United States Patent
Altmann et al.

(10) Patent No.: US 9,487,483 B2
(45) Date of Patent: Nov. 8, 2016

(54) COMPLEMENT PATHWAY MODULATORS AND USES THEREOF

(71) Applicant: Novartis AG, Basel (CH)

(72) Inventors: Eva Altmann, Reinach (CH); Ulrich Hommel, Mulheim (DE); Edwige Liliane Jeanne Lorthiois, Niffer (FR); Jeurgen Klaus Maibaum, Weil-Haltingen (DE); Nils Ostermann, Binzen (DE); Jean Quancard, Huningue (FR); Stefan Andreas Randl, Frankfurt am Main (DE); Olivier Rogel, Hesingue (FR); Anna Vulpetti, Basel (CH); Stefanie Flohr, Lorrach (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/409,911

(22) PCT Filed: Jun. 27, 2013

(86) PCT No.: PCT/IB2013/055300
§ 371 (c)(1),
(2) Date: Dec. 19, 2014

(87) PCT Pub. No.: WO2014/002058
PCT Pub. Date: Jan. 3, 2014

(65) Prior Publication Data
US 2015/0148349 A1 May 28, 2015

Related U.S. Application Data

(60) Provisional application No. 61/665,479, filed on Jun. 28, 2012, provisional application No. 61/774,229, filed on Mar. 7, 2013.

(51) Int. Cl.
| | |
|---|---|
| C07D 209/52 | (2006.01) |
| C07D 471/04 | (2006.01) |
| C07D 401/14 | (2006.01) |
| C07D 403/06 | (2006.01) |
| C07D 403/14 | (2006.01) |
| C07D 487/04 | (2006.01) |
| A61K 45/06 | (2006.01) |

(52) U.S. Cl.
CPC ............ *C07D 209/52* (2013.01); *A61K 45/06* (2013.01); *C07D 401/14* (2013.01); *C07D 403/06* (2013.01); *C07D 403/14* (2013.01); *C07D 471/04* (2013.01); *C07D 487/04* (2013.01)

(58) Field of Classification Search
None
See application file for complete search history.

(56) References Cited

U.S. PATENT DOCUMENTS

| | | | |
|---|---|---|---|
| 5,596,000 | A | 1/1997 | Esser |
| 5,872,135 | A | 2/1999 | Desolms |
| 6,274,617 | B1 | 8/2001 | Hamilton |
| 6,933,316 | B2 | 8/2005 | Hsieh et al. |
| 7,417,063 | B2 | 8/2008 | Smallheer et al. |
| 2001/0041733 | A1 | 11/2001 | Hamilton |
| 2005/0107319 | A1 | 5/2005 | Bansal |
| 2006/0020000 | A1 | 1/2006 | Tynebor |
| 2008/0003214 | A1 | 1/2008 | Cezanne et al. |
| 2012/0295884 | A1* | 11/2012 | Altmann ............ C07D 401/14 514/210.18 |

FOREIGN PATENT DOCUMENTS

| | | |
|---|---|---|
| DE | 102004045796 | 3/2006 |
| EP | 0039051 A2 | 11/1981 |
| EP | 0394989 A2 | 10/1990 |
| FR | 2876692 A1 | 4/2006 |
| WO | 9320099 | 10/1993 |
| WO | 9610035 | 4/1996 |
| WO | 9639137 | 12/1996 |
| WO | 9962484 | 12/1999 |
| WO | 9962487 | 12/1999 |
| WO | 9962879 | 12/1999 |
| WO | 0009112 | 2/2000 |
| WO | 0226697 | 4/2002 |
| WO | 0232879 | 4/2002 |
| WO | 03045912 A1 | 6/2003 |
| WO | 2004034769 A1 | 4/2004 |
| WO | 2004045518 A2 | 6/2004 |
| WO | 2004062601 A2 | 7/2004 |

(Continued)

OTHER PUBLICATIONS

Morikis et al., Biochemical Society Transactions, 30(6):1026-1036 (2002).
Ricklin et al., Nature Biotechnology, 25(11):1265-1275 (2007).

*Primary Examiner* — Timothy R Rozof
(74) *Attorney, Agent, or Firm* — John B. Alexander

(57) ABSTRACT

The present invention provides a compound of formula (I): a method for manufacturing the compounds of the invention, and its therapeutic uses. The present invention further provides a combination of pharmacologically active agents and a pharmaceutical composition.

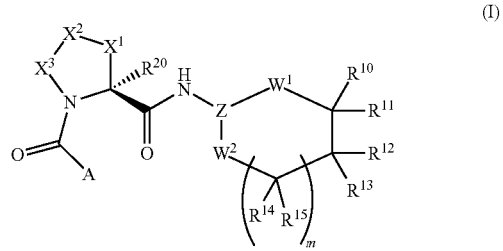

17 Claims, No Drawings

(56) References Cited

FOREIGN PATENT DOCUMENTS

| WO | 2004062607 | A2 | 7/2004 |
|----|------------|----|--------|
| WO | 2004065367 | A1 | 8/2004 |
| WO | 2004078163 | A2 | 9/2004 |
| WO | 2004083174 | A2 | 9/2004 |
| WO | 2004087646 | A2 | 10/2004 |
| WO | 2005077417 | A1 | 8/2005 |
| WO | 2006090192 | A1 | 8/2006 |
| WO | 2006127550 | A1 | 11/2006 |
| WO | 2006129199 | A1 | 12/2006 |
| WO | 2007016589 | A2 | 2/2007 |
| WO | 2007044668 | A2 | 4/2007 |
| WO | 2007070600 | A2 | 6/2007 |
| WO | 2007103549 | A2 | 9/2007 |
| WO | 2008036967 | A2 | 3/2008 |
| WO | 2008055206 | A2 | 5/2008 |
| WO | 2008064218 | A2 | 5/2008 |
| WO | 2008132153 | A1 | 11/2008 |
| WO | 2008147883 | A1 | 12/2008 |
| WO | 2009106980 | A2 | 9/2009 |
| WO | 2010020675 | A1 | 2/2010 |
| WO | 2011082077 | A1 | 7/2011 |
| WO | 2012/093101 |  | 7/2012 |

* cited by examiner

COMPLEMENT PATHWAY MODULATORS AND USES THEREOF

This application is a U.S. National Phase filing of International Application No. PCT/IB2013/055300 filed 27 Jun. 2013, which claims priority to U.S. Application No. 61/665,479 filed 28 Jun. 2012 and 61/774,229 filed 07 Mar. 2013, the contents of which are incorporated herein by reference in their entirety.

FIELD OF THE INVENTION

The invention relates to the inhibition of the complement alternative pathway and particularly to inhibition of Factor D, in patients suffering from conditions and diseases associated with complement alternative pathway activation such as age-related macular degeneration, diabetic retinopathy and related ophthalmic diseases.

BACKGROUND OF THE INVENTION

The complement system is a crucial component of the innate immunity system and comprises a group of proteins that are normally present in an inactive state. These proteins are organized in three activation pathways: the classical, the lectin, and the alternative pathways (V. M. Holers, In Clinical Immunology: Principles and Practice, ed. R. R. Rich, Mosby Press; 1996, 363-391). Molecules from microorganisms, antibodies or cellular components can activate these pathways resulting in the formation of protease complexes known as the C3-convertase and the C5-convertase. The classical pathway is a calcium/magnesium-dependent cascade, which is normally activated by the formation of antigen-antibody complexes. It can also be activated in an antibody-independent manner by the binding of C-reactive protein complexed to ligand and by many pathogens including gram-negative bacteria. The alternative pathway is a magnesium-dependent cascade which is activated by deposition and activation of C3 on certain susceptible surfaces (e.g., cell wall polysaccharides of yeast and bacteria, and certain biopolymer materials).

Factor D may be a suitable target for the inhibition of this amplification of the complement pathways because its plasma concentration in humans is very low (about 1.8 μg/mL), and it has been shown to be the limiting enzyme for activation of the alternative complement pathway (P. H. Lesavre and H. J. Müller-Eberhard. J. Exp. Med., 1978; 148: 1498-1510; J. E. Volanakis et al., New Eng. J. Med., 1985; 312:395-401).

Macular degeneration is a clinical term that is used to describe a family of diseases that are characterized by a progressive loss of central vision associated with abnormalities of Bruch's membrane, the choroid, the neural retina and/or the retinal pigment epithelium. In the center of the retina is the macula lutea, which is about ⅓ to ½ cm in diameter. The macula provides detailed vision, particularly in the center (the fovea), because the cones are higher in density and because of the high ratio of ganlion cells to photoreceptor cells. Blood vessels, ganglion cells, inner nuclear layer and cells, and the plexiform layers are all displaced to the side (rather than resting above the photoreceptor cells), thereby allowing light a more direct path to the cones. Under the retina is the choroid, a part of the uveal tract, and the retinal pigmented epithelium (RPE), which is between the neural retina and the choroid. The choroidal blood vessels provide nutrition to the retina and its visual cells.

Age-related macular degeneration (AMD), the most prevalent form of macular degeneration, is associated with progressive loss of visual acuity in the central portion of the visual field, changes in color vision, and abnormal dark adaptation and sensitivity. Two principal clinical manifestations of AMD have been described as the dry, or atrophic, form and the neovascular, or exudative, form. The dry form is associated with atrophic cell death of the central retina or macula, which is required for fine vision used for activities such as reading, driving or recognizing faces. About 10-20% of these AMD patients progress to the second form of AMD, known as neovascular AMD (also referred to as wet AMD).

Neovascular AMD is characterized by the abnormal growth of blood vessels under the macula and vascular leakage, resulting in displacement of the retina, hemorrhage and scarring. This results in a deterioration of sight over a period of weeks to years. Neovascular AMD cases originate from intermediate or advanced dry AMD. The neovascular form accounts for 85% of legal blindness due to AMD. In neovascular AMD, as the abnormal blood vessels leak fluid and blood, scar tissue is formed that destroys the central retina.

The new blood vessels in neovascular AMD are usually derived from the choroid and are referred to as choroidal neovascularizaton (CNV). The pathogenesis of new choroidal vessels is poorly understood, but such factors as inflammation, ischemia, and local production of angiogenic factors are thought to be important. A published study suggests that CNV is caused by complement activation in a mouse laser model (Bora P. S., J. Immunol. 2005; 174; 491-497).

Human genetic evidence implicates the involvement of the complement system, particularly the alternative pathway, in the pathogenesis of Age-related Macular Degeneration (AMD). Significant associations have been found between AMD and polymorphisms in complement factor H (CFH) (Edwards A O, et al. Complement factor H polymorphism and age-related macular degeneration. Science. 2005 Apr. 15; 308(5720):421-4; Hageman G S, et al A common haplotype in the complement regulatory gene factor H (HF1/CFH) predisposes individuals to age-related macular degeneration. Proc Natl Acad Sci USA. 2005 May 17; 102(20):7227-32; Haines J L, et al. Complement factor H variant increases the risk of age-related macular degeneration. Science. 2005 Apr. 15; 308(5720):419-21; Klein R J, et al Complement factor H polymorphism in age-related macular degeneration. Science. 2005 Apr. 15; 308(5720):385-9; Lau L I, et al. Association of the Y402H polymorphism in complement factor H gene and neovascular age-related macular degeneration in Chinese patients. Invest Ophthalmol Vis Sci. 2006 August; 47(8):3242-6; Simonelli F, et al. Polymorphism p. 402Y>H in the complement factor H protein is a risk factor for age related macular degeneration in an Italian population. Br J Ophthalmol. 2006 September; 90(9):1142-5; and Zareparsi S, et al Strong association of the Y402H variant in complement factor H at 1q32 with susceptibility to age-related macular degeneration. Am J Hum Genet. 2005 July; 77(1):149-53. Complement factor B (CFB) and complement C2 (Gold B, et al. Variation in factor B (BF) and complement component 2 (C2) genes is associated with age-related macular degeneration. Nat Genet. 2006 April; 38(4):458-62 and Jakobsdottir J, et al. C2 and CFB genes inage-related maculopathy and joint action with CFH and LOC387715 genes. PLoS One. 2008 May 21; 3(5):e2199), and most recently in complement C3 (Despriet D D, et al Complement component C3 and risk of age-related macular degeneration. Ophthalmology. 2009 March; 116(3):474-480.e2; Mailer J B, et al Variation in complement factor 3 is associated with risk of age-related macular degeneration. Nat Genet. 2007 October; 39(10):1200-1 and Park K H, et al Complement component 3 (C3) haplotypes and risk of advanced age-related macular degeneration. Invest Ophthalmol Vis Sci. 2009 July; 50(7):3386-93. Epub 2009 Feb. 21. Taken together, the genetic variations in the alternative pathway components CFH, CFB, and C3 can predict clinical outcome in nearly 80% of cases.

Currently there is no proven medical therapy for dry AMD and many patients with neovascular AMD become legally blind despite current therapy with anti-VEGF agents such as Lucentis. Thus, it would be desirable to provide therapeutic agents for the treatment or prevention of complement mediated diseases and particularly for the treatment of AMD.

SUMMARY OF THE INVENTION

The present invention provides compounds that modulate, and preferably inhibit, activation of the alternative complement pathway. In certain embodiments, the present invention provides compounds that modulate, and preferably inhibit, Factor D activity and/or Factor D mediated complement pathway activation. Such Factor D modulators are preferably high affinity Factor D inhibitors that inhibit the catalytic activity of complement Factor Ds, such as primate Factor D and particularly human Factor D.

The compounds of the present invention inhibit or suppress the amplification of the complement system caused by C3 activation irrespective of the inital mechanism of activation (including for example activation of the classical, lectin or ficolin pathways).

Various embodiments of the invention are described herein. It will be recognized that features specified in each embodiment may be combined with other specified features to provide further embodiments.

Within certain aspects, Factor D modulators provided herein are compounds of Formula I and salts thereof:

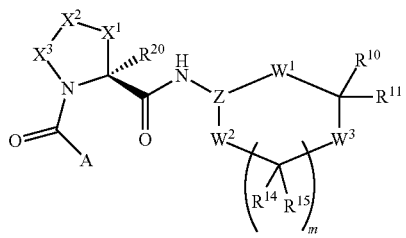

(I)

Within certain other aspects, Factor D modulators provided herein are compounds of Formula II, and salts thereof:

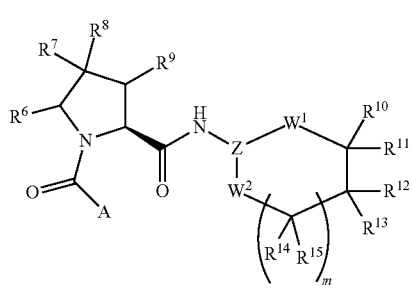

(II)

In another embodiment, the invention provides a pharmaceutical composition comprising a therapeutically effective amount of a compound according to the definition of formula (I) or formula (II) or subformulae thereof and one or more pharmaceutically acceptable carriers.

In another embodiment, the invention provides a combination, in particular a pharmaceutical combination, comprising a therapeutically effective amount of the compound according to the definition of formula (I) or formula (II) or subformulae thereof and one or more therapeutically active.

The invention further provides methods of treating or preventing complement mediated diseases, the method comprising the steps of identifying a patient in need of complement modulation therapy and administering a compound of Formula (I) or formula (II) or a subformulae thereof. Complement mediated diseases include ophthalmic diseases (including early or neovascular age-related macular degeneration and geographic atrophy), autoimmune diseases (including arthritis, rheumatoid arthritis), Respiratory diseases, cardiovascular diseases.

Other aspects of the invention are discussed infra.

DETAILED DESCRIPTION OF THE INVENTION

As noted above, the present invention provides compounds that modulate Factor D activation and/or Factor D-mediated signal transduction of the complement system. Such compounds may be used in vitro or in vivo to modulate (preferably inhibit) Factor D activity in a variety of contexts.

In a first embodiment, the invention provides compounds of Formula I and pharmaceutically acceptable salts thereof, which modulate the alternative pathway of the complement system. Compounds of Formula I are represented by the structure:

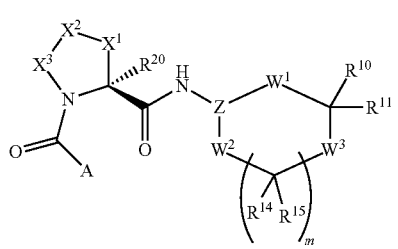

(I)

Wherein
A is a group selected from:

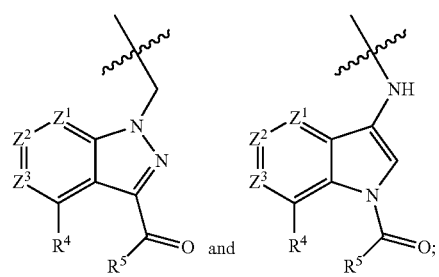

Wherein
$Z^1$ is $C(R^1)$ or N;
$Z^2$ is $C(R^2)$ or N;

$Z^3$ is $C(R^3)$ or N, wherein at least one of $Z^1$, $Z^2$ or $Z^3$ is not N;

$R^1$ is selected from the group consisting of hydrogen, halogen, $C_1$-$C_6$alkyl, $C_1$-$C_6$alkoxy, haloC-$C_6$alkyl, haloC-$C_6$alkoxy, $C_1$-$C_6$alkoxycarbonyl, $CO_2H$ and $C(O)NR^AR^B$;

$R^2$ and $R^3$ are independently selected from the group consisting of hydrogen, halogen, hydroxy, $NR^CR^D$, cyano, $CO_2H$, $CONR^AR^B$, $SO_2C_1$-$C_6$alkyl, and $SO_2NH_2$, $SO_2NR^AR^B$, $C_1$-$C_6$alkoxycarbonyl, —$C(NR^A)NR^CR^D$, $C_1$-$C_6$alkyl, haloC$_1$-$C_6$alkyl, $C_2$-$C_6$alkenyl, $C_1$-$C_6$alkoxy, haloC$_1$-$C_6$alkoxy, $C_2$-$C_6$alkenyloxy, wherein each alkyl, alkenyl, alkoxy and alkenyloxy is unsubstituted or substituted with up to 4 substituents independently selected from halogen, hydroxy, cyano, tetrazole, $C_1$-$C_4$alkoxy, $C_1$-$C_4$haloalkoxy, $CO_2H$, $C_1$-$C_6$alkoxycarbonyl, $C(O)NR^AR^B$, $NR^CR^D$, optionally substituted phenyl, heterocycle having 4 to 7 ring atoms and 1, 2 or 3 ring heteroatoms selected from N, O or S, heteroaryl having 5 or 6 ring atoms and 1, 2 or 3 ring heteroatoms selected from N, O or S, and wherein optional phenyl and heteroaryl substituents are selected from halogen, hydroxy, $C_1$-$C_4$alkyl, $C_1$-$C_4$alkoxy and $CO_2H$;

$R^4$ is selected from the group consisting of hydrogen, halogen, and $C_1$-$C_6$alkyl;

$R^5$ is $C_1$-$C_4$alkyl, hydroxyC$_1$-$C_4$alkyl, haloC$_1$-$C_4$alkyl $C_1$-$C_4$alkoxyC$_1$-$C_4$alkyl, amino, methylamino;

$X^1$ is $CR^9R^{22}$ or sulfur;

$X^2$ is $CR^7R^8$, oxygen, sulfur, N(H) or N($C_1$-$C_6$alkyl), wherein at least one of $X^1$ and $X^2$ is carbon; or $X^1$ and $X^2$, in combination, forms an olefin of the formula —$C(R^7)$=$C(H)$— or —$C(R^7)$=$C(C_1$-$C_4$alkyl)-, wherein the $C(R^7)$ is attached to $X^3$;

$X^3$ is $(CR^6R^{21})_q$ or N(H) wherein q is 0, 1 or 2, wherein $X^3$ is $CR^6R^{21}$ or $(CR^6R^{21})_2$ when either $X^1$ or $X^2$ is sulfur or $X^2$ is oxygen; or $X^2$ and $X^3$, taken in combination, are —N=C(H)— or —N=C($C_1$-$C_4$alkyl)- in which the C(H) or C($C_1$-$C_4$alkyl) is attached to $X^1$;

$R^6$ is selected from the group consisting of hydrogen and $C_1$-$C_6$alkyl;

$R^7$ is hydrogen, halogen, hydroxy, cyano, $C_1$-$C_6$alkyl, $C_1$-$C_6$alkoxy, hydroxyC$_1$-$C_6$alkyl, $C_1$-$C_6$alkoxyC$_1$-$C_6$alkyl, haloC$_1$-$C_6$alkyl, or $C_1$-$C_6$haloalkoxy;

$R^8$ is hydrogen, halogen, hydroxy, azide, cyano, COOH, $C_1$-$C_6$alkoxycarbonyl, $C_1$-$C_6$alkyl, $C_1$-$C_6$alkoxy, $C_1$-$C_6$haloalkyl, $C_1$-$C_6$haloalkoxy, $NR^AR^B$, N(H)C(O)$C_1$-$C_6$alkyl, hydroxyC$_1$-$C_6$alkyl, $C_1$-$C_6$alkoxyC$_1$-$C_6$alkyl or $C_1$-$C_6$alkyl substituted with $NR^AR^B$, N(H)C(O)H or N(H)C(O)($C_1$-$C_4$alkyl);

$R^9$ is selected from the group consisting of hydrogen, hydroxy, halogen, $C_1$-$C_6$alkyl, haloC$_1$-$C_6$alkyl, $C_2$-$C_6$alkenyl, $C_2$-$C_6$alkynyl, $C_1$-$C_6$alkoxy, haloC$_1$-$C_6$alkoxy, $NR^AR^B$, N(H)C(O)$C_1$-$C_6$alkyl, N(H)C(O)O$C_1$-$C_6$alkyl and OC(O)$NR^CR^D$ each of alkyl, alkoxy, alkenyl, and alkynyl substituents may be substituted with 0, 1 or 2 groups independently selected at each occurrence from the group consisting of halogen, hydroxy, $C_1$-$C_6$alkyl, $C_1$-$C_6$alkoxy and $NR^AR^B$;

$R^{20}$ is hydrogen or $C_1$-$C_6$alkyl;

$R^{21}$ is selected from the group consisting of hydrogen, phenyl and $C_1$-$C_6$alkyl, wherein the alkyl group is unsubstituted or substituted with hydroxy, amino, azide, and NHC(O)$C_1$-$C_6$alkyl;

$R^{22}$ is selected from the group consisting of hydrogen, halogen, hydroxy, amino and $C_1$-$C_6$alkyl;

$CR^7R^8$, taken in combination forms a spirocyclic 3 to 6 membered carbocycle which is substituted with 0, 1, or 2 substituents independently selected from the group consisting of halogen and methyl; or $R^7$ and $R^8$, taken in combination, form an exocyclic methylidene (=$CH_2$);

$R^7$ and $R^{22}$ or $R^8$ and $R^9$, taken in combination form an epoxide ring or a 3 to 6 membered carbocyclic ring system which carbocyclic ring is substituted with 0, 1 or 2 substituents independently selected from the group consisting of halogen, methyl, ethyl, hydroxyC$_1$-$C_4$alkyl, $C_1$-$C_6$alkoxyC$_1$-$C_4$alkyl, $C_1$-$C_4$alkoxycarbonyl, $CO_2H$ and $C_1$-$C_4$alkyl substituted with $NR^AR^B$;

$R^6$ and $R^7$ or $R^8$ and $R^{21}$, taken in combination, form a fused 3 membered carbocyclic ring system which is substituted with 0, 1 or 2 substituents independently selected from the group consisting of halogen, methyl, ethyl, hydroxyC$_1$-$C_4$alkyl, $C_1$-$C_6$alkoxyC$_1$-$C_4$alkyl, $C_1$-$C_4$alkoxycarbonyl, $CO_2H$ and $C_1$-$C_4$alkyl substituted with $NR^AR^B$; or $R^{20}$ and $R^{22}$ taken in combination form a fused 3 carbocyclic ring system;

$R^9$ and $R^{21}$ taken in combination form a form 1 to 3 carbon alkylene linker;

$R^7$ and $R^{20}$ taken in combination form 1 to 3 carbon alkylene linker;

Z is N or $CR^{16}$;

$W^1$ is a bond or $CR^{17}R^{18}$;

$W^2$ is a bond or $CH_2$;

$W^3$ is $CR^{12}R^{13}$; or $W^3$ is oxygen when (a) neither $W^1$ or $W^2$ is a bond and m is 1 or (b) $W^1$ is a bond, $W^2$ is $CH_2$ and m is 2;

$R^{10}$ is selected from the group consisting of hydrogen, $C_1$-$C_4$alkyl, $C_1$-$C_4$alkoxy, halogen, hydroxyC$_1$-$C_4$alkyl, haloC$_1$-$C_4$alkyl, haloC$_1$-$C_4$alkoxy, $CO_2C_1$-$C_4$alkyl, and $C(O)NH_2$;

$R^{11}$ is selected from the group consisting of hydrogen, $C_1$-$C_4$alkyl, haloC$_1$-$C_4$alkyl, $C_1$-$C_4$alkoxy, hydroxy and halogen;

or $CR^{10}R^{11}$, taken in combination form a spirocyclic carbocycle having 3 to 6 ring carbon atoms or a spirocyclic heterocycle having 3 to 6 ring atoms and one ring heteroatom selected from N, O or S;

$R^{12}$ and $R^{13}$ are independently selected from the group consisting of hydrogen, $C_1$-$C_4$alkyl, haloC$_1$-$C_4$alkyl, $C_1$-$C_4$alkoxy, haloC$_1$-$C_4$alkoxy and halogen;

$R^{14}$ and $R^{15}$ are independently selected from hydrogen, $C_1$-$C_4$alkyl, $C_1$-$C_4$alkoxy, halogen, haloC$_1$-$C_4$alkyl and hydroxy;

$R^{16}$ is hydrogen, $C_1$-$C_4$alkyl optionally substituted by fluoro, hydroxy or methoxy;

$R^{17}$ is hydrogen or fluoro;

$R^{18}$ is hydrogen or fluoro; or $CR^{17}R^{18}$—$CR^{10}R^{11}$, taken in combination, form a vinyl group of the formula—$C(R^{18})$=$C(R^{11})$—;

$R^A$ and $R^B$, are each independently selected from the group consisting of hydrogen, $C_1$-$C_6$alkyl, haloC$_1$-$C_6$alkyl, $C_1$-$C_6$alkoxyC$_1$-$C_6$alkyl or hydroxyC$_1$-$C_6$alkyl; and $R^C$ and $R^D$ are independently selected from the group consisting of hydrogen, and $C_1$-$C_6$alkyl, haloC$_1$-$C_6$alkyl, $C_1$-$C_6$alkoxyC$_1$-$C_6$alkyl, hydroxyC$_1$-$C_6$alkyl or $NR^CR^D$, taken in combination, form a heterocycle having 4 to 7 ring atoms and 0 or 1 additional ring N, O or S atoms, which heterocycle is substituted with 0, 1, or 2 substituents independently selected from the group consisting of $C_1$-$C_4$alkyl, halogen, hydroxy, $C_1$-$C_4$alkoxy; and m is 0, 1, or 2.

In a second embodiment, the invention provides compounds of Formula II and pharmaceutically acceptable salts thereof, which modulate the alternative pathway of the complement system. Compounds of Formula II are represented by the structure:

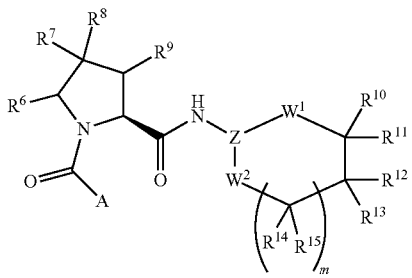

(II)

Wherein
A is a group selected from:

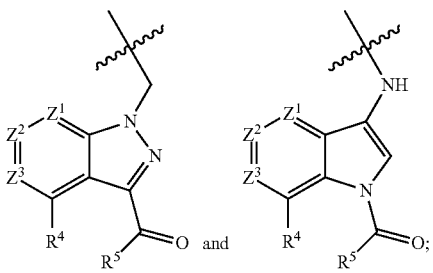

$Z^1$ is $C(R^1)$ or N;
$Z^2$ is $C(R^2)$ or N;
$Z^3$ is $C(R^3)$ or N, wherein at least one of $Z^1$, $Z^2$ or $Z^3$ is not N;
$R^1$ is selected from the group consisting of hydrogen, halogen, $C_1$-$C_6$alkyl, $C_1$-$C_6$alkoxy, haloC-$C_6$alkyl, haloC-$C_6$alkoxy $C_1$-$C_6$alkoxycarbonyl, $CO_2H$ and $C(O)NR^AR^B$;
$R^2$ and $R^3$ are independently selected from the group consisting of hydrogen, halogen, hydroxy, $NR^CR^D$, cyano, $CO_2H$, $CONR^AR^B$, $SO_2C_1$-$C_6$alkyl, and $SO_2NH_2$, $SO_2NR^AR^B$, $C_1$-$C_6$alkoxycarbonyl, —$C(NR^A)NR^CR^D$, $C_1$-$C_6$alkyl, halo$C_1$-$C_6$alkyl, $C_2$-$C_6$alkenyl, $C_1$-$C_6$alkoxy, halo$C_1$-$C_6$alkoxy, $C_2$-$C_6$alkenyloxy, wherein each alkyl, alkenyl, alkoxy and alkenyloxy is unsubstituted or substituted with up to 4 substitutents independently selected from halogen, hydroxy, cyano, tetrazole, $C_1$-$C_4$alkoxy, $C_1$-$C_4$haloalkoxy, $CO_2H$, $C_1$-$C_6$alkoxycarbonyl, $C(O)NR^AR^B$, $NR^CR^D$, optionally substituted phenyl, heterocycle having 4 to 7 ring atoms and 1, 2 or 3 ring heteroatoms selected from N, O or S, heteroaryl having 5 or 6 ring atoms and 1, 2 or 3 ring heteroatoms selected from N, O or S, and wherein optional phenyl and heteroaryl substituents are selected from halogen, hydroxy, $C_1$-$C_4$alkyl, $C_1$-$C_4$alkoxy and $CO_2H$;
$R^4$ is selected from the group consisting of hydrogen, halogen, and $C_1$-$C_6$alkyl;
$R^5$ is $C_1$-$C_4$alkyl, haloC-$C_4$alkyl, hydroxy$C_1$-$C_4$alkyl, $C_1$-$C_4$alkoxy$C_1$-$C_4$alkyl, amino, and methylamino;
$R^6$ is hydrogen;
$R^7$ is hydrogen or fluoro;
$R^8$ is hydrogen, methyl or hydroxymethyl;
$R^9$ is hydrogen, halogen, hydroxy or methoxy; or
$R^6$ and $R^7$, taken in combination, form a cyclopropane ring; or $R^8$ and $R^9$, taken in combination, form a cyclopropane ring;
Z is N or $CR^{16}$;
$W^1$ is a bond or $CR^{17}R^{18}$;
$W^2$ is a bond or $CH_2$;
$R^{10}$ is selected from the group consisting of hydrogen, $C_1$-$C_4$alkyl, $C_1$-$C_4$alkoxy, halogen, hydroxy$C_1$-$C_4$alkyl, halo$C_1$-$C_4$alkyl, halo$C_1$-$C_4$alkoxy, $CO_2C_1$-$C_4$alkyl and $C(O)NH_2$;
$R^{11}$ is selected from the group consisting of hydrogen, $C_1$-$C_4$alkyl, halo$C_1$-$C_4$alkyl, $C_1$-$C_4$alkoxy, hydroxy and halogen;
or $CR^{10}R^{11}$, taken in combination form a spirocyclic carbocycle having 3 to 6 ring carbon atoms or a spirocyclic heterocycle having 3 to 6 ring atoms and one ring heteroatom selected from N, O or S;
$R^{12}$ and $R^{13}$ are independently selected from the group consisting of hydrogen, $C_1$-$C_4$alkyl and halogen;
$R^{14}$ and $R^{15}$ are independently selected from hydrogen, $C_1$-$C_4$alkyl, $C_1$-$C_4$alkoxy, halogen, halo$C_1$-$C_4$alkyl and hydroxy;
$R^{16}$ is hydrogen, $C_1$-$C_4$alkyl optionally substituted by fluoro, hydroxy or methoxy;
$R^{17}$ is hydrogen or fluoro;
$R^{18}$ is hydrogen or fluoro; or
$CR^{17}R^{18}$—$CR^{10}R^{11}$, taken in combination, form a vinyl group of the formula—$C(R^{18})$=$C(R^{11})$—;
$R^A$ and $R^B$, are each independently selected from the group consisting of hydrogen, $C_1$-$C_6$alkyl, halo$C_1$-$C_6$alkyl, $C_1$-$C_6$alkoxy$C_1$-$C_6$alkyl, or hydroxy$C_1$-$C_6$alkyl; and
$R^C$ and $R^D$ are independently selected from the group consisting of hydrogen, and $C_1$-$C_6$alkyl, halo$C_1$-$C_6$alkyl, $C_1$-$C_6$alkoxy$C_1$-$C_6$alkyl, hydroxy$C_1$-$C_6$alkyl or $NR^CR^D$, taken in combination, form a heterocycle having 4 to 7 ring atoms and 0 or 1 additional ring N, O or S atoms, wherein heterocycle is substituted with 0, 1 or 2 substituents independently selected from the group consisting of $C_1$-$C_4$alkyl, halogen, hydroxy, $C_1$-$C_4$alkoxy; and
m is 0, 1 or 2.

In a third embodiment, compounds, or salts thereof, according to embodiment one or two are provided. Compounds of the third embodiment are represented by formula (III) or (IV):

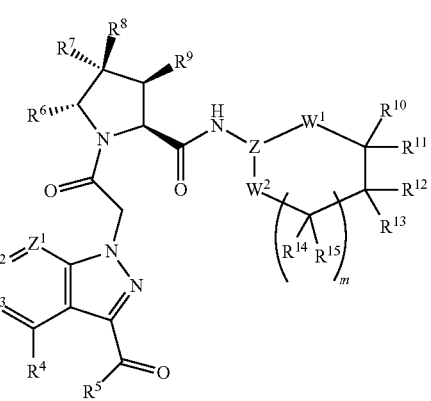

(III)

or

-continued

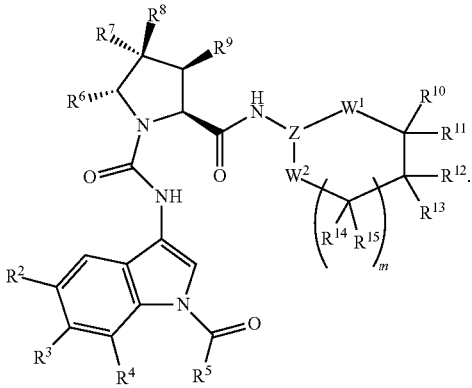

(IV)

In a fourth embodiment, a compound or salt thereof according to any one of embodiments one to three is provided in which at least two of $Z^1$, $Z^2$ and $Z^3$ are not N.

In a fifth embodiment, a compound or salt thereof according to any one of embodiments one to four is provided in which $R^4$ is hydrogen.

In a sixth embodiment, a compound or salt thereof according to any one of embodiments one to five is provided in which $Z^1$ is N or $CR^1$; $Z^2$ is N or $CR^2$, wherein at least one of $Z^1$ and $Z^2$ are not N;

$Z^3$ is $CR^3$;

$R^1$ is hydrogen, halogen or $C_1$-$C_4$alkyl;

$R^2$ is selected from the group consisting of hydrogen, halogen, $CO_2H$, $C_1$-$C_4$alkyl and $C_1$-$C_4$alkoxy;

$R^3$ is selected from the group consisting of hydrogen, halogen, $CO_2H$, $C_1$-$C_4$alkyl and $C_1$-$C_4$alkoxy, wherein the alkoxy is optionally substituted by pyridyl or pyrimidinyl;

$R^4$ is hydrogen; and $R^5$ is amino or $C_1$-$C_4$alkyl.

In a seventh embodiment, a compound or salt thereof according to any one of embodiments one to five is provided in which $Z^1$ is $CR^1$; $Z^2$ is $CR^2$; and $Z^3$ is $CR^3$;

$R^1$ is hydrogen, halogen or $C_1$-$C_4$alkyl;

$R^2$ is selected from the group consisting of hydrogen, halogen, $CO_2H$, $C_1$-$C_4$alkyl and $C_1$-$C_4$alkoxy;

$R^3$ is selected from the group consisting of hydrogen, halogen, $CO_2H$, $C_1$-$C_4$alkyl and $C_1$-$C_4$alkoxy, wherein the alkoxy is optionally substituted by pyridyl or pyrimidinyl;

$R^4$ is hydrogen; and $R^5$ is amino or $C_1$-$C_4$alkyl.

In an eighth embodiment, a compound or salt thereof according to any one of embodiments one to five is provided in which $Z^1$ and $Z^2$ are CH; and $Z^3$ is $CR^3$;

$R^3$ is $C_1$-$C_4$alkoxy substituted by pyridyl or pyrimidinyl;

$R^4$ is hydrogen; and $R^5$ is amino or $C_1$-$C_4$alkyl.

In a ninth embodiment, a compound or salt thereof according to any one of embodiments one to six is provided in which $Z^1$ is N or $CR^1$; $Z^2$ is N or $CR^2$, wherein at least one of $Z^1$ and $Z^2$ are not N;

$Z^3$ is $CR^3$;

$R^1$ is hydrogen, halogen or $C_1$-$C_4$alkyl;

$R^2$ is selected from the group consisting of hydrogen, halogen, $CO_2H$, $C_1$-$C_4$alkyl and $C_1$-$C_4$alkoxy; and $R^3$ is selected from from the group consisting of hydrogen and $C_1$-$C_4$alkyl (in certain compounds, $R^3$ is hydrogen, methyl or ethyl, or $R^3$ is methyl or ethyl;

In a tenth embodiment, a compound or salt thereof according to any one of embodiments one to nine is provided in which $R^6$ and $R^7$ taken in combination form a cyclopropane ring;

$R^8$ is hydrogen, methyl or hydroxymethyl; and $R^9$ is hydrogen.

In an eleventh embodiment, a compound or salt thereof according to any one of embodiments one to nine is provided in which $R^6$ and $R^7$ are hydrogen; and $R^8$ and $R^9$ taken in combination form a cyclopropane ring;

In a twelfth embodiment, a compound or salt thereof according to any one of embodiments one to nine is provided in which $R^6$ and $R^8$ are hydrogen;

$R^7$ is fluoro; and $R^9$ is hydrogen or methoxy.

In a thirteenth embodiment, a compound or salt thereof according to any one of embodiments one to twelve is provided in which $W^1$ is $CH_2$ and $W^2$ is a bond or $CH_2$.

In a fourteenth embodiment, a compound or salt thereof according to any one of embodiments one to thirteen is provided in which $R^{10}$ is selected from the group consisting of hydrogen, $C_1$-$C_4$alkyl, $C_1$-$C_4$alkoxy, halogen and halo$C_1$-$C_4$alkyl;

$R^{11}$ is selected from the group consisting of hydrogen, $C_1$-$C_4$alkyl, $C_1$-$C_4$alkoxy and halogen;

or $CR^{10}R^{11}$, taken in combination form a spirocyclic cyclopropyl;

$R^{12}$ and $R^{13}$ are hydrogen; and $R^{14}$ and $R^{15}$ are independently selected from hydrogen, hydroxyl, $C_1$-$C_4$alkyl and $C_1$-$C_4$alkoxy.

In a fifteenth embodiment, a compound or salt thereof according to any one of embodiments one to fourteen is provided in which Z is N.

In a sixteenth embodiment, a compound or salt thereof according to any one of embodiments one to fourteen is provided in which Z is CH.

In a seventeenth embodiment, a compound or salt thereof according to any one of embodiments one to fourteen is provided in which the compound is represented by formula (V) or (VI):

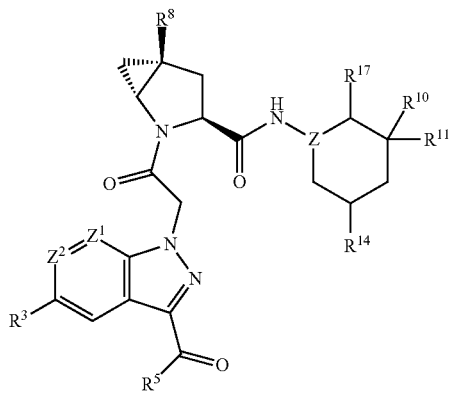

(V)

or

-continued

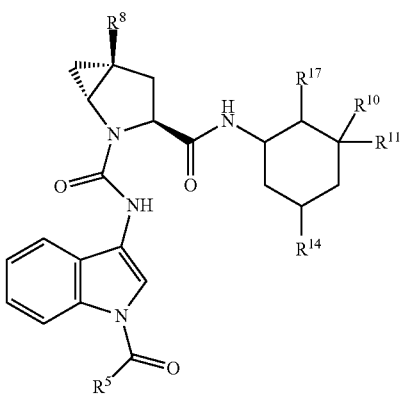

(VI)

Wherein
$Z^1$ is CH or N;
$Z^2$ is $CR^2$ or N;
$R^2$ is hydrogen, $C_1$-$C_4$alkyl, or halogen;
$R^3$ is hydrogen, $C_1$-$C_4$alkyl, or pyrimidinylmethoxy;
$R^5$ is methyl or amino;
$R^8$ is hydrogen or hydroxymethyl;
$R^{10}$ is $C_1$-$C_4$alkyl, halogen, or trifluoromethyl;
$R^{11}$ is hydrogen, halogen, $C_1$-$C_4$alkyl or methoxy; or
$R^{10}$ and $R^{11}$ together form a spirocyclopropyl;
$R^{14}$ is hydrogen, hydroxyl, $C_1$-$C_4$alkyl or methoxy;
$R^{17}$ is hydrogen; or
$CHR^{17}CR^{10}R^{11}$, taken in combination forms a vinyl group of the formula $CH=CR^{11}$.

In a eighteenth embodiment, a compound or salt thereof according to any one of embodiments one or two is provided in which the compound is selected:
(1R,3S,5R)-2-[2-(3-Acetyl-pyrazolo[3,4-c]pyridin-1-yl)-acetyl]-2-aza-bicyclo[3.1.0]hexane-3-carboxylic acid (3,3-dimethyl-cyclobutyl)-amide;
(1R,3S,5R)-2-[2-(3-Acetyl-pyrazolo[3,4-b]pyridin-1-yl)-acetyl]-2-aza-bicyclo[3.1.0]hexane-3-carboxylic acid (2,2-dimethyl-cyclopropyl)-amide;
(1R,3S,5R)-2-[2-(3-Acetyl-pyrazolo[3,4-b]pyridin-1-yl)-acetyl]-2-aza-bicyclo[3.1.0]hexane-3-carboxylic acid (2,2-difluoro-cyclopropyl)-amide;
(1R,3S,5R)-2-[2-(3-Acetyl-pyrazolo[3,4-b]pyridin-1-yl)-acetyl]-2-aza-bicyclo[3.1.0]hexane-3-carboxylic acid ((1R,2S)-2-fluoro-cyclopropyl)-amide;
(1R,3S,5R)-2-[2-(3-Acetyl-pyrazolo[3,4-b]pyridin-1-yl)-acetyl]-2-aza-bicyclo[3.1.0]hexane-3-carboxylic acid (3,3,5-trimethyl-cyclohexyl)-amide;
(1R,3S,5R)-2-[2-(3-Acetyl-pyrazolo[3,4-b]pyridin-1-yl)-acetyl]-2-aza-bicyclo[3.1.0]hexane-3-carboxylic acid (3,3,5,5-tetramethyl-cyclohexyl)-amide;
(1R,3S,5R)-2-[2-(3-Acetyl-pyrazolo[3,4-c]pyridin-1-yl)-acetyl]-2-aza-bicyclo[3.1.0]hexane-3-carboxylic acid (2,2-dimethyl-tetrahydro-pyran-4-yl)-amide;
(1R,3S,5R)-2-[2-(3-Acetyl-pyrazolo[3,4-c]pyridin-1-yl)-acetyl]-2-aza-bicyclo[3.1.0]hexane-3-carboxylic acid (3,3-difluoro-cyclobutyl)-amide;
(1R,3S,5R)-2-[2-(3-Acetyl-pyrazolo[3,4-c]pyridin-1-yl)-acetyl]-2-aza-bicyclo[3.1.0]hexane-3-carboxylic acid (3,3-difluoro-cyclohexyl)-amide;
(1R,3S,5R)-2-[2-(3-Acetyl-pyrazolo[3,4-c]pyridin-1-yl)-acetyl]-2-aza-bicyclo[3.1.0]hexane-3-carboxylic acid (1-hydroxymethyl-cyclohexyl)-amide;
(1R,3S,5R)-2-[2-(3-Acetyl-pyrazolo[3,4-c]pyridin-1-yl)-acetyl]-2-aza-bicyclo[3.1.0]hexane-3-carboxylic acid (4,4-difluoro-cyclohexyl)-amide;
(1R,3S,5R)-2-[2-(3-Acetyl-pyrazolo[3,4-b]pyridin-1-yl)-acetyl]-2-aza-bicyclo[3.1.0]hexane-3-carboxylic acid ((1R,3R)-3-carbamoyl-cyclopentyl)-amide;
(1R,3R)-3-({(1R,3S,5R)-2-[2-(3-Acetyl-pyrazolo[3,4-b]pyridin-1-yl)-acetyl]-2-aza-bicyclo[3.1.0]hexane-3-carbonyl}-amino)-cyclopentanecarboxylic acid methyl ester;
(1R,3S)-3-({(1R,3S,5R)-2-[2-(3-Acetyl-pyrazolo[3,4-b]pyridin-1-yl)-acetyl]-2-aza-bicyclo[3.1.0]hexane-3-carbonyl}-amino)-cyclohexanecarboxylic acid methyl ester;
(1R,3S,5R)-2-Aza-bicyclo[3.1.0]hexane-2,3-dicarboxylic acid 2-[(1-carbamoyl-1H-indol-3-yl)-amide]3-cyclohexylamide;
(1R,3S,5R)-2-Aza-bicyclo[3.1.0]hexane-2,3-dicarboxylic acid 2-[(1-carbamoyl-1H-indol-3-yl)-amide]3-(S)-cyclohex-2-enylamide;
(1R,3S,5R)-2-Aza-bicyclo[3.1.0]hexane-2,3-dicarboxylic acid 2-[(1-carbamoyl-1H-indol-3-yl)-amide]3-{[(1S,3R)-3-(2,2,2-trifluoro-ethoxy)-cyclohexyl]-amide};
(1R,3S,5R)-2-Aza-bicyclo[3.1.0]hexane-2,3-dicarboxylic acid 2-[(1-carbamoyl-1H-indol-3-yl)-amide]3-{[(1R,3S)-3-(2,2,2-trifluoro-ethoxy)-cyclohexyl)-amide};
(1R,3S,5R)-2-Aza-bicyclo[3.1.0]hexane-2,3-dicarboxylic acid 2-[(1-carbamoyl-1H-indol-3-yl)-amide]3-{[(1S,3S)-3-(2,2,2-trifluoro-ethoxy)-cyclohexyl]-amide};
(1R,3S,5R)-2-Aza-bicyclo[3.1.0]hexane-2,3-dicarboxylic acid 2-[(1-carbamoyl-1H-indol-3-yl)-amide]3-{[(1R,3R)-3-(2,2,2-trifluoro-ethoxy)-cyclohexyl]-amide};
(1R,3S,5R)-2-Aza-bicyclo[3.1.0]hexane-2,3-dicarboxylic acid 2-[(1-carbamoyl-1H-indol-3-yl)-amide]3-[((1R,3S)-3-methoxy-cyclohexyl)-amide];
(1R,3S,5R)-2-Aza-bicyclo[3.1.0]hexane-2,3-dicarboxylic acid 2-[(1-carbamoyl-1H-indol-3-yl)-amide]3-[((R)-3,3-dimethyl-cyclohexyl)-amide];
(1R,3S,5R)-2-Aza-bicyclo[3.1.0]hexane-2,3-dicarboxylic acid 2-[(1-carbamoyl-1H-indol-3-yl)-amide]3-[((1R,3S)-3-ethyl-cyclohexyl)-amide];
(1R,3S,5R)-2-Aza-bicyclo[3.1.0]hexane-2,3-dicarboxylic acid 2-[(1-carbamoyl-1H-indol-3-yl)-amide]3-[((1S,3R)-3-ethyl-cyclohexyl)-amide];
(1R,3S,5R)-2-Aza-bicyclo[3.1.0]hexane-2,3-dicarboxylic acid 2-[(1-carbamoyl-1H-indol-3-yl)-amide]3-[((1R,3S)-3-methyl-cyclohexyl)-amide];
(1R,3S,5R)-2-Aza-bicyclo[3.1.0]hexane-2,3-dicarboxylic acid 2-[(1-carbamoyl-1H-indol-3-yl)-amide]3-[((1R,3S)-3-trifluoromethyl-cyclohexyl)-amide];
(2S,4R)-4-Fluoro-pyrrolidine-1,2-dicarboxylic acid 1-[(1-carbamoyl-1H-indol-3-yl)-amide]2-[((R)-3,3-dimethyl-cyclohexyl)-amide];
1-{2-[(1R,3S,5R)-3-(3,3-Dimethyl-piperidin-1-ylcarbamoyl)-2-aza-bicyclo[3.1.0]hex-2-yl]-2-oxo-ethyl}-6-methyl-1H-indazole-3-carboxylic acid amide;
1-{2-[(1R,3S,5R)-3-(3,3-Dimethyl-piperidin-1-ylcarbamoyl)-2-aza-bicyclo[3.1.0]hex-2-yl]-2-oxo-ethyl}-5-methyl-1H-pyrazolo[3,4-c]pyridine-3-carboxylic acid amide;
(1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid (3,3-dimethyl-piperidin-1-yl)-amide;
(1R,3S,5R)-2-[2-(3-Acetyl-pyrazolo[3,4-c]pyridin-1-yl)-acetyl]-2-aza-bicyclo[3.1.0]hexane-3-carboxylic acid (3-hydroxy-3-trifluoromethyl-cyclohexyl)-amide;
(1R,3S,5R)-2-[2-(3-Acetyl-indazol-1-yl)-acetyl]-2-aza-bicyclo[3.1.0]hexane-3-carboxylic acid (trans-3-trifluoromethoxy-cyclohexyl)-amide;

1-{2-Oxo-2-[(1R,3S,5R)-3-(trans-3-trifluoromethoxy-cyclohexylcarbamoyl)-2-aza-bicyclo[3.1.0]hex-2-yl]-ethyl}-1H-indazole-3-carboxylic acid amide;

1-{2-[(1R,3S,5R)-3-(3-Hydroxy-3-trifluoromethyl-cyclohexylcarbamoyl)-2-aza-bicyclo[3.1.0]hex-2-yl]-2-oxo-ethyl}-1H-pyrazolo[3,4-c]pyridine-3-carboxylic acid amide;

1-{2-[(1R,3S,5R)-3-(2,2-Difluoro-cyclohexylcarbamoyl)-2-aza-bicyclo[3.1.0]hex-2-yl]-2-oxo-ethyl}-1H-pyrazolo[3,4-c]pyridine-3-carboxylic acid amide;

(1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((S)-2,2-difluoro-cyclohexyl)-amide;

(1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((R)-2,2-difluoro-cyclohexyl)-amide;

(1R,3S,5R)-2-{2-[3-acetyl-5-(pyrimidin-2-ylmethoxy)-indazol-1-yl]-acetyl}-2-aza-bicyclo[3.1.0]hexane-3-carboxylic acid (2-fluoro-cyclohex-2-enyl)-amide;

1-{2-[(1R,3S,5R)-3-(3-Methoxy-3-trifluoromethyl-cyclohexylcarbamoyl)-2-aza-bicyclo[3.1.0]hex-2-yl]-2-oxo-ethyl}-1H-indazole-3-carboxylic acid amide;

1-{2-[(1R,3S,5R)-3-(3-Methoxy-3-trifluoromethyl-cyclohexylcarbamoyl)-2-aza-bicyclo[3.1.0]hex-2-yl]-2-oxo-ethyl}-1H-indazole-3-carboxylic acid amide;

1-{2-Oxo-2-[(1R,3S,5R)-3-((1R,3S)-3-trifluoromethyl-cyclohexylcarbamoyl)-2-aza-bicyclo[3.1.0]hex-2-yl]-ethyl}-1H-pyrazolo[3,4-c]pyridine-3-carboxylic acid amide;

(1R,3S,5R)-2-[2-(3-Acetyl-indazol-1-yl)-acetyl]-2-aza-bicyclo[3.1.0]hexane-3-carboxylic acid ((1S,3S)-3-methoxy-cyclohexyl)-amide;

(1R,3S,5R)-2-[2-(3-Acetyl-indazol-1-yl)-acetyl]-2-aza-bicyclo[3.1.0]hexane-3-carboxylic acid ((1R,3R)-3-methoxy-cyclohexyl)-amide;

(1R,3S,5R)-2-[2-(3-Acetyl-indazol-1-yl)-acetyl]-2-aza-bicyclo[3.1.0]hexane-3-carboxylic acid ((1S,3R)-3-methoxy-cyclohexyl)-amide;

(1R,3S,5R)-2-[2-(3-Acetyl-indazol-1-yl)-acetyl]-2-aza-bicyclo[3.1.0]hexane-3-carboxylic acid ((1R,3S)-3-methoxy-cyclohexyl)-amide;

1-{2-[(1R,3S,5R)-3-((1R,3S)-3-Methoxy-cyclohexylcarbamoyl)-2-aza-bicyclo[3.1.0]hex-2-yl]-2-oxo-ethyl}-1H-indazole-3-carboxylic acid amide;

1-{2-[(1R,3S,5R)-3-((1R,3S)-3-Methyl-cyclohexylcarbamoyl)-2-aza-bicyclo[3.1.0]hex-2-yl]-2-oxo-ethyl}-1H-indazole-3-carboxylic acid amide;

1-{2-[(1R,3S,5R)-3-((1S,3R)-3-Methyl-cyclohexylcarbamoyl)-2-aza-bicyclo[3.1.0]hex-2-yl]-2-oxo-ethyl}-1H-indazole-3-carboxylic acid amide;

1-{2-Oxo-2-[(1R,3S,5R)-3-((1R,3S)-3-trifluoromethyl-cyclohexylcarbamoyl)-2-aza-bicyclo[3.1.0]hex-2-yl]-ethyl}-1H-indazole-3-carboxylic acid amide;

5-Methyl-1-{2-oxo-2-[(1R,3S,5R)-3-((1R,3S)-3-trifluoromethyl-cyclohexylcarbamoyl)-2-aza-bicyclo[3.1.0]hex-2-yl]-ethyl}-1H-pyrazolo[3,4-c]pyridine-3-carboxylic acid amide;

1-{2-[(1R,3S,5R)-3-((1R,3S)-3-Methyl-cyclohexylcarbamoyl)-2-aza-bicyclo[3.1.0]hex-2-yl]-2-oxo-ethyl}-1H-pyrazolo[3,4-c]pyridine-3-carboxylic acid amide;

1-{2-[(1R,3S,5R)-3-(3,3-Difluoro-cyclopentylcarbamoyl)-2-aza-bicyclo[3.1.0]hex-2-yl]-2-oxo-ethyl}-1H-indazole-3-carboxylic acid amide;

1-{2-[(1R,3S,5R)-3-((S)-3,3-Dimethyl-cyclohexylcarbamoyl)-2-aza-bicyclo[3.1.0]hex-2-yl]-2-oxo-ethyl}-1H-indazole-3-carboxylic acid amide;

1-{2-[(1R,3S,5R)-3-((R)-3,3-Dimethyl-cyclohexylcarbamoyl)-2-aza-bicyclo[3.1.0]hex-2-yl]-2-oxo-ethyl}-1H-indazole-3-carboxylic acid amide;

1-{2-[(1R,3S,5R)-3-((S)-3,3-Dimethyl-cyclohexylcarbamoyl)-2-aza-bicyclo[3.1.0]hex-2-yl]-2-oxo-ethyl}-1H-pyrazolo[3,4-c]pyridine-3-carboxylic acid amide;

1-{2-[(1R,3S,5R)-3-((R)-3,3-Dimethyl-cyclohexylcarbamoyl)-2-aza-bicyclo[3.1.0]hex-2-yl]-2-oxo-ethyl}-1H-pyrazolo[3,4-c]pyridine-3-carboxylic acid amide;

1-{2-Oxo-2-[(1R,3S,5R)-3-((S)-spiro[2.5]oct-5-ylcarbamoyl)-2-aza-bicyclo[3.1.0]hex-2-yl]-ethyl}-1H-indazole-3-carboxylic acid amide;

1-{2-Oxo-2-[(1R,3S,5R)-3-((R)-spiro[2.5]oct-5-ylcarbamoyl)-2-aza-bicyclo[3.1.0]hex-2-yl]-ethyl}-1H-indazole-3-carboxylic acid amide;

1-{2-[(1R,3S,5R)-3-((R)-3,3-Dimethyl-cyclohexylcarbamoyl)-2-aza-bicyclo[3.1.0]hex-2-yl]-2-oxo-ethyl}-5-methyl-1H-indazole-3-carboxylic acid amide;

1-{2-[(1R,3S,5R)-3-((R)-3,3-Dimethyl-cyclohexylcarbamoyl)-2-aza-bicyclo[3.1.0]hex-2-yl]-2-oxo-ethyl}-6-fluoro-1H-indazole-3-carboxylic acid amide;

1-{2-[(1R,3S,5R)-3-((R)-3,3-Dimethyl-cyclohexylcarbamoyl)-2-aza-bicyclo[3.1.0]hex-2-yl]-2-oxo-ethyl}-6-methyl-1H-indazole-3-carboxylic acid amide;

6-Chloro-1-{2-[(1R,3S,5R)-3-((R)-3,3-dimethyl-cyclohexylcarbamoyl)-2-aza-bicyclo[3.1.0]hex-2-yl]-2-oxo-ethyl}-1H-indazole-3-carboxylic acid amide;

1-{2-[(1R,3S,5R)-3-((R)-3,3-Dimethyl-cyclohexylcarbamoyl)-2-aza-bicyclo[3.1.0]hex-2-yl]-2-oxo-ethyl}-5-methyl-1H-pyrazolo[3,4-c]pyridine-3-carboxylic acid amide;

1-{2-[(1R,3S,5R)-3-((R)-3,3-Dimethyl-cyclohexylcarbamoyl)-2-aza-bicyclo[3.1.0]hex-2-yl]-2-oxo-ethyl}-5-ethyl-1H-pyrazolo[3,4-c]pyridine-3-carboxylic acid amide;

1-{2-[(1R,3S,5R)-3-((R)-3,3-Dimethyl-cyclohexylcarbamoyl)-2-aza-bicyclo[3.1.0]hex-2-yl]-2-oxo-ethyl}-7-methyl-1H-pyrazolo[3,4-c]pyridine-3-carboxylic acid amide;

(1R,3S,5R)-2-[2-(5-Acetyl-pyrrolo[2,3-c]pyridazin-7-yl)-acetyl]-2-aza-bicyclo[3.1.0]hexane-3-carboxylic acid ((R)-3,3-dimethyl-cyclohexyl)-amide;

1-{2-[(1R,3S,5R)-3-((S)-3,3-Dimethyl-cyclopentylcarbamoyl)-2-aza-bicyclo[3.1.0]hex-2-yl]-2-oxo-ethyl}-1H-pyrazolo[3,4-c]pyridine-3-carboxylic acid amide;

1-{2-[(1R,3S,5R)-3-((R)-3,3-Dimethyl-cyclopentylcarbamoyl)-2-aza-bicyclo[3.1.0]hex-2-yl]-2-oxo-ethyl}-1H-pyrazolo[3,4-c]pyridine-3-carboxylic acid amide;

(1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((1R,3R)-3-methoxy-cyclohexyl)-amide;

1-{2-[(2S,4R)-2-((S)-3,3-Dimethyl-cyclohexylcarbamoyl)-4-fluoro-pyrrolidin-1-yl]-2-oxo-ethyl}-1H-pyrazolo[3,4-c]pyridine-3-carboxylic acid amide;

1-{2-[(2S,4R)-2-((R)-3,3-Dimethyl-cyclohexylcarbamoyl)-4-fluoro-pyrrolidin-1-yl]-2-oxo-ethyl}-1H-pyrazolo[3,4-c]pyridine-3-carboxylic acid amide;

1-{2-[(1R,3S,5R)-3-((1S,3R)-3-Ethyl-cyclohexylcarbamoyl)-2-aza-bicyclo[3.1.0]hex-2-yl]-2-oxo-ethyl}-1H-pyrazolo[3,4-c]pyridine-3-carboxylic acid amide;

1-{2-[(1R,3S,5R)-3-((1R,3S)-3-Ethyl-cyclohexylcarbamoyl)-2-aza-bicyclo[3.1.0]hex-2-yl]-2-oxo-ethyl}-1H-pyrazolo[3,4-c]pyridine-3-carboxylic acid amide;

1-{2-[(1R,3S,5R)-3-(3-Methyl-cyclohex-2-enylcarbamoyl)-2-aza-bicyclo[3.1.0]hex-2-yl]-2-oxo-ethyl}-1H-indazole-3-carboxylic acid amide;

1-{2-Oxo-2-[(1R,3S,5R)-3-((S)-spiro[2.5]oct-5-ylcarbamoyl)-2-aza-bicyclo[3.1.0]hex-2-yl]-ethyl}-1H-pyrazolo[3,4-c]pyridine-3-carboxylic acid amide;

1-{2-Oxo-2-[(1R,3S,5R)-3-((R)-spiro[2.5]oct-5-ylcarbamoyl)-2-aza-bicyclo[3.1.0]hex-2-yl]-ethyl}-1H-pyrazolo[3,4-c]pyridine-3-carboxylic acid amide;

1-{2-[(1R,3S,5R)-3-((1S,3R)-3-Methyl-cyclopentylcarbamoyl)-2-aza-bicyclo[3.1.0]hex-2yl]-2-oxo-ethyl}-1H-indazole-3-carboxylic acid amide;

1-{2-[(1R,3S,5R)-3-((1S,3S)-3-Methyl-cyclopentylcarbamoyl)-2-aza-bicyclo[3.1.0]hex-2-yl]-2-oxo-ethyl}-1H-indazole-3-carboxylic acid amide;

1-{2-[(1R,3S,5R)-3-((1R,3R)-3-Methyl-cyclopentylcarbamoyl)-2-aza-bicyclo[3.1.0]hex-2-yl]-2-oxo-ethyl}-1H-indazole-3-carboxylic acid amide;

1-{2-[(1R,3S,5R)-3-((1R,3S)-3-Methyl-cyclopentylcarbamoyl)-2-aza-bicyclo[3.1.0]hex-2-yl]-2-oxo-ethyl}-1H-indazole-3-carboxylic acid amide;

1-{2-[(2S,4R)-2-((R)-3,3-Dimethyl-cyclohexylcarbamoyl)-4-fluoro-pyrrolidin-1-yl]-2-oxo-ethyl}-5-ethyl-1H-pyrazolo[3,4-c]pyridine-3-carboxylic acid amide;

1-{2-[(2S,4R)-2-((R)-3,3-Dimethyl-cyclohexylcarbamoyl)-4-fluoro-pyrrolidin-1-yl]-2-oxo-ethyl}-1H-indazole-3-carboxylic acid amide;

1-{2-[(1R,3S,5R)-3-((1R,3S)-3-Ethyl-cyclohexylcarbamoyl)-2-aza-bicyclo[3.1.0]hex-2-yl]-2-oxo-ethyl}-5-methyl-1H-pyrazolo[3,4-c]pyridine-3-carboxylic acid amide;

1-{2-[(2S,3S,4S)-2-((R)-3,3-Dimethyl-cyclohexylcarbamoyl)-4-fluoro-3-methoxy-pyrrolidin-1-yl]-2-oxo-ethyl}-1H-indazole-3-carboxylic acid amide;

1-{2-[(2S,3S,4S)-2-((S)-3,3-Dimethyl-cyclohexylcarbamoyl)-4-fluoro-3-methoxy-pyrrolidin-1-yl]-2-oxo-ethyl}-1H-indazole-3-carboxylic acid amide;

1-{2-[(1R,2S,5S)-2-((R)-3,3-Dimethyl-cyclohexylcarbamoyl)-3-aza-bicyclo[3.1.0]hex-3-yl]-2-oxo-ethyl}-1H-pyrazolo[3,4-c]pyridine-3-carboxylic acid amide;

1-{2-[(1R,2S,5S)-2-((S)-3,3-Dimethyl-cyclohexylcarbamoyl)-3-aza-bicyclo[3.1.0]hex-3-yl]-2-oxo-ethyl}-1H-pyrazolo[3,4-c]pyridine-3-carboxylic acid amide;

1-{2-[(1R,2S,5S)-2-((R)-3,3-Dimethyl-cyclohexylcarbamoyl)-3-aza-bicyclo[3.1.0]hex-3-yl]-2-oxo-ethyl}-1H-indazole-3-carboxylic acid amide;

1-{2-[(1R,2S,5S)-2-((S)-3,3-Dimethyl-cyclohexylcarbamoyl)-3-aza-bicyclo[3.1.0]hex-3-yl]-2-oxo-ethyl}-1H-indazole-3-carboxylic acid amide;

(1R,3S,5R)-2-[2-(3-Acetyl-indazol-1-yl)-acetyl]-2-aza-bicyclo[3.1.0]hexane-3-carboxylic acid ((S)-3,3-dichloro-cyclohexyl)-amide;

(1R,3S,5R)-2-[2-(3-Acetyl-indazol-1-yl)-acetyl]-2-aza-bicyclo[3.1.0]hexane-3-carboxylic acid ((R)-3,3-dichloro-cyclohexyl)-amide;

1-{2-[(2S,4R)-4-Fluoro-2-((S)-spiro[2.5]oct-5-ylcarbamoyl)-pyrrolidin-1-yl]-2-oxo-ethyl}-1H-indazole-3-carboxylic acid amide;

1-{2-[(2S,4R)-4-Fluoro-2-((R)-spiro[2.5]oct-5-ylcarbamoyl)-pyrrolidin-1-yl]-2-oxo-ethyl}-1H-indazole-3-carboxylic acid amide;

(1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((1R,3S)-3-methoxy-cyclohexyl)-amide;

(1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((1R,3S)-3-trifluoromethyl-cyclohexyl)-amide;

(1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((1R,3S)-3-methyl-cyclohexyl)-amide;

(1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((S)-3,3-dimethyl-cyclohexyl)-amide;

(1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((R)-3,3-dimethyl-cyclohexyl)-amide;

(1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((1R,3R)-3-methoxy-cyclopentyl)-amide;

(1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((1S,3S)-3-methoxy-cyclopentyl)-amide;

(1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((1S,3R)-3-methoxy-cyclopentyl)-amide;

(1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((1R,3S)-3-methoxy-cyclopentyl)-amide;

(1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid (3,3-dimethyl-cyclobutyl)-amide;

(1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid (3,3-difluoro-cyclobutyl)-amide;

1-{2-[(1R,3S,5R)-3-((1S,5S)-5-Methoxy-3,3-dimethyl-cyclohexylcarbamoyl)-2-aza-bicyclo[3.1.0]hex-2-yl]-2-oxo-ethyl}-1H-indazole-3-carboxylic acid amide;

1-{2-[(1R,3S,5R)-3-((1R,5R)-5-Methoxy-3,3-dimethyl-cyclohexylcarbamoyl)-2-aza-bicyclo[3.1.0]hex-2-yl]-2-oxo-ethyl}-1H-indazole-3-carboxylic acid amide;

1-{2-[(1R,3S,5R)-3-(cis-5-Methoxy-3,3-dimethyl-cyclohexylcarbamoyl)-2-aza-bicyclo[3.1.0]hex-2-yl]-2-oxo-ethyl}-1H-indazole-3-carboxylic acid amide;

1-{2-[(1R,3S,5R)-3-((1S,5S)-5-Hydroxy-3,3-dimethyl-cyclohexylcarbamoyl)-2-aza-bicyclo[3.1.0]hex-2-yl]-2-oxo-ethyl}-1H-indazole-3-carboxylic acid amide;

1-{2-[(1R,3S,5R)-3-((1R,5R)-5-Hydroxy-3,3-dimethyl-cyclohexylcarbamoyl)-2-aza-bicyclo[3.1.0]hex-2-yl]-2-oxo-ethyl}-1H-indazole-3-carboxylic acid amide;

1-{2-[(1R,3S,5S)-3-(3,3-dimethyl-cyclohexylcarbamoyl)-5-hydroxymethyl-2-aza-bicyclo[3.1.0]hex-2-yl]-2-oxo-thyl}-1H-indazole-3-carboxylic acid amide;

1-{2-[(1R,3S,5S)-3-((R)-3,3-Dimethyl-cyclohexylcarbamoyl)-5-hydroxymethyl-2-aza-bicyclo[3.1.0]hex-2-yl]-2-oxo-ethyl}-1H-indazole-3-carboxylic acid amide;

1-{2-[(1R,3S,5S)-3-((S)-3,3-Dimethyl-cyclohexylcarbamoyl)-5-hydroxymethyl-2-aza-bicyclo[3.1.0]hex-2-yl]-2-oxo-ethyl}-1H-indazole-3-carboxylic acid amide;

(1R,3S,5S)-2-[2-(3-Acetyl-pyrazolo[3,4-c]pyridin-1-yl)-acetyl]-5-hydroxymethyl-2-aza-bicyclo[3.1.0]hexane-3-carboxylic acid (S)-spiro[2.5]oct-5-ylamide;

(1R,3S,5S)-2-[2-(3-Acetyl-pyrazolo[3,4-c]pyridin-1-yl)-acetyl]-5-hydroxymethyl-2-aza-bicyclo[3.1.0]hexane-3-carboxylic acid (R)-spiro[2.5]oct-5-ylamide;

(1R,3S,5S)-2-[2-(3-Acetyl-pyrazolo[3,4-b]pyridin-1-yl)-acetyl]-5-hydroxymethyl-2-aza-bicyclo[3.1.0]hexane-3-carboxylic acid ((R)-3,3-dimethyl-cyclohexyl)-amide;

(1R,3S,5S)-2-[2-(3-Acetyl-pyrazolo[3,4-b]pyridin-1-yl)-acetyl]-5-hydroxymethyl-2-aza-bicyclo[3.1.0]hexane-3-carboxylic acid ((S)-3,3-dimethyl-cyclohexyl)-amide;

1-{2-[(1R,3S,5S)-3-((1S,3R)-3-Ethyl-cyclohexylcarbamoyl)-5-hydroxymethyl-2-aza-bicyclo[3.1.0]hex-2-yl]-2-oxo-ethyl}-1H-indazole-3-carboxylic acid amide;

1-{2-[(1R,3S,5S)-3-((1S,3S)-3-Ethyl-cyclohexylcarbamoyl)-5-hydroxymethyl-2-aza-bicyclo[3.1.0]hex-2-yl]-2-oxo-ethyl}-1H-indazole-3-carboxylic acid amide;

1-{2-[(1R,3S,5S)-3-((1R,3R)-3-Ethyl-cyclohexylcarbamoyl)-5-hydroxymethyl-2-aza-bicyclo[3.1.0]hex-2-yl]-2-oxo-ethyl}-1H-indazole-3-carboxylic acid amide;

1-{2-[(1R,3S,5S)-3-((1R,3S)-3-Ethyl-cyclohexylcarbamoyl)-5-hydroxymethyl-2-aza-bicyclo[3.1.0]hex-2-yl]-2-oxo-ethyl}-1H-indazole-3-carboxylic acid amide;

(1R,3S,5S)-2-[2-(3-Acetyl-pyrazolo[3,4-c]pyridin-1-yl)-acetyl]-5-hydroxymethyl-2-aza-bicyclo[3.1.0]hexane-3-carboxylic acid ((R)-3,3-dimethyl-cyclohexyl)-amide;

(1R,3S,5S)-2-[2-(3-Acetyl-pyrazolo[3,4-c]pyridin-1-yl)-acetyl]-5-hydroxymethyl-2-aza-bicyclo[3.1.0]hexane-3-carboxylic acid ((S)-3,3-dimethyl-cyclohexyl)-amide;

1-(2-((1R,3S,5R)-3-(3-hydroxy-3-methylcyclohexylcarbamoyl)-2-azabicyclo[3.1.0]hexan-2-yl)-2-oxoethyl)-1H-indazole-3-carboxamide;

(1R,3S,5R)-2-(2-(3-acetyl-1H-indazol-1-yl)acetyl)-N-((1R,5R)-5-hydroxy-3,3-dimethylcyclohexyl)-2-azabicyclo[3.1.0]hexane-3-carboxamide;

(1R,3S,5R)-2-(2-(3-acetyl-1H-indazol-1-yl)acetyl)-N-((1S,5S)-5-hydroxy-3,3-dimethylcyclohexyl)-2-azabicyclo[3.1.0]hexane-3-carboxamide;

1-(2-((1R,3S,5R)-3-((3-methoxy-3-methylcyclohexyl)carbamoyl)-2-azabicyclo[3.1.0]hexan-2-yl)-2-oxoethyl)-1H-indazole-3-carboxamide;

1-(2-((1R,3S,5R)-3-(((1R,3S)-3-(hydroxymethyl)-3-methylcyclohexyl)carbamoyl)-2-azabicyclo[3.1.0]hexan-2-yl)-2-oxoethyl)-1H-indazole-3-carboxamide; and 1-(2-((1R,3S,5R)-3-(((1S,3R)-3-(hydroxymethyl)-3-methylcyclohexyl)carbamoyl)-2-azabicyclo[3.1.0]hexan-2-yl)-2-oxoethyl)-1H-indazole-3-carboxamide.

Some of the compounds listed supra have been prepared in enantiopure form (i.e., greater than about 80%, greater than 90% or greater than 95% enantiomeric purity). Other compounds have been isolated as mixtures of stereoisomers, e.g., diastereoisomeric mixtures of two or more diastereoisomers. Each compound isolated as a mixture of stereoisomers has marked as mixture in the foregoing list.

In one embodiment, the invention provides a combination, in particular a pharmaceutical combination, comprising a therapeutically effective amount of the compound according to the definition of formula (I), (II), (IIa), (IIb), (III), (IIIa), and (IIIb) or subformulae thereof or any one of the specifically disclosed compounds of the invention and one or more therapeutically active agents (preferably selected from those listed infra).

For purposes of interpreting this specification, the following definitions will apply and whenever appropriate, terms used in the singular will also include the plural and vice versa.

As used herein, the term "alkyl" refers to a fully saturated branched or unbranched hydrocarbon moiety having up to 20 carbon atoms. Unless otherwise provided, alkyl refers to hydrocarbon moieties having 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

As used herein, the term "alkylene" refers to divalent alkyl group as defined herein above having 1 to 20 carbon atoms. It comprises 1 to 20 carbon atoms, Unless otherwise provided, alkylene refers to moieties having 1 to 16 carbon atoms, 1 to 10 carbon atoms, 1 to 7 carbon atoms, or 1 to 4 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like.

As used herein, the term "haloalkyl" refers to an alkyl as defined herein, that is substituted by one or more halo groups as defined herein. The haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

The term "aryl" refers to an aromatic hydrocarbon group having 6-20 carbon atoms in the ring portion. Typically, aryl is monocyclic, bicyclic or tricyclic aryl having 6-20 carbon atoms.

Furthermore, the term "aryl" as used herein, refers to an aromatic substituent which can be a single aromatic ring, or multiple aromatic rings that are fused together.

Non-limiting examples include phenyl, naphthyl or tetrahydronaphthyl, each of which may optionally be substituted by 1-4 substituents, such as alkyl, trifluoromethyl, cycloalkyl, halogen, hydroxy, alkoxy, acyl, alkyl-C(O)—O—, aryl-O—, heteroaryl-O—, amino, thiol, alkyl-S—, aryl-S—, nitro, cyano, carboxy, alkyl-O—C(O)—, carbamoyl, alkyl-S(O)—, sulfonyl, sulfonamido, phenyl, and heterocyclyl.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Typically, alkoxy groups have about 1-7, more preferably about 1-4 carbons.

As used herein, the term "heterocyclyl" or "heterocyclo" refers to a saturated or unsaturated non-aromatic ring or ring system, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. The heterocyclic group can be attached at a heteroatom or a carbon atom. The heterocyclyl can include fused or bridged rings as well as spirocyclic rings. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

The term "heterocyclyl" further refers to heterocyclic groups as defined herein substituted with 1 to 5 substituents independently selected from the groups consisting of the following:
  (a) alkyl;
  (b) hydroxy (or protected hydroxy);
  (c) halo;
  (d) oxo, i.e., =O;
  (e) amino, alkylamino or dialkylamino;

(f) alkoxy;
(g) cycloalkyl;
(h) carboxyl;
(i) heterocyclooxy, wherein heterocyclooxy denotes a heterocyclic group bonded through an oxygen bridge;
(j) alkyl-O—C(O)—;
(k) mercapto;
(l) nitro;
(m) cyano;
(n) sulfamoyl or sulfonamido;
(o) aryl;
(p) alkyl-C(O)—O—;
(q) aryl-C(O)—O—;
(r) aryl-S—;
(s) aryloxy;
(t) alkyl-S—;
(u) formyl, i.e., HC(O)—;
(v) carbamoyl;
(w) aryl-alkyl-; and
(x) aryl substituted with alkyl, cycloalkyl, alkoxy, hydroxy, amino, alkyl-C(O)—NH—, alkylamino, dialkylamino or halogen.

As used herein, the term "cycloalkyl" refers to saturated or unsaturated monocyclic, bicyclic or tricyclic hydrocarbon groups of 3-12 carbon atoms. Unless otherwise provided, cycloalkyl refers to cyclic hydrocarbon groups having between 3 and 9 ring carbon atoms or between 3 and 7 ring carbon atoms, each of which can be optionally substituted by one, or two, or three, or more substituents independently selected from the group consisting of alkyl, halo, oxo, hydroxy, alkoxy, alkyl-C(O)—, acylamino, carbamoyl, alkyl-NH—, (alkyl)$_2$N—, thiol, alkyl-S—, nitro, cyano, carboxy, alkyl-O—C(O)—, sulfonyl, sulfonamido, sulfamoyl, and heterocyclyl. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

As used herein, the term "aryloxy" refers to both an —O-aryl and an —O-heteroaryl group, wherein aryl and heteroaryl are defined herein.

As used herein, the term "heteroaryl" refers to a 5-14 membered monocyclic- or bicyclic- or tricyclic-aromatic ring system, having 1 to 8 heteroatoms selected from N, O or S. Typically, the heteroaryl is a 5-10 membered ring system (e.g., 5-7 membered monocycle or an 8-10 membered bicycle) or a 5-7 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, and 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, or 7-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenanthrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroary groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, and 2-, 4-, 5-, 6-, or 7-benzothiazolyl.

A heteroaryl group may be substituted with 1 to 5 substituents independently selected from the groups consisting of the following:
(a) alkyl;
(b) hydroxy (or protected hydroxy);
(c) halo;
(d) oxo, i.e., =O;
(e) amino, alkylamino or dialkylamino;
(f) alkoxy;
(g) cycloalkyl;
(h) carboxyl;
(i) heterocyclooxy, wherein heterocyclooxy denotes a heterocyclic group bonded through an oxygen bridge;
(j) alkyl-O—C(O)—;
(k) mercapto;
(l) nitro;
(m) cyano;
(n) sulfamoyl or sulfonamido;
(o) aryl;
(p) alkyl-C(O)—O—;
(q) aryl-C(O)—O—;
(r) aryl-S—;
(s) aryloxy;
(t) alkyl-S—;
(u) formyl, i.e., HC(O)—;
(v) carbamoyl;
(w) aryl-alkyl-; and
(x) aryl substituted with alkyl, cycloalkyl, alkoxy, hydroxy, amino, alkyl-C(O)—NH—, alkylamino, dialkylamino or halogen.

As used herein, the term "halogen" or "halo" refers to fluoro, chloro, bromo, and iodo.

As used herein, the term "optionally substituted" unless otherwise specified refers to a group that is unsubstituted or is substituted by one or more, typically 1, 2, 3 or 4, suitable non-hydrogen substituents, each of which is independently selected from the group consisting of:
- (a) alkyl;
- (b) hydroxy (or protected hydroxy);
- (c) halo;
- (d) oxo, i.e., =O;
- (e) amino, alkylamino or dialkylamino;
- (f) alkoxy;
- (g) cycloalkyl;
- (h) carboxyl;
- (i) heterocyclooxy, wherein heterocyclooxy denotes a heterocyclic group bonded through an oxygen bridge;
- (j) alkyl-O—C(O)—;
- (k) mercapto;
- (l) nitro;
- (m) cyano;
- (n) sulfamoyl or sulfonamido;
- (o) aryl;
- (p) alkyl-C(O)—O—;
- (q) aryl-C(O)—O—;
- (r) aryl-S—;
- (s) aryloxy;
- (t) alkyl-S—;
- (u) formyl, i.e., HC(O)—;
- (v) carbamoyl;
- (w) aryl-alkyl-; and
- (x) aryl substituted with alkyl, cycloalkyl, alkoxy, hydroxy, amino, alkyl-C(O)—NH—, alkylamino, dialkylamino or halogen.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. The asterisk (*) indicated in the name of a compound designate a racemic mixture.

"Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfornate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts. Inorganic acids from which salts can be derived include, for example, hydrochloric acid, hydrobromic acid, sulfuric acid, nitric acid, and phosphoric acid. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$, $^{31}P$, $^{32}P$, $^{35}S$, $^{36}Cl$, $^{125}I$ respectively. The invention includes various isotopically labeled compounds as defined herein, for example those into which radioactive isotopes, such as $^{3}H$, $^{13}C$, and $^{14}C$, are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In certain embodiments, selective deuteration of compounds of Formula (I) or formula (II), or subformulae thereof, include deuteration of $R^{10}$, $R^{11}$, $R^{12}$, $R^{13}$, $R^{14}$, $R^{15}$, $R^{16}$, and/or $R^{17}$ when each of these variables is hydrogen (e.g., $^{2}H$ or D), alkyl (e.g., $CD_3$) or alkoxy (e.g., $OCD_3$). For example, when any of of $R^{10}$, $R^{11}$, $R^{12}$, $R^{13}$, $R^{14}$, $R^{15}$, $R^{16}$, and/or $R^{17}$ are methyl or ethyl, the alkyl residue is preferably deuterated, e.g., $CD_3$ or $CD_2CD_3$. In certain other compounds when $R^{10}$, $R^{14}$ or $R^{15}$ is methoxy, the methyl residue is preferably deuterated, e.g., $OCD_3$. In certain other compounds, when any of of $R^{10}$, $R^{11}$, $R^{12}$, $R^{13}$, $R^{14}$, $R^{15}$, $R^{16}$, and/or $R^{17}$ are hydrogen, the hydrogen may be isotopically enriched as deuterium (i.e., $^{2}H$). In certain other compounds, when $W^{2}$ is methylene, the hydrogen may be isotopically enriched as deuterium (i.e., $C(^{2}H)_2$).

In certain embodiments, selective deuteration of compounds of Formula (I) or formula (II) include deuteration of $R^{5}$, when $R^{5}$ is alkanoyl, e.g., $C(O)CD_3$. In other embodiments, certain substitutents on the proline ring are selectively deuterated. For example, when any of $R^{8}$ or $R^{9}$ are methyl or methoxy, the alkyl residue is preferably deuterated, e.g., $CD_3$ or $OCD_3$. In certain other compounds, when two substituents of the proline ring are combined to form a cyclopropyl ring, the unsubstituted methylene carbon is selectively deuterated.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

The compounds of the present invention may inherently or by design form solvates with solvents (including water). Therefore, it is intended that the invention embrace both solvated and unsolvated forms. The term "solvate" refers to a molecular complex of a compound of the present invention (including salts thereof) with one or more solvent molecules. Such solvent molecules are those commonly used in the pharmaceutical art, which are known to be innocuous to a recipient, e.g., water, ethanol, dimethylsulfoxide, acetone and other common organic solvents. The term "hydrate" refers to a molecular complex comprising a compound of the invention and water. Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder, or a disease or biological process (e.g., tissue regeneration and reproduction) (i) mediated by Factor D, or (ii) associated with Factor D activity, or (iii) characterized by activity (normal or abnormal) of the complement alternative pathway; or (2) reducing or inhibiting the activity of Factor D; or (3) reducing or inhibiting the expression of Factor D; or (4) reducing or inhibiting activation of the complement system and particularly reducing or inhibiting generation of C3a, iC3b, C5a or the membrane attack complex generated by activation of the complement alternative pathway. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of Factor D and/or the complement alternative pathway; or at least partially reducing or inhibiting the expression of Factor D and/or the complement alternative pathway. The meaning of the term "a therapeutically effective amount" as illustrated in the above embodiment for Factor D and/or the complement alternative pathway.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Suitable prodrugs are often pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Furthermore, the compounds of the present invention, including their salts, can also be obtained in the form of their hydrates, or include other solvents used for their crystallization.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosäuren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide und Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Salts of compounds of the present invention having at least one salt-forming group may be prepared in a manner known to those skilled in the art. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted into the free compounds in accordance with methods known to those skilled in the art. Metal and ammonium salts can be converted, for example, by treatment with suitable acids, and acid addition salts, for example, by treatment with a suitable basic agent.

Mixtures of isomers obtainable according to the invention can be separated in a manner known to those skilled in the art into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150 ºC, for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed. 1952, Methods of Organic Synthesis, Thieme, Volume 21).

Typically, the compounds of formula (I) can be prepared according to the Schemes provided infra.

A compound of the formula IV or V can, for example, be prepared from a corresponding N-protected aminoacid as described below:

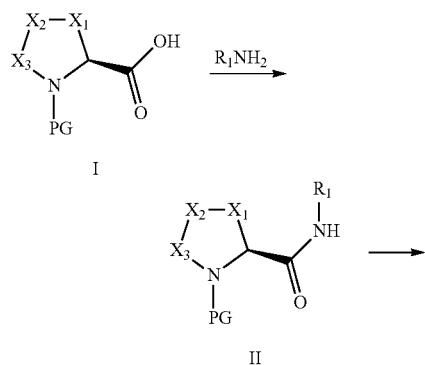

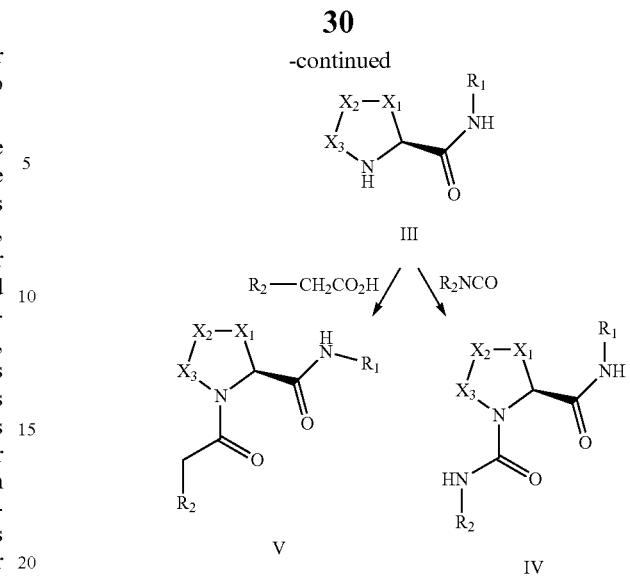

By reacting an N-protected aminoacid I wherein PG is a protecting group or a reactive derivative thereof with an amino compound, under condensation conditions to obtain a compound of the formula II. Removing the protecting group and reacting the compound of the formula III with an isocyanate to obtain a compound of the formula IV or with an acid or a reactive derivative thereof under condensation conditions to obtain a compound of the formula V.

A A compound of the formula IV or V can, for example, be prepared from a corresponding protected aminoacid as described below

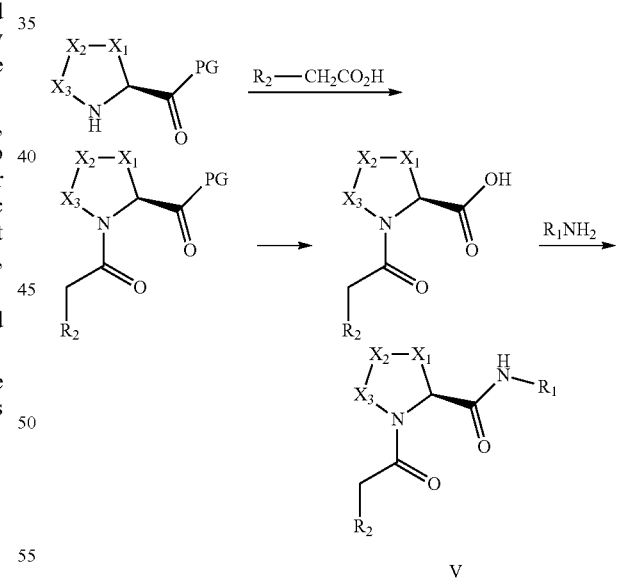

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure materials.

Compounds of the invention and intermediates can also be converted into each other according to methods generally known to those skilled in the art.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and ophthalmic administration, etc. In addition, the pharmaceutical compositions of the present invention can be made up in a solid form (including without limitation capsules, tablets, pills, granules, powders or suppositories), or in a liquid form (including without limitation solutions, suspensions, emulsions, each of which may be suitable for ophthalmic administration). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with
  a) diluents, e.g., lactose, dextrose, sucrose, mannitol, sorbitol, cellulose and/or glycine;
  b) lubricants, e.g., silica, talcum, stearic acid, its magnesium or calcium salt and/or polyethyleneglycol; for tablets also
  c) binders, e.g., magnesium aluminum silicate, starch paste, gelatin, tragacanth, methylcellulose, sodium carboxymethylcellulose and/or polyvinylpyrrolidone; if desired
  d) disintegrants, e.g., starches, agar, alginic acid or its sodium salt, or effervescent mixtures; and/or
  e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for ophthalmic application, e.g., for the treatment of eye diseases e.g., for therapeutic or prophylactic use in treating age related macular degeneration and other complement mediated ophthalmic disorders. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be desirable.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

Prophylactic and Therapeutic Uses

The compounds of formula I in free form or in pharmaceutically acceptable salt form, exhibit valuable pharmacological properties, e.g. Factor D modulating properties, complement pathway modulating properties and modulation of the complement alternative pathway properties, e.g. as indicated in in vitro and in vivo tests as provided in the next sections and are therefore indicated for therapy.

The present invention provides methods of treating a disease or disorder associated with increased complement activity by administering to a subject in need thereof an effective amount of the compounds of Formula (I) of the invention. In certain aspects, methods are provided for the treatment of diseases associated with increased activity of the C3 amplification loop of the complement pathway. In certain embodiments, methods of treating or preventing complement mediated diseases are provided in which the complement activation is induced by antibody-antigen interactions, by a component of an autoimmune disease, or by ischemic damage.

In a specific embodiment, the present invention provides a method of treating or preventing age-related macular degeneration (AMD) by administering to a subject in need thereof an effective amount of the compound of Formula (I) of the invention. In certain embodiments, patients who are currently asymptomatic but are at risk of developing a symptomatic macular degeneration related disorder are suitable for administration with a compound of the invention. The methods of treating or preventing AMD include, but are not limited to, methods of treating or preventing one or more symptoms or aspects of AMD selected from formation of ocular drusen, inflammation of the eye or eye tissue, loss of photoreceptor cells, loss of vision (including loss of visual acuity or visual field), neovascularization (including CNV), retinal detachment, photoreceptor degeneration, RPE degeneration, retinal degeneration, chorioretinal degeneration, cone degeneration, retinal dysfunction, retinal damage in response to light exposure, damage of the Bruch's membrane, and/or loss of RPE function.

The compound of Formula (I) of the invention can be used, inter alia, to prevent the onset of AMD, to prevent the progression of early AMD to advanced forms of AMD including neovascular AMD or geographic atrophy, to slow and/or prevent progression of geographic atrophy, to treat or prevent macular edema from AMD or other conditions (such as diabetic retinopathy, uveitis, or post surgical or non-surgical trauma), to prevent or reduce the loss of vision from AMD, and to improve vision lost due to pre-existing early or advanced AMD. It can also be used in combination with anti-VEGF therapies for the treatment of neovascular AMD patients or for the prevention of neovascular AMD. The present invention further provides methods of treating a complement related disease or disorder by administering to a subject in need thereof an effective amount of the compound(s) of the invention, wherein said disease or disorder is selected from uveitis, adult macuar degeneration, diabetic retinopathy, retinitis pigmentosa, macular edema, Behcet's uveitis, multifocal choroiditis, Vogt-Koyangi-Harada syndrome, intermediate uveitis, birdshot retino-choroiditis, sympathetic ophthalmia, ocular dicatricial pemphigoid, ocular pemphigus, nonartertic ischemic optic neuropathy, post-operative inflammation, and retinal vein occlusion.

In some embodiments, the present invention provides methods of treating a complement related disease or disorder by administering to a subject in need thereof an effective amount of the compounds of the invention. Examples of known complement related diseases or disorders include: neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, thermal injury including burns or frostbite, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration and neural regeneration. In addition, other known complement related disease are lung disease and disorders such as dyspnea, hemoptysis, ARDS, asthma, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), asthma, allergy, bronchoconstriction, hypersensitivity pneumonitis, parasitic diseases, Goodpasture's Syndrome, pulmonary vasculitis, Pauci-immune vasculitis, immune complex-associated inflammation, uveitis (including Behcet's disease and other sub-types of uveitis), antiphospholipid syndrome.

In a specific embodiment, the present invention provides methods of treating a complement related disease or disorder by administering to a subject in need thereof an effective amount of the compounds of the invention, wherein said disease or disorder is asthma, arthritis (e.g., rheumatoid arthritis), autoimmune heart disease, multiple sclerosis, inflammatory bowel disease, ischemia-reperfusion injuries, Barraquer-Simons Syndrome, hemodialysis, systemic lupus, lupus erythematosus, psoriasis, multiple sclerosis, transplantation, diseases of the central nervous system such as Alzheimer's disease and other neurodegenerative conditions, atypicaly hemolytic uremic syndrome (aHUS), glomerulonephritis (including membrane proliferative glomerulonephritis), blistering cutaneous diseases (including bullous pemphigoid, pemphigus, and epidermolysis bullosa), ocular cicatrical pemphigoid or MPGN II.

In a specific embodiment, the present invention provides methods of treating glomerulonephritis by administering to a subject in need thereof an effective amount of a composition comprising a compound of the present invention. Symptoms of glomerulonephritis include, but not limited to, proteinuria; reduced glomerular filtration rate (GFR); serum electrolyte changes including azotemia (uremia, excessive blood urea nitrogen—BUN) and salt retention, leading to water retention resulting in hypertension and edema; hematuria and abnormal urinary sediments including red cell casts; hypoalbuminemia; hyperlipidemia; and lipiduria. In a specific embodiment, the present invention provides methods of treating paroxysmal nocturnal hemoglobinuria (PNH) by administering to a subject in need thereof an effective amount of a composition comprising an compound of the present invention with or without concomitent administration of a complement C5 inhibitor or C5 convertase inhibitor such as Soliris.

In a specific embodiment, the present invention provides methods of reducing the dysfunction of the immune and/or hemostatic systems associated with extracorporeal circulation by administering to a subject in need thereof an effective amount of a composition comprising an compound of the present invention. The compounds of the present invention can be used in any procedure which involves circulating the patient's blood from a blood vessel of the patient, through a conduit, and back to a blood vessel of the patient, the conduit having a luminal surface comprising a material capable of causing at least one of complement activation, platelet activation, leukocyte activation, or platelet-leukocyte adhesion. Such procedures include, but are not limited to, all forms of ECC, as well as procedures involving the introduction of an artificial or foreign organ, tissue, or vessel into the blood circuit of a patient. More particularly, such procedures include, but are not limited to, transplantation procedures including kidney, liver, lung or heart transplant procedures and islet cell transplant procedures.

In other embodiments, the compounds of the invention are suitable for use in the treatment of diseases and disorders associated with fatty acid metabolism, including obesity and other metabolic disorders.

In another embodiment, the compounds of the invention may be used in blood ampules, diagnostic kits and other equipment used in the collection and sampling of blood. The use of the compounds of the invention in such diagnostic kits may inhibit the ex vivo activation of the complement pathway associated with blood sampling.

The pharmaceutical composition or combination of the present invention can be in unit dosage of about 1-1000 mg of active ingredient(s) for a subject of about 50-70 kg, or about 1-500 mg or about 1-250 mg or about 1-160 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the following in vitro & in vivo methods.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by alternative complement pathway. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by the complement alternative pathway, wherein the medicament is prepared for administration with another therapeutic agent. The invention also provides the use of another therapeutic agent for treating a disease or condition mediated by the complement alternative pathway, wherein the medicament is administered with a compound of formula (I).

The invention also provides a compound of formula (I) for use in a method of treating a disease or condition mediated by the complement alternative pathway, wherein the compound of formula (I) is prepared for administration with another therapeutic agent. The invention also provides another therapeutic agent for use in a method of treating a disease or condition mediated by the complement alternative pathway and/or Factor D, wherein the other therapeutic agent is prepared for administration with a compound of formula (I). The invention also provides a compound of formula (I) for use in a method of treating a disease or condition mediated by the complement alternative pathway and/or Factor D, wherein the compound of formula (I) is administered with another therapeutic agent. The invention also provides another therapeutic agent for use in a method of treating a disease or condition mediated by the complement alternative pathway and/or Factor D, wherein the other therapeutic agent is administered with a compound of formula (I).

The invention also provides the use of a compound of formula (I) for treating a disease or condition mediated by the complement alternative pathway and/or Factor D, wherein the patient has previously (e.g. within 24 hours) been treated with another therapeutic agent. The invention also provides the use of another therapeutic agent for treating a disease or condition mediated by the complement alternative pathway and/or Factor D wherein the patient has previously (e.g. within 24 hours) been treated with a compound of formula (I).

The pharmaceutical compositions can be administered alone or in combination with other molecules known to have a beneficial effect on retinal attachment or damaged retinal tissue, including molecules capable of tissue repair and regeneration and/or inhibiting inflammation. Examples of useful, cofactors include anti-VEGF agents (such as an antibody or FAB against VEGF, e.g., Lucentis or Avastin), basic fibroblast growth factor (bFGF), ciliary neurotrophic factor (CNTF), axokine (a mutein of CNTF), leukemia inhibitory factor (LIF), neutrotrophin 3 (NT-3), neurotrophin-4 (NT-4), nerve growth factor (NGF), insulin-like growth factor II, prostaglandin E2, 30 kD survival factor, taurine, and vitamin A. Other useful cofactors include symptom-alleviating cofactors, including antiseptics, antibiotics, antiviral and antifungal agents and analgesics and anesthetics Suitable agents for combination treatment with the compounds of the invention include agents known in the art that are able to modulate the activities of complement components.

A combination therapy regimen may be additive, or it may produce synergistic results (e.g., reductions in complement pathway activity more than expected for the combined use of the two agents). In some embodiments, the present invention provide a combination therapy for preventing and/or treating AMD or another complement related ocular disease as described above with a compound of the invention and an anti-angiogenic, such as anti-VEGF agent (including Lucentis and Avastin) or photodynamic therapy (such as verteporfin).

In some embodiments, the present invention provide a combination therapy for preventing and/or treating autoimmune disease as described above with a compound of the invention and a B-Cell or T-Cell modulating agent (for example cyclosporine or analogs thereof, rapamycin, RAD001 or analogs thereof, and the like). In particular, for multiple sclerosis therapy may include the combination of a compound of the invention and a second MS agent selected from fingolimod, cladribine, tysarbi, laquinimod, rebif, avonex and the like.

In one embodiment, the invention provides a method of modulating activity of the complement alternative pathway in a subject, wherein the method comprises administering to the subject a therapeutically effective amount of the compound according to the definition of formula (I). The invention further provides methods of modulating the activity of the complement alternative pathway in a subject by modulating the activity of Factor D, wherein the method comprises administering to the subject a therapeutically effective amount of the compound according to the definition of Formula (I).

In one embodiment, the invention provides a compound according to the definition of formula (I), (Ia), (VII) or any subformulae thereof, for use as a medicament.

In one embodiment, the invention provides the use of a compound according to the definition of formula (I), (Ia), (VII) or any subformulae thereof, for the treatment of a disorder or disease in a subject mediated by complement activation. In particular, the invention provides the use of a compound according to the definition of formula (I), (Ia), (VII) or any subformulae thereof, for the treatment of a disorder or disease mediated by activation of the complement alternative pathway.

In one embodiment, the invention provides the use of a compound according to the definition of formula (I), (Ia), in the manufacture of a medicament for the treatment of a disorder or disease in a subject characterized by activation of the complement system. More particularly in the manufacture of a medicament for the treatment of a disease or disorder in a subject characterized by over activation of the complement alternative pathway.

In one embodiment, the invention provides the use of a compound according to the definition of formula (I), (Ia), or subformulae thereof for the treatment of a disorder or disease in a subject characterized by activation of the complement system. More particularly, the invention provides uses of the compounds provided herein in the treatment of a disease or disorder characterized by over activation of the complement alternative pathway or the $C_3$ amplification loop of the alternative pathway. In certain embodiments, the use is in the treatment of a disease or disorder is selected from retinal diseases (such as age-related macular degeneration).

The present invention provides use of the compounds of the invention for treating a disease or disorder associated with increased complement activity by administering to a subject in need thereof an effective amount of the compounds of Formula (I) of the invention. In certain aspects, uses are provided for the treatment of diseases associated with increased activity of the $C_3$ amplification loop of the complement pathway. In certain embodiments, uses of treating or preventing complement mediated diseases are provided in which the complement activation is induced by antibody-antigen interactions, by a component of an autoimmune disease, or by ischemic damage.

In a specific embodiment, the present invention provides use of the compounds of the invention for treating or preventing age-related macular degeneration (AMD). In certain embodiments, patients who are currently asymptomatic but are at risk of developing a symptomatic macular degeneration related disorder are suitable for administration with a compound of the invention. The use in treating or preventing AMD include, but are not limited to, uses in treating or preventing one or more symptoms or aspects of AMD selected from formation of ocular drusen, inflammation of the eye or eye tissue, loss of photoreceptor cells, loss of vision (including loss of visual acuity or visual field), neovascularization (including CNV), retinal detachment, photoreceptor degeneration, RPE degeneration, retinal degeneration, chorioretinal degeneration, cone degeneration, retinal dysfunction, retinal damage in response to light exposure, damage of the Bruch's membrane, and/or loss of RPE function.

The compound of Formula (I) of the invention can be used, inter alia, to prevent the onset of AMD, to prevent the progression of early AMD to advanced forms of AMD including neovascular AMD or geographic atrophy, to slow and/or prevent progression of geographic atrophy, to treat or prevent macular edema from AMD or other conditions (such as diabetic retinopathy, uveitis, or post surgical or nonsurgical trauma), to prevent or reduce the loss of vision from AMD, and to improve vision lost due to pre-existing early or advanced AMD. It can also be used in combination with anti-VEGF therapies for the treatment of neovascular AMD patients or for the prevention of neovascular AMD. The present invention further provides methods of treating a complement related disease or disorder by administering to a subject in need thereof an effective amount of the compound(s) of the invention, wherein said disease or disorder is selected from uveitis, adult macuar degeneration, diabetic retinopathy, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, postoperative inflammation, and retinal vein occlusion.

In some embodiments, the present invention provides uses for treating a complement related disease or disorder. Examples of known complement related diseases or disorders include: neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, thermal injury including burns or frostbite, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration and neural regeneration. In addition, other known complement related disease are lung disease and disorders such as dyspnea, hemoptysis, ARDS, asthma, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), asthma, allergy, bronchoconstriction, hypersensitivity pneumonitis, parasitic diseases, Goodpasture's Syndrome, pulmonary vasculitis, Pauci-immune vasculitis, immune complex-associated inflammation, uveitis (including Behcet's disease and other sub-types of uveitis), antiphospholipid syndrome.

In a specific embodiment, the present invention provides use of the compounds of the invention for treating a complement related disease or disorder, wherein said disease or disorder is asthma, arthritis (e.g., rheumatoid arthritis), autoimmune heart disease, multiple sclerosis, inflammatory bowel disease, ischemia-reperfusion injuries, Barraquer-Simons Syndrome, hemodialysis, systemic lupus, lupus erythematosus, psoriasis, multiple sclerosis, transplantation, diseases of the central nervous system such as Alzheimer's disease and other neurodegenerative conditions, atypicaly hemolytic uremic syndrome (aHUS), glomerulonephritis (including membrane proliferative glomerulonephritis), blistering cutaneous diseases (including bullous pemphigoid, pemphigus, and epidermolysis bullosa), ocular cicatrical pemphigoid or MPGN II.

In a specific embodiment, the present invention provides use of the compounds of the invention for treating glomerulonephritis. Symptoms of glomerulonephritis include, but not limited to, proteinuria; reduced glomerular filtration rate (GFR); serum electrolyte changes including azotemia (uremia, excessive blood urea nitrogen—BUN) and salt retention, leading to water retention resulting in hypertension and edema; hematuria and abnormal urinary sediments including red cell casts; hypoalbuminemia; hyperlipidemia; and lipiduria. In a specific embodiment, the present invention provides methods of treating paroxysmal nocturnal hemoglobinuria (PNH) by administering to a subject in need thereof an effective amount of a composition comprising an compound of the present invention with or without concomitant administration of a complement C5 inhibitor or C5 convertase inhibitor such as Soliris.

In a specific embodiment, the present invention provides use of the compounds of the invention for reducing the dysfunction of the immune and/or hemostatic systems associated with extracorporeal circulation. The compounds of the present invention can be used in any procedure which involves circulating the patient's blood from a blood vessel of the patient, through a conduit, and back to a blood vessel of the patient, the conduit having a luminal surface comprising a material capable of causing at least one of complement activation, platelet activation, leukocyte activation, or platelet-leukocyte adhesion. Such procedures include, but are not limited to, all forms of ECC, as well as procedures involving the introduction of an artificial or foreign organ, tissue, or vessel into the blood circuit of a patient. More particularly, such procedures include, but are not limited to, transplantation procedures including kidney, liver, lung or heart transplant procedures and islet cell transplant procedures.

The following examples are intended to illustrate the invention and are not to be construed as being limitations thereon. Temperatures are given in degrees centrigrade (° C.). If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

InterAlia the Following in vitro Tests May be Used
Human Complement Factor D Assay: Method 1

Recombinant human factor D (expressed in *E. coli* and purified using standard methods) at 10 nM concentration is incubated with test compound at various concentrations for 1 hour at room temperature in 0.1 M Hepes buffer, pH 7.5, containing 1 mM $MgCl_2$, 1 M NaCl and 0.05% CHAPS. A synthetic substrate Z-Lys-thiobenzyl and 2,4-dinitrobenzenesulfonyl-fluoresceine are added to final concentrations of 200 µM and 25 µM, respectively. The increase in fluorescence is recorded at excitation of 485 nm and emission at 535 nm in a microplate spectrofluorimeter. $IC_{50}$ values are calculated from percentage of inhibition of complement factor D-activity as a function of test compound concentration.

Human Complement Factor D Assay: Method 2

Recombinant human factor D (expressed in *E. coli* and purified using standard methods) at a 10 nM concentration is incubated with test compound at various concentrations for 1 hour at room temperature in 0.1 M PBS pH 7.4 containing 7.5 mM $MgCl_2$ and 0.075% (w/v) CHAPS. Cobra venom factor and human complement factor B substrate complex is added to a final concentration of 200 nM. After 1 hour incubation at room temperature, the enzyme reaction was stopped by addition of 0.1 M sodium carbonate buffer pH 9.0 containing 0.15 M NaCl and 40 mM EDTA. The product of the reaction, Ba, was quantified by means of an enzyme-linked-immunosorbent assay. $IC_{50}$ values are calculated from percentage of inhibition of factor D-activity as a function of test compound concentration.

The following Examples, while representing preferred embodiments of the invention, serve to illustrate the invention without limiting its scope.

Abbreviations
abs. absolute
Ac acetyl
AcOH acetic acid
aq. aqueous
cc concentrated
c-hexane cyclohexane
CSA Camphor sulfonic acid
DBU 1,8-diazabicyclo[5.4.0]undec-7-ene
DCC N,N'-dicyclohexylcarbodiimide
DCE Dichloroethane
DEA Diethylamine
DEAD Diethyl azodicarboxylate
Dia Diastereoisomer
DIBALH diisobutylaluminium hydride
DIPEA N,N-diisopropylethylamine
DMAP 4-dimethylaminopyridine
DME dimethoxyethane
DMF dimethylformamide
DMME dimethoxymethane
DMSO dimethylsulfoxide
DPPA diphenylphosphoryl azide
EDCI 1-(3-dimethylaminopropyl)-3-ethylcarbodiimide hydrochloride
$Et_3N$ triethylamine
$Et_2O$ diethylether
EtOAc ethyl acetate
EtOH ethanol
Flow flow rate
h hour(s)
HMPA hexamethylphosphoroamide
HOBt 1-hydroxybenzotriazole
HBTU 2-(1H-benzotriazol-1-yl)-1,1,3,3-tetramethyluronium tetrafluoroborate
HPLC High Performance Liquid Chromatography
HV high vacuum
IPA isopropylamine
i-PrOH isopropanol
KHMDS potassium hexamethyldisilazane
L liter(s)
LC/MS Liquid Chromatography/Mass Spectrometry
LDA lithium diisopropylamine
mCPBA 3-chloroperoxybenzoic acid
Me methyl
MeI methyl iodide
MeOH methanol
MesCl Mesyl Chloride
min minute(s)
mL milliliter
MS Mass Spectrometry
NBS N-Bromo succinimide
NMM 4-methylmorpholine
NMR Nuclear Magnetic Resonance
Pd/C palladium on charcoal
Prep Preparative
Ph phenyl
RP reverse phase
RT room temperature
sat. aq. a saturated aqueous solution of
$scCO_2$ super critical carbone dioxide
SEM-Cl 2-(Trimethylsilyl)ethoxymethyl chloride
SFC Supercritical Fluid Chromatography
TBAF tetra-butylammonium fluoride
TBDMS-Cl tert-butyldimethylsilyl chloride
TBDMS tert-butyldimethylsilyl
TBME tert-butylmethylether
TEA triethylamine
TFA trifluoroacetic acid
THF tetrahydrofurane
TLC Thin Layer Chromatography
TMEDA tetramethylethylenediamine
$T_3P$ Propylphosphonic anhydride
$t_R$ retention time
Trademarks
Celite=Celite® (The Celite Corporation)=filtering aid based on diatomaceous earth
$NH_2$ Isolute (=Isolute® $NH_2$, Isolute® is registered for Argonaut Technologies, Inc.)=ion exchange with amino groups based on silica gel
Nucleosil=Nucleosil®, trademark of Machery & Nagel, Düren, FRG for HPLC materials
PTFE membrane=Chromafil O-45/15MS Polytetrafluoroethylene Machereynagel)
PL Thiol Cartridge=Stratosphere® SPE, PL-Thiol MP SPE+, 500 mg per 6 mL tube, 1.5 mmol (nominal)
Q-Tube Pressure tube reactor, SigmaAldrich Gold column RediSep Rf Gold™ Colums, Teledyne ISCO Temperatures are measured in degrees Celsius. Unless otherwise indicated, the reactions take place at RT.

Phase Separator: Biotage—Isolute Phase separator (Part Nr: 120-1908-F for 70 mL and Part Nr: 120-1909-J for 150 mL)

TLC Conditions: $R_f$ values for TLC are measured on 5×10 cm TLC plates, silica gel $F_{254}$, Merck, Darmstadt, Germany.

HPLC Conditions:

HPLC were performed using an Agilent 1100 or 1200 series instrument. Mass spectra and LC/MS were determined using an Agilent 1100 series instrument.

a: Agilent Eclipse XDB-C18, 1.8 μm, 4.6×50 mm 20-100% $CH_3CN/H_2O/6$ min, 100% $CH_3CN/1.5$ min, $CH_3CN$ and $H_2O$ containing 0.1% of TFA, flow: 1 mL/min.

b. Agilent Eclipse XDB-C18, 1.8 μm, 4.6×50 mm, 5-100% $CH_3CN/H_2O/6$ min, 100% $CH_3CN/1.5$ min, $CH_3CN$ and $H_2O$ containing 0.1% TFA, flow: 1 mL/min.

c. Waters Sunfire C18, 2.5 μm, 3×30 mm, 10-98% in 2.5 min, $CH_3CN$ and $H_2O$ containing 0.1% TFA, flow: 1.4 mL/min.

d. Agilent Eclipse XDB-C18, 1.8 μm, 2.1×30 mm 5-100% $CH_3CN/H_2O/3$ min, 100% $CH_3CN/0.75$ min, $CH_3CN$ and $H_2O$ containing 0.1% of TFA, flow: 0.6 mL/min e. Agilent Eclipse XDB-C18, 1.8 μm, 2.1×30 mm 20-100% $CH_3CN/H_2O/3$ min, 100% $CH_3CN/0.75$ min, $CH_3CN$ and $H_2O$ containing 0.1% of TFA, flow: 0.6 mL/min f. Waters X-Bridge C18, 2.5 μm, 3×50 mm, 10-98% $CH_3CN/H_2O/8.6$ min, 98% $CH_3CN/1.4$ min, $CH_3CN$ and $H_2O$ containing 0.1% of TFA, flow: 1.4 mL/min.

g. UPLC/MS: Waters Acquity; UPLC column: Waters Acquility HSS T3, 1.8 μm, 2.1×50 mm 10-95% $CH_3CN/H_2O/1.5$ min, $H_2O$ containing 0.05% HCOOH+3.75 mM $NH_4OAc$ and $CH_3CN$ containing 0.04% HCOOH, flow: 1.2 mL/min.

h. UPLC/MS: Waters Acquity; UPLC column: Waters Acquility HSS T3, 1.8 μm, 2.1×50 mm 2-98% $CH_3CN/H_2O/1.4$ min, $H_2O$ containing 0.05% HCOOH+3.75 mM $NH_4OAc$ and $CH_3CN$ containing 0.04% HCOOH, flow: 1.4 mL/min.

i. Waters X-Bridge C18, 2.5 μm, 3×30 mm, 10-98% $CH_3CN/H_2O/3$ min, 98% $CH_3CN/0.5$ min, $CH_3CN$ and $H_2O$ containing 0.1% of TFA, flow: 1.4 mL/min.

j. Waters Symmetry C18, 3.5 μm, 2.1×50 mm, 20-95% $CH_3CN/H_2O/3.5$ min, 95% $CH_3CN/2$ min, $CH_3CN$ and $H_2O$ containing 0.1% TFA, flow: 0.6 mL/min.

Part A: Synthesis of Substituted Aromatic or Heteroaromatic Building Blocks

Scheme A1: Preparation of 2-(3-Acetyl-1h-indazol-1-yl)acetic acid

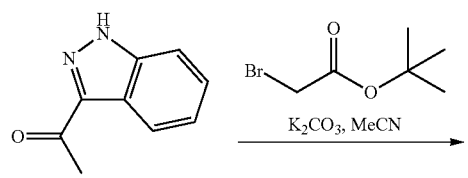

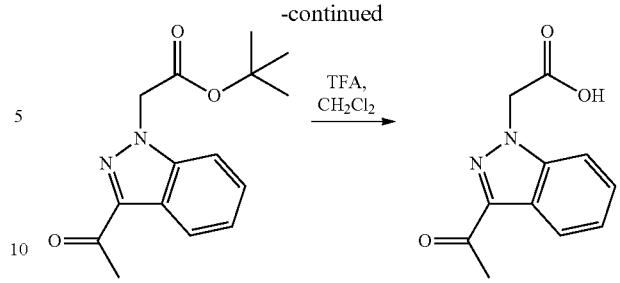

A. Tert-butyl 2-(3-acetyl-1H-indazol-1-yl)acetate

To a solution of 1-(1H-indazol-3-yl)ethanone [4498-72-0] (2 g, 12.46 mmol) in $CH_3CN$ (50 mL) was added potassium carbonate (3.97 g, 28.7 mmol) and tert-butyl 2-bromoacetate (2.58 mL, 17.48 mmol). The reaction mixture was stirred at 90° C. overnight. The reaction mixture was filtered, the solid was washed with $CH_3CN$ and the filtrate was concentrated under vacuum. The material thus obtained was used in the next step without further purification. MS: 275 [M+H]+; $t_R$ (HPLC conditions d): 3.78 min.

B. 2-(3-Acetyl-1H-indazol-1-yl)acetic acid

To a solution of tert-butyl 2-(3-acetyl-1H-indazol-1-yl)acetate (4 g, 12.4 mmol) in $CH_2Cl_2$ (45 mL) was added TFA (15 mL, 195 mmol), and the reaction mixture was stirred at RT overnight. The reaction mixture was diluted with $CH_2Cl_2$ and MeOH and volatiles were evaporated under reduced pressure to afford the title compound: MS: 219 [M+H]+; $t_R$ (HPLC conditions d): 2.78 min.

Scheme A2: General protocol described for the preparation of (3-acetyl-pyrazolo[3,4-c]pyridin-1-yl)-acetic acid trifluoroacetate

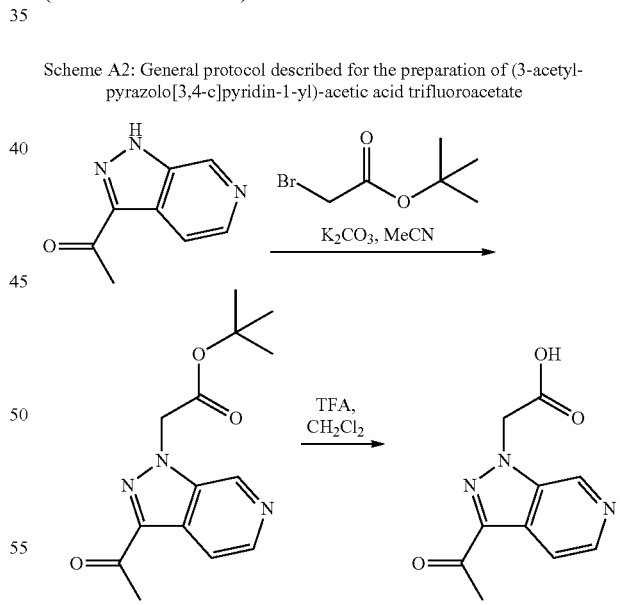

A. (3-Acetyl-pyrazolo[3,4-c]pyridin-1-yl)-acetic acid tert-butyl ester

To a solution of 1-(1H-pyrazolo[3,4-c]pyridin-3-yl)-ethanone (Sphinx Scientific laboratory LLC, catalog number: PPY-1-CS01) (2.45 g 14.44 mmol) in $CH_3CN$ (50 mL) were added potassium carbonate (3.99 g, 28.9 mmol) and tert-butyl 2-bromoacetate (2.34 mL, 15.88 mmol). The reaction mixture was stirred at RT overnight, poured into water and extracted with EtOAc (×3). The combined organic extracts were dried (Na$_2$SO$_4$), filtered and concentrated. The crude residue was purified by flash column chromatography on silica gel to afford the title compound (c-hexane/EtOAc 1:0 to 0:1). TLC, R$_f$(EtOAc)=0.7; MS: 276 [M+H]+; t$_R$ (HPLC conditions e): 2.06 min.

B. (3-Acetyl-pyrazolo[3,4-c]pyridin-1-yl)-acetic acid trifluoroacetate

The title compound was prepared from (3-acetyl-pyrazolo[3,4-c]pyridin-1-yl)-acetic acid tert-butyl ester in a similar manner as described in step B of Scheme A1 for the preparation of 2-(3-acetyl-1H-indazol-1-yl)acetic acid. MS: 220 [M+H]+; t$_R$ (HPLC conditions e): 0.69 min.

(3-Acetyl-pyrazolo[3,4-b]pyridin-1-yl)-acetic acid

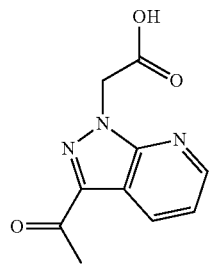 [SMILES: CC(=O)c1nn(CC(=O)O)c2ncccc12]

The title compound was prepared using similar procedures as described for the synthesis of (3-acetyl-pyrazolo[3,4-c]pyridin-1-yl)-acetic acid trifluoroacetate in Scheme A2 starting from 1-(1H-pyrazolo[3,4-b]pyridin-3-yl)-ethanone (Sphinx Scientific Laboratory LLC, [889451-31-4], PYP-3-0043). MS (UPLC/MS): 220 [M+H]+, 218.2 [M−H]−; t$_R$ (HPLC conditions d): 2.51 min.

Scheme A3: General protocol described for the preparation of 2-(3-acetyl-5-(pyrimidin-2-ylmethoxy)-1H-indazol-1-yl)acetic acid

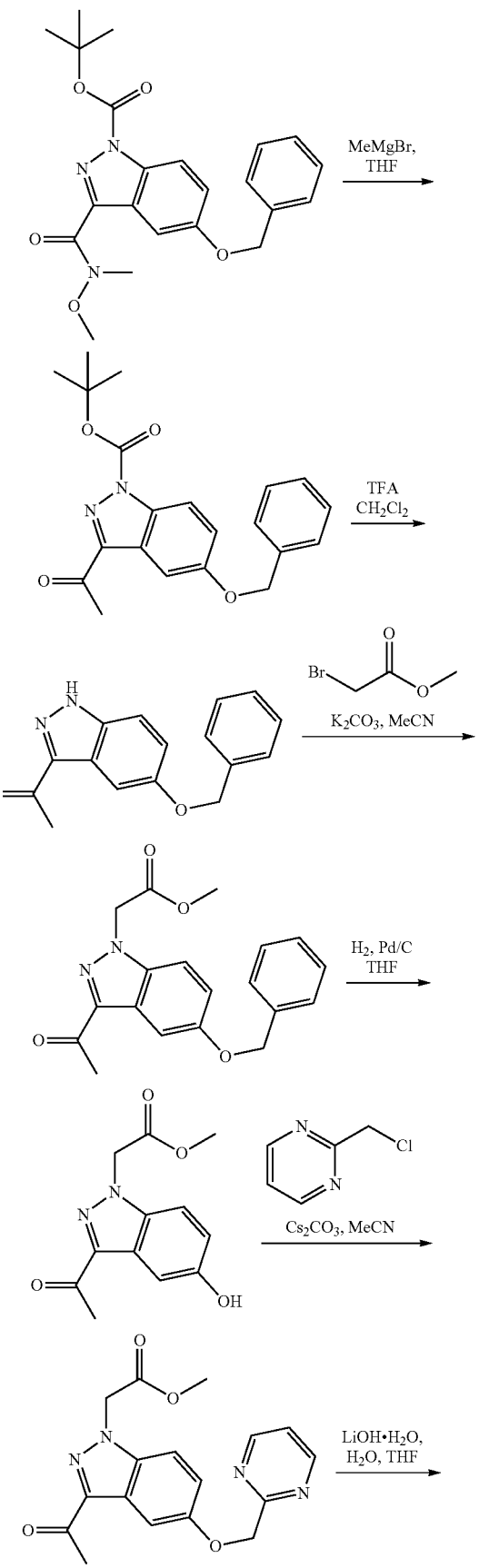

-continued

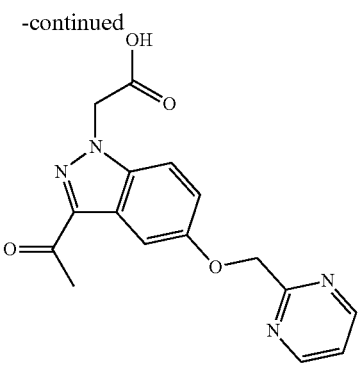

A. 5-(Benzyloxy)-N-methoxy-N-methyl-1H-indazole-3-carboxamide

The title compound was prepared in a similar manner as described by F. Crestey et al., *Tetrahedron* 2007, 63, 419-428: To a solution of 5-(benzyloxy)-1H-indazole-3-carboxylic acid [177941-16-1](3.50 g, 13.1 mmol) in THF (70 mL) was added N,O-dimethylhydroxylamine (1.40 g, 14.4 mmol). The mixture was cooled to 0° C. before the addition of pyridine (2.30 mL, 28.7 mmol). The solution was stirred at 0° C. for 1.5 h, and then at RT for 1 h. Pyridine (2.10 mL, 26.1 mmol) and EDCI (5.00 g, 26.1 mmol) were added and the mixture was stirred at RT overnight. Water was added to the reaction mixture followed by extraction with $CH_2Cl_2$ (3×). The combined organic extracts were washed with sat. aq. $NaHCO_3$, dried (phase separator) and evaporated to give the title compound. MS (LC/MS): 312.0 [M+H]+, 334.0 [M+Na]+, 645.1 [2M+Na]+, 310.0 [M−H]−; $t_R$ (HPLC conditions b): 4.44 min.

B. Tert-butyl 5-(benzyloxy)-3-(methoxy(methyl)carbamoyl)-1H-indazole-1-carboxylate The title compound was prepared in a similar manner as described by F. Crestey et al., *Tetrahedron* 2007, 63, 419-428: To a solution of 5-(benzyloxy)-N-methoxy-N-methyl-1H-indazole-3-carboxamide (3.40 g, 10.9 mmol) in $CH_2Cl_2$ (70 mL) was added DMAP (0.13 g, 1.09 mmol), TEA (1.67 mL, 12.0 mmol) and $Boc_2O$ (3.80 mL, 16.4 mmol) at 0° C. The reaction mixture was stirred at 0° C. for 1 h and allowed to return to RT overnight. The reaction mixture was diluted with $CH_2Cl_2$ and washed successively with 50 mL of 0.1 M aq. HCl and water. The organic layer was dried (phase separator) and concentrated to give the title compound. MS (LC/MS): 434.0 [M+Na]+, 845.0 [2M+Na]+; $t_R$ (HPLC conditions b): 5.79 min.

C. Tert-butyl 3-acetyl-5-(benzyloxy)-1H-indazole-1-carboxylate and 1-(5-(benzyloxy)-1H-indazol-3-yl)ethanone The title compound was prepared in a similar manner as described by F. Crestey et al., *Tetrahedron* 2007, 63, 419-428. To a solution of tert-butyl 5-(benzyloxy)-3-(methoxy(methyl)carbamoyl)-1H-indazole-1-carboxylate (4.70 g, 11.4 mmol) in THF (60 mL), cooled to −78° C., was added a 3 M solution of MeMgBr in $Et_2O$ (22.9 mL, 68.5 mmol). The reaction mixture was stirred at −78° C. for 1 h. Sat. aq. $NH_4Cl$ was added and the temperature was allowed to raise to RT. The mixture was extracted with $CH_2Cl_2$, (2×), the combined organic layers were dried (phase separator) and concentrated to give a mixture of tert-butyl 3-acetyl-5-(benzyloxy)-1H-indazole-1-carboxylate and 1-(5-(benzyloxy)-1H-indazol-3-yl)ethanone which was used in the next step without purification. MS (LC/MS): 267.0 [M+H]+, 289.0 [M+Na]+, 265.1 [M−H]− for 1-(5-(benzyloxy)-1H-indazol-3-yl)ethanone, 389.0 [M+Na]+, 310.9 [M-tBu]+, 267.1 [M-Boc]+ for tert-butyl 3-acetyl-5-(benzyloxy)-1H-indazole-1-carboxylate; $t_R$ (HPLC conditions b): 4.72 min for 1-(5-(benzyloxy)-1H-indazol-3-yl)ethanone and 6.12 min for tert-butyl 3-acetyl-5-(benzyloxy)-1H-indazole-1-carboxylate.

D. 1-(5-(Benzyloxy)-1H-indazol-3-yl)ethanone

To a mixture of tert-butyl 3-acetyl-5-(benzyloxy)-1H-indazole-1-carboxylate and 1-(5-(benzyloxy)-1H-indazol-3-yl)ethanone (3.80 g, 10.4 mmol) in $CH_2Cl_2$ (50 mL) was added TFA (7.99 mL, 104 mmol). The reaction mixture was stirred at RT overnight, diluted with $CH_2Cl_2$ and washed with 100 mL of 2 N aq. NaOH. The aq. layer was extracted with $CH_2Cl_2$ (2×), the combined organic extracts were dried (phase separator) and evaporated to give the title compound. MS (LC/MS): 267.0 [M+H]+, 289.0 [M+Na]+, 265.1 [M−H]−; $t_R$ (HPLC conditions b): 4.71 min.

E. Methyl 2-(3-acetyl-5-(benzyloxy)-1H-indazol-1-yl)acetate

To a solution of 1-(5-(benzyloxy)-1H-indazol-3-yl)ethanone (3.50 g, 13.1 mmol) in $CH_3CN$ (100 mL) was added potassium carbonate (4.54 g, 32.9 mmol) and methyl 2-bromoacetate (1.33 mL, 14.5 mmol). The reaction mixture was stirred at 90° C. for 90 min. The reaction mixture was filtered and the solid was washed with $CH_3CN$. The filtrate was concentrated and the product was purified by flash column chromatography on silica gel (c-hexane/EtOAc 1:1 to 1:3). TLC, $R_f$(c-hexane/EtOAc 1:3)=0.64; MS (LC/MS): 339.0 [M+H]+, 361.0 [M+Na]+; $t_R$ (HPLC conditions b): 5.09 min.

F. Methyl 2-(3-acetyl-5-hydroxy-1H-indazol-1-yl)acetate

To a solution of methyl 2-(3-acetyl-5-(benzyloxy)-1H-indazol-1-yl)acetate (3.70 g, 10.9 mmol) in THF (80 mL) was added Pd/C (10%, 400 mg). The reaction mixture was stirred at 50° C. overnight under a $H_2$ atmosphere. The reaction mixture was filtered over Celite and washed with $CH_2Cl_2$, then the filtrate was evaporated to give the title compound. MS (LC/MS): 248.9 [M+H]+, 271.0 [M+Na]+; $t_R$ (HPLC conditions b): 3.36 min.

G. Methyl 2-(3-acetyl-5-(pyrimidin-2-ylmethoxy)-1H-indazol-1-yl)acetate

To a solution of methyl 2-(3-acetyl-5-hydroxy-1H-indazol-1-yl)acetate (1.80 g, 7.25 mmol) in $CH_3CN$ (75 mL) was added 2-(chloromethyl)pyrimidine hydrochloride (1.32 g, 7.98 mmol) and $Cs_2CO_3$ (5.91 g, 18.13 mmol). The reaction mixture was stirred at 70° C. for 2 h, cooled to RT, filtered and washed with $CH_3CN$. The filtrate was evaporated and the residue was purified by flash column chromatography on silica gel (c-hexane/EtOAc 1:1 to 1:3) to afford the title compound. TLC, $R_f$(c-hexane/EtOAc 1:3)=0.35; MS (LC/MS): 340.9 [M+H]+, 363.0 [M+Na]+; $t_R$ (HPLC conditions b): 3.64 min.

H. 2-(3-Acetyl-5-(pyrimidin-2-ylmethoxy)-1H-indazol-1-yl)acetic acid

To a solution of methyl 2-(3-acetyl-5-(pyrimidin-2-ylmethoxy)-1H-indazol-1-yl)acetate (1.93 g, 5.67 mmol) in THF (15 mL) and water (15 mL) was added LiOH.H$_2$O (0.25 g, 5.95 mmol). The reaction mixture was stirred at RT for 1.5 h. Volatiles were evaporated and the residue was lyophilized to give the title compound as a lithium salt. MS (LC/MS): 327.0 [M+H]+; t$_R$ (HPLC conditions b): 3.24 min.

Scheme A4: Preparation of (5-acetyl-pyrrolo[2,3-c]pyridazin-7-yl)-acetic acid trifluoroacetate

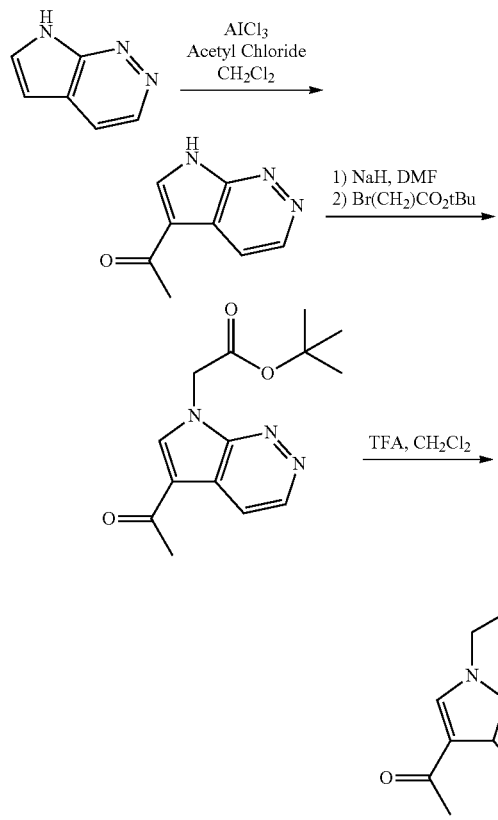

A. 1-(7H-Pyrrolo[2,3-c]pyridazin-5-yl)-ethanone

To a stirred suspension of AlCl$_3$ (2.24 g, 16.79 mmol) in CH$_2$Cl$_2$ (80 mL), was added 7H-pyrrolo[2,3-c]pyridazine (400 mg, 3.36 mmol). After stirring at RT for 30 min, acetyl chloride (1.20 mL, 16.79 mmol) was added dropwise and the resulting mixture was stirred at RT for 3 days. The reaction mixture was cooled to 00° C. and slowly quenched by addition of MeOH (20 mL). The reaction mixture was concentrated and purified by flash chromatography on silica gel (CH$_2$Cl$_2$/MeOH 10/0 to 8/2) to give the title compound. TLC, R$_f$(CH$_2$Cl$_2$/MeOH 9:1)=0.47; MS (UPLC/MS): 162.0 [M+H]+, 160.1 [M−H]−; t$_R$ (HPLC conditions c): 1.30 min.

B. (5-Acetyl-pyrrolo[2,3-c]pyridazin-7-yl)-acetic acid tert-butyl ester

A suspension of NaH (60% in mineral oil, 91 mg, 2.28 mmol) in DMF (3 mL) was cooled to 0° C. and a solution of 1-(7H-pyrrolo[2,3-c]pyridazin-5-yl)-ethanone (350 mg, 2.17 mmol) in DMF (8 mL) was added. The resulting suspension was stirred at for 30 min at 0° C. subsequently tert-butyl 2-bromoacetate (337 μL, 2.28 mmol) was added slowly. The reaction mixture was stirred at RT for 3.5 h, poured into water and extracted with EtOAc (2×). The combined organic layers were washed with water, dried (Na$_2$SO$_4$), filtered, concentrated and the product was purified by flash chromatography on silica gel (CH$_2$Cl$_2$/MeOH 100/0 to 93/7) to give the title compound. TLC, R$_f$(CH$_2$Cl$_2$/MeOH 9:1)=0.54; MS (UPLC/MS): 276.1 [M+H]+; t$_R$ (HPLC conditions c): 1.30 min.

C. (5-Acetyl-pyrrolo[2,3-c]pyridazin-7-yl)-acetic acid trifluoroacetate

To a solution of (5-acetyl-pyrrolo[2,3-c]pyridazin-7-yl)-acetic acid tert-butyl ester (340 mg, 1.11 mmol) in CH$_2$Cl$_2$ (4 mL) was added TFA (1.7 mL, 22.23 mmol). The reaction mixture was stirred at RT for 6 h and concentrated. The residue was dissolved in CH$_2$Cl$_2$, concentrated again and dried under HV. MS (UPLC/MS): 220.1 [M+H]+, 218.1 [M−H]−, 437.2 [2M−H]−.

Scheme A5: Preparation of 3-Isocyanato-indole-1-carboxylic acid

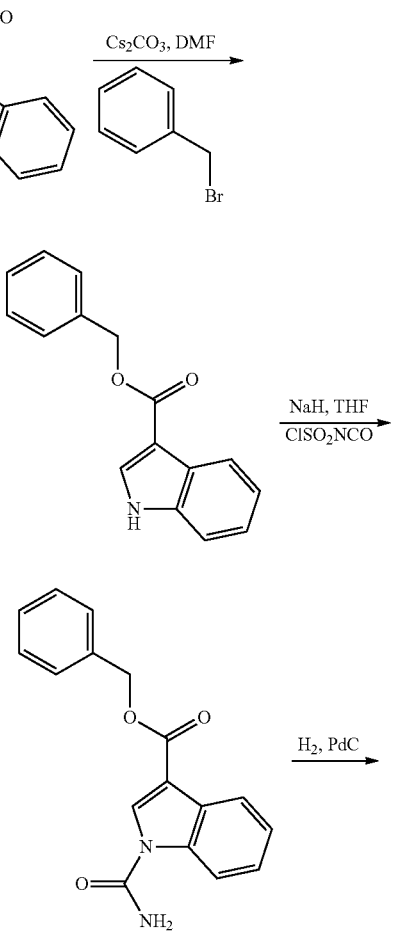

-continued

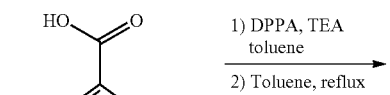

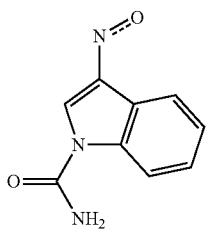

A. 1H-Indole-3-carboxylic acid benzyl ester

To a solution of 1H-indole-3-carboxylic acid (5 g, 31 mmol) in DMF (70 mL) under nitrogen atmosphere at 0° C. was added cesium carbonate (11 g, 31 mmol) and benzyl bromide (4.05 mL, 34.1 mmol). The reaction mixture was stirred at RT for 48 h and poured into water. EtOAc was added and the layers were separated, the aq. layer was extracted with EtOAc (3×). The combined organic layers were washed with water, dried ($Na_2SO_4$), filtered and concentrated. The residue was taken up in $Et_2O$ and the resulting precipitate was filtered-to afford the title compound. TLC, $R_f$ (c-hexane/EtOAc 1:1)=0.55; MS (LC/MS): 252.1 [M+H]+, 274.0 [M+Na]+; $t_R$ (HPLC conditions j) 3.77 min.

B. 1-Carbamoyl-1H-indole-3-carboxylic acid benzyl ester

To a solution of 1H-indole-3-carboxylic acid benzyl ester (3.5 g, 13.9 mmol) in THF (70 mL) at 5° C., was added NaH (60% in mineral oil, 557 mg, 13.9 mmol). The mixture was stirred at 5° C. for 30 min before slow dropwise addition of chlorosulfonyl isocyanate (2.42 mL, 27.9 mmol) maintaining the temperature between 5° C. and 10° C. The pale yellow solution was subsequently stirred at RT for 3.5 h. Acetic acid (22.5 mL) was added (exothermic), and the resulting solution was stirred at RT for 1.5 h before addition of ice and water (100 mL). The white thick suspension was stirred at RT for 30 min and the precipitate was filtered, taken up in MeOH and filtered again to afford the desired compound. $^1$H-NMR (400 MHz, DMSO) δ (ppm): 8.64 (s, 1H), 8.29 (d, 1H), 8.04 (d, 1H), 7.90 (m, 2H), 7.50 (d, 2H), 7.42 (t, 2H), 7.36-7.30 (m, 3H), 5.38 (s, 2H).

C. 1-carbamoyl-1H-indole-3-carboxylic acid

1-Carbamoyl-1H-indole-3-carboxylic acid benzyl ester (1.33 g, 4.52 mmol) was dissolved in a mixture of DMF/THF 1:1 (28 mL), Pd/C (10%, 250 mg) was added and the solution was degassed 3 times replacing air with nitrogen and then nitrogen with hydrogen. The reaction mixture was further stirred under hydrogen atmosphere overnight and the catalyst was removed through a pad of Celite and washed with THF. The solvents were concentrated to give a yellow solid which was taken up in $Et_2O$ and filtered to afford the title compound. $^1$H-NMR (400 MHz, DMSO) δ (ppm): 12.6 (m, 1H), 8.54 (bs, 1H), 8.28 (d, 1H), 8.05 (d, 1H), 7.85 (m, 2H), 7.34-7.27 (m, 2H).

D. 3-isocyanato-indole-1-carboxylic acid amide

To a suspension of 1-carbamoyl-1H-indole-3-carboxylic acid (1.31 g, 6.42 mmol) in toluene (30 mL) under nitrogen was added TEA (893 µl, 6.42 mmol). After 15 min, DPPA (1.54 mL, 6.42 mmol) was added and the reaction mixture was further stirred at RT overnight. The solvent was concentrated, the residue was taken up in $CH_2Cl_2$ and the precipitate was filtered to give the acyl azide intermediate (565 mg). Toluene (20 mL) was added and the suspension refluxed for 1.5 h under nitrogen atmosphere. The reaction was monitored by TLC (disappearance of the acyl azide). Toluene was concentrated under vacuum and the desired isocyanate was directly used in the next step without further purification. $^1$H-NMR (400 MHz, $CDCl_3$) δ (ppm) 8.18 (d, 1H), 7.61 (d, 1H), 7.44 (t, 1H), 7.35 (t, 1H), 7.23 (s, 1H), 5.39 (bs, 2H).

Scheme A6: Preparation of (3-carbamoyl-indazol-1-yl)-acetic acid

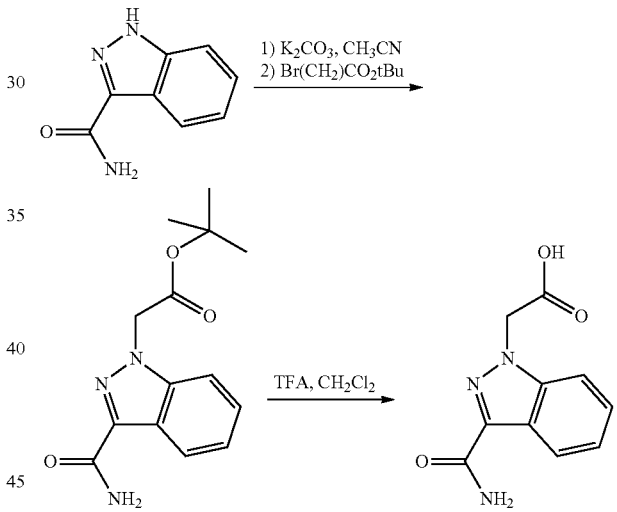

A. Tert-butyl 2-(3-carbamoyl-1H-indazol-1-yl)acetate

To a suspension of 1H-indazole-3-carboxamide [90004-04-9](2.00 g, 12.4 mmol) and potassium carbonate (4.12 g, 29.8 mmol) in $CH_3CN$ (60 mL) was added tert-butyl 2-bromoacetate (2.20 mL, 14.9 mmol) dropwise at RT, subsequently the resulting mixture was kept under reflux for 16 h. Then the reaction mixture was cooled to RT and filtered, the solid was washed with $CH_3CN$ and the filtrate was concentrated under vacuum. The residual oil was used directly in the next reaction step without further purification. MS (LC/MS): 276.0 [M+H]+; $t_R$ (HPLC conditions d): 3.22 min.

B. (3-Carbamoyl-indazol-1-yl)-acetic acid

To a solution of tert-butyl 2-(3-carbamoyl-1H-indazol-1-yl)acetate (3.42 g, 12.4 mmol) in $CH_2Cl_2$ (20 mL) was added TFA (10 mL, 130 mmol) and the resulting mixture was stirred at RT for 16 h. The reaction mixture was concentrated in vacuo, the residual solid was suspended in MeOH and concentrated again in vacuo to give the title compound. MS (LC/MS): 220 [M+H]+; $t_R$ (HPLC conditions d): 1.79 min.

Scheme A7: General protocol for the preparation of 2-(3-carbamoyl-1H-pyrazolo[3,4-c]pyridin-1-yl)acetic acid

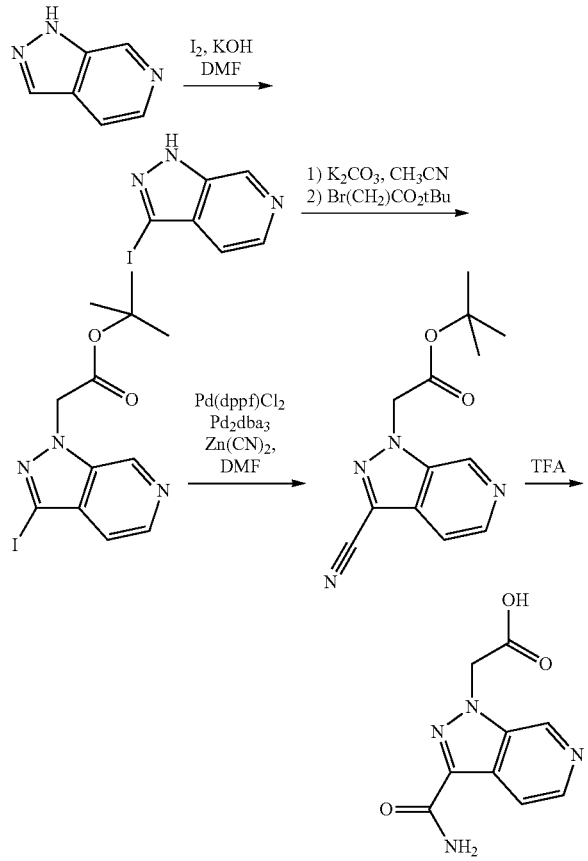

A. 3-Iodo-1H-pyrazolo[3,4-c]pyridine

To a solution of 1H-pyrazolo[3,4-c]pyridine[271-47-6] (4.00 g, 33.6 mmol) in DMF (50 mL) were added iodine (12.8 g, 50.4 mmol) and potassium hydroxide (4.70 g, 84.0 mmol). The reaction mixture was stirred at RT for 16 h. The mixture was diluted with 10% sodium thiosulfate and water and extracted with EtOAc (3×). The combined organic extracts were washed with brine, dried (phase separator) and concentrated to afford the title compound. MS (LC/MS): 246.0 [M+H]+; $t_R$ (HPLC conditions d): 0.48 min.

B. Tert-butyl 2-(3-iodo-1H-pyrazolo[3,4-c]pyridin-1-yl)acetate

To a suspension of 3-iodo-1H-pyrazolo[3,4-c]pyridine (6.24 g, 22.9 mmol) and potassium carbonate (7.29 g, 52.7 mmol) in CH$_3$CN (50 mL) was added tert-butyl 2-bromo-acetate (4.06 mL, 27.5 mmol) dropwise. The resulting mixture was heated to reflux for 2 h, cooled to RT and filtered, the solid was washed with CH$_3$CN and the filtrate was concentrated and the product was purified by flash column chromatography on silica gel (c-hexane/EtOAc 4:1 to 1:1). MS (LC/MS): 360.0 [M+H]+; $t_R$ (HPLC conditions d): 2.93 min.

C. Tert-butyl 2-(3-cyano-1H-pyrazolo[3,4-c]pyridin-1-yl)acetate

A mixture of tert-butyl 2-(3-iodo-1H-pyrazolo[3,4-c]pyridin-1-yl)acetate (3.76 g, 10.5 mmol), Zn(CN)$_2$ (1.35 g, 11.5 mmol), Pd(dppf)C$_2$ (855 mg, 1.05 mmol), Pd$_2$(dba)$_3$ (959 mg, 1.05 mmol) in water (4 mL) and DMF (30 mL) was stirred at 100° C. for 16 h under argon. After cooling to RT, the reaction mixture was diluted with EtOAc and washed with water, sat. aq. NaHCO$_3$ (2×) and brine, dried (phase separator), concentrated and purified by flash column chromatography on silica gel (c-hexane/EtOAc 1/1 to 0/1) to give the title compound. MS (LC/MS): 259.0 [M+H]+; $t_R$ (HPLC conditions d): 3.10 min. Further elution of the column with CH$_2$Cl$_2$/MeOH 8:2 and subsequent purification by preparative HPLC (Macherey-Nagel Nucleosil 100-10 C18, 5 µm, 40×250 mm, flow: 40 mL/min, eluent: 5-100% CH$_3$CN/H$_2$O/20 min, 100% CH$_3$CN/2 min, CH$_3$CN and H$_2$O containing 0.1% TFA) afforded tert-butyl 2-(3-carbamoyl-1H-pyrazolo[3,4-c]pyridin-1-yl)acetate as side-product. MS (LC/MS): 277.0 [M+H]+; $t_R$ (HPLC conditions d): 2.39 min.

D. 2-(3-Carbamoyl-1H-pyrazolo[3,4-c]pyridin-1-yl)acetic acid

A solution of tert-butyl 2-(3-cyano-1H-pyrazolo[3,4-c]pyridin-1-yl)acetate (663 mg, 2.40 mmol) in TFA (6 mL) was subjected to microwave irradiation at 140° C. for 90 min. The reaction mixture was concentrated, the residual solid was suspended in MeOH and volatiles were removed in vacuo. MS: 221.0 [M+H]+; $t_R$ (HPLC conditions d): 0.23 min.

From tert-butyl 2-(3-carbamoyl-1H-pyrazolo[3,4-c]pyridin-1-yl)acetate:

To a solution of tert-butyl 2-(3-carbamoyl-1H-pyrazolo[3,4-c]pyridin-1-yl)acetate (663 mg, 2.40 mmol) in CH$_2$Cl$_2$ (20 mL) was added TFA (10 mL, 130 mmol), and the resulting mixture was stirred at RT for 6 h. The reaction mixture was concentrated in vacuo, the residual solid was suspended in methanol and volatiles were removed again in vacuo to give the title compound.

(3-Carbamoyl-5-ethyl-pyrazolo[3,4-c]pyridin-1-yl)-acetic acid

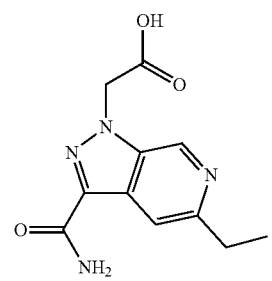 [SMILES: CCc1cc2c(C(N)=O)nn(CC(=O)O)c2cn1]

The title compound was prepared from 5-ethyl-1H-pyrazolo[3,4-c]pyridine as described in Scheme A7 for the preparation of 2-(3-carbamoyl-1H-pyrazolo[3,4-c]pyridin-1-yl)acetic acid. MS (LC/MS): 249 [M+H]+, $t_R$ (HPLC conditions d): 0.49 min.

5-Ethyl-1H-pyrazolo[3,4-c]pyridine

Triethylaluminum (21.7 mL, 40.4 mmol, 25 wt % solution in toluene) was added to a vigorously stirred solution of 5-bromo-1H-pyrazolo[3,4-c]pyridine[929617-35-6](4.00 g, 20.2 mmol) and Pd(PPh₃)₄ (1.17 g, 1.01 mmol) in THF (100 mL) under argon. The reaction mixture was stirred at 65° C. for 60 h, cooled to RT and poured into sat. aq. NH₄Cl. The resulting suspension was filtered, the solid was washed with water and discarded. The filtrate and combined washings were extracted with EtOAc (3×). The combined organic extracts were washed with brine, then dried (Phase separator), concentrated and purified by flash column chromatography on silica gel (c-hexane/EtOAc 5/5 to 0/10) to give the title compound. TLC, R$_f$ (c-hexane/EtOAc 1:3)=0.22; MS (LC/MS): 148 [M+H]+, t$_R$ (HPLC conditions d): 0.71 min.

(3-Carbamoyl-7-methyl-pyrazolo[3,4-c]pyridin-1-yl)-acetic acid

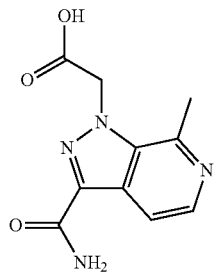 [SMILES: Cc1nccc2c(C(N)=O)nn(CC(=O)O)c12]

The title compound was prepared from 7-methyl-1H-pyrazolo[3,4-c]pyridine using the same procedure as in Scheme A7 for the preparation of (3-carbamoyl-1H-pyrazolo[3,4-c]pyridin-1-yl)acetic acid. MS (LC/MS): 235 [M+H]+, t$_R$ (HPLC conditions d): 0.6 min.

7-Methyl-1H-pyrazolo[3,4-c]pyridine

Trimethylaluminum (23.9 mL, 47.8 mmol, 2M sol. in toluene) was added to a vigorously stirred solution of 7-chloro-1H-pyrazolo[3,4-c]pyridine (3.67 g, 23.9 mmol) and Pd(PPh₃)₄ (1.38 g, 1.19 mmol) in THF (109 mL) under argon. The reaction mixture was stirred at 65° C. for 16 h, cooled to RT and poured into sat. aq. NH₄Cl. The resulting suspension was filtered, the solid washed with water and discarded. The filtrate and the combined washings were extracted with EtOAc (3×). The combined organic extracts were washed with brine then dried (phase separator) and concentrated to give 7-methyl-1H-pyrazolo[3,4-c]pyridine as a solid. MS (LC/MS): 134 [M+H]+, t$_R$ (HPLC conditions d): 0.25 min.

7-Chloro-1H-pyrazolo[3,4-c]pyridine

A solution of 2-chloro-4-methylpyridin-3-amine [133627-45-9](3.0 g, 21.0 mmol) in acetic acid (300 mL) was treated with a solution of sodium nitrite (1.45 g, 21.0 mmol) in water (2.5 mL). The reaction mixture was stirred at RT for 24 h. An additional solution of sodium nitrite (500 mg, 7.25 mmol) in water (1 mL) was added to the mixture which was allowed to stir at RT for 3 h. Acetic acid was evaporated under reduced pressure and the residual aq. solution was partitioned between EtOAc and sat. aq. NaHCO₃. The solid was filtered and dried under vacuum to yield batch 1 of product. The organic filtrate was washed with water and brine, then dried (phase separator) and concentrated to afford batch 2. The two batches were combined to give 7-chloro-1H-pyrazolo[3,4-c]pyridine as a solid. MS (LC/MS): 153 [M+H]+, t$_R$ (HPLC conditions d): 0.9 min.

Scheme A8: Preparation of (3-carbamoyl-5-methyl-pyrazolo[3,4-c]pyridin-1-yl)-acetic acid

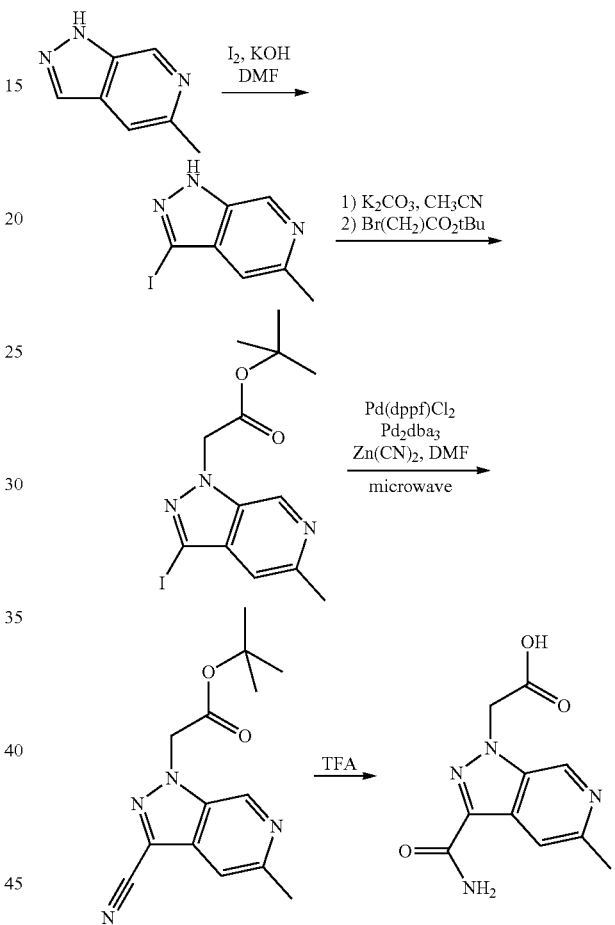

A. 3-Iodo-5-methyl-1H-pyrazolo[3,4-c]pyridine

To a solution of 5-methyl-1H-pyrazolo[3,4-c]pyridine [76006-06-9](1.00 g, 7.51 mmol) in DMF (15 mL) were added iodine (2.86 g, 11.3 mmol) and potassium hydroxide (1.05 g, 18.8 mmol). The reaction mixture was stirred at RT for 60 h. The mixture was diluted with 10% sodium thiosulfate and water, the resulting suspension was filtered. The solid was washed with water and then dried under vacuum. MS (LC/MS): 260.0 [M+H]+; t$_R$ (HPLC conditions d): 0.28 min.

B. Tert-butyl 2-(3-iodo-5-methyl-1H-pyrazolo[3,4-c]pyridin-1-yl)acetate

To a suspension of 3-iodo-5-methyl-H-pyrazolo[3,4-c]pyridine (1.00 g, 3.86 mmol) and potassium carbonate (1.28 g, 9.26 mmol) in CH₃CN (40 mL) was added tert-butyl 2-bromoacetate (0.685 mL, 4.63 mmol) dropwise at RT and the resulting mixture was heated under reflux for 16 h. The mixture was cooled to RT and filtered, the solid was washed with CH$_3$CN and the filtrate was concentrated. The residual oil was used directly in the next step without further purification. MS (LC/MS): 374.0 [M+H]+; $t_R$ (HPLC conditions d): 2.96 min.

C. Tert-butyl 2-(3-cyano-5-methyl-1H-pyrazolo[3,4-c]pyridin-1-yl)acetate

A mixture of tert-butyl 2-(3-iodo-5-methyl-1H-pyrazolo [3,4-c]pyridin-1-yl)acetate (1.00 g, 2.55 mmol), Zn(CN)$_2$ (329 mg, 2.55 mmol), Pd(dppf)Cl$_2$ (208 mg, 0.25 mmol), Pd$_2$(dba)$_3$ (233 mg, 0.25 mmol) in water (2.7 mL) and DMF (20 mL) was subjected to microwave irradiation at 120° C. for 30 min under argon. The reaction mixture was filtered through a pad of Celite and the filtrate was diluted with water and EtOAc. The phases were separated and the aq. layer was extracted with EtOAc. The combined organic extracts were washed with brine, then dried (phase separator), concentrated and purified by flash chromatography on silica gel (c-hexane/EtOAc 2:1 to 1:1). MS (LC/MS): 273.0 [M+H]+; $t_R$ (HPLC conditions d): 3.04 min.

D. (3-Carbamoyl-5-methyl-pyrazolo[3,4-c]pyridin-1-yl)-acetic acid

A solution of tert-butyl 2-(3-cyano-5-methyl-1H-pyrazolo [3,4-c]pyridin-1-yl)acetate (250 mg, 0.92 mmol) in TFA (4 mL) was subjected to microwave irradiation at 140° C. for 90 min. The reaction mixture was concentrated, the residual solid was suspended in MeOH and concentrated in vacuo to give the title compound. MS: 235.0 [M+H]+; $t_R$ (HPLC conditions d): 0.24 min.

Scheme A9: General protocol for the preparation of (3-carbamoyl-6-chloro-indazol-1-yl)-acetic acid

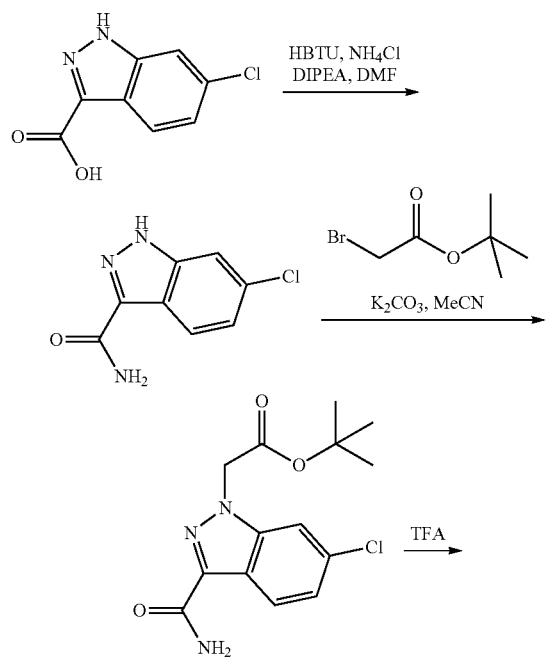

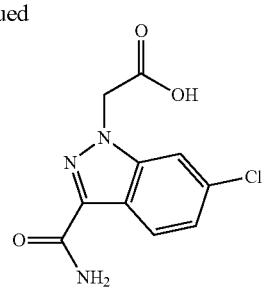

A. 6-Chloro-1H-indazole-3-carboxylic acid amide

To a solution of 6-chloro-1H-indazole-3-carboxylic acid (500 mg, 2.54 mmol), NH$_4$Cl (408 mg, 7.63 mmol) and HBTU (144 mg, 3.82 mmol) in DMF (10 mL) was added DIPEA (1.33 mL, 7.63 mmol). The reaction mixture was stirred for 16 h at RT, concentrated, the residue was diluted with EtOAc and washed with aq. 1N HCl. The organic layer was dried (Na$_2$SO$_4$), filtered, concentrated and the product purified by flash column chromatography on silica gel (CH$_2$Cl$_2$/MeOH 10/0 to 8/2). MS (UPLC/MS): 196.2 [M+H]+; $t_R$ (HPLC conditions c): 1.47 min.

B. (3-Carbamoyl-6-chloro-indazol-1-yl)-acetic acid tert-butyl ester

To a solution of 6-chloro-1H-indazole-3-carboxylic acid amide (400 mg, 2.045 mmol) in CH$_3$CN (10 mL) were added potassium carbonate (565 mg, 4.09 mmol) and tert-butyl 2-bromoacetate (0.362 mL, 2.454 mmol). The reaction mixture was stirred for 3 h at RT, diluted with water (50 mL) and extracted with EtOAc. The combined organic extracts were dried (Na$_2$SO$_4$), filtered and concentrated. The residue was purified by flash column chromatography on silica gel (c-hexane/EtOAc 10/0 to 5/5) to afford the title compound. MS (UPLC/MS): 327.2 [M+NH$_4$]+; $t_R$ (HPLC conditions c): 2.03 min.

C. (3-Carbamoyl-6-chloro-indazol-1-yl)-acetic acid

To a solution of (3-carbamoyl-6-chloro-indazol-1-yl)-acetic acid tert-butyl ester (280 mg, 0.904 mmol) in CH$_2$Cl$_2$ (5 mL) was added TFA (0.69 mL, 9.04 mmol). The reaction mixture was stirred 16 h at RT, concentrated and the product was purified by preparative HPLC (Waters Sunfire C18-OBD, 5 µm, 30×100 mm, flow: 40 mL/min, eluent: 5% to 100% CH$_3$CN in H$_2$O in 20 min, CH$_3$CN and H$_2$O containing 0.1% TFA). MS (UPLC/MS): 254.2 [M+H]+, $t_R$ (HPLC conditions c): 1.43 min.

(3-Carbamoyl-6-methyl-indazol-1-yl)-acetic acid

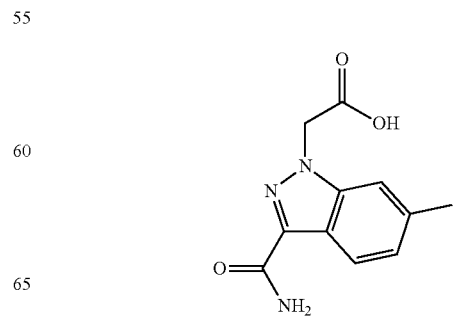

The title compound was prepared from 6-methyl-1H-indazole-3-carboxylic acid as described in Scheme A9 for the preparation of (3-carbamoyl-6-chloro-indazol-1-yl)-acetic acid. MS (UPLC/MS): 234.3 [M+H]+; $t_R$ (HPLC conditions c): 1.33 min.

(3-Carbamoyl-6-fluoro-indazol-1-yl)-acetic acid

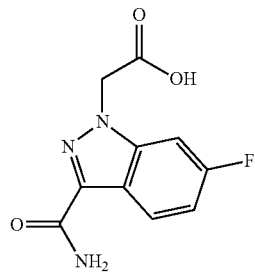 [SMILES: NC(=O)c1nn(CC(=O)O)c2cc(F)ccc12]

The title compound was prepared from 6-fluoro-1H-indazole-3-carboxylic acid as described in Scheme A9 for the preparation of (3-carbamoyl-6-chloro-indazol-1-yl)-acetic acid. MS (UPLC/MS): 238.1 [M+H]+; $t_R$ (UPLC conditions h): 0.55 min.

Scheme A10: Preparation of (3-Carbamoyl-5-methyl-indazol-1-yl)-acetic acid

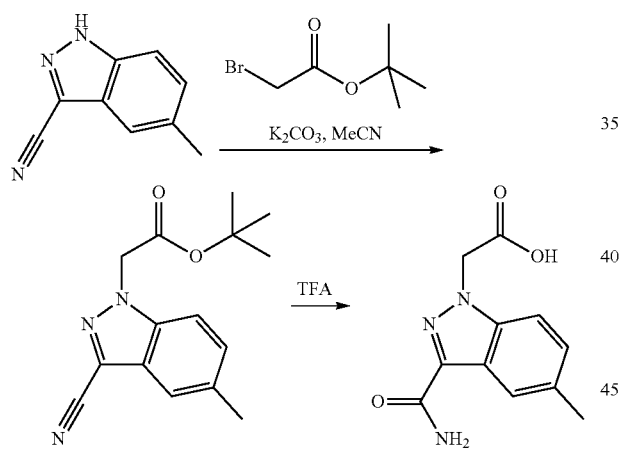

A. (3-Cyano-5-methyl-indazol-1-yl)-acetic acid tert-butyl ester

To a solution of 5-methyl-1H-indazole-3-carbonitrile (260 mg, 1.654 mmol) in CH₃CN (6 mL) were added potassium carbonate (457 mg, 3.31 mmol) and tert-butyl 2-bromoacetate (0.244 mL, 1.654 mmol). The reaction mixture was stirred at RT for 5 h then poured into water and extracted with EtOAc (3×). The combined organic extracts were dried (phase separator) and concentrated. The crude residue was purified by flash column chromatography on silica gel (c-hexane/EtOAc 1:0 to 7:3). MS: 294.0 [M+Na]+, 215.9 [M-tBu]+; $t_R$ (HPLC conditions d): 3.98 min.

B. (3-Carbamoyl-5-methyl-indazol-1-yl)-acetic acid

A solution of (3-cyano-5-methyl-indazol-1-yl)-acetic acid tert-butyl ester (221 mg, 0.815 mmol) in TFA (3.9 mL) was subjected to microwave irradiation at 140° C. for 90 min. The reaction mixture was concentrated, the residual solid was suspended in MeOH and concentrated in vacuo to afford the title compound. MS: 234.0 [M+H]+, 255.9 [M+Na]+; $t_R$ (HPLC conditions d): 2.60 min.

Part B: Synthesis of Various 5-Membered Heterocycles:

Scheme B1: Preparation of (1R,3S,5S)-5-hydroxymethyl-2-azabicyclo[3.1.0]hexane-2,3-dicarboxylic acid 2-tert-butyl ester

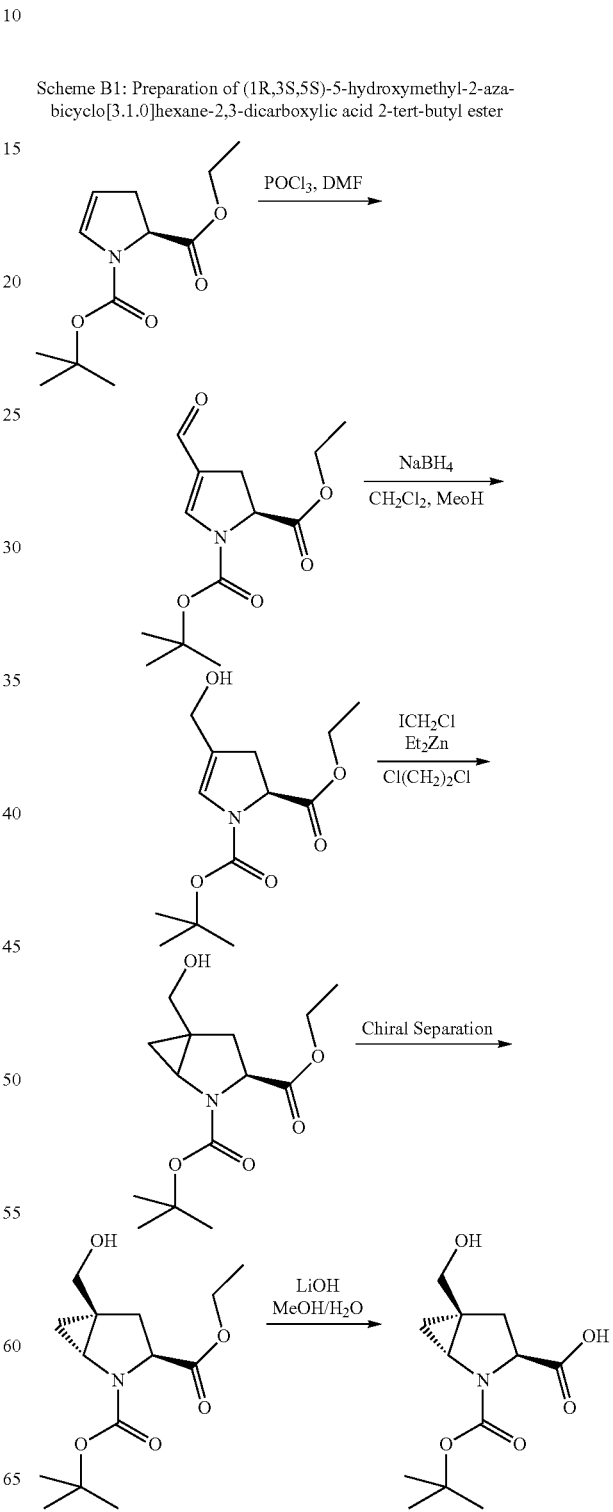

A. (S)-4-Formyl-2,3-dihydro-pyrrole-1,2-dicarboxylic acid 1-tert-butyl ester 2-ethyl ester POCl$_3$ (7.59 mL, 83 mmol) was added in 25 min at 0° C. under N$_2$ atmosphere to DMF (6.39 mL, 83 mmol) and the mixture was stirred at RT for 20 min. Dry CH$_2$Cl$_2$ (150 mL) was added at 0° C., followed by a solution of (S)-2,3-dihydro-pyrrole-1,2-dicarboxylic acid 1-tert-butyl ester 2-ethyl ester (10 g, 41.4 mmol) in CH$_2$Cl$_2$ (50 mL). The mixture was stirred 30 min at RT until completion. The mixture was slowly poured into an ice cold aqueous solution of NaOH 10 N (150 mL) and extracted with CH$_2$Cl$_2$ (×3). The combined organic extracts were washed with brine (×2), with water, dried (Na$_2$SO$_4$), filtered and concentrated. The crude residue was purified by flash column chromatography on silica gel (c-hexane/EtOAc 10:0 to 9:1) to give the desired material as a yellow oil. R$_f$, TLC (c-hexane/EtOAc 4:1)=0.2; MS (UPLC/MS): 270 [M+H]+, 170 [M-Boc]+; t$_R$ (HPLC conditions c): 1.93 min.

B. (S)-4-Hydroxymethyl-2,3-dihydro-pyrrole-1,2-dicarboxylic acid 1-tert-butyl ester 2-ethyl ester A solution of (S)-4-formyl-2,3-dihydro-pyrrole-1,2-dicarboxylic acid 1-tert-butyl ester 2-ethyl ester (3.32 g, 12.3 mmol) in CH$_2$Cl$_2$ (51.4 mL) was cooled at −78° C. under a nitrogen atmosphere, solid NaBH$_4$ (1 g, 24.7 mmol) was added portionwise maintaining the temperature at −78° C. MeOH (25.7 mL) was added dropwise and the reaction mixture was allowed to reach 0° C. and was stirred 1.5 h at 0° C. The reaction mixture was quenched with sat. aq. NH$_4$Cl and extracted with CH$_2$Cl$_2$ (×3). The combined organic layers were washed with brine, dried (Na$_2$SO$_4$), filtered and concentrated. The crude residue was purified by flash column chromatography on silica gel (c-hexane/EtOAc 10:0 to 0:10) to give the desired material as a yellow oil. R$_f$, TLC (c-hexane/EtOAc 1:1)=0.30; MS (UPLC/MS): 272.2 [M+H]+, 316 [M+HCOO]−; t$_R$ (HPLC conditions c): 1.74 min.

C. (1R,3S,5S) and (1S,3S,5R)-5-Hydroxymethyl-2-aza-bicyclo[3.1.0]hexane-2,3-dicarboxylic acid 2-tert-butyl ester 3-ethyl ester To a solution of (S)-4-hydroxymethyl-2,3-dihydro-pyrrole-1,2-dicarboxylic acid 1-tert-butyl ester 2-ethyl ester (1.12 g, 4.13 mmol) in CH$_2$Cl$_2$ (115 mL) under argon at −20° C. were slowly added diethylzinc (1M in hexanes, 8.26 mL, 8.26 mmol) and diiodomethane (0.73 mL, 9.08 mmol) and the reaction mixture was further stirred at −10° C. for 2 h. Diethylzinc (1M in hexanes, 8.26 mL, 8.26 mmol) and diiodomethane (0.73 mL, 9.08 mmol) were again added and the reaction mixture was further stirred at −10° C. for 2 h to complete the reaction. Sat. aq. NH$_4$Cl was added slowly (exothermic) at −20° C. followed by CH$_2$Cl$_2$. The layers were separated and the aqueous layer was extracted with CH$_2$Cl$_2$ (×2). To the combined organic layers were added few crystals of Na$_2$S and water (ratio CH$_2$Cl$_2$/H$_2$O 20:1) and the biphasic mixture was stirred for 30 min. Water was added, the layers were separated and the organic layer was dried (Na$_2$SO$_4$), filtered and concentrated. The crude residue was purified by flash column chromatography on silica gel (c-hexane/EtOAc 1:1) to give a mixture of diastereoisomers (4:6 (1R,3S,5S)/(1S,3S,5R)). The absolute stereochemistry of the diastereoisomers was determined by NMR. R$_f$, TLC (c-hexane/EtOAc 1:1)=0.25; MS (UPLC/MS): 186.1 [M-Boc]+, 230.2 [M-tBu]+, 286.3 [M+H]+; t$_R$ (HPLC conditions c): 1.75 min.

D. (1R,3S,5S)-5-Hydroxymethyl-2-aza-bicyclo[3.1.0]hexane-2,3-dicarboxylic acid 2-tert-butyl ester 3-ethyl ester The mixture of (1R,3S,5S) and (1S,3S,5R)-5-hydroxymethyl-2-aza-bicyclo[3.1.0]hexane-2,3-dicarboxylic acid 2-tert-butyl ester 3-ethyl ester (360 g) was separated into its diastereoisomers by preparative chiral HPLC (column SMB columns Chiralpak AD, 20 um, 250×30 mm; eluent: heptane/EtOH 80/20) to give (1R,3S,5S)-5-hydroxymethyl-2-aza-bicyclo[3.1.0]hexane-2,3-dicarboxylic acid 2-tert-butyl ester 3-ethyl ester: t$_R$ (Chiralpak AD-prep, 20 um, 250×4.6 mm, n-heptane/EtOH 80/20, flow rate: 1 mL/min, detection: UV at 210 nm): 6.94 min and (1 S,3S,5R)-5-hydroxymethyl-2-aza-bicyclo[3.1.0]hexane-2,3-dicarboxylic acid 2-tert-butyl ester 3-ethyl ester: t$_R$ (Chiralpak AD-prep, 20 um, 250×4.6 mm, n-heptane/EtOH 80/20, flow rate: 1 mL/min, detection: UV at 210 nm): 4.20 min.

E. (1R,3S,5S)-5-Hydroxymethyl-2-aza-bicyclo[3.1.0]hexane-2,3-dicarboxylic acid 2-tert-butyl ester To (1R,3S,5S)-5-hydroxymethyl-2-aza-bicyclo[3.1.0]hexane-2,3-dicarboxylic acid 2-tert-butyl ester 3-ethyl ester (100 mg, 0.31 mmol) in THF (1.5 mL) and H$_2$O (0.15 mL) at 0° C. was added NaOH (1 M in water, 0.63 mL, 0.63 mmol). The solution was stirred 1 h at RT and poured into 10% KHSO$_4$ (until pH 1), EtOAc was added and the layers were separated (×3). The combined organic layers were dried (Na$_2$SO$_4$), filtered and concentrated to give the title compound. MS: 258.3 [M+H]+; $^1$H-NMR (400 MHz, DMSO-d$_6$) δ (ppm): 12.5 (m, 1H), 4.71 (m, 1H), 3.92 (m, 1H), 3.42-3.35 (m, 2H), 3.17 (m, 1H), 2.31 (m, 1H), 2.08 (m, 1H), 1.41 and 1.33 (2 s, 9H), 0.79 (m, 1H), 0.67 (m, 1H).

Scheme B2: Preparation of (1R,3S,5R)-2-[2-(3-acetyl-pyrazolo[3,4-b]pyridin-1-yl)-acetyl]-2]azabicyclo[3.1.0]hexane-3-carboxylic acid

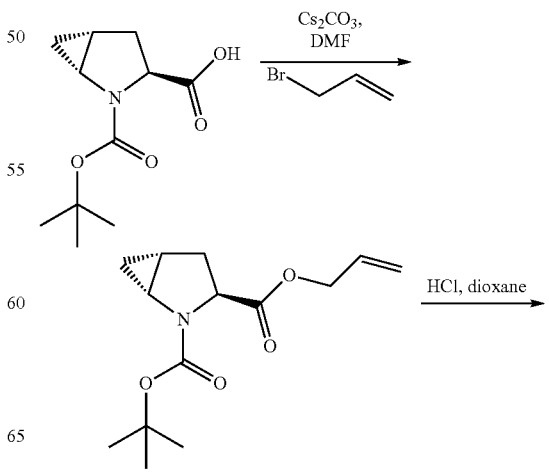

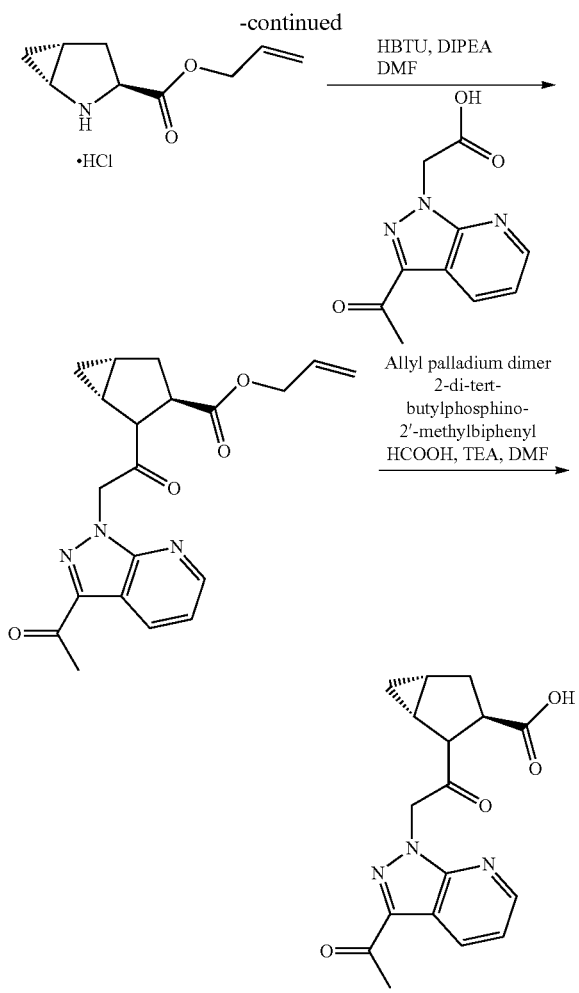

A. (1R,3S,5R)-2-Azabicyclo[3.1.0]hexane-2,3-dicarboxylic acid 3-allyl ester 2-tert-butyl ester To a solution of (1R,3S,5R)-2-azabicyclo[3.1.0]hexane-2,3-dicarboxylic acid 2-tert-butyl ester (1.5 g, 3.6 mmol) and Cs$_2$CO$_3$ (2.26 g, 6.9 mmol) in DMF (20 mL), allyl bromide (0.6 mL, 3.9 mmol) was added. The reaction mixture was stirred for 40 h at RT. DMF was evaporated. The residue was dissolved in EtOAc and washed with 1N aq. HCl, dried (Na$_2$SO$_4$), filtered, concentrated and the product was purified by flash column chromatography on silica gel (c-hexane/EtOAc 10:0 to 4:6). MS (LC/MS):167.9 [M-Boc]+, 290.0 [M+Na]+.

B. (1R,3S,5R)-2-Azabicyclo[3.1.0]hexane-3-carboxylic acid allyl ester hydrochloride To (1R,3S,5R)-2-azabicyclo[3.1.0]hexane-2,3-dicarboxylic acid 3-allyl ester 2-tert-butyl ester (1.69 g, 6.32 mmol) was added 4N HCl in dioxane (15.8 mL, 63.2 mmol). The reaction mixture was stirred for 6 h at RT and subsequently lyophilized to afford the title compound. MS: 168.0 [M+H]+.

C. (1R,3S,5R)-2-[2-(3-Acetyl-pyrazolo[3,4-b]pyridin-1-yl)-acetyl]-2-aza-bicyclo[3.1.0]hexane-3-carboxylic acid allyl ester To a solution of (1R,3S,5R)-2-azabicyclo[3.1.0]hexane-2,3-dicarboxylic acid 3-allyl ester hydrochloride (1.03 g, 6.43 mmol), (3-acetyl-pyrazolo[3,4-b]pyridin-1-yl)-acetic acid (prepared as described in Part A, 1.3 g, 5.93 mmol) and HBTU (2.70 g, 7.12 mmol) in DMF (19.7 mL) was added DIPEA (3.11 mL, 17.8 mmol). The reaction mixture was stirred for 16 h at RT. DMF was evaporated. The residue was poured into sat. aq. NH$_4$Cl and extracted with EtOAc (3×50 mL). The combined organic extracts were dried (Na$_2$SO$_4$), filtered, concentrated and the product purified by flash column chromatography on silica gel (c-hexane/EtOAc 10:0 to 0:10). R$_f$, TLC (EtOAc)=0.6; MS (LC/MS): 369.0 [M+H]+, 391.0 [M+Na]+; t$_R$ (HPLC conditions d): 2.78 min.

D. (1R,3S,5R)-2-[2-(3-Acetyl-pyrazolo[3,4-b]pyridin-1-yl)-acetyl]-2-aza-bicyclo[3.1.0]hexane-3-carboxylic acid Allyl palladium chloride dimer (0.084 g, 0.231 mmol) and 2-di-tert-butylphosphino-2'-methylbiphenyl (0.288 g, 0.923 mmol) were dissolved in DMF (7.69 mL) under argon atmosphere. The reaction mixture was stirred at RT for 10 min. After cooling the reaction mixture to 10° C., formic acid (0.513 mL, 13.38 mmol) was added followed by TEA (1.86 mL, 13.38 mmol) and a solution of (1R,3S,5R)-2-[2-(3-acetyl-pyrazolo[3,4-b]pyridin-1-yl)acetyl]-2-azabicyclo[3.1.0]hexane-3-carboxylic acid allyl ester (1 g, 2.3 mmol) in DMF (15.38 mL). The reaction mixture was stirred at 10° C. for 1 h. DMF was evaporated. The residue was poured into sat. aq. NH$_4$Cl and extracted with EtOAc (3×50 mL). The combined organic extracts were dried (Na$_2$SO$_4$), filtered and concentrated. The residue was dissolved in MeOH and filtered over a PL-Thiol cartridge. The filtrate was concentrated. The residue was purified by preparative HPLC (Waters Sunfire C18-OBD, 5 μm, 30×100 mm, flow: 40 mL/min, eluent: 5% to 80% CH$_3$CN in H$_2$O in 20 min, CH$_3$CN and H$_2$O containing 0.1% TFA) and the pure fractions were combined and lyophilized to afford the title compound. MS (LC/MS): 328.9 [M+H]+, 351.0 [MH+Na]; t$_R$ (HPLC conditions e): 1.84 min. $^1$H-NMR (400 MHz, DMSO-d$_6$) δ (ppm): 8.66 (dd, 1H), 8.58 (m, 1H), 7.35-7.50 (m, 1H), 8.54-8.61 (m, 1H), 5.88 (d, 1H), 5.55 (d, 1 H), 4.14-4.24 (m, 1H), 3.75-3.83 (m, 1H), 2.64 (s, 3H), 2.26-2.36 (m, 1H), 2.10-2.23 (m, 1H), 1.80-1.95 (m, 1H), 0.95-1.07 (m, 1H), 0.67-0.81 (m, 1H).

Scheme B3: Preparation of (1R,3S,5R)-2-[2-(3-Acetyl-pyrazolo[3,4-c]pyridin-1-yl)-acetyl]-2-aza-bicyclo[3.1.0]hexane-3-carboxylic acid

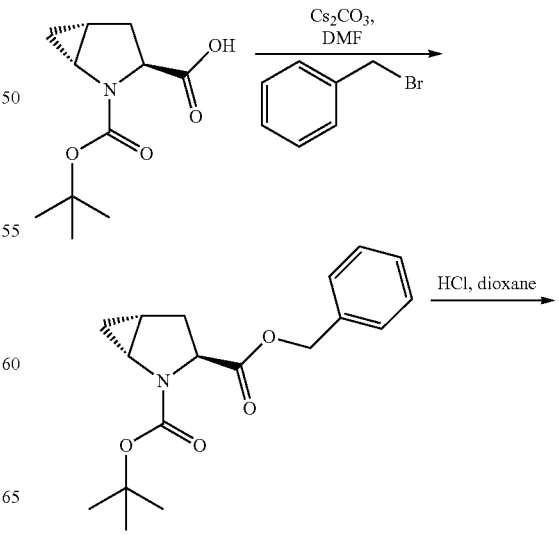

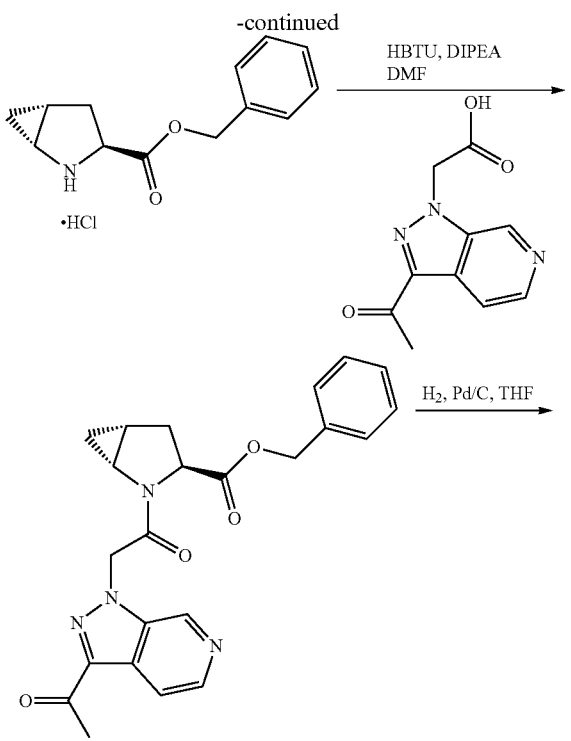

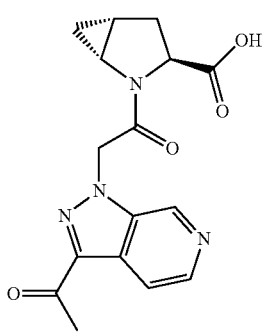

A. (1R,3S,5R)-2-Aza-bicyclo[3.1.0]hexane-2,3-dicarboxylic acid 3-benzyl ester 2-tert-butyl ester To a cold solution of (1R,3S,5R)-2-aza-bicyclo[3.1.0]hexane-2,3-dicarboxylic acid 2-tert-butyl ester (2 g, 8.8 mmol) at 0° C. was added a solution of $Cs_2CO_3$ (2.87 g, 8.8 mmol) in water (12.3 mL). After 30 min stirring, the resulting mixture was concentrated and the residue was suspended in DMF (41 mL). The suspension was cooled to 0° C., then benzyl bromide (1.045 mL, 8.80 mmol) was added. The reaction mixture was stirred at RT for 16 h. DMF was evaporated, the residue was poured into water and extracted with EtOAc (3×50 mL). The combined organic extracts were dried (phase separator), concentrated and the product purified by flash column chromatography on silica gel (c-hexane/EtOAc 10:0 to 8:2). TLC, $R_f$ (c-hexane/EtOAc 8:2)=0.45; MS (UPLC/MS): 318 [M+H]+, $t_R$ (HPLC conditions d): 3.89 min.

B. (1R,3S,5R)-2-Aza-bicyclo[3.1.0]hexane-3-carboxylic acid benzyl ester hydrochloride To a solution of (1R,3S,5R)-2-aza-bicyclo[3.1.0]hexane-2,3-dicarboxylic acid 3-benzyl ester 2-tert-butyl ester (2.69 g, 8.48 mmol) in dioxane was added 4N HCl in dioxane (10.6 mL, 42.4 mmol). The reaction mixture was stirred at RT overnight and subsequently lyophilized to afford the title compound. MS (LC/MS): 218 [M+H]+.

C. (1R,3S,5R)-2-[2-(3-Acetyl-pyrazolo[3,4-c]pyridin-1-yl)-acetyl]-2-aza-bicyclo[3.1.0]hexane-3-carboxylic acid benzyl ester To a solution of (1R,3S,5R)-2-aza-bicyclo[3.1.0]hexane-3-carboxylic acid benzyl ester hydrochloride (2.98 g, 9.06 mmol), (3-acetyl-pyrazolo[3,4-c]pyridin-1-yl)-acetic acid (prepared as described in Part A, 3.2 g, 9.06 mmol) and HBTU (5.15 g, 13.59 mmol) in DMF (30.2 mL) was added DIPEA (4.75 mL, 27.2 mmol). The reaction mixture was stirred for 16 h at RT. DMF was evaporated. The residue was diluted with EtOAc and washed successively with 1N aq. HCl and 5% aq. $NaHCO_3$. The organic layer was dried (phase separator), concentrated and the product was purified by flash column chromatography on silica gel (c-hexane/EtOAc 10:0 to 0:10). TLC, $R_f$ (EtOAc)=0.33; MS (UPLC/MS): 419 [M+H]+, $t_R$ (HPLC conditions d): 2.97 min.

D. (1R,3S,5R)-2-[2-(3-Acetyl-pyrazolo[3,4-c]pyridin-1-yl)-acetyl]-2-aza-bicyclo[3.1.0]hexane-3-carboxylic acid To a solution of (1R,3S,5R)-2-[2-(3-acetyl-pyrazolo[3,4-c]pyridin-1-yl)-acetyl]-2-aza-bicyclo[3.1.0]hexane-3-carboxylic acid benzyl ester (2.26 g, 5.4 mmol) in THF (20 mL) was added Pd/C 10% (60 mg). The reaction was placed under hydrogen atmosphere and was stirred for 72 h. The reaction mixture was filtered over Celite and washed with MeOH. Filtrate and washing were concentrated to afford the title compound. MS (UPLC/MS): 329 [M+H]+, $t_R$ (HPLC conditions d): 2.29 min.

Scheme B4: Preparation of (2S,3S,4S)-2-(3,3-dimethyl-cyclohexylcarbamoyl)-4-fluoro-3-methoxy-pyrrolidine-1-carboxylic acid tert-butyl ester

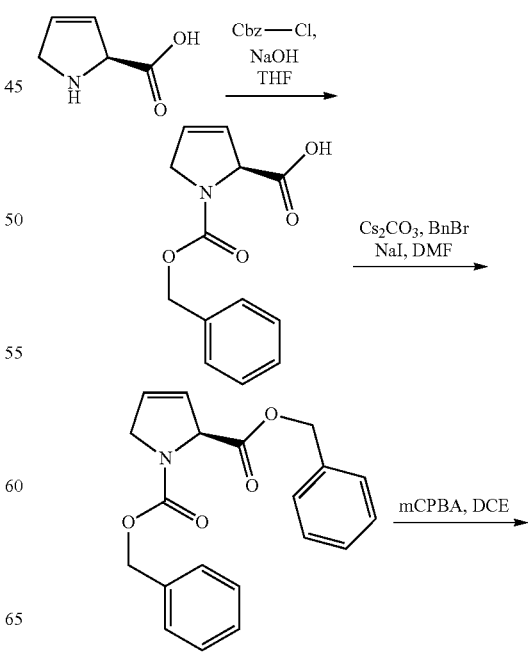

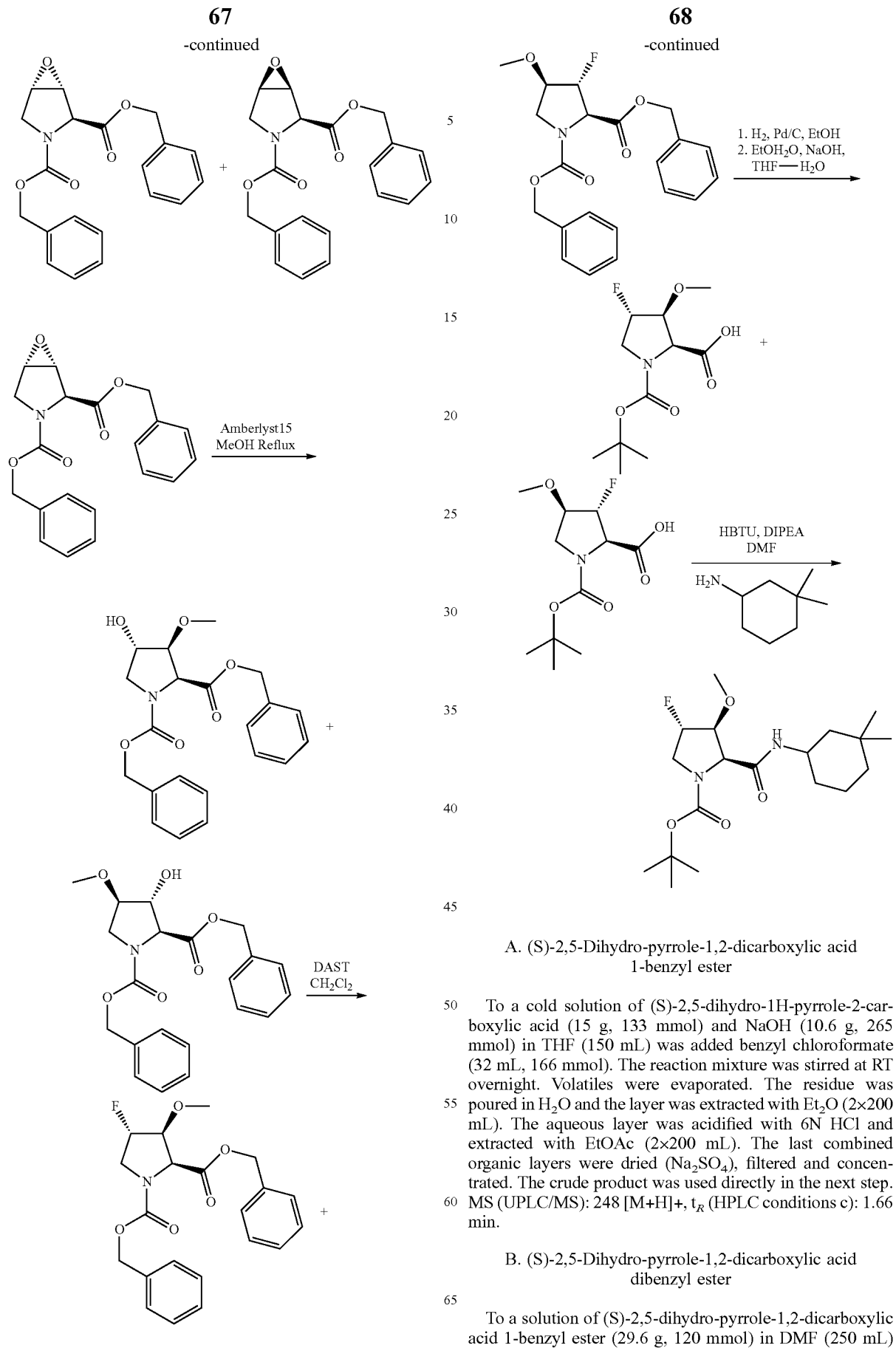

A. (S)-2,5-Dihydro-pyrrole-1,2-dicarboxylic acid 1-benzyl ester

To a cold solution of (S)-2,5-dihydro-1H-pyrrole-2-carboxylic acid (15 g, 133 mmol) and NaOH (10.6 g, 265 mmol) in THF (150 mL) was added benzyl chloroformate (32 mL, 166 mmol). The reaction mixture was stirred at RT overnight. Volatiles were evaporated. The residue was poured in $H_2O$ and the layer was extracted with $Et_2O$ (2×200 mL). The aqueous layer was acidified with 6N HCl and extracted with EtOAc (2×200 mL). The last combined organic layers were dried ($Na_2SO_4$), filtered and concentrated. The crude product was used directly in the next step. MS (UPLC/MS): 248 [M+H]+, $t_R$ (HPLC conditions c): 1.66 min.

B. (S)-2,5-Dihydro-pyrrole-1,2-dicarboxylic acid dibenzyl ester

To a solution of (S)-2,5-dihydro-pyrrole-1,2-dicarboxylic acid 1-benzyl ester (29.6 g, 120 mmol) in DMF (250 mL)

were added NaI (2.15 g, 14.37 mmol), Cs₂CO₃ (42.9 g, 132 mmol) and benzyl bromide (17.09 mL, 144 mmol). The reaction mixture was stirred at RT during 72 h. The reaction was quenched by addition of H₂O (500 mL) and extracted with EtOAc (3×200 mL). The combined organic layers were dried (Na₂SO₄), filtered and concentrated. The crude residue was purified by flash column chromatography on silica gel (c-hexane/EtOAc 10:0 to 8:2). MS (UPLC/MS): 338 [M+H]+, $t_R$ (HPLC conditions c): 2.31 min.

C. (1R,2S,5S)-6-Oxa-3-aza-bicyclo[3.1.0]hexane-2,3-dicarboxylic acid dibenzyl ester and (1S,2S,5R)-6-Oxa-3-aza-bicyclo[3.1.0]hexane-2,3-dicarboxylic acid dibenzyl ester The title compound was prepared in a similar manner as described by J. Kenneth Robinson and al., *Tetrahedron*, 1998, 54, 981-996: To a solution of (S)-2,5-dihydro-pyrrole-1,2-dicarboxylic acid dibenzyl ester (7.5 g, 22.23 mmol) in DCE (80 mL) were added mCPBA (7.67 g, 44.5 mmol) and 4,4'-thiobis(6-tert-butyl-m-cresol) (0.797 g, 2.22 mmol). The reaction mixture was then heated to 90° C. overnight. Then was concentrated. The crude residue was diluted in CH₂Cl₂ (200 mL) and washed with aq. solution of Na₂S₂O₅ 5% and with a sat. aq. solution of NaHCO₃. The organic layer was dried (Na₂SO₄), filtered and concentrated. The crude residue was purified by flash column chromatography on silica gel (c-hexane/EtOAc 10:0 to 8:2). MS (UPLC/MS): 354 [M+H]+, $t_R$ (HPLC conditions c): 2.24 min. (1S,2S,5R)-6-Oxa-3-aza-bicyclo[3.1.0]hexane-2,3-dicarboxylic acid dibenzyl ester was also isolated. MS (UPLC/MS): 354 [M+H]+, $t_R$ (HPLC conditions c): 2.15 min.

D. (2S,3S,4S)-4-Hydroxy-3-methoxy-pyrrolidine-1,2-dicarboxylic acid dibenzyl ester and (2S,3R,4R)-3-hydroxy-4-methoxy-pyrrolidine-1,2-dicarboxylic acid dibenzyl ester To a solution of (1R,2S,5S)-6-oxa-3-aza-bicyclo[3.1.0]hexane-2,3-dicarboxylic acid dibenzyl ester (30 g, 85 mmol) in MeOH (150 mL) was added Amberlyst 15 (30 g). The reaction mixture was heated overnight at 65° C., then allowed to cool to RT and filtered. Amberlyst 15 residue was washed with MeOH. The combined filtrates were concentrated and purified by flash column chromatography on silica gel (c-hexane/EtOAc 10:0 to 5:5) to give a mixture of the 2 regioisomers as a yellow oil. MS (UPLC/MS): 386 [M+H]+, 430 [M+HCOO]−; $t_R$ (HPLC conditions c): 2.072 min.

E. (2S,3S,4S)-4-Fluoro-3-methoxy-pyrrolidine-1,2-dicarboxylic acid dibenzyl ester and (2R,3R,4R)-3-fluoro-4-methoxy-pyrrolidine-1,2-dicarboxylic acid dibenzyl ester A solution of (2S,3S,4S)-4-hydroxy-3-methoxy-pyrrolidine-1,2-dicarboxylic acid dibenzyl ester and (2S,3R,4R)-3-hydroxy-4-methoxy-pyrrolidine-1,2-dicarboxylic acid dibenzyl ester (17.8 g, 46.2 mmol) in CH₂Cl₂ (250 mL) was cooled under Argon at −78° C. then DAST (12.2 mL, 92 mmol) was added dropwise. The reaction mixture was allowed to reach RT and further stirred for 16 h. The reaction mixture was diluted with CH₂Cl₂ and carefully quenched with a sat. aq. solution of NaHCO₃. The layers were separated, the aqueous layer extracted twice with CH₂Cl₂, the combined organic layers were dried (Na₂SO₄), filtered, concentrated and purified by flash column chromatography on silica gel (c-hexane/EtOAc 10:0 to 0:10) to give a mixture of the 2 regioisomers as a yellow solid. MS (UPLC/MS): 388.3 [M+H]+, 405.3 [M+NH₄]+; $t_R$ (HPLC conditions c): 2.34 min.

F. (2S,3S,4S)-4-Fluoro-3-methoxy-pyrrolidine-1,2-dicarboxylic acid 1-tert-butyl ester and (2R,3R,4R)-3-Fluoro-4-methoxy-pyrrolidine-1,2-dicarboxylic acid 1-tert-butyl ester To a solution of (2S,3S,4S)-4-fluoro-3-methoxy-pyrrolidine-1,2-dicarboxylic acid dibenzyl ester (430 mg, 1.11 mmol) in MeOH (25 mL) was added Pd/C 10% (100 mg). The reaction was placed under hydrogen atmosphere and was stirred for 2 h then was filtered over glass-fiber, rinsed with MeOH (25 mL) and water (25 mL). After concentration, the residue was lyophilized overnight. The powder obtained was dissolved in THF/Water 1/1 (20 mL) then aq. 1N NaOH (0.755 mL) and Boc anhydride (412 mg, 2.22 mmol) were added and the reaction mixture was stirred at RT overnight. After concentration, the crude residue was purified by flash column chromatography on silica gel (c-hexane/EtOAc 10:0 to 6:4) to give the title compound. MS (UPLC/MS): 264 [M+H]+; $t_R$ (HPLC conditions c): 0.65 min.

G: (2S,3S,4S)-2-(3,3-Dimethyl-cyclohexylcarbamoyl)-4-fluoro-3-methoxy-pyrrolidine-1-carboxylic acid tert-butyl ester To a solution of (2S,3S,4S)-4-fluoro-3-methoxy-pyrrolidine-1,2-dicarboxylic acid 1-tert-butyl ester and (2R,3R,4R)-3-fluoro-4-methoxy-pyrrolidine-1,2-dicarboxylic acid 1-tert-butyl ester (500 mg, 1.899 mmol), 3,3-dimethylcyclohexanamine (342 mg, 2.089 mmol) and HBTU (1080 mg, 2.85 mmol) in DMF (6.3 mL) was added DIPEA (995 μL, 5.70 mmol). The reaction mixture was stirred at RT overnight and concentrated. The crude residue was taken up in EtOAc and washed successively with aq. HCl 1N and aq. NaHCO₃ 5%. The organic layer was dried (phase separator), concentrated and purified by flash column chromatography on silica gel (c-hexane/EtOAc 10:0 to 8:2 then isocratic 8:2) to give the title compound. TLC, $R_f$ (c-hexane/EtOAc 5/5)= 0.39; MS (UPLC/MS): 317.0 [M-tBu]+, 395.0 [M+Na]+.

Part C: Synthesis of Cycloalkyl-Amine Intermediates:

Scheme C1: Preparation of 3,3-dimethyl-cyclobutylamine hydrochloride

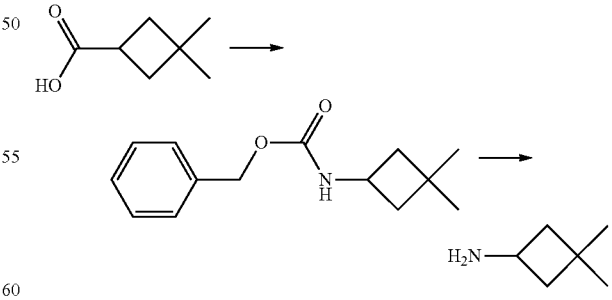

A. (3,3-Dimethyl-cyclobutyl)-carbamic acid benzyl ester

To a solution of 3,3-dimethylcyclobutanecarboxylic acid (200 mg, 1.560 mmol) and TEA (261 μL, 1.873 mmol) in THF (5.2 mL) was added DPPA (405 µL, 1.873 mmol). The reaction mixture was stirred at RT overnight and concentrated. The residue was dissolved in toluene (5.2 mL) then benzyl alcohol (487 µL, 4.68 mmol) was added and the reaction mixture was stirred at 80° C. for 8 h. After cooling to RT, the reaction mixture was concentrated and the crude residue was purified by flash column chromatography on silica gel (c-hexane/EtOAc 10:0 to 8:2) followed by preparative HPLC (XBridge C18OBD, 5 µm, 30×100, eluent: 20 to 100% CH$_3$CN in H$_2$O in 12 min, CH$_3$CN and H$_2$O containing 7.3 mM of NH$_3$, flow 45 mL/min). The pure fractions were lyophilized to afford the title compound. TLC, R$_f$ (c-hexane/AcOEt 8/2) =0.41; MS (UPLC/MS): 234.2 [M+H]+; t$_R$ (HPLC conditions b): 5.02 min.

B. 3,3-Dimethyl-cyclobutylamine hydrochloride

To a solution of (3,3-dimethyl-cyclobutyl)-carbamic acid benzyl ester (142 mg, 0.65 mmol) in EtOH (3 mL) and 4N HCl in dioxane (0.020 mL, 0.65 mmol) was added Pd/C (34.5 mg, 0.032 mmol). The reaction mixture was placed under an hydrogen atmosphere and stirred for 16 h. Subsequently the reaction mixture was filtered over a pad of Celite and washed with EtOH. The filtrate was adjusted to acidic pH by addition of 2 mL of 4N HCl in dioxane and concentrated. The title compound was used in the next step without further purification. $^1$H NMR (400 MHz, DMSO-d$_6$) δ ppm: 8.13 (bs., 3 H), 3.58-3.70 (m, 1 H), 1.86-2.05 (m, 4 H), 1.10 (d, 6 H).

Scheme C2: Preparation of (1R,3R)-3-amino-cyclopentanecarboxylic acid amide trifluoroacetate

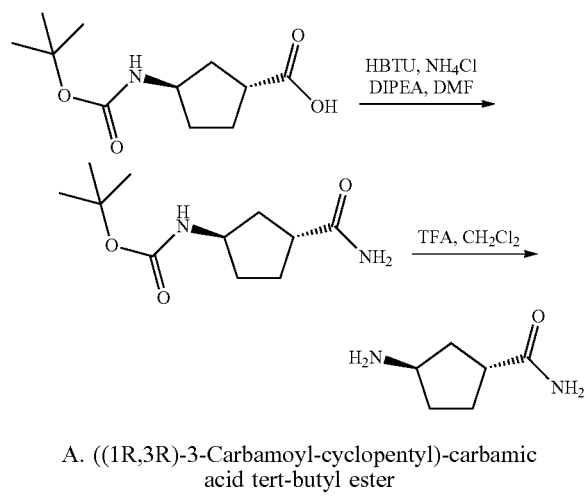

A. ((1R,3R)-3-Carbamoyl-cyclopentyl)-carbamic acid tert-butyl ester

To a solution of (1R,3R)-3-tert-butoxycarbonylamino-cyclopentanecarboxylic acid (250 mg, 1.09 mmol), NH$_4$Cl (117 mg, 2.18 mmol) and HBTU (620 mg, 1.63 mmol) in DMF (3.6 mL) was added DIPEA (0.57 mL, 3.27 mmol). The reaction mixture was stirred at RT for 16 h and then concentrated. The residue was taken up in EtOAc and successively washed with 1N aq. HCl and 5% aq. NaHCO$_3$. The organic layer was dried (Na$_2$SO$_4$), filtered, concentrated and the product was purified by flash column chromatography on silica gel (CH$_2$Cl$_2$/MeOH 10:0 to 95:5). MS (LC/MS): 246.3 [M+NH$_4$]+, 173.0 [M-tBu]+.

B. (1R,3R)-3-Amino-cyclopentanecarboxylic acid amide trifluoroacetate

To a solution of ((1R,3R)-3-carbamoyl-cyclopentyl)-carbamic acid tert-butyl ester (160 mg, 0.70 mmol) in CH$_2$Cl$_2$ (2.33 mL) was added TFA (1 mL, 12.98 mmol). The reaction mixture was stirred at RT for 2 h and concentrated to dryness to afford the title compound. MS (LC/MS): 129.0 [M+H]+.

Scheme C3: General protocol for the preparation of (1R,3R)-3-Amino-cyclopentanecarboxylic acid methyl ester trifluoroacetate

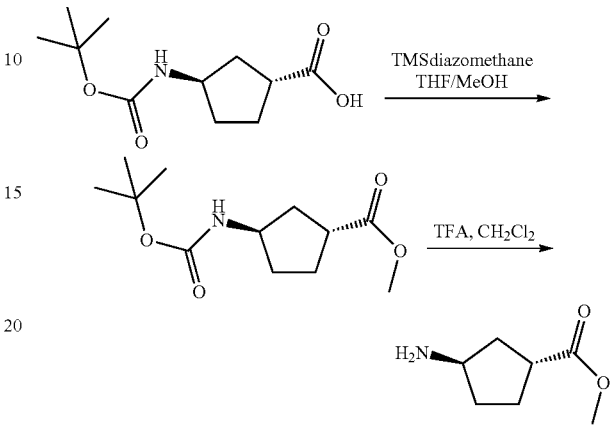

A. (1R,3R)-3-tert-Butoxycarbonylamino-cyclopentanecarboxylic acid methyl ester

To a solution of (1R,3R)-3-tert-butoxycarbonylamino-cyclopentanecarboxylic acid (250 mg, 1.09 mmol) in THF/MeOH (1/1, 3.6 mL) was added dropwise, at 0° C., trimethylsilyldiazomethane (2M in diethylether, 1.09 mL, 2.18 mmol). The reaction mixture was stirred at 0° C. for 1 h and concentrated. The product was purified by flash column chromatography on silica gel (c-hexane/EtOAc 10:0 to 7:3). MS (LC/MS): 266.0 [M+Na]+, 188.1 [M-tBu]+.

B. (1R,3R)-3-Amino-cyclopentanecarboxylic acid methyl ester trifluoroacetate

The title compound was prepared from (1R,3R)-3-tert-butoxycarbonylamino-cyclopentanecarboxylic acid methyl ester in a similar manner as described in step B of Scheme C2 for the preparation of (1R,3R)-3-amino-cyclopentanecarboxylic acid amide trifluoroacetate. MS: 144.1 [M+H]+.

(1R,3S)-3-Amino-cyclohexanecarboxylic acid methyl ester trifluoroacetate

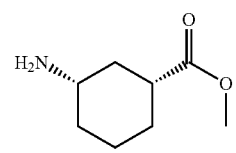

The title compound was prepared using the same procedures as described for the synthesis of (1R,3R)-3-amino-cyclopentanecarboxylic acid methyl ester trifluoroacetate in Scheme C3 starting from (1R,3S)-3-(tert-butoxycarbonylamino)cyclohexanecarboxylic acid. MS: 158.0 [M+H]+.

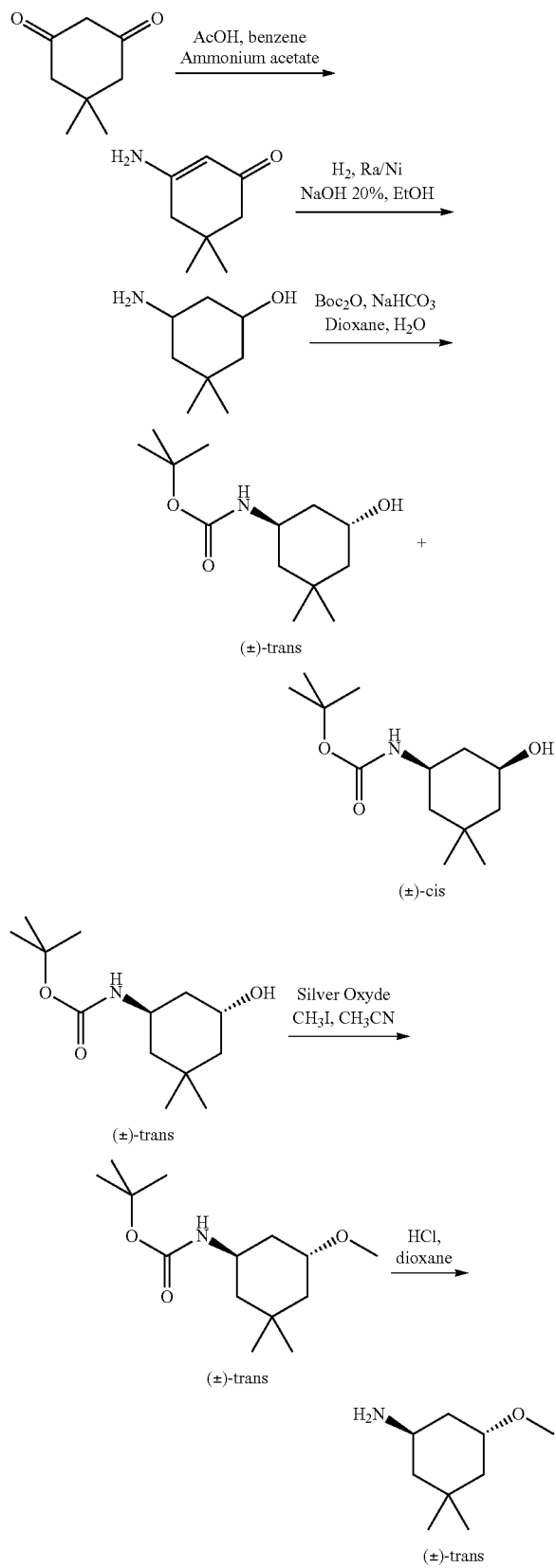

Scheme C4: General protocol for the preparation of (±)-trans-5-methoxy-3,3-dimethyl-cyclohexylamine hydrochloride

A. 3-Amino-5,5-dimethyl-cyclohex-2-enone

The title compound was prepared in a similar manner as described by P. G. Baraldi, *Synthetic Communications*, 1983, 902. To a suspension of 5,5-dimethylcyclohexane-1,3-dione (10 g, 71.3 mmol) in benzene (180 mL) were added acetic acid (1.84 mL, 31.2 mmol) and ammonium acetate (11.0 g, 143 mmol). The reaction mixture was refluxed for 5 h and the water formed was removed azeotropically using a Dean-Stark apparatus. Subsequently the reaction mixture was cooled to RT, quenched with sat. aq. $Na_2CO_3$ and 1N aq. NaOH and extracted with $CH_2Cl_2$ several times. The combined organic extracts were dried ($Na_2SO_4$), filtered and concentrated to afford the title compound. MS (UPLC/MS): 139.9 [M+H]+; $t_R$ (HPLC conditions i): 0.48 min

B. 5-Amino-3,3-dimethyl-cyclohexanol

To a solution of 3-amino-5,5-dimethyl-cyclohex-2-enone (2 g, 14.37 mmol) in EtOH (20 mL) and aq. NaOH 20% (0.6 mL) was added Raney-Nickel (1.8 g). The reaction mixture was placed under an hydrogen atmosphere (5 bars) at 60° C. and stirred for 2 days. Subsequently the reaction mixture was cooled to RT and filtered through Hyflo Super Gel medium with EtOH. The filtrate was concentrated to give the mixture of diastereoisomers directly engaged in the next step without purification. MS (UPLC/MS): 144.1 [M+H]+.

C. ((±)-Trans-5-hydroxy-3,3-dimethyl-cyclohexyl)-carbamic acid tert-butyl ester and ((±)-cis-5-hydroxy-3,3-dimethyl-cyclohexyl)-carbamic acid tert-butyl ester To 5-amino-3,3-dimethyl-cyclohexanol (2.05 g, 14.3 mmol) in dioxane/$H_2O$ (1:1; 200 mL) were added $NaHCO_3$ (1.2 g, 14.3 mmol) and $Boc_2O$ (3.75 g, 17.18 mmol). The reaction mixture was stirred at RT for 1 h, saturated with NaCl and extracted twice with $CH_2Cl_2$. The combined organic layers were dried ($Na_2SO_4$), filtered, concentrated and the product was purified by flash column chromatography on silica gel (c-hexane/EtOAc 10:0 to 5:5) to give ((±)-trans-5-hydroxy-3,3-dimethyl-cyclohexyl)-carbamic acid tert-butyl ester:TLC, $R_f$ (Cyclo/AcOEt 5/1)=0.23; MS (UPLC/MS): 261.1 [M+$NH_4$]+; $t_R$ (UPLC conditions h): 0.93 min and ((±)-cis-5-hydroxy-3,3-dimethyl-cyclohexyl)-carbamic acid tert-butyl ester:TLC, $R_f$ (Cyclo/AcOEt 5/1)= 0.16; MS (UPLC/MS): 244.1 [M+H]+; $t_R$ (UPLC conditions h): 0.88 min.

D. ((±)-Trans-5-methoxy-3,3-dimethyl-cyclohexyl)-carbamic acid tert-butyl ester A mixture of ((±)-trans-5-hydroxy-3,3-dimethyl-cyclohexyl)-carbamic acid tert-butyl ester (800 mg, 3.29 mmol), silver(I) oxide (1.676 g, 7.23 mmol) and iodomethane (2.06 mL, 32.9 mmol) in $CH_3CN$ (11 mL) was stirred at 80° C. overnight. The reaction mixture was taken to RT and subsequently filtered. $H_2O$ and brine were added to the filtrate and extracted 2 times with EtOAc. The combined organic extracts were dried ($Na_2SO_4$), filtered, concentrated and the product was purified by flash column chromatography on silica gel (c-hexane/EtOAc 10:0 to 7:3). TLC, $R_f$ (Cyclo/AcOEt 5/1)=0.56; MS (UPLC/MS): 275.3 [M+$NH_4$]+; $t_R$ (UPLC conditions h): 1.13 min.

E. (±)-Trans-5-methoxy-3,3-dimethyl-cyclohexylamine hydrochloride

To a solution of ((±)-trans-5-methoxy-3,3-dimethyl-cyclohexyl)-carbamic acid tert-butyl ester (390 mg, 1.51 mmol) in dioxane (0.5 mL) was added 4M HCl in dioxane (0.55 mL, 18.18 mmol). The reaction mixture was stirred at RT for 2 h and concentrated to afford the title compound. MS (UPLC/MS): 158.1 [M+H]+; $t_R$ (UPLC conditions h): 0.48 min.

(±)-Cis-5-methoxy-3,3-dimethyl-cyclohexylamine hydrochloride

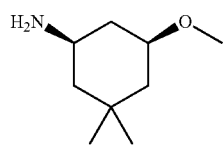

The title compound was prepared as described for the synthesis of (±)-trans-5-methoxy-3,3-dimethyl-cyclohexylamine hydrochloride in Scheme C4 step D and E starting from ((±)-cis-5-hydroxy-3,3-dimethyl-cyclohexyl)-carbamic acid tert-butyl ester (prepared as described in Scheme C4 step C). MS (UPLC/MS): 158.1 [M+H]+; $t_R$ (UPLC conditions h): 0.44 min.

(±)-Trans-5-amino-3,3-dimethyl-cyclohexanol hydrochloride

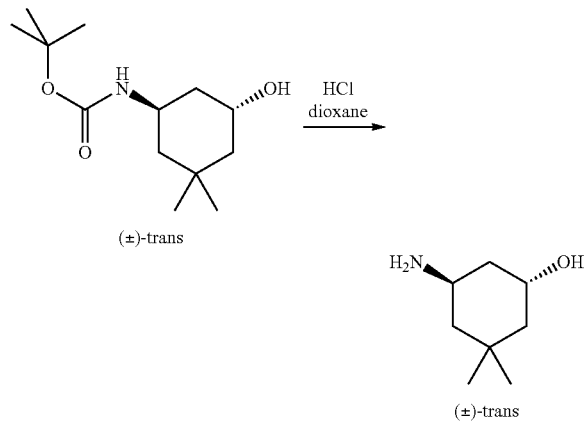

(±)-Trans-5-amino-3,3-dimethyl-cyclohexanol hydrochloride was prepared using the same procedure as described for the synthesis of (±)-trans-5-methoxy-3,3-dimethyl-cyclohexylamine hydrochloride in Scheme C4 step E starting from ((±)-trans-5-hydroxy-3,3-dimethyl-cyclohexyl)-carbamic acid tert-butyl ester synthetised in Scheme C4 step C. MS (UPLC/MS): 144.1 [M+H]+; $t_R$ (UPLC conditions h): 0.33 min.

Scheme C5: Prepartion of (1R,3S)-3-trifluoromethyl-cyclohexylamine hydrochloride

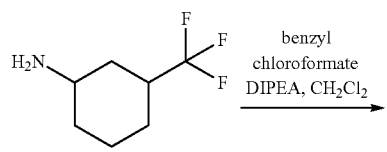

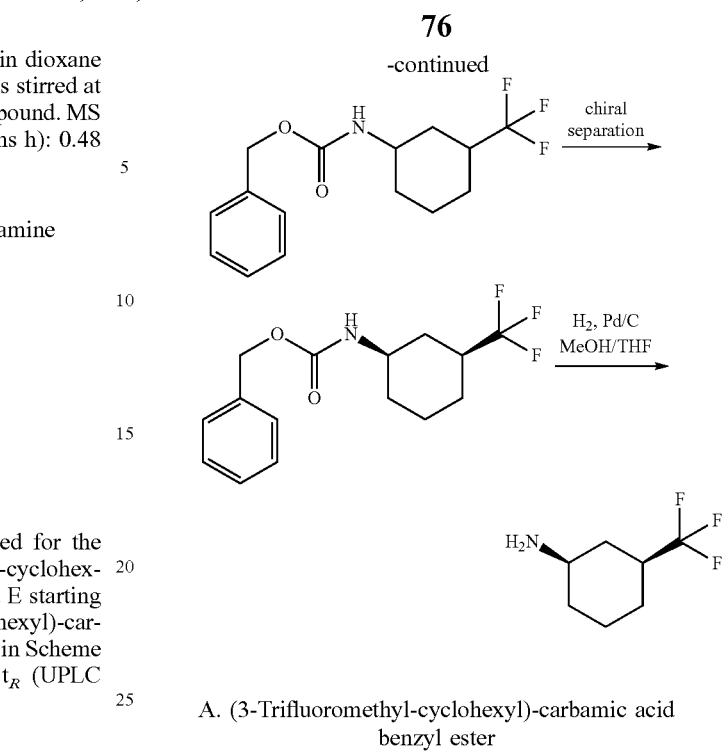

A. (3-Trifluoromethyl-cyclohexyl)-carbamic acid benzyl ester

To a solution of 3-trifluoromethyl-cyclohexylamine (2.5 g, 14.95 mmol) and DIPEA (3.92 mL, 22.43 mmol) in CH$_2$Cl$_2$ (20 mL) was added benzyl chloroformate (2.348 mL, 16.45 mmol). at 0° C. The reaction mixture stirred at 0° C. for 1 h and subsequently at RT overnight. The solvent was evaporated and the residue was poured into water and extracted with EtOAc (2×). The combined organic extracts were dried (phase separator), concentrated and the product purified by flash column chromatography on silica gel (c-hexane/EtOAc 10:0 to 6:4). MS (LC/MS): 301.9 [M+H]+, 324.0 [M+Na]+; $t_R$ (HPLC conditions d): 3.91 min.

B. ((1R,3S)-3-Trifluoromethyl-cyclohexyl)-carbamic acid benzyl ester (Dia 4 from chiral separation)

The mixture of (3-trifluoromethyl-cyclohexyl)-carbamic acid benzyl ester was separated into its diastereoisomers by preparative chiral HPLC (Column: Chiralpak AD, 20 um, 393×76.5 mm; eluent: heptane:MeOH 99:1, flow rate: 80 mL/min) to give ((1R,3R) or (1S,3S)-3-trifluoromethyl-cyclohexyl)-carbamic acid benzyl ester—Dia 1: $t_R$ (Chiralpak AD-H, 5 um, 250×4.6 mm, heptane:MeOH 99:1, flow rate: 1 mL/min, detection: UV at 220 nm): 23.14 min, ((1R,3R) or (1S,3S)-3-trifluoromethyl-cyclohexyl)-carbamic acid benzyl ester—Dia 2: $t_R$ (Chiralpak AD-H, 5 um, 250×4.6 mm, heptane:MeOH 99:1, flow rate: 1 mL/min, detection: UV at 220 nm): 26.84 min, ((1S,3R)-3-trifluoromethyl-cyclohexyl)-carbamic acid benzyl ester—Dia 3: $t_R$ (Chiralpak AD-H, 5 um, 250×4.6 mm, heptane:MeOH 99:1, flow rate: 1 mL/min, detection: UV at 220 nm): 38.78 min and ((1R,3S)-3-trifluoromethyl-cyclohexyl)-carbamic acid benzyl ester—Dia 4: $t_R$ (Chiralpak AD-H, 5 um, 250×4.6 mm, heptane:MeOH 99:1, flow rate: 1 mL/min, detection: UV at 220 nm): 48.92 min.

Cis/trans relative stereochemistry was assigned based on NMR. Dia 1 and Dia 2 display a trans relative stereochemistry, Dia 3 and Dia 4 display a cis relative stereochemistry. The absolute stereochemistry of Dia 4: ((1R,3S)-3-trifluoromethyl-cyclohexyl)-carbamic acid benzyl ester was assigned by X-ray crystallography of Example 49 prepared from Dia 4. As a consequence Dia 3 is ((1S,3R)-3-trifluoromethyl-cyclohexyl)-carbamic acid benzyl ester.

C. (1R,3S)-3-Trifluoromethyl-cyclohexylamine hydrochloride

To a solution of ((1R,3S)-3-trifluoromethyl-cyclohexyl)-carbamic acid benzyl ester (Dia 4) (745 mg, 2.47 mmol) in MeOH/THF (1/1, 50 mL) was added Pd/C (105 mg, 0.1 mmol), the reaction mixture was placed under an hydrogen atmosphere and stirred at RT for 18 h. The reaction mixture was filtered over a pad of Celite, and washed with a solution of THF/MeOH. The combined filtrate and washings were adjusted to acidic pH by addition of 3N aq. HCl and subsequently concentrated to afford the title compound. $^1$H NMR (400 MHz, DMSO-$d_6$) δ ppm: 8.11 (bs., 3 H), 3.11 (m, 1 H), 2.5 (m, 1 H, under DMSO residual peak), 2.13 (d, 1 H), 1.96 (d, 1 H), 1.83 (d, 2 H), 1.21-1.43 (m, 3 H), 1.13 (m, 1 H).

Scheme C6: Preparation of spiro[2.5]oct-5-ylamine hydrochloride

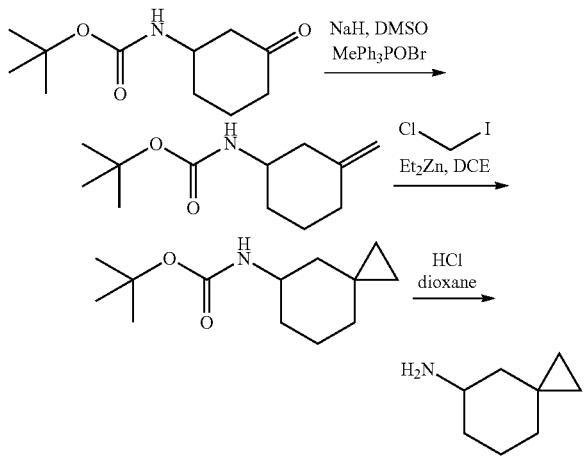

A. (3-Methylene-cyclohexyl)-carbamic acid tert-butyl ester

NaH (60% in mineral oil, 0.375 g, 9.38 mmol) was dissolved under an argon atmosphere in DMSO (5.21 mL). The mixture was stirred at RT for 1 h and cooled to 0° C. Then a suspension of methyltriphenylphosphonium bromide (3.52 g, 9.85 mmol) in DMSO (10.42 mL) was warmed until complete dissolution and added dropwise. The resulting yellow solution was stirred at RT for 30 min. Then a solution of (3-oxo-cyclohexyl)-carbamic acid tert-butyl ester (1 g, 4.69 mmol) in DMSO (5.21 mL) was added and the mixture was stirred at RT for 1 h. Subsequently water was added and the crude mixture was extracted several times with EtOAc. The combined organic layers were dried (phase separator), concentrated and the product purified by flash column chromatography on silica gel (c-hexane/EtOAc 10:0 to 95:5). TLC, $R_f$ (c-hexane/EtOAc 9/1)=0.73; MS (LC/MS): 155.9 [M-tBu]+, 234.1 [M+Na]+; $^1$H NMR (400 MHz, DMSO-$d_6$) δ ppm: 6.75 (d, 1 H), 4.65 (d, 2 H), 3.14-3.24 (m, 1 H), 2.25-2.42 (m, 1 H), 2.15 (d, 1 H), 1.70-1.90 (m, 4 H), 1.38 (s, 9 H), 1.06-1.30 (m, 2 H).

B. Spiro[2.5]oct-5-yl-carbamic acid tert-butyl ester

Chloroiodomethane (440 µL, 6.06 mmol) was added at 0° C. to a solution of (3-methylene-cyclohexyl)-carbamic acid tert-butyl ester (400 mg, 1.89 mmol) in dry DCE (6.3 mL) under an inerte atmosphere. Then, diethylzinc 1M in hexane (3.03 mL, 3.03 mmol) was added and the reaction mixture was stirred at RT for 3 h. The reaction mixture was poured into water and extracted several times with CH$_2$Cl$_2$. The combined organic layers were dried (phase separator), concentrated and the product purified by flash column chromatography on silica gel (c-hexane/EtOAc 10:0 to 8:2). TLC, $R_f$ (c-hexane/EtOAc 9/1)=0.45; MS (LC/MS): 170.1 [M-tBu]+, 248.1 [M+Na]+; $^1$H NMR (400 MHz, DMSO-$d_6$) δ ppm: 6.66 (br. s., 1 H), 3.28 (m, 1 H, under H$_2$O residual peak), 1.77 (d, 1 H), 1.63 (m, 1 H), 1.42-1.58 (m, 2 H), 1.23-1.42 (m, 10 H), 1.10 (m, 1 H), 0.97 (d, 1 H), 0.75 (d, 1 H), 0.13-0.29 (m, 4 H).

C. Spiro[2.5]oct-5-ylamine hydrochloride

To a solution of spiro[2.5]oct-5-yl-carbamic acid tert-butyl ester (495 mg, 2.197 mmol) in dioxane (7.3 mL) was added 4M HCl in dioxane (2.7 mL, 10.98 mmol) and the reaction mixture was stirred at RT overnight. The reaction mixture was lyophilized to afford the title compound. MS (LC/MS): 125.9 [M+H]+; $^1$H NMR (400 MHz, DMSO-$d_6$) δ ppm: 7.92 (bs., 1 H), 3.04 (t, 1 H), 1.96 (d, 1 H), 1.61-1.83 (m, 2 H), 1.46-1.61 (m, 1 H), 1.20-1.46 (m, 2 H), 1.16 (d, 1 H), 0.83 (d, 1 H), 0.28-0.43 (m, 2 H), 0.06-0.28 (m, 2 H).

Scheme C7: Preparation of 3-methyl-cyclohex-2-enylamine hydrochloride

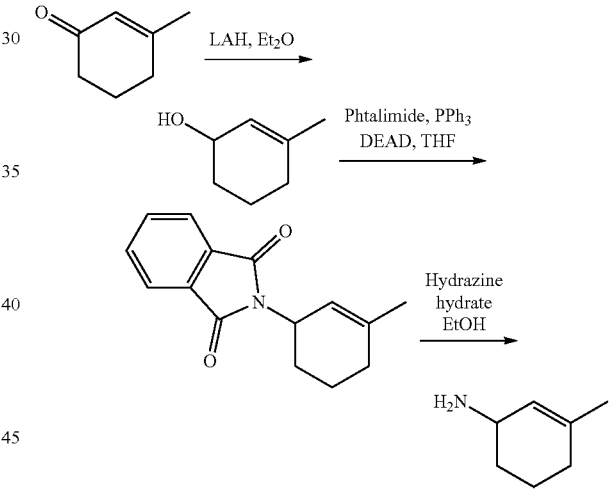

A. 3-Methyl-cyclohex-2-enol

To a solution of lithium aluminum hydride (4M in Et$_2$O, 7.49 mL, 30 mmol) at 0° C. was added dropwise a solution of 3-methylcyclohex-2-enone (3 g, 27.2 mmol) in Et$_2$O (20 mL). The reaction mixture was stirred for 3 h at RT, quenched with sat. aq. NH$_4$Cl and extracted with Et$_2$O. The combined organic extracts were washed with water and brine, dried (Na$_2$SO$_4$), filtered and concentrated. The product was used in the next step without further purification. $^1$H NMR (400 MHz, DMSO-$d_6$) δ ppm: 5.36 (d, 1 H), 4.44 (d, 1 H), 3.96 (bs., 1 H), 1.73-1.95 (m, 2 H), 1.52-1.73 (m, 5 H), 1.26-1.52 (m, 2 H).

B. 2-(3-Methyl-cyclohex-2-enyl)-isoindole-1,3-dione

To a solution of 3-methyl-cyclohex-2-enol (1.6 g, 14.26 mmol), phthalimide (2.52 g, 17.12 mmol) and triphenylphosphine (5.61 g, 21.40 mmol) in THF (30 mL) was added DEAD (9.03 mL, 22.82 mmol). The reaction mixture was stirred for 16 h at RT, concentrated and the crude residue was purified by flash column chromatography on silica gel (c-hexane/EtOAc 10:0 to 7:3) to afford the title compound. MS (UPLC/MS): 242.1 [M+H]+; $t_R$ (HPLC conditions c): 2.18 min.

C. 3-Methyl-cyclohex-2-enylamine hydrochloride

To a solution of 2-(3-methyl-cyclohex-2-enyl)-isoindole-1,3-dione (300 mg, 1.24 mmol) in EtOH (10 ml) was added hydrazine hydrate (0.064 mL, 1.306 mmol) and the reaction mixture was stirred for 16 h at RT. The precipitate formed was filtered and discarded. 4N HCl in dioxane was added to the filtrate and evaporation of the volatils afforded the title compound, which was used in the next step without further purification.

Scheme C8: Preparation of 3,3-dichloro-cyclohexylamine

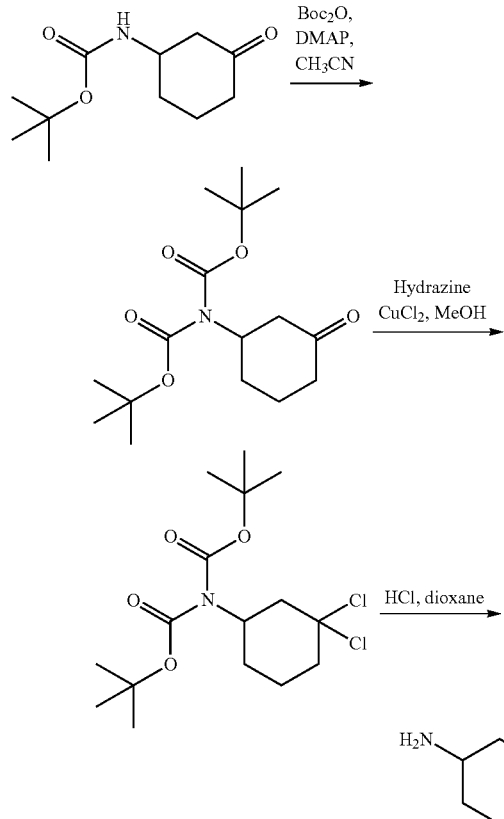

A. (3-Oxo-cyclohexyl)-biscarbamic acid tert-butyl ester

To a solution of (3-oxo-cyclohexyl)-carbamic acid tert-butyl ester (480 mg, 2.25 mmol) and DMAP (13.7 mg, 0.113 mmol) in CH₃CN (22.5 mL) was added Boc₂O (614 mg, 2.81 mmol). The reaction mixture was stirred at RT overnight, poured into H₂O/brine and extracted with EtOAc (2×). The combined organic layers were dried (Na₂SO₄), filtered, concentrated and the crude residue was purified by flash column chromatography on silica gel (c-hexane/EtOAc 10:0 to 8:2). TLC, $R_f$ (c-hexane/AcOEt 2/1)=0.70; MS (UPLC/MS): 314.2 [M+H]+; $t_R$ (UPLC conditions h): 1.20 min.

B. (3,3-Dichloro-cyclohexyl)-biscarbamic acid tert-butyl ester

The title compound was prepared in a similar manner as described in WO2007/3056 A1, 2007. Hydrazine hydrate (1.55 mL, 31.9 mmol) was added to a suspension of 4 Å molecular sieve powder (1.3 g) in MeOH (5 mL). The mixture was stirred for 15 min, then a solution of (3-oxo-cyclohexyl)-biscarbamic acid tert-butyl ester (500 mg, 1.595 mmol) in MeOH (5 mL) was added. The reaction mixture was stirred for 5 h at RT. The suspension was filtered and the filtrate was concentrated to give the intermediate hydrazone.

A solution of CuCl₂ (150 mg, 11.17 mmol) in MeOH (5 mL) was treated with TEA (0.78 mL, 5.58 mmol) at 0° C. The mixture was stirred for 15 min at RT and cooled to 0° C. Then a solution of the crude hydrazone dissolved in MeOH (7 mL) was added dropwise over 20 min and the reaction mixture was stirred at 0° C. for 1 h, quenched with brine and aq. NH₃ solution. The blue reaction mixture was extracted twice with CH₂Cl₂. The combined organic layers were washed with sat. aq. NH₄Cl, brine, dried (Na₂SO₄), filtered and concentrated. The product was used in the next step without further purification.

C. 3,3-Dichloro-cyclohexylamine hydrochloride

To a solution of (3,3-dichloro-cyclohexyl)-biscarbamic acid tert-butyl ester (410 mg, 1.1 mmol) in dioxane (1.5 mL) was added 4N HCl in dioxane (1.67 mL, 6.68 mmol). The reaction mixture was stirred at RT for 2 h. The precipitate formed was filtered and the filtrate was evaporated to dryness to give the title compound. MS (UPLC/MS): 168.1-170.1 [M+H]+.

Scheme C9: Preparation of 3,3-dimethyl-piperidin-1-ylamine

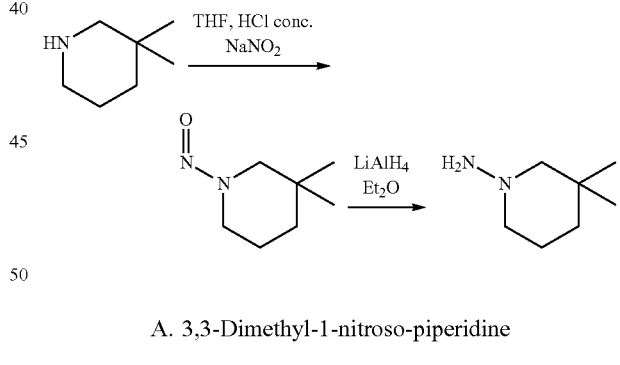

A. 3,3-Dimethyl-1-nitroso-piperidine

To a solution of 3,3-dimethylpiperidine (1 g, 8.83 mmol) in THF (50 mL) and conc HCl. (17.67 mL, 44.2 mmol) was added sodium nitrite (0.792 g, 11.48 mmol) portionwise at RT. The reaction mixture was stirred for 48 h at RT. The crude mixture was extracted several times with Et₂O. The combined organic layers were dried (Na₂SO₄), filtered and concentrated. The crude product was used in the next step without further purification. MS (UPLC/MS): 143.1 [M+H]+; $t_R$ (HPLC conditions c): 1.42 min.

B. 3,3-Dimethyl-piperidin-1-ylamine

To a solution of lithium aluminum hydride (0.64 g, 16.88 mmol) in Et₂O (35.0 mL) was added, at 0° C., a solution of 3,3-dimethyl-1-nitroso-piperidine (1.2 g, 8.44 mmol) in Et₂O (17.50 ml). The reaction mixture was stirred for 3 h at RT, quenched with water and extracted with Et₂O. The organic layer was washed with water and brine, dried (Na₂SO₄), filtered and concentrated. The crude product was used in the next step without further purification. ¹H NMR filtrate, which was subsequently concentrated to dryness. The residue was suspended in Et₂O and filtered to give the product as a white solid, which was used in the next step without further purification. ¹H NMR (400 MHz, DMSO-d₆) δ ppm: 8.10 (bs., 2 H), 3.37-3.61 (m, 1 H), 1.04-2.26 (m, 7 H), 0.88-1.03 (m, 3 H).

Scheme C11: Preparation fo 3-Amino-1-methylcyclohexanol and of 3-methoxy-3-methylcyclohexan-amine

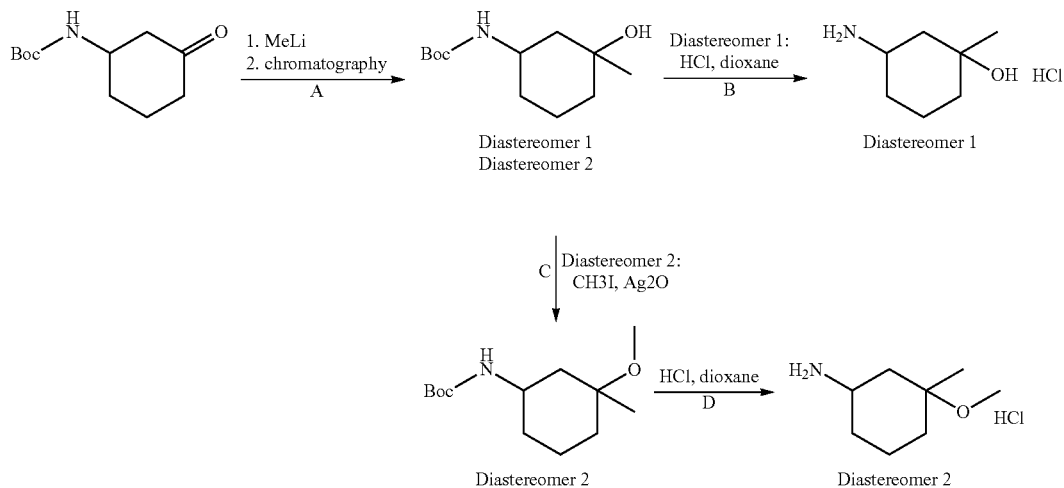

(400 MHz, DMSO-d₆) δ ppm: 3.33 (m, 2 H, under H₂O residual peak), 3.23 (bs., 2 H), 1.44-1.59 (m, 2H), 1.00-1.16 (m, 2 H), 0.89 (s, 6 H).

Scheme C10: Preparation of 3-methyl-cyclopentylamine hydrochloride

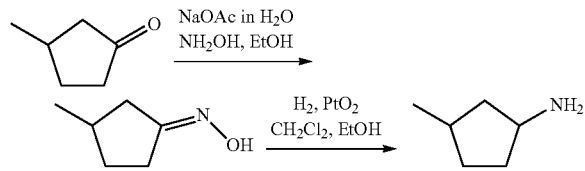

A. 3-Methyl-cyclopentanone oxime

To a solution of 3-methylcyclopentanone (3.28 mL, 30.6 mmol) in EtOH (18 mL) were added hydroxylamine hydrochloride (3.61 g, 52.0 mmol) and a solution of sodium acetate (4.26 g, 52.0 mmol) in H₂O (36 mL). The reaction mixture was refluxed for 3 h, cooled to RT and concentrated. To the aq. residue was added brine and it was extracted several times with CH₂Cl₂. The combined organic layers were dried (phase separator) and concentrated. The crude product was used in the next step without further purification. MS (LC/MS): 113.9 [M+H]+; $t_R$ (HPLC conditions d): 2.33 min.

B. 3-Methyl-cyclopentylamine hydrochloride

To a solution of 3-methyl-cyclopentanone oxime (3.47 g, 30.7 mmol) in CH₂Cl₂ (3 mL) and EtOH (155 mL) was added PtO₂ (1.5 g, 30.7 mmol). The mixture was placed under an hydrogen atmosphere and stirred for 16 h. The reaction mixture was filtered through a pad of Celite and washed with EtOH. HCl in MeOH (5 mL) was added to the A. tert-Butyl 3-hydroxy-3-methylcyclohexylcarbamate—Diastereoisomer 1 and Diastereoisomer 2

To a solution of racemic tert-butyl 3-oxocyclohexylcarbamate (2.0 g, 9.38 mmol) in dry THF (100 mL) at −78° C. was added MeLi (1.6 M in diethyl ether, 24.62 mL, 39.4 mmol) dropwise during 30 min. The resulting mixture was stirred for 45 min at −78° C. A second portion of MeLi (1.6 M in diethyl ether, 24.62 mL, 39.4 mmol) was added and the mixture was stirred for 45 min at −78° C. The reaction mixture was quenched with saturated solution of NH₄Cl and extracted with EtOAc (×3). The combined organic layers were dried (Na₂SO₄), filtered and evaporated to dryness. The crude material was purified by flash column chromatography on silica gel (RediSep® Rf, Teledyne Isco, 120 g; gradient: c-hexane/EtOAc 100/0 to 70/30) to afford the title compounds: Diastereomer 1: TLC, $R_f$(c-hexane/AcOEt 1/1, sprayed with vanilline)=0.45 and Diastereomer 2 (as a mixture with the starting material): TLC, $R_f$ (c-hexane/AcOEt 1/1, sprayed with vanilline)=0.55.

B. 3-Amino-1-methylcyclohexanol, hydrochloride salt—Diastereomer 1

A mixture of tert-butyl 3-hydroxy-3-methylcyclohexylcarbamate—Diastereomer 1 (100 mg, 0.436 mmol) in dioxane (1 mL) and HCl (4N in dioxane, 1.58 mL, 6.32 mmol) was stirred at RT under nitrogen for 2 h. The mixture was concentrated to dryness to afford the crude title compound which was used without further purification in the next step. TLC, $R_f$(c-hexane/AcOEt 1/1, sprayed with vanilline)=0.06.

C. tert-Butyl 3-methoxy-3-methylcyclohexylcarbamate—Diastereomer 2

To a solution of tert-butyl 3-hydroxy-3-methylcyclohexylcarbamate—Diastereomer 2 (containing tert-butyl 3-oxocyclohexylcarbamate, 670 mg) in acetonitrile (20 mL) was added silver oxide (1747 mg, 7.54 mmol) and iodomethane (2.95 mL, 47.1 mmol). The suspension was stirred for 16 h at 80° C. The reaction mixture was cooled down to 23° C., filtered and evaporated to dryness. The crude material was purified by flash column chromatography on silica gel (24 g) (gradient: c-hexane/EtOAc 100/0 to 50/50) to afford the title compound as a colorless oil. TLC, $R_f$ (c-hexane/AcOEt 8/2, sprayed with vanilline)=0.5; MS (UPLC/MS): 244.3 [M+H]+, 487.4 [2M+H]+.

D. 3-Methoxy-3-methylcyclohexanamine hydrochloride salt—Diastereomer 2

To a solution of tert-butyl(3-methoxy-3-methylcyclohexyl)carbamate—Diastereoisomer 2 (73 mg, 0.30 mmol) in dioxane (0.3 mL) was added HCl (4 N in dioxane, 0.45 mL) and the reaction mixture was stirred at RT for 4 h. The reaction solution was concentrated to afford the crude title compound which was used without purification in the next step. MS (UPLC/MS): 144.2 [M+H]+.

Scheme C12: Preparation of (3-Amino-1-methylcyclohexyl)methanol, salt withhydrochloride

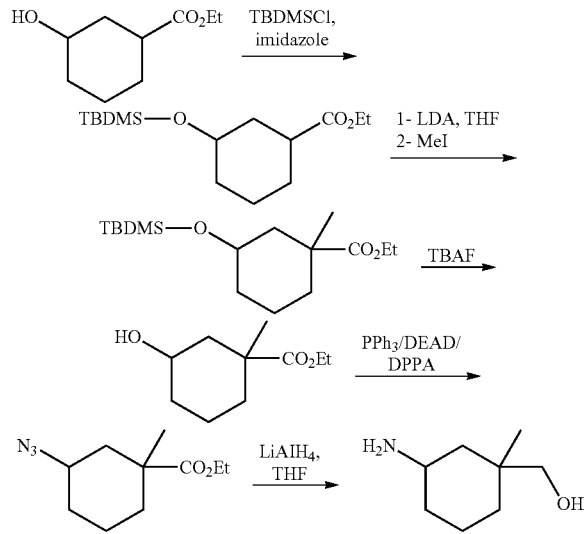

A. Ethyl 3-(tert-butyldimethylsilyloxy)cyclohexanecarboxylate

To a solution of ethyl 3-hydroxycyclohexanecarboxylate (13.0 g, 75 mmol) and imidazole (12.85 g, 189 mmol) in acetonitrile (377 mL) was added tert-butylchlorodimethylsilane (11.95 g, 79 mmol) at 5° C. The reaction mixture was stirred at 23° C. overnight. Then was quenched with brine and extracted with CH$_2$Cl$_2$ (×2). The combined organic layers were dried (Na$_2$SO$_4$), filtered and concentrated under vacuum. The crude material was treated with hexane (30 mL) in an ultra sonic bath and filtered. The filtrate was concentrated under vacuum and the crude title compound was purified by flash-chromatography on silica gel ((RediSep® Rf, Teledyne Isco, 125 g; gradient c-hexane/EtOAc 100/0 to 80/20) to afford ethyl 3-(tert-butyldimethylsilyloxy)cyclohexanecarboxylate as a diastereomeric mixture. TLC, Rf (c-hexane/AcOEt 5/1)=0.75.

B. Ethyl 3-(tert-butyldimethylsilyloxy)-1-methylcyclohexanecarboxylate

To a solution of ethyl 3-(tert-butyldimethylsilyloxy)cyclohexanecarboxylate (17 g, 59.3 mmol) in THF (400 mL) under a nitrogen atmosphere was added LDA (1.8 M in THF, 49.5 ml, 89 mmol) at −78° C. The reaction mixture was stirred at −78° C. for 10 min and iodomethane (6.5 mL, 104 mmol) was added. The yellow solution was slowly allowed to reach 0° C. and was stirred at 0° C. for 1 h. The reaction mixture was quenched with a saturated solution of NH$_4$Cl and extracted with EtOAc (×2). The combined organic layers were dried (Na$_2$SO$_4$), filtered and concentrated under vacuum to afford the title compound which was used in the subsequent step without further purification.

C. Ethyl 3-hydroxy-1-methylcyclohexanecarboxylate

To a solution of ethyl 3-(tert-butyldimethylsilyloxy)-1-methylcyclohexanecarboxylate (18.3 gl) in THF (300 mL) was added TBAF-trihydrate (22.36 g, 70.9 mmol) and the reaction mixture was stirred at RT for 12 h. The reaction solution was diluted with MTBE (500 mL) and washed successively with with brine and H$_2$O. The aqueous layer was extracted again with MTBE. The combined organic layers were dried (Na$_2$SO$_4$), filtered and concentrated under vacuum. The crude product was purified by flash column chromatography on silica gel (67 g) (gradient: c-hexane/EtOAc 100/0 to 70/30) to afford the title compound. MS (UPLC/MS): 187.2 [M+H]+.

D. Ethyl 3-azido-1-methylcyclohexanecarboxylate

To an ice-cooled solution of ethyl 3-hydroxy-1-methylcyclohexanecarboxylate (5.5 g, 28.1 mmol) and triphenylphosphine (7.36 g, 28.1 mmol) in THF (281 mL) under a nitrogen atmosphere was added DEAD (97%, 4.58 mL, 28.1 mmol). After 5 minutes diphenylphosphoryl azide (6.06 mL, 28.1 mmol) was added. The yellow solution was stirred at 0° C. for 1 h and subsequently at RT for 4 h. The reaction mixture was quenched with H$_2$O/brine and extracted with MTBE (×2). The combined organic layers were dried (Na$_2$SO$_4$), filtered and concentrated under vacuum. The crude product was purified by flash column chromatography on silica gel (RediSep® Rf, Teledyne Isco, 120 g; gradient: c-hexane/EtOAc 100/0 to 60/40) to afford the crude title compound, which was used without further purification in the next step. TLC, Rf (c-hexane/AcOEt 2/1)=0.75.

E. (3-Amino-1-methylcyclohexyl)methanol, hydrochloride salt

To a solution of ethyl 3-azido-1-methylcyclohexanecarboxylate (3.62 g) in THF (120 mL) under a nitrogen atmosphere was added LiAlH$_4$ (1 M in THF, 12 mL, 12 mmol) at 0° C. The reaction mixture was stirred at 0° C. for 4 h. Sodiumsulfate decahydrate was added to the reaction mixture to destroy the excess of lithiumaluminiumhydride and the mixture was stirred for 15 min. Then methanol and dry sodiumsulfate were slowly added and the fine suspension was filtered through a pad of Celite. The filtrate was concentrated under vacuum and was taken up in diethylether (180 mL) and filtered. To the filtrate was added HCl (4 N, 6.5 mL, 26 mol) at 0° C. A white precipitate formed immediately and was filtered through a sintered glass funnel. The solid was dried under vacuum to afford the 3-amino-1-methylcyclohexyl)methanol, hydrochloride salt. MS (UPLC/MS): 144.2 [M+H]+; 1H-NMR (400 MHz, DMSO-d$_6$) δ ppm: 7.97 (s, 3 H), 3.06-3.09 (m, 3 H), 1.91 (m, 1 H), 1.55-1.59 (m, 2 H), 1.42 (m, 1 H), 1.24 (m, 1 H), 1.13-1.15 (m, 3 H), 0.8 (s, 3 H). The relative stereochemistry was tentatively assigned based on NMR-ROESY experiments to a racemic mixture of ((1S,3R)-3-(aminomethyl)-1-methyl-cyclohexyl)methanol and ((1R,3S)-3-(aminomethyl)-1-methylcyclohexyl)methanol (hydrochloride salts).

Part D: Synthesis Of Examples 1 To 128

1H NMR data for selected compounds can be found at the end of part D.

Scheme D1: General protocol described for the preparation of Example 1: (1R,3S,5R)-2-[2-(3-Acetyl-pyrazolo[3,4-c]pyridin-1-yl)-acetyl]-2-aza-bicyclo[3.1.0]hexane-3-carboxylic acid (3,3-dimethyl-cyclobutyl)-amide

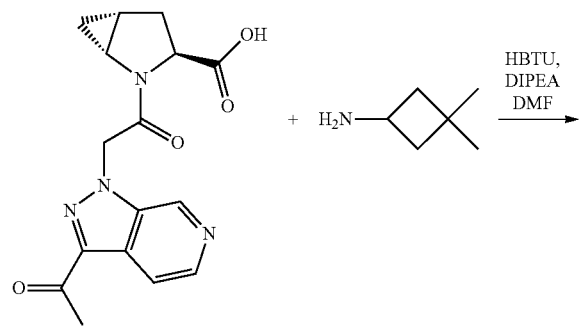

To a solution of (1R,3S,5R)-2-[2-(3-acetyl-pyrazolo[3,4-c]pyridin-1-yl)-acetyl]-2-aza-bicyclo[3.1.0]hexane-3-carboxylic acid (prepared as described in part B, 261 mg, 0.64 mmol), 3,3-dimethyl-cyclobutylamine hydrochloride (prepared as described in part C, 108 mg, 0.637 mmol) and HBTU (290 mg, 0.764 mmol) in DMF (1.5 mL) was added DIPEA (334 µL, 1.91 mmol). The reaction mixture was stirred at RT overnight and the product was purified by preparative HPLC (XBridge C18OBD, 5 µm, 30×100, flow: 45 ml/min, eluent: 5 to 99% CH$_3$CN in H$_2$O in 12 min, CH$_3$CN and H$_2$O containing 7.3 mM of NH$_3$). The pure fractions were combined and lyophilized to afford the title compound. MS (UPLC/MS): 410.3 [M+H]+, t$_R$ (HPLC conditions b): 3.58 min.

The examples below were prepared according to the general procedures described in Scheme D1 for the preparation of Example 1 from commercially available building blocks, if not otherwise stated (see notes at the end of table 1):

TABLE 1

| Example | Structure | Name | Characterization (end-table notes); MS (LC/MS); t$_R$ (HPLC conditions) |
|---|---|---|---|
| 2 | 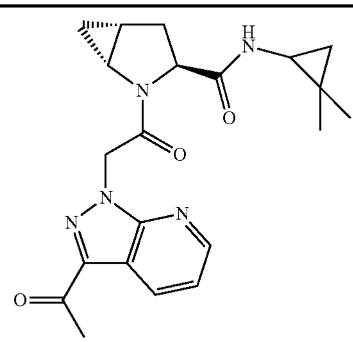 | (1R,3S,5R)-2-[2-(3-Acetyl-pyrazolo[3,4-b]pyridin-1-yl)-acetyl]-2-aza-bicyclo[3.1.0]hexane-3-carboxylic acid (2,2-dimethyl-cyclopropyl)-amide | (1[B2]); 396.1 [M+H]+, 418.0 [M+Na]+; t$_R$ (e): 2.49 min. |
| 3 | 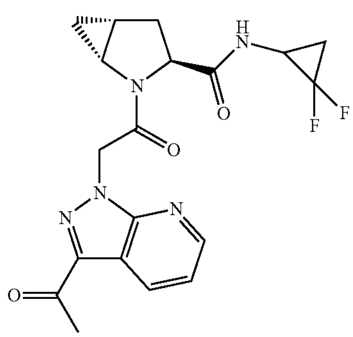 [SMILES: CC(=O)c1nn(CC(=O)N2[C@@H]3C[C@@H]3C[C@H]2C(=O)NC2CC2(F)F)c2ncccc12] | (1R,3S,5R)-2-[2-(3-Acetyl-pyrazolo[3,4-b]pyridin-1-yl)-acetyl]-2-aza-bicyclo[3.1.0]hexane-3-carboxylic acid (2,2-difluoro-cyclopropyl)-amide | (1[B2], 3); 404.3 [M+H]+, 448.4 [M+HCOO]−; t$_R$ (c): 1.59 min. |

TABLE 1-continued

| Example | Structure | Name | Characterization (end-table notes); MS (LC/MS); $t_R$ (HPLC conditions) |
|---|---|---|---|
| 4 | 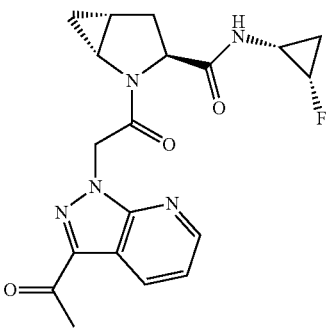 [SMILES: CC(=O)c1nn(CC(=O)N2[C@@H]3C[C@@H]3C[C@H]2C(=O)N[C@@H]2C[C@@H]2F)c2ncccc12] | (1R,3S,5R)-2-[2-(3-Acetyl-pyrazolo[3,4-b]pyridin-1-yl)-acetyl]-2-aza-bicyclo[3.1.0]hexane-3-carboxylic acid ((1R,2S)-2-fluoro-cyclopropyl)-amide | (1[B2], 3); 386.4 [M+H]+, 408.3 [M+Na]+; $t_R$ (c): 1.48 min. |
| 5 | 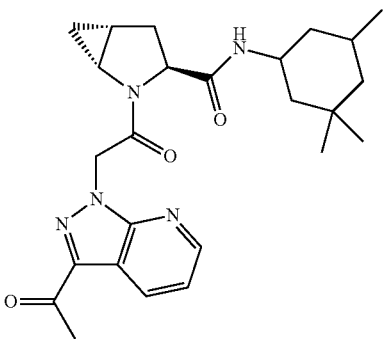 [SMILES: CC(=O)c1nn(CC(=O)N2[C@@H]3C[C@@H]3C[C@H]2C(=O)NC2CC(C)CC(C)(C)C2)c2ncccc12] | (1R,3S,5R)-2-[2-(3-Acetyl-pyrazolo[3,4-b]pyridin-1-yl)-acetyl]-2-aza-bicyclo[3.1.0]hexane-3-carboxylic acid (3,3,5-trimethyl-cyclohexyl)-amide (mixture of 4 diastereoisomers) | (1[B2]); 452.0 [M+H]+, 474.1 [M+Na]+; $t_R$ (e): 3.35 min. |
| 6 | 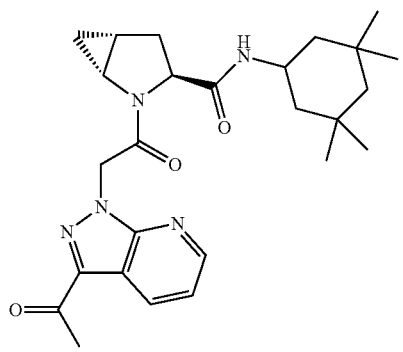 [SMILES: CC(=O)c1nn(CC(=O)N2[C@@H]3C[C@@H]3C[C@H]2C(=O)NC2CC(C)(C)CC(C)(C)C2)c2ncccc12] | (1R,3S,5R)-2-[2-(3-Acetyl-pyrazolo[3,4-b]pyridin-1-yl)-acetyl]-2-aza-bicyclo[3.1.0]hexane-3-carboxylic acid (3,3,5,5-tetramethyl-cyclohexyl)-amide | (1[B2]); 466.1 [M+H]+, 488.0 [M+Na]+; $t_R$ (e): 3.46 min. |
| 7 | 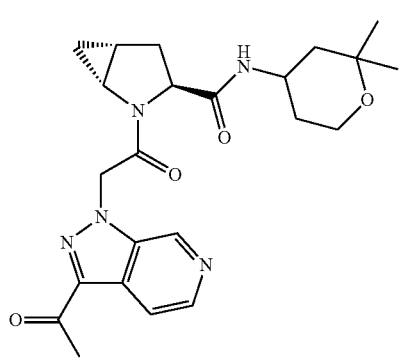 [SMILES: CC(=O)c1nn(CC(=O)N2[C@@H]3C[C@@H]3C[C@H]2C(=O)NC2CCOC(C)(C)C2)c2cnccc12] | (1R,3S,5R)-2-[2-(3-Acetyl-pyrazolo[3,4-c]pyridin-1-yl)-acetyl]-2-aza-bicyclo[3.1.0]hexane-3-carboxylic acid (2,2-dimethyl-tetrahydro-pyran-4-yl)-amide | (1[B3]); 440.0 [M+H]+, 462.1 [M+Na]+; $t_R$ (b): 2.98 min. |

TABLE 1-continued

| Example | Structure | Name | Characterization (end-table notes); MS (LC/MS); $t_R$ (HPLC conditions) |
|---|---|---|---|
| 8 | 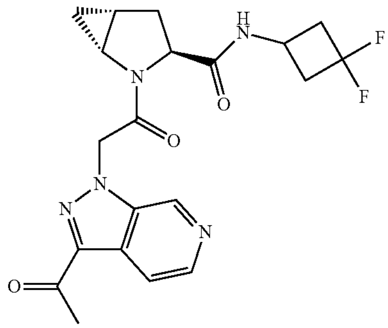 [SMILES: CC(=O)c1nn(CC(=O)N2[C@@H]3C[C@@H]3C[C@H]2C(=O)NC2CC(F)(F)C2)c2cnccc12] | (1R,3S,5R)-2-[2-(3-Acetyl-pyrazolo[3,4-c]pyridin-1-yl)-acetyl]-2-aza-bicyclo[3.1.0]hexane-3-carboxylic acid (3,3-difluoro-cyclobutyl)-amide | (1[B3]); 418.0 [M+H]+, 439.9 [M+Na]+; $t_R$ (d): 2.55 min. |
| 9 | 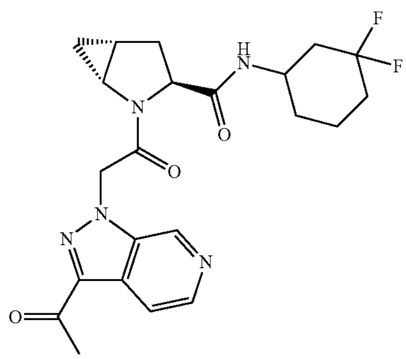 [SMILES: CC(=O)c1nn(CC(=O)N2[C@@H]3C[C@@H]3C[C@H]2C(=O)NC2CCCC(F)(F)C2)c2cnccc12] | (1R,3S,5R)-2-[2-(3-Acetyl-pyrazolo[3,4-c]pyridin-1-yl)-acetyl]-2-aza-bicyclo[3.1.0]hexane-3-carboxylic acid (3,3-difluoro-cyclohexyl)-amide | (1[B3]); 446.0 [M+H]+, 468.0 [M+Na]+; $t_R$ (b): 3.39 min. |
| 10 | 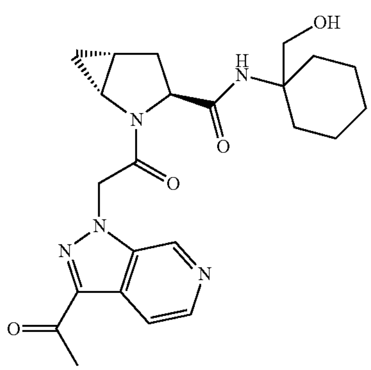 [SMILES: CC(=O)c1nn(CC(=O)N2[C@@H]3C[C@@H]3C[C@H]2C(=O)NC2(CO)CCCCC2)c2cnccc12] | (1R,3S,5R)-2-[2-(3-Acetyl-pyrazolo[3,4-c]pyridin-1-yl)-acetyl]-2-aza-bicyclo[3.1.0]hexane-3-carboxylic acid (1-hydroxymethyl-cyclohexyl)-amide | (1[B3]); 440.0 [M+H]+, 462.0 [M+Na]+; $t_R$ (e): 1.54 min. |
| 11 | 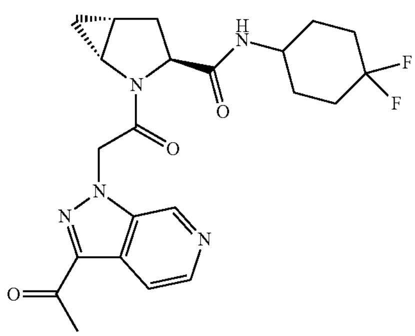 [SMILES: CC(=O)c1nn(CC(=O)N2[C@@H]3C[C@@H]3C[C@H]2C(=O)NC2CCC(F)(F)CC2)c2cnccc12] | (1R,3S,5R)-2-[2-(3-Acetyl-pyrazolo[3,4-c]pyridin-1-yl)-acetyl]-2-aza-bicyclo[3.1.0]hexane-3-carboxylic acid (4,4-difluoro-cyclohexyl)-amide | (1[B3]); 446.0 [M+H]+, 468.0 [M+Na]+; $t_R$ (e): 1.75 min. |

TABLE 1-continued

| Example | Name | Characterization (end-table notes); MS (LC/MS); $t_R$ (HPLC conditions) |
|---|---|---|
| 12 | (1R,3S,5R)-2-[2-(3-Acetyl-pyrazolo[3,4-b]pyridin-1-yl)-acetyl]-2-aza-bicyclo[3.1.0]hexane-3-carboxylic acid ((1R,3R)-3-carbamoyl-cyclopentyl)-amide | (1[B2], 2[C2]); 439.0 [M+H]+, 483.3 [M+HCOO]−; $t_R$ (e): 1.26 min. |
| 13 | (1R,3R)-3-({(1R,3S,5R)-2-[2-(3-Acetyl-pyrazolo[3,4-b]pyridin-1-yl)-acetyl]-2-aza-bicyclo[3.1.0]hexane-3-carbonyl}-amino)-cyclopentane carboxylic acid methyl ester | (1[B2], 2[C3]); 454.0 [M+H]+, 476.0 [M+Na]+; $t_R$ (e): 2.35 min. |
| 14 | (1R,3S)-3-({(1R,3S,5R)-2-[2-(3-Acetyl-pyrazolo[3,4-b]pyridin-1-yl)-acetyl]-2-aza-bicyclo[3.1.0]hexane-3-carbonyl}-amino)-cyclohexanecarboxylic acid methyl ester | (1[B2], 2[C3]); 468.1 [M+H]+, 490.0 [M+Na]+; $t_R$ (e): 2.60 min. |

(1) The substituted acid derivative was prepared as described in Part B [Scheme];
(2) The substituted amine derivative was prepared as described in Part C [Scheme];
(3) T$_3$P was used instead of HBTU in step A.

Scheme D2: General protocol described for the preparation of Example 15: (1R, 3S, 5R)-2-Aza-bicyclo[3.1.0]hexane-2,3-dicarboxylic acid 2-[(1-carbamoyl-1H-indol-3-yl)-amide]3-cyclohexylamide

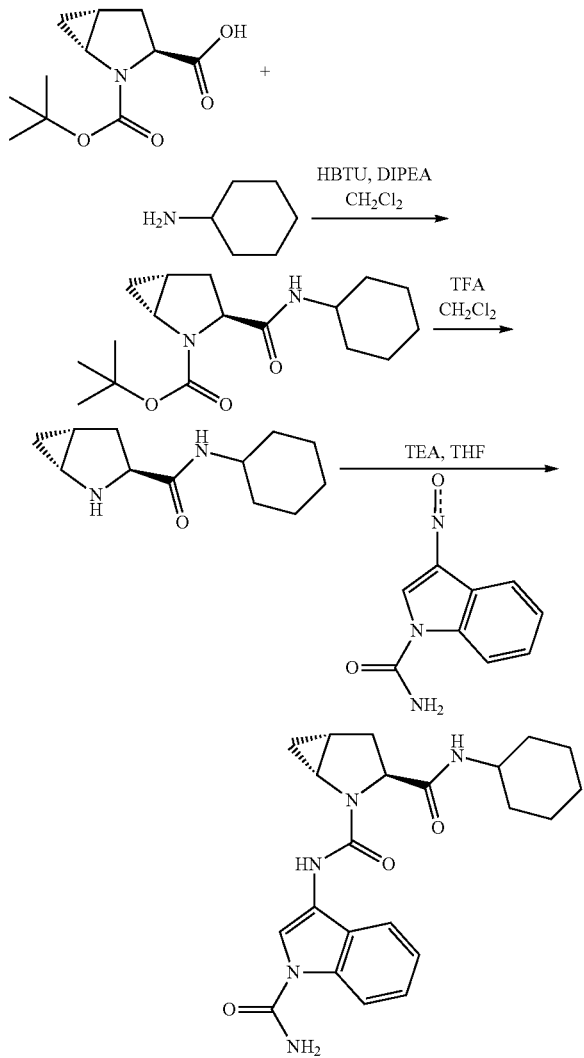

A. (1R,3S,5R)-3-Cyclohexylcarbamoyl-2-aza-bicyclo[3.1.0]hexane-2-carboxylic acid tert-butyl ester To a solution of (1R,3S,5R)-2-aza-bicyclo[3.1.0]hexane-2,3-dicarboxylic acid 2-tert-butyl ester (250 mg, 1.1 mmol), cyclohexylamine (0.132 mL, 1.15 mmol) and HBTU (621 mg, 1.65 mmol) in $CH_2Cl_2$ (11 mL) was added DIPEA (0.576 mL, 3.3 mmol). The reaction mixture was stirred at RT overnight, concentrated and the product was purified by preparative HPLC (Waters Sunfire, C18-OBD, 5 μm, 30×100 mm, flow: 40 mL/min, eluent: 20 to 100% $CH_3CN$ in $H_2O$ in 20 min, $CH_3CN$ and $H_2O$ containing 0.1% TFA). The pure fractions were combined and lyophilized to afford the title compound. MS (UPLC/MS): 309.4 [M+H]+; $t_R$ (HPLC conditions c): 2.01 min.

B. (1R,3S,5R)-2-Aza-bicyclo[3.1.0]hexane-3-carboxylic acid cyclohexylamide trifluoroacetate To a solution of (1R,3S,5R)-3-cyclohexylcarbamoyl-2-aza-bicyclo[3.1.0]hexane-2-carboxylic acid tert-butyl ester (341 mg, 1.10 mmol) in $CH_2Cl_2$ (10 mL) was added TFA (5 mL) and the resulting mixture was stirred at RT for 3 h. The reaction mixture was concentrated, suspended in MeOH and concentrated again to give the title compound which was used in the next step without further purification. MS (UPLC/MS): 209.3 [M+H]+; $t_R$ (HPLC conditions c): 1.10 min.

C. Example 15: (1R,3S,5R)-2-Aza-bicyclo[3.1.0]hexane-2,3-dicarboxylic acid 2-[(1-carbamoyl-1H-indol-3-yl)-amide]3-cyclohexylamide To a solution of (1R,3S,5R)-2-aza-bicyclo[3.1.0]hexane-3-carboxylic acid cyclohexylamide trifluoroacetate (100 mg, 0.31 mmol) and TEA (0.108 mL, 0.77 mmol) in THF (5 mL) was added 3-isocyanato-indole-1-carboxylic acid amide (prepared as described in part A, 62 mg, 0.31 mmol). The reaction mixture was stirred at RT under inert atmosphere for 1 h, subsequently concentrated and the product was purified by preparative HPLC (Waters Sunfire, C18-OBD, 5 μm, 30×100 mm, flow: 40 mL/min, eluent: 20 to 100% $CH_3CN$ in $H_2O$ in 20 min, $CH_3CN$ and $H_2O$ containing 0.1% TFA). The pure fractions were combined and lyophilized to afford the title compound. MS (UPLC/MS): 410.4 [M+H]+; $t_R$ (HPLC conditions c): 1.80 min.

The examples below were prepared according to the general procedure described in Scheme D2 for the preparation of Example 15 from commercially available building blocks, if not otherwise stated (see notes at the end of table 2). In case a racemic amine is used in step A, the mixture of diastereoisomers can be separated either in step A or C (for details, refer to Separation method section).

TABLE 2

| Example | Structure | Name | Characterization (end-table notes); MS (LC/MS); $t_R$ (HPLC conditions) |
|---|---|---|---|
| 16 | 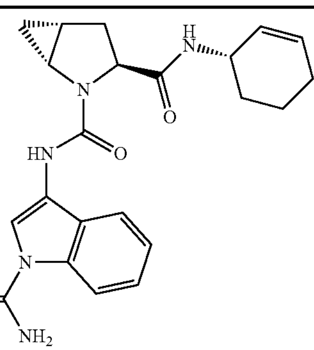 | (1R,3S,5R)-2-Aza-bicyclo[3.1.0]hexane-2,3-dicarboxylic acid 2-[(1-carbamoyl-1H-indol-3-yl)-amide] 3-(S)-cyclohex-2-enylamide | 408 [M+H]+; $t_R$ (d): 3.79 min. |

TABLE 2-continued

| Example | Structure | Name | Characterization (end-table notes); MS (LC/MS); $t_R$ (HPLC conditions) |
|---|---|---|---|
| 17 | 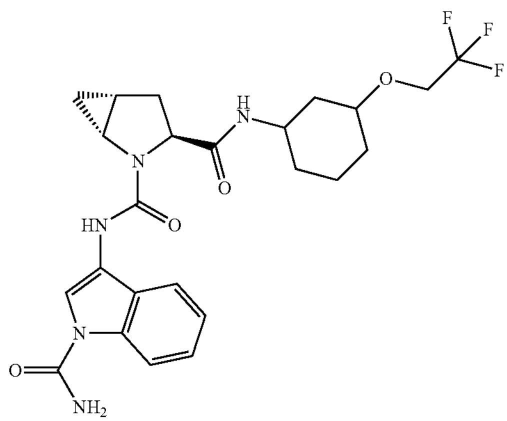 [SMILES: NC(=O)n1cc(NC(=O)N2[C@@H]3C[C@@H]3C[C@H]2C(=O)NC2CCCC(OCC(F)(F)F)C2)c2ccccc21] | (1R,3S,5R)-2-Aza-bicyclo[3.1.0]hexane-2,3-dicarboxylic acid 2-[(1-carbamoyl-1H-indol-3-yl)-amide] 3-{[3-(2,2,2-trifluoro-ethoxy)-cyclohexyl]-amide}-Dia 1 | (4[Method 1]); 508.0 [M+H]+; $t_R$ (b): 4.43 min. |
| 18 | 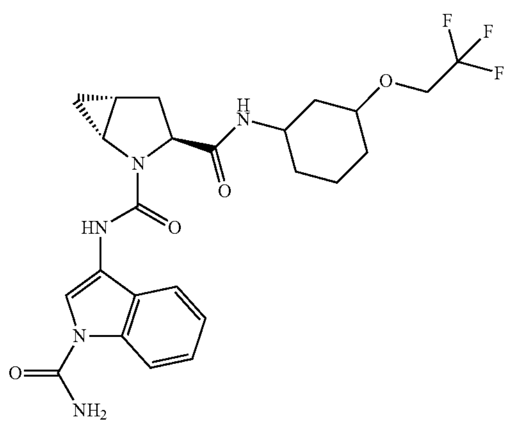 [SMILES: NC(=O)n1cc(NC(=O)N2[C@@H]3C[C@@H]3C[C@H]2C(=O)NC2CCCC(OCC(F)(F)F)C2)c2ccccc21] | (1R,3S,5R)-2-Aza-bicyclo[3.1.0]hexane-2,3-dicarboxylic acid 2-[(1-carbamoyl-1H-indol-3-yl)-amide] 3-{[3-(2,2,2-trifluoro-ethoxy)-cyclohexyl]-amide}-Dia 2 | (4[Method 1]); 508.0 [M+H]+; $t_R$ (b): 4.38 min. |
| 19 | 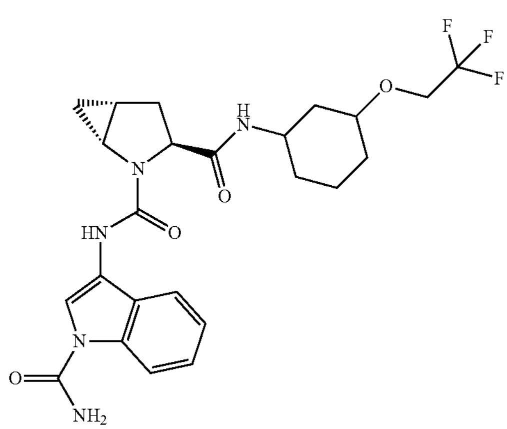 [SMILES: NC(=O)n1cc(NC(=O)N2[C@@H]3C[C@@H]3C[C@H]2C(=O)NC2CCCC(OCC(F)(F)F)C2)c2ccccc21] | (1R,3S,5R)-2-Aza-bicyclo[3.1.0]hexane-2,3-dicarboxylic acid 2-[(1-carbamoyl-1H-indol-3-yl)-amide] 3-{[3-(2,2,2-trifluoro-ethoxy)-cyclohexyl]-amide}-Dia 3 | (4[Method 1]); 508.0 [M+H]+; $t_R$ (b): 4.44 min. |

TABLE 2-continued

| Example | Structure | Name | Characterization (end-table notes); MS (LC/MS); $t_R$ (HPLC conditions) |
|---|---|---|---|
| 20 | 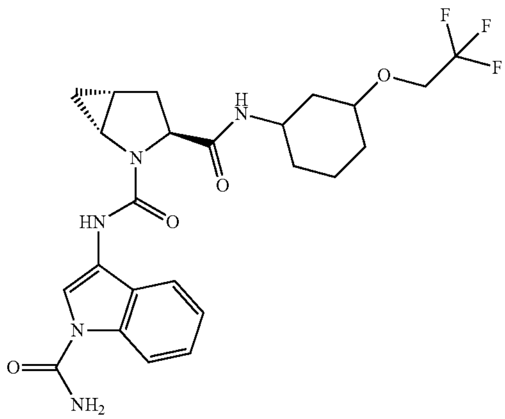 [SMILES: NC(=O)n1cc(NC(=O)N2[C@@H]3C[C@@H]3C[C@H]2C(=O)NC2CCCC(OCC(F)(F)F)C2)c2ccccc21] | (1R,3S,5R)-2-Aza-bicyclo[3.1.0]hexane-2,3-dicarboxylic acid 2-[(1-carbamoyl-1H-indol-3-yl)-amide] 3-{[3-(2,2,2-trifluoro-ethoxy)-cyclohexyl]-amide}-Dia 4 | (4[Method 1]); 508.0 [M+H]+; $t_R$ (b): 4.39 min. |
| 21 | 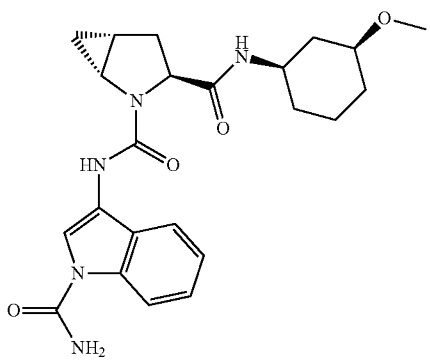 [SMILES: CO[C@H]1CCC[C@@H](NC(=O)[C@@H]2C[C@H]3C[C@H]3N2C(=O)Nc2cn(C(N)=O)c3ccccc23)C1] | (1R,3S,5R)-2-Aza-bicyclo[3.1.0]hexane-2,3-dicarboxylic acid 2-[(1-carbamoyl-1H-indol-3-yl)-amide] 3-[((1R,3S)-3-methoxy-cyclohexyl)-amide] | 440.0 [M+H]+; $t_R$ (b): 3.76 min. |
| 22 | 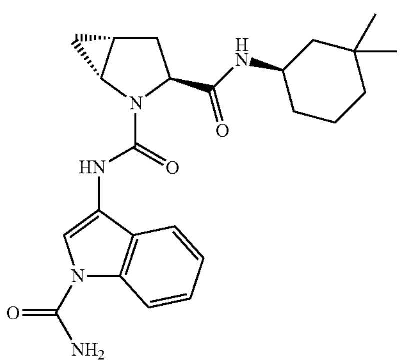 [SMILES: CC1(C)CCC[C@@H](NC(=O)[C@@H]2C[C@H]3C[C@H]3N2C(=O)Nc2cn(C(N)=O)c3ccccc23)C1] | (1R,3S,5R)-2-Aza-bicyclo[3.1.0]hexane-2,3-dicarboxylic acid 2-[(1-carbamoyl-1H-indol-3-yl)-amide] 3-[((R)-3,3-dimethyl-cyclohexyl)-amide] | (1,2,4[Method 2]); 438.1 [M+H]+, 460.0 [M+Na]+; $t_R$ (d): 3.39 min. |
| 23 | 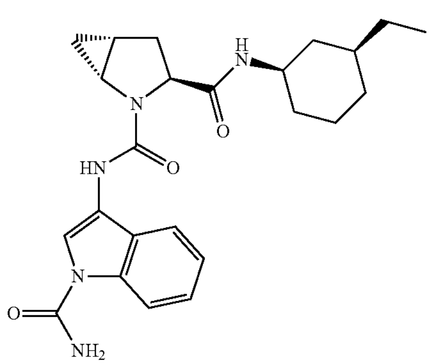 [SMILES: CC[C@H]1CCC[C@@H](NC(=O)[C@@H]2C[C@H]3C[C@H]3N2C(=O)Nc2cn(C(N)=O)c3ccccc23)C1] | (1R,3S,5R)-2-Aza-bicyclo[3.1.0]hexane-2,3-dicarboxylic acid 2-[(1-carbamoyl-1H-indol-3-yl)-amide] 3-[((1R,3S)-3-ethyl-cyclohexyl)-amide] | (1, 2, 4[Method 3]); 438.1 [M+H]+; $t_R$ (b): 4.64 min. |

TABLE 2-continued

| Example | Structure | Name | Characterization (end-table notes); MS (LC/MS); $t_R$ (HPLC conditions) |
|---|---|---|---|
| 24 | 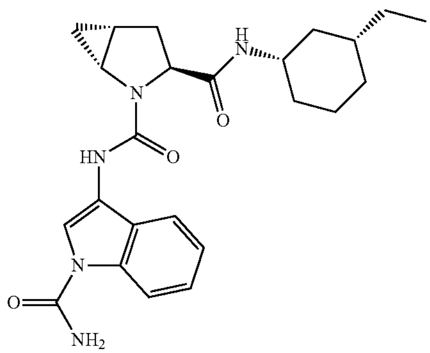 [SMILES: CC[C@@H]1CCC[C@H](NC(=O)[C@@H]2C[C@H]3C[C@H]3N2C(=O)Nc2cn(C(N)=O)c3ccccc23)C1] | (1R,3S,5R)-2-Aza-bicyclo[3.1.0]hexane-2,3-dicarboxylic acid 2-[(1-carbamoyl-1H-indol-3-yl)-amide] 3-[((1S,3R)-3-ethyl-cyclohexyl)-amide] | (1, 2, 4[Method 3]); 438.1 [M+H]+; $t_R$ (b): 4.60 min. |
| 25 | 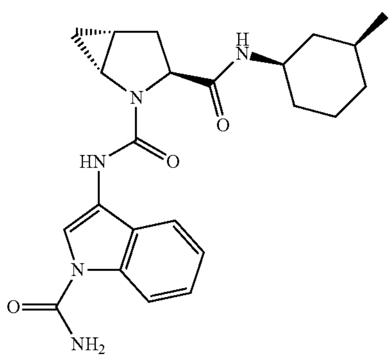 [SMILES: C[C@H]1CCC[C@@H](NC(=O)[C@@H]2C[C@H]3C[C@H]3N2C(=O)Nc2cn(C(N)=O)c3ccccc23)C1] | (1R,3S,5R)-2-Aza-bicyclo[3.1.0]hexane-2,3-dicarboxylic acid 2-[(1-carbamoyl-1H-indol-3-yl)-amide] 3-[((1R,3S)-3-methyl-cyclohexyl)-amide] | (1, 2, 4[Method 4]); 424.0 [M+H]+, 446.0 [M+Na]+; $t_R$ (b): 4.37 min. |
| 26 | 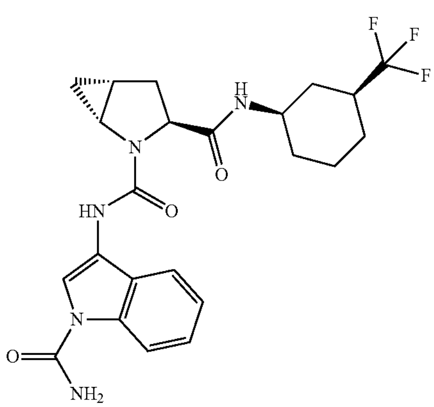 [SMILES: NC(=O)n1cc(NC(=O)N2[C@@H]3C[C@@H]3C[C@H]2C(=O)N[C@@H]2CCC[C@H](C(F)(F)F)C2)c2ccccc21] | (1R,3S,5R)-2-Aza-bicyclo[3.1.0]hexane-2,3-dicarboxylic acid 2-[(1-carbamoyl-1H-indol-3-yl)-amide] 3-[((1R,3S)-3-trifluoromethyl-cyclohexyl)-amide] | (1, 2, 3[C5]); 478.0 [M+H]+, 500.0 [M+Na]+; $t_R$ (b): 4.41 min. |

TABLE 2-continued

| Example | Structure | Name | Characterization (end-table notes); MS (LC/MS); $t_R$ (HPLC conditions) |
|---|---|---|---|
| 27 | 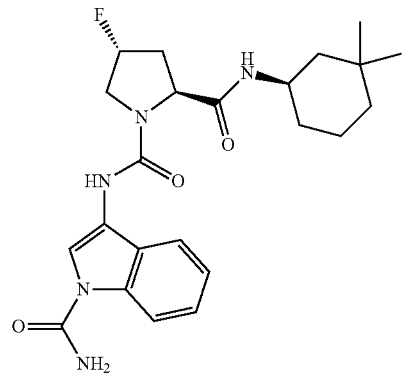 [SMILES: CC1(C)CCC[C@@H](NC(=O)[C@@H]2C[C@@H](F)CN2C(=O)Nc2cn(C(N)=O)c3ccccc23)C1] | (2S,4R)-4-Fluoro-pyrrolidine-1,2-dicarboxylic acid 1-[(1-carbamoyl-1H-indol-3-yl)-amide] 2-[((R)-3,3-dimethyl-cyclohexyl)-amide] | (1, 2, 4[Method 5]); 444.3 [M+H]+, 442.4 [M−H]−; $t_R$ (b): 4.33 min. |

(1) DMF was used instead of CH₂Cl₂ in step A;
(2) HCl (4 M/dioxane) in dioxane was used instead of TFA in CH₂Cl₂ in step B;
(3) The substituted amine derivative used in step A was prepared as described in Part C [Scheme];
(4) For details concerning the separation of diastereoisomers and assignement of stereochemistry see Separation section [Method].

Scheme D3: General protocol described for the preparation of Example 28: 1-{2-[(1R, 3S, 5R)-3-(3,3-Dimethyl-piperidin-1-ylcarbamoyl)-2-aza-bicyclo[3.1.0]hex-2-yl]-2-oxo-ethyl}-6-methyl-1H-indazole-3-carboxylic acid amide

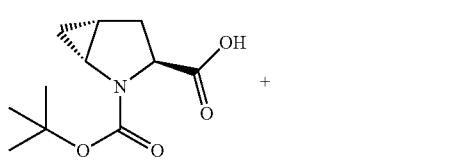

+

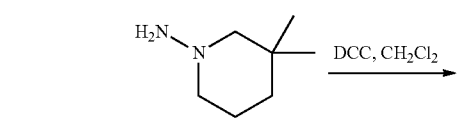

DCC, CH₂Cl₂ →

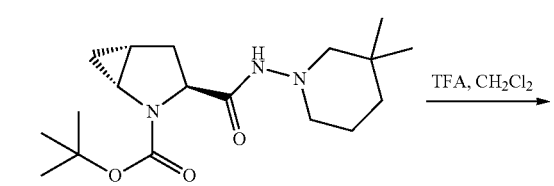

TFA, CH₂Cl₂ →

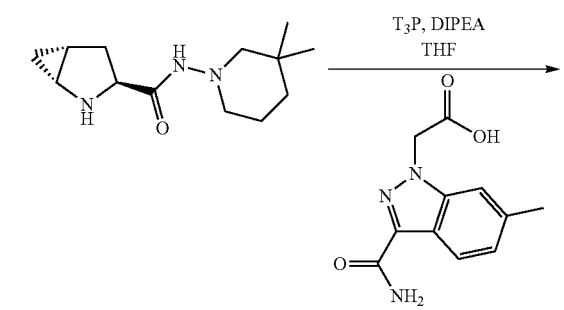

T₃P, DIPEA
THF
→

-continued

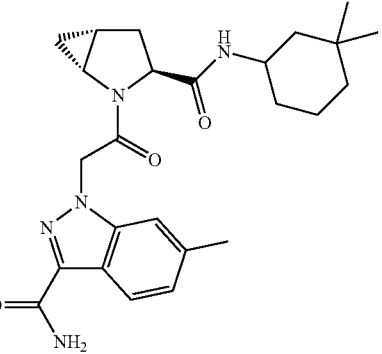

A. (1R,3S,5R)-3-(3,3-Dimethyl-piperidin-1-ylcarbamoyl)-2-aza-bicyclo[3.1.0]hexane-2-carboxylic acid tert-butyl ester To a solution of (1R,3S,5R)-2-aza-bicyclo[3.1.0]hexane-2,3-dicarboxylic acid 2-tert-butyl ester (650 mg, 2.86 mmol) in THF (30 mL) was added DCC (590 mg, 2.86 mmol). After 5 min stirring, 3,3-dimethyl-piperidin-1-ylamine (prepared as described in part C, 403 mg, 3.15 mmol) was added and the reaction mixture was stirred overnight at RT. The precipitate formed was filtered and the filtrate evaporated to dryness. The crude residue was purified by flash column chromatography on silica gel (c-hexane/EtOAc 10:0 to 6:4) to afford the title compound. MS (UPLC/MS): 338.3 [M+H]+; $t_R$ (UPLC conditions g): 1.10 min.

B. (1R,3S,5R)-2-Aza-bicyclo[3.1.0]hexane-3-carboxylic acid (3,3-dimethyl-piperidin-1-yl)-amide trifluoroacetate To a solution of (1R,3S,5R)-3-(3,3-dimethyl-piperidin-1-ylcarbamoyl)-2-aza-bicyclo[3.1.0]hexane-2-carboxylic acid tert-butyl ester (620 mg, 1.84 mmol) in CH₂Cl₂ (10 mL) was added TFA (1.41 mL, 18.37 mmol). The reaction mixture was stirred overnight at RT and concentrated. The product was used in the next step without further purification. MS (UPLC/MS): 238.2 [M+H]+; $t_R$ (UPLC conditions g): 0.53 min.

C. Example 28: 1-{2-[(1R,3S,5R)-3-(3,3-Dimethyl-piperidin-1-ylcarbamoyl)-2-aza-bicyclo[3.1.0]hex-2-yl]-2-oxo-ethyl}-6-methyl-1H-indazole-3-carboxylic acid amide To a solution of (1R,3S,5R)-2-aza-bicyclo[3.1.0]hexane-3-carboxylic acid (3,3-dimethyl-piperidin-1-yl)-amide trifluoroacetate (100 mg, 0.14 mmol), (3-carbamoyl-6-methyl-indazol-1-yl)-acetic acid (prepared as described in part A, 41.7 mg, 0.15 mmol) and $T_3P$ (50% in EtOAc, 0.123 ml, 0.210 mmol) in $CH_2Cl_2$ (5 mL) was added DIPEA (0.07 mL, 0.42 mmol). The reaction mixture was stirred for 1 h at RT, concentrated and the product purified by preparative HPLC (Waters Sunfire C18 OBD, 5 μm, 30×100 mm, gradient: 5 to 100% $CH_3CN$ in $H_2O$ in 20 min, Flow 40 mL/min). MS (UPLC/MS): 453.2 [M+H]+; $t_R$ (HPLC conditions c): 1.63 min.

The examples below were prepared according to the general procedures described in Scheme D3 for the preparation of Example 28 from commercially available building blocks, if not otherwise stated (see notes at the end of table 3):

Scheme D4: General protocol described for the preparation of Example 31: (1R,3S,5R)-2-[2-(3-Acetyl-pyrazolo[3,4-c]pyridin-1-yl)-acetyl]-2-aza-bicyclo[3.1.0]hexane-3-carboxylic acid (3-hydroxy-3-trifluoromethyl-cyclohexyl)-amide

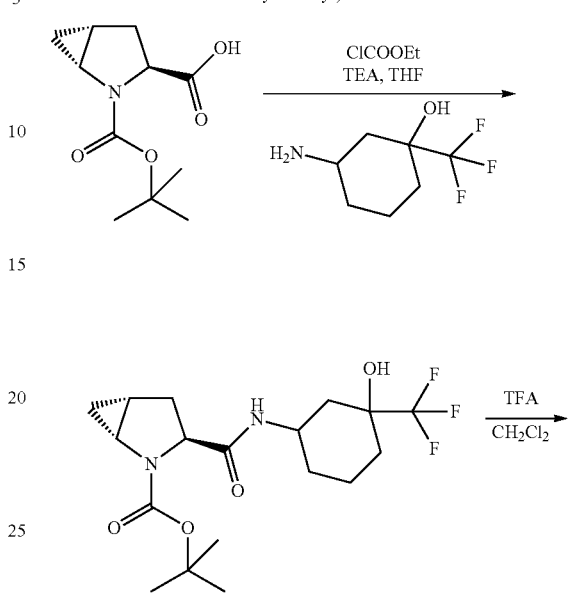

TABLE 3

| Example | Structure | Name | Characterization (end-table notes); MS (LC/MS); $t_R$ (HPLC conditions) |
|---|---|---|---|
| 29 | 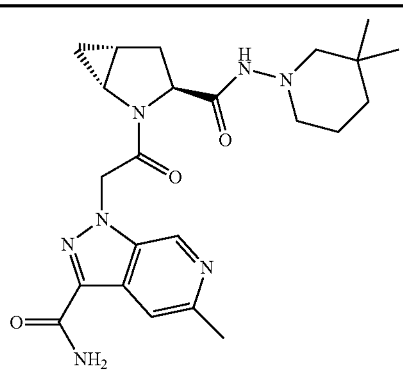 | 1{2-[(1R,3S,5R)-3-(3,3-Dimethyl-pipendin-1-ylcarbamoyl)-2-aza-bicyclo[3.1.0]hex-2-yl]-2-oxo-ethyl}-5-methyl-1H-pyrazolo[3,4-c]pyridine-3-carboxylic acid amide | (1[A8]); 454.3 [M+H]+, 498.2 [M+HCOO]−; $t_R$ (c): 1.19 min. |
| 30 | 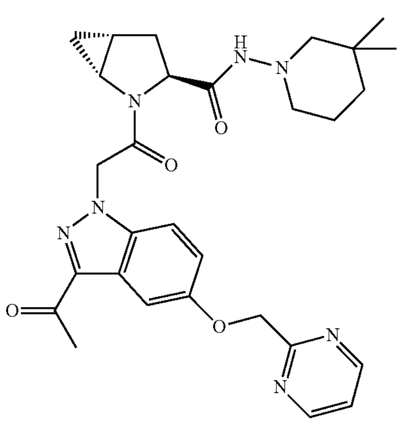 [SMILES: CC(=O)c1nn(CC(=O)N2[C@@H]3C[C@@H]3C[C@H]2C(=O)NN2CCCC(C)(C)C2)c2ccc(OCc3ncccn3)cc12] | (1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid (3,3-dimethyl-piperidin-1-yl)-amide | (1[A3]); 546.3 [M+H]+, 590.3 [M+HCOO]−; $t_R$ (c): 1.73 min. |

(1) The substituted acid derivative used in step C was prepared as described in Part A [Scheme]

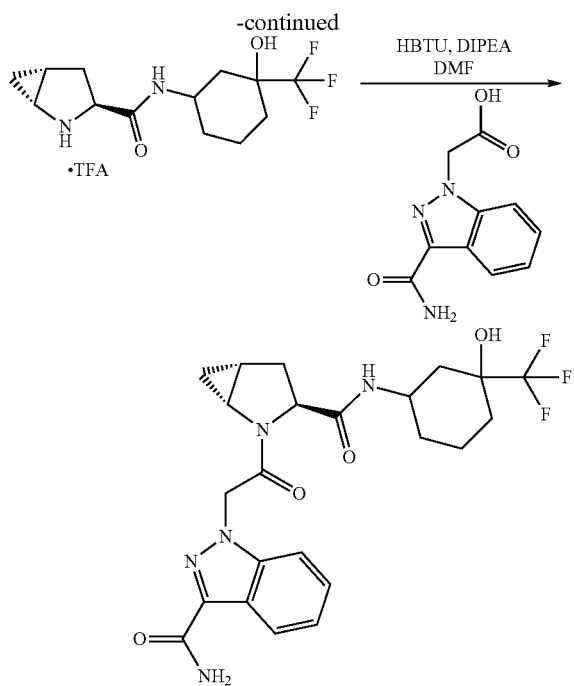

A. (1R,3S,5R)-3-(3-Hydroxy-3-trifluoromethyl-cyclohexylcarbamoyl)-2-aza-bicyclo[3.1.0]hexane-2-carboxylic acid tert-butyl ester To a solution of (1R,3S,5R)-2-aza-bicyclo[3.1.0]hexane-2,3-dicarboxylic acid 2-tert-butyl ester (0.087 g, 0.38 mmol) in dry THF (2 mL) at −20° C. under nitrogen atmosphere was added TEA (0.11 mL, 0.764 mmol) and subsequently in a dropwise manner ethylchloroformate (0.37 mL, 0.382 mmol). The reaction mixture was stirred at −20° C. for 90 min, and a solution of 3-amino-1-trifluoromethyl-cyclohexanol (0.07 g, 0.382 mmol) in dry THF (2 mL) was added. The reaction mixture was further stirred at −20° C. for 1 h, warmed up to RT and stirred at 65° C. for 16 h. The reaction mixture was diluted with EtOAc, washed with sat. aq. NH$_4$Cl and brine, dried (phase separator) and concentrated to give the title compound as a mixture of diastereoisomers which was used without further purification in the next step. MS: 393.0 [M+H]+, 391.9 [M−H]−.

B. (1R,3S,5R)-2-Aza-bicyclo[3.1.0]hexane-3-carboxylic acid (3-hydroxy-3-trifluoromethyl-cyclohexyl)-amide trifluoroacetate To a solution of (1R,3S,5R)-3-(3-hydroxy-3-trifluoromethyl-cyclohexylcarbamoyl)-2-aza-bicyclo[3.1.0]hexane-2-carboxylic acid tert-butyl ester (0.15 g, 0.38 mmol) in CH$_2$Cl$_2$ (2.5 mL) was added TFA (0.29 mL, 3.82 mmol). The reaction mixture was stirred at RT for 16 h and concentrated in vacuo. The residue was suspended in MeOH, concentrated and dried under vacuo to give the title compound as a yellow oil, which was used without further purification in the next step. MS: 293.0 [M+H]+.

C. Example 31: 1-{2-[(1R,3S,5R)-3-(3-Hydroxy-3-trifluoromethyl-cyclohexylcarbamoyl)-2-aza-bicyclo[3.1.0]hex-2-yl]-2-oxo-ethyl}-1H-indazole-3-carboxylic acid amide To a solution of (3-carbamoyl-indazol-1-yl)-acetic acid (prepared as described in Part A, 34.4 mg, 0.10 mmol) in DMF (1 mL) were successively added (1R,3S,5R)-2-aza-bicyclo[3.1.0]hexane-3-carboxylic acid (3-hydroxy-3-trifluoromethyl-cyclohexyl)-amide trifluoroacetate (40 mg, 0.098 mmol), DIPEA (0.69 mL, 0.394 mmol) and HBTU (44.8 mg, 0.118 mmol). The reaction mixture was stirred at RT for 2 h, concentrated and the product was purified by preparative HPLC (Waters Sunfire C18-OBD, 5 µm, 30×100 mm, flow: 40 mL/min, eluent: 5% to 100% CH$_3$CN in H$_2$O in 20 min, CH$_3$CN and H$_2$O containing 0.1% TFA). The pure fractions were combined, CH$_3$CN was evaporated and the resulting aq. solution was lyophilized to give the title compound as a mixture of diastereoisomers. MS: 494.0 [M+H]+, 492.1 [M−H]−; t$_R$ (HPLC conditions b): 3.37/3.47 min.

The examples below were prepared according to the general procedures described in Scheme D4 for the preparation of Example 31 from commercially available building blocks, if not otherwise stated (see notes at the end of table 4):

TABLE 4

| Example | Structure | Name | Characterization (end-table notes); MS (LC/MS); t$_R$ (HPLC conditions) |
|---------|-----------|------|----|
| 32 | 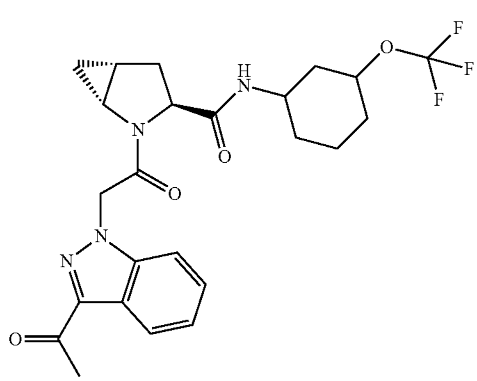 [SMILES: CC(=O)c1nn(CC(=O)N2[C@@H]3C[C@@H]3C[C@H]2C(=O)NC2CCCC(OC(F)(F)F)C2)c2ccccc12] | (1R,3S,5R)-2-[2-(3-Acetyl-indazol-1-yl)-acetyl]-2-aza-bicyclo[3.1.0]hexane-3-carboxylic acid (trans-3-trifluoromethoxy-cyclohexyl)-amide | 493.0 [M+H]+, 515.0 [M+Na]+; t$_R$ (b): 4.76 min |

TABLE 4-continued

| Example | Structure | Name | Characterization (end-table notes); MS (LC/MS); $t_R$ (HPLC conditions) |
|---|---|---|---|
| 33 | 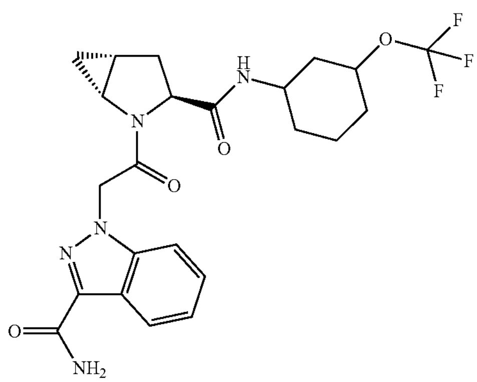 [SMILES: NC(=O)c1nn(CC(=O)N2[C@@H]3C[C@@H]3C[C@H]2C(=O)NC2CCCC(OC(F)(F)F)C2)c2ccccc12] | 1-{2-Oxo-2-[(1R,3S,5R)-3-(trans-3-trifluoromethoxy-cyclohexylcarbamoyl)-2-aza-bicyclo[3.1.0]hex-2-yl]ethyl}-1H-indazole-3-carboxylic acid amide | 494.3 [M+H]+, 516.3 [M+Na]+; $t_R$ (b): 4.26 min |
| 34 | 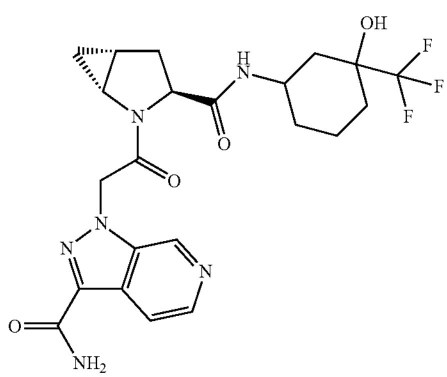 [SMILES: NC(=O)c1nn(CC(=O)N2[C@@H]3C[C@@H]3C[C@H]2C(=O)NC2CCCC(O)(C(F)(F)F)C2)c2cnccc12] | 1-{2-[(1R,3S,5R)-3-(3-Hydroxy-3-trifluoromethyl-cyclohexylcarbamoyl)-2-aza-bicyclo[3.1.0]hex-2-yl]-2-oxo-ethyl}-1H-pyrazolo[3,4-c]pyridine-3-carboxylic acid amide (mixture of diastereoisomers) | 495.1 [M+H]+, 493.1 [M–H]–; $t_R$ (b): 2.97/3.07 min |
| 35 | 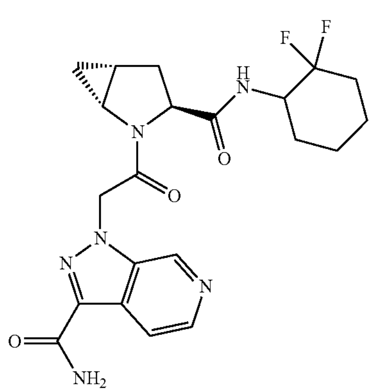 [SMILES: NC(=O)c1nn(CC(=O)N2[C@@H]3C[C@@H]3C[C@H]2C(=O)NC2CCCCC2(F)F)c2cnccc12] | 1-{2-[(1R,3S,5R)-3-(2,2-Difluoro-cyclohexylcarbamoyl)-2-aza-bicyclo[3.1.0]hex-2-yl]-2-oxo-ethyl}-1H-pyrazolo[3,4-c]pyridine-3-carboxylic acid amide | (1); 347.1 [M+H]+, 445.1 [M–H]–; tR (b): 2.97 min. |

(1) The title compound was synthetised from (1R,3S,5R)-3-(2,2-difluoro-cyclohexylcarbamoyl)-2-aza-bicyclo[3.1.0]hexane-2-carboxylic acid tert-butyl ester (described in Example 36) using the procedure described in step B and C of scheme D4 and using HCl in dioxane instead of TFA in step B.

Example 36: (1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid (2,2-difluoro-cyclohexyl)-amide—Dia 1

Example 37: (1R,3S,5R)-2-{2-[3-acetyl-5-(pyrimidin-2-ylmethoxy)-indazol-1-yl]-acetyl}-2-aza-bicyclo[3.1.0]hexane-3-carboxylic acid (2,2-difluoro-cyclohexyl)-amide—Dia 2 and Example 38: (1R,3S,5R)-2-{2-[3-acetyl-5-(pyrimidin-2-ylmethoxy)-indazol-1-yl]-acetyl}-2-aza-bicyclo[3.1.0]hexane-3-carboxylic acid (2-fluoro-cyclohex-2-enyl)-amide

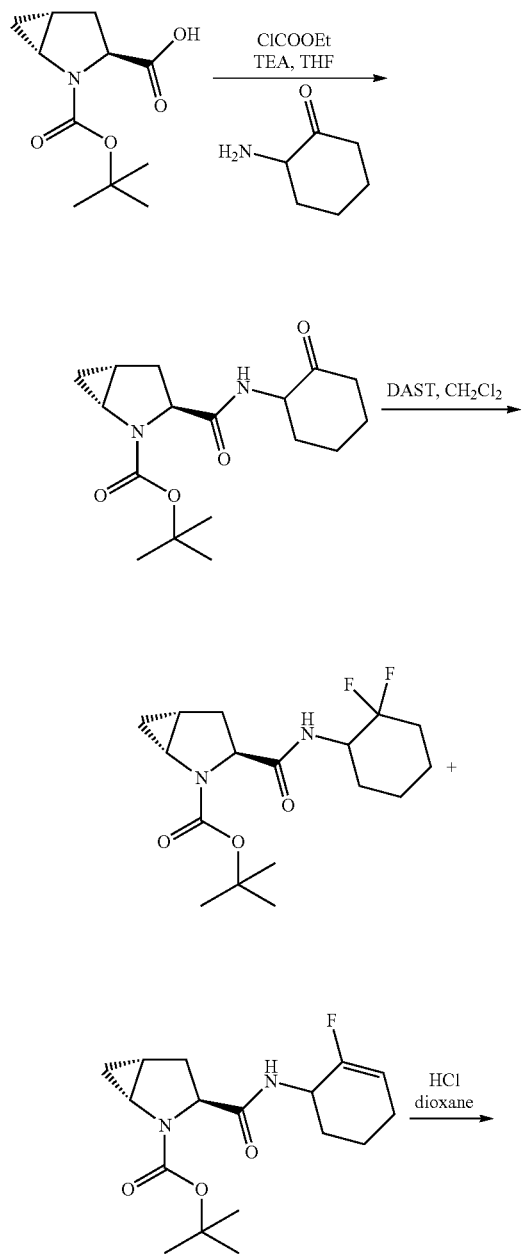

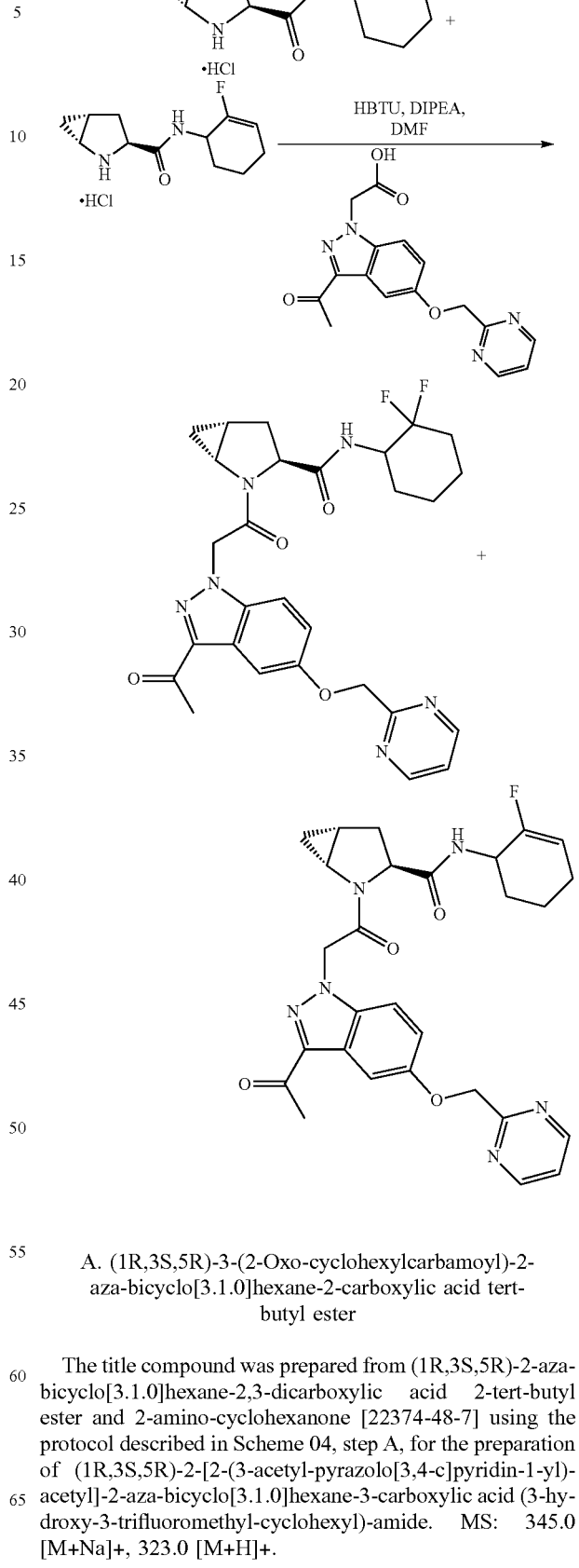

A. (1R,3S,5R)-3-(2-Oxo-cyclohexylcarbamoyl)-2-aza-bicyclo[3.1.0]hexane-2-carboxylic acid tert-butyl ester The title compound was prepared from (1R,3S,5R)-2-aza-bicyclo[3.1.0]hexane-2,3-dicarboxylic acid 2-tert-butyl ester and 2-amino-cyclohexanone [22374-48-7] using the protocol described in Scheme 04, step A, for the preparation of (1R,3S,5R)-2-[2-(3-acetyl-pyrazolo[3,4-c]pyridin-1-yl)-acetyl]-2-aza-bicyclo[3.1.0]hexane-3-carboxylic acid (3-hydroxy-3-trifluoromethyl-cyclohexyl)-amide. MS: 345.0 [M+Na]+, 323.0 [M+H]+.

B. (1R,3S,5R)-3-(2,2-Difluoro-cyclohexylcarbamoyl)-2-aza-bicyclo[3.1.0]hexane-2-carboxylic acid tert-butyl ester and (1R,3S,5R)-3-(2-fluoro-cyclohex-2-enylcarbamoyl)-2-aza-bicyclo[3.1.0]hexane-2-carboxylic acid tert-butyl ester To an ice-cold solution of (1R,3S,5R)-3-(2-oxo-cyclohexylcarbamoyl)-2-aza-bicyclo[3.1.0]hexane-2-carboxylic acid tert-butyl ester (1.15 g, 3.57 mmol) in $CH_2Cl_2$ (30 mL) was added dropwise diethylaminosulfur trifluoride (1.55 mL, 11.8 mmol). The reaction mixture was stirred at 5° C. for 15 min, then at RT for 18 h. The reaction mixture was quenched with 10 mL of sat. aq. $NaHCO_3$. Layers were separated and the organic layer was dried (phase separator) and concentrated. The crude residue was purified by flash chromatography on silica gel (c-hexane/EtOAc 66/33) to isolate a mixture of (1R,3S,5R)-3-(2,2-difluoro-cyclohexylcarbamoyl)-2-aza-bicyclo[3.1.0]hexane-2-carboxylic acid tert-butyl ester, MS: 367.0 [M+Na]+, 245.2 [M-Boc]+ and (1R,3S,5R)-3-(2-fluoro-cyclohex-2-enylcarbamoyl)-2-aza-bicyclo[3.1.0]hexane-2-carboxylic acid tert-butyl ester, MS: 347.2 [M+Na]+. Alternatively, (1R,3S,5R)-3-(2,2-difluoro-cyclohexylcarbamoyl)-2-aza-bicyclo[3.1.0]hexane-2-carboxylic acid tert-butyl ester was isolated from the crude mixture prepared as described in step B, by preparative HPLC-Mass (XBridge C18OBD, 5 µm, 30×100, flow: 45 ml/min, eluent: 5 to 99% $CH_3CN$ in $H_2O$ in 12 min, $CH_3CN$ and $H_2O$ containing 7.3 mM of $NH_3$). MS: 367.0 [M+Na]+, 245.1 [M-Boc]+.

C. (1R,3S,5R)-2-Aza-bicyclo[3.1.0]hexane-3-carboxylic acid (2,2-difluoro-cyclohexyl)-amide hydrochloride and (1R,3S,5R)-2-aza-bicyclo[3.1.0]hexane-3-carboxylic acid (2-fluoro-cyclohex-2-enyl)-amide hydrochloride To the mixture of (1R,3S,5R)-3-(2,2-difluoro-cyclohexylcarbamoyl)-2-aza-bicyclo[3.1.0]hexane-2-carboxylic acid tert-butyl ester and (1R,3S,5R)-3-(2-fluoro-cyclohex-2-enylcarbamoyl)-2-aza-bicyclo[3.1.0]hexane-2-carboxylic acid tert-butyl ester (0.9 g, 2.61 mmol) in dioxane (20 mL) was added 4N HCl in dioxane (6.53 mL, 26.1 mmol). The reaction mixture was stirred at RT for 16 h, frozen and lyophilized to afford a mixture of (1R,3S,5R)-2-aza-bicyclo[3.1.0]hexane-3-carboxylic acid (2,2-difluoro-cyclohexyl)-amide hydrochloride, MS: 245.1 [M+H]+ and (1R,3S,5R)-2-aza-bicyclo[3.1.0]hexane-3-carboxylic acid (2-fluoro-cyclohex-2-enyl)-amide hydrochloride, MS: 225.1 [M+H]+.

D. Example 36: (1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid (2,2-difluoro-cyclohexyl)-amide—Dia 1

Example 37: (1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid (2,2-difluoro-cyclohexyl)-amide—Dia 2 and Example 38: (1R,3S,5R)-2-{2-[3-acetyl-5-(pyrimidin-2-ylmethoxy)-indazol-1-yl]-acetyl}-2-aza-bicyclo[3.1.0]hexane-3-carboxylic acid (2-fluoro-cyclohex-2-enyl)-amide To the mixture of (1R,3S,5R)-2-aza-bicyclo[3.1.0]hexane-3-carboxylic acid (2,2-difluoro-cyclohexyl)-amide hydrochloride and (1R,3S,5R)-2-aza-bicyclo[3.1.0]hexane-3-carboxylic acid (2-fluoro-cyclohex-2-enyl)-amide hydrochloride (0.75 g, 2.09 mmol) in DMF (10 mL) were added [3-acetyl-5-(pyrimidin-2-ylmethoxy)-indazol-1-yl]-acetic acid (prepared as described in part A, 0.73 mg, 2.20 mmol), HBTU (1.19 g, 3.14 mmol) and DIPEA (1.46 mL, 8.37 mmol). The reaction mixture was stirred at RT for 18 h. The crude reaction mixture was directly subjected to purification by preparative HPLC-Mass (XBridge C18OBD, 5 µm, 30×100, flow: 45 mL/min, eluent: 5 to 99% $CH_3CN$ in $H_2O$ in 12 min, $CH_3CN$ and $H_2O$ containing 7.3 mM of $NH_3$) to give (1R,3S,5R)-2-{2-[3-acetyl-5-(pyrimidin-2-ylmethoxy)-indazol-1-yl]-acetyl}-2-aza-bicyclo[3.1.0]hexane-3-carboxylic acid (2-fluoro-cyclohex-2-enyl)-amide, MS: 533.2 [M+H]+; $t_R$ (HPLC conditions f): 3.27 min and (1R,3S,5R)-2-{2-[3-acetyl-5-(pyrimidin-2-ylmethoxy)-indazol-1-yl]-acetyl}-2-aza-bicyclo[3.1.0]hexane-3-carboxylic acid (2,2-difluoro-cyclohexyl)-amide as a mixture of 2 diastereoisomers, MS: 553.2 [M+H]+; $t_R$ (HPLC conditions f): 3.33 min. Preparative chiral SFC (column: Chiralpak AS-H, 250×30 mm; eluent: $scCO_2$: MeOH 83:17, flow rate: 80 mL/min, pressure: 150 bar) provided the single diastereoisomer: (1R,3S,5R)-2-{2-[3-acetyl-5-(pyrimidin-2-ylmethoxy)-indazol-1-yl]-acetyl}-2-aza-bicyclo[3.1.0]hexane-3-carboxylic acid (2,2-difluoro-cyclohexyl)-amide—Dia 1: $t_R$ (SFC, Chiralpak AS-H, 250×4.6 mm, $scCO_2$:MeOH 75:25, flow rate: 3 mL/min, detection: UV at 215 nm, pressure. 150 bar): 1.65 min and (1R,3S,5R)-2-{2-[3-acetyl-5-(pyrimidin-2-ylmethoxy)-indazol-1-yl]-acetyl}-2-aza-bicyclo[3.1.0]hexane-3-carboxylic acid (2,2-difluoro-cyclohexyl)-amide—Dia 2: $t_R$ (SFC, Chiralpak AS-H, 250×4.6 mm, $scCO_2$:MeOH 75:25, flow rate: 3 mL/min, detection: UV at 215 nm, pressure: 150 bar): 2.37 min.

Example 39: 1-{2-[(1R,3S,5R)-3-(3-Methoxy-3-trifluoromethyl-cyclohexylcarbamoyl)-2-aza-bicyclo[3.1.0]hex-2-yl]-2-oxo-ethyl}-1H-indazole-3-carboxylic acid amide—Dia mix 1

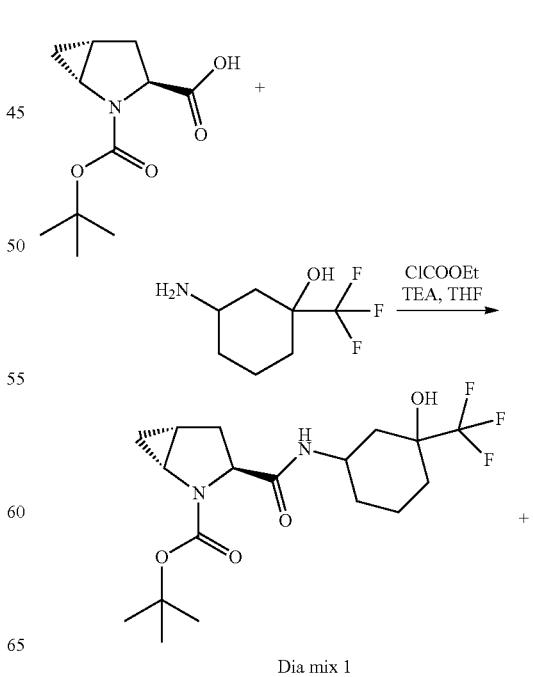

Dia mix 1

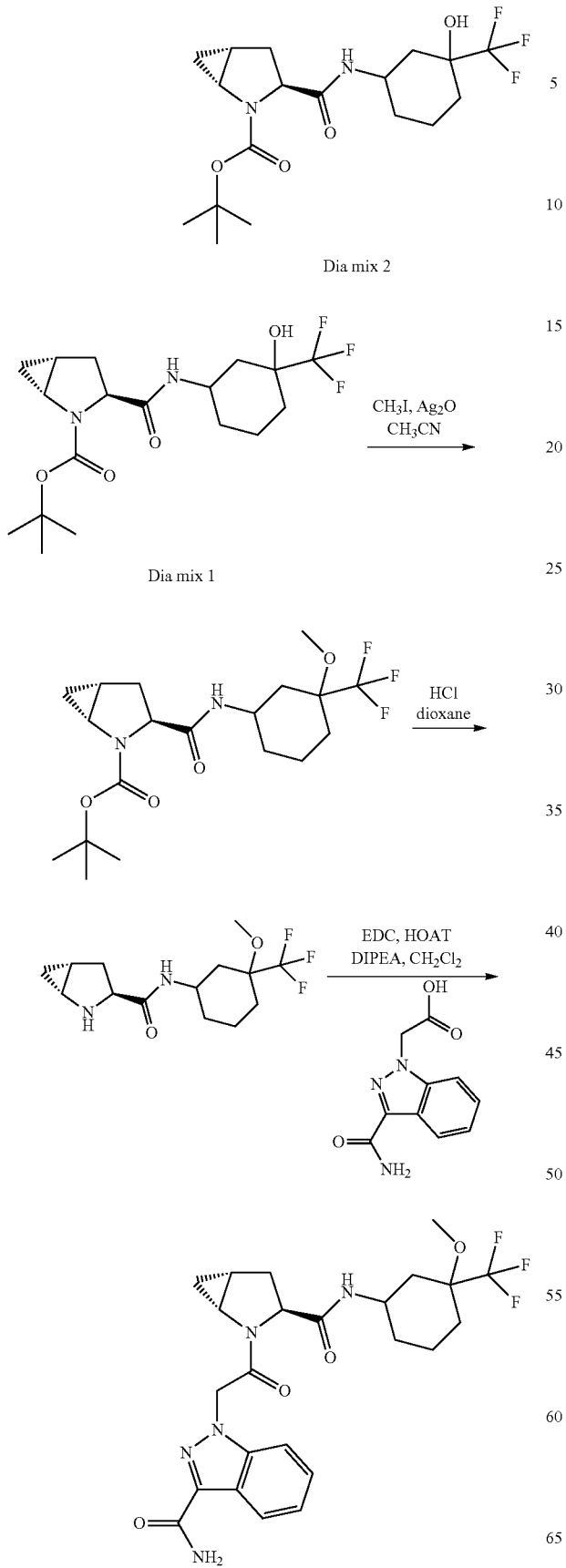

A. (1R,3S,5R)-3-(3-Hydroxy-3-trifluoromethyl-cyclohexylcarbamoyl)-2-aza-bicyclo[3.1.0]hexane-2-carboxylic acid tert-butyl ester—Dia mix 1 and Dia mix 2

The title compound was prepared from (1R,3S,5R)-2-aza-bicyclo[3.1.0]hexane-2,3-dicarboxylic acid 2-tert-butyl ester and 3-amino-1-trifluoromethyl-cyclohexanol using the protocol described in Scheme D4 step A for the preparation of (1R,3S,5R)-2-[2-(3-acetyl-pyrazolo[3,4-c]pyridin-1-yl)-acetyl]-2-aza-bicyclo[3.1.0]hexane-3-carboxylic acid (3-hydroxy-3-trifluoromethyl-cyclohexyl)-amide to give after purification by flash chromatography on silica gel (c-hexane/EtOAc 10/0 to 0/10): (1R,3S,5R)-3-(3-hydroxy-3-trifluoromethyl-cyclohexylcarbamoyl)-2-aza-bicyclo[3.1.0]hexane-2-carboxylic acid tert-butyl ester—Dia mix 1, TLC, $R_f$ (c-hexane/EtOAc 5/5)=0.26, MS: 393.0 [M+H]+ and (1R,3S,5R)-3-(3-hydroxy-3-trifluoromethyl-cyclohexylcarbamoyl)-2-aza-bicyclo[3.1.0]hexane-2-carboxylic acid tert-butyl ester—Dia mix 2, TLC, $R_f$ (c-hexane/EtOAc 5/5)=0.21, MS: 393.0 [M+H]+.

B. (1R,3S,5R)-3-(3-Methoxy-3-trifluoromethyl-cyclohexylcarbamoyl)-2-aza-bicyclo[3.1.0]hexane-2-carboxylic acid tert-butyl ester—Dia mix 1

To a solution of (1R,3S,5R)-3-(3-hydroxy-3-trifluoromethyl-cyclohexylcarbamoyl)-2-aza-bicyclo[3.1.0]hexane-2-carboxylic acid tert-butyl ester—Dia mix 1 (84 mg, 0.214 mmol) in CH$_3$CN (5 mL) in a Q-Tube, were added silver oxide (119 mg, 0.514 mmol) and iodomethane (0.201 mL, 3.21 mmol). The suspension was stirred for 4 h at 80° C. (50% conversion). Then iodomethane (0.201 mL, 3.21 mmol) and silver oxide (119 mg, 0.514 mmol) were added again and the reaction mixture was stirred at 80° C. overnight. The crude reaction mixture was filtered, concentrated and purified by flash column chromatography on silica gel (c-hexane/EtOAc 10/0 to 4/6) to afford the title compound. MS: 407.0 [M+H]+.

C. (1R,3S,5R)-2-Aza-bicyclo[3.1.0]hexane-3-carboxylic acid (3-methoxy-3-trifluoromethyl-cyclohexyl)-amide hydrochloride—Dia mix 1

To a solution of (1R,3S,5R)-3-(3-methoxy-3-trifluoromethyl-cyclohexylcarbamoyl)-2-aza-bicyclo[3.1.0]hexane-2-carboxylic acid tert-butyl ester—Dia mix 1 (82 mg, 0.202 mmol) in dioxane (0.250 mL) was added HCl (4 N in dioxane, 0.6 mL). The reaction mixture was stirred for 4 h at RT and concentrated to dryness to give the title compound. MS: 307.2 [M+H]+.

D. Example 39: 1-{2-[(1R,3S,5R)-3-(3-Methoxy-3-trifluoromethyl-cyclohexylcarbamoyl)-2-aza-bicyclo[3.1.0]hex-2-yl]-2-oxo-ethyl}-1H-indazole-3-carboxylic acid amide—Dia mix 1

To a solution of (1R,3S,5R)-2-aza-bicyclo[3.1.0]hexane-3-carboxylic acid (3-methoxy-3-trifluoromethyl-cyclohexyl)-amide hydrochloride—Dia mix 1 (82 mg, 0.20 mmol), (3-carbamoyl-indazol-1-yl)-acetic acid (prepared as described in part A, 44.0 mg, 0.20 mmol), HOAT (31.5 mg, 0.23 mmol) and DIPEA (0.105 mL, 0.60 mmol) in CH$_2$Cl$_2$ (4 mL) was added EDC (42.4 mg, 0.22 mmol). The reaction mixture was stirred at RT for 7 h, poured into H$_2$O and aq. HCl 0.1N and extracted with CH$_2$Cl$_2$ (2×). The combined extracts were washed with sat. aq. Na$_2$CO$_3$, dried (Na$_2$SO$_4$), filtered, concentrated and the product was purified by preparative HPLC (Waters Sunfire C18 OBD, 5 μm, 30×100 mm, flow 40 mL/min, eluent 5 to 100% CH₃CN in H₂O in 20 min, CH₃CN and H₂O containing 0.1% TFA). The pure fractions were combined, poured into sat. aq. Na₂CO₃ and extracted with CH₂Cl₂ (2×). The combined extracts were dried (Na₂SO₄), filtered and concentrated to afford the title compound. MS (UPLC/MS): 508.2 [M+H]+, 552.2 [M+HCOO]−; $t_R$ (HPLC conditions f): 3.64 min.

Example 40: 1-{2-[(1R,3S,5R)-3-(3-Methoxy-3-trifluoromethyl-cyclohexylcarbamoyl)-2-aza-bicyclo[3.1.0]hex-2-yl]-2-oxo-ethyl}-1H-indazole-3-carboxylic acid amide—Dia mix 2

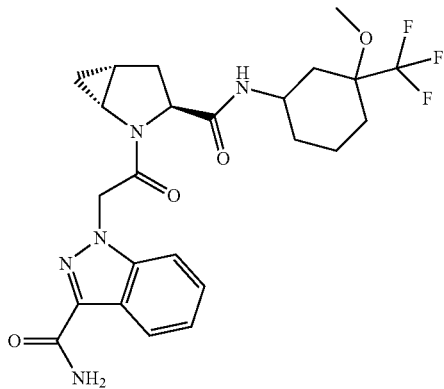 [SMILES: COC1(C(F)(F)F)CCCC(NC(=O)[C@@H]2C[C@H]3C[C@H]3N2C(=O)Cn2nc(C(N)=O)c3ccccc32)C1]

The title compound was prepared from (1R,3S,5R)-3-(3-hydroxy-3-trifluoromethyl-cyclohexylcarbamoyl)-2-aza-bicyclo[3.1.0]hexane-2-carboxylic acid tert-butyl ester—Dia mix 2 (prepared in step A of Example 39) using the same protocol as described for Example 39 step B, C and D. MS (UPLC/MS): 508.2 [M+H]+, 552.2 [M+HCOO]−; $t_R$ (HPLC conditions f): 3.67 min.

Scheme D5: General protocol described for the preparation of Example 41: 1-{2-Oxo-2-[(1R,3S,5R)-3-((1R,3S)-3-trifluoromethyl-cyclohexylcarbamoyl)-2-aza-bicyclo[3.1.0]hex-2-yl]-ethyl}-1H-pyrazolo[3,4-c]pyridine-3-carboxylic acid amide

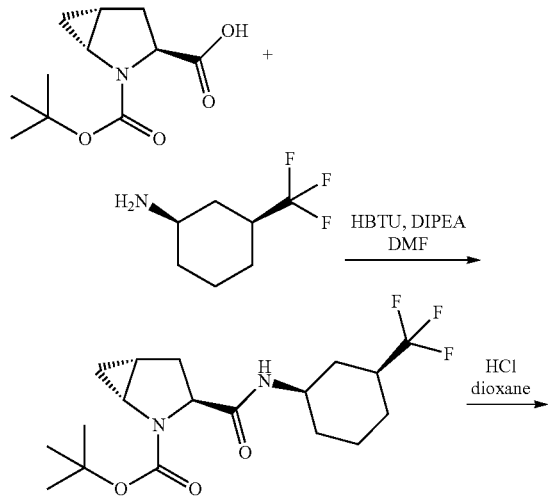

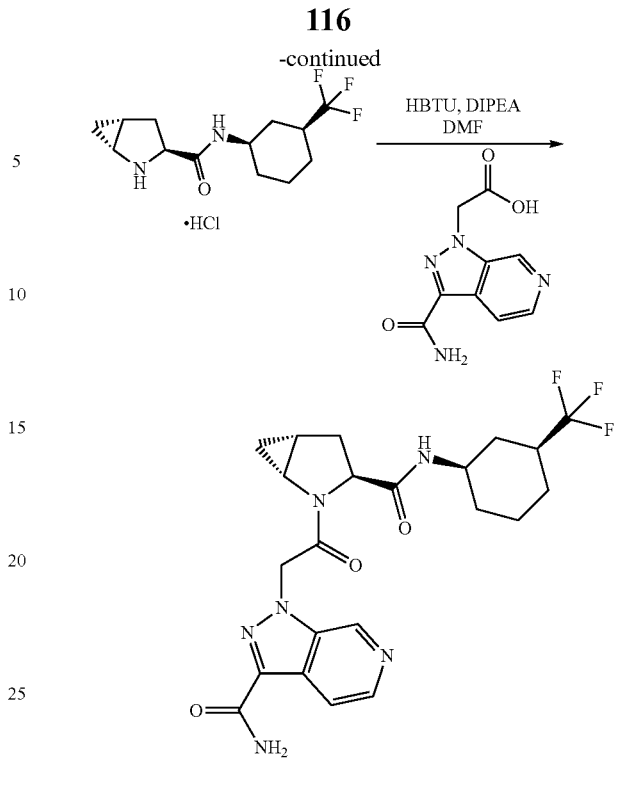

A. (1R,3S,5R)-3-((1R,3S)-3-Trifluoromethyl-cyclohexylcarbamoyl)-2-aza-bicyclo[3.1.0]hexane-2-carboxylic acid tert-butyl ester To a solution of (1R,3S,5R)-2-aza-bicyclo[3.1.0]hexane-2,3-dicarboxylic acid 2-tert-butyl ester (536 mg, 2.357 mmol), (1R,3S)-3-trifluoromethyl-cyclohexylamine hydrochloride (prepared as described in part C, 480 mg, 2.357 mmol) and HBTU (1073 mg, 2.83 mmol) in DMF (10 mL) was added DIPEA (1.24 mL, 7.07 mmol). The reaction mixture was stirred at RT overnight, concentrated and purified by flash column chromatography on silica gel (c-hexane/EtOAc 10/0 to 5/5) to afford the title compound. MS (LC/MS): 277.0 [M-Boc]+, 399.0 [M+Na]+; $t_R$ (HPLC conditions d): 3.62 min.

B. (1R,3S,5R)-2-Aza-bicyclo[3.1.0]hexane-3-carboxylic acid ((1R,3S)-3-trifluoromethyl-cyclohexyl)-amide hydrochloride To (1R,3S,5R)-3-((1R,3S)-3-trifluoromethyl-cyclohexylcarbamoyl)-2-aza-bicyclo[3.1.0]hexane-2-carboxylic acid tert-butyl ester (768 mg, 2.04 mmol) was added 4N HCl in dioxane (20 mL). The reaction mixture was stirred for 2 h at RT and concentrated to give the title compound which was directly used in the next step without further purification. MS (LC/MS): 277.0 [M+H]+.

C. Example 41: 1-{2-Oxo-2-[(1R,3S,5R)-3-((1R,3S)-3-trifluoromethyl-cyclohexylcarbamoyl)-2-aza-bicyclo[3.1.0]hex-2-yl]-ethyl}-1H-pyrazolo[3,4-c]pyridine-3-carboxylic acid amide To a solution of (3-carbamoyl-pyrazolo[3,4-c]pyridin-1-yl)-acetic acid trifluoroacetate (prepared as described in part A, 30 mg, 0.09 mmol), (1R,3S,5R)-2-aza-bicyclo[3.1.0]hexane-3-carboxylic acid ((1R,3S)-3-trifluoromethyl-cyclohexyl)-amide hydrochloride (28.1 mg, 0.09 mmol) and HBTU (40.9 mg, 0.108 mmol) in DMF (1 mL) was added DIPEA (0.047 mL, 0.269 mmol). The reaction mixture was stirred at RT for 4 h and the product was purified by preparative HPLC (XBridge C18OBD, 5 μm, 30×100 mm, flow: 45 mL/min, eluent: 5 to 100% CH$_3$CN in H$_2$O in 12 min, CH$_3$CN and H$_2$O containing 7.3 mM of NH$_3$). The pure fractions were lyophilized to afford the title compound. MS (LC/MS): 479.0 [M+H]+, 501.1 [M+Na]+; t$_R$ (HPLC conditions b): 3.49 min.

The examples below were prepared according to the general procedures described in Scheme D5 for the preparation of Example 41 from commercially available building blocks, if not otherwise stated (see notes at the end of table 5). In case a racemic amine is used in step A, the mixture of diastereoisomers can be separated either in step A or C (for details, refer to Separation method section).

TABLE 5

| Example | Structure | Name | Characterization (end-table notes); MS (LC/MS); t$_R$ (HPLC conditions) |
|---|---|---|---|
| 42 | 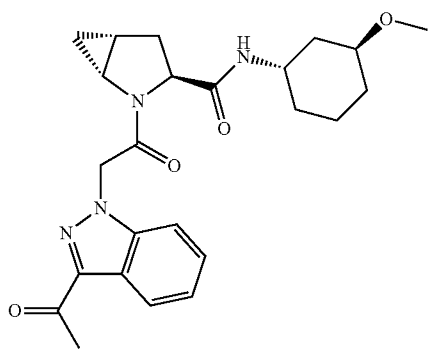 [SMILES: CO[C@H]1CCC[C@H](NC(=O)[C@@H]2C[C@H]3C[C@H]3N2C(=O)Cn2nc(C(C)=O)c3ccccc32)C1] | (1R,3S,5R)-2-[2-(3-Acetyl-indazol-1-yl)-acetyl]-2-aza-bicyclo[3.1.0]hexane-3-carboxylic acid ((1S,3S)-3-methoxy-cyclohexyl)-amide | (4, 7, 11); 461.0 [M+Na]+, 483.3 [M+HCOO]−; t$_R$ (b): 4.18 min |
| 43 | 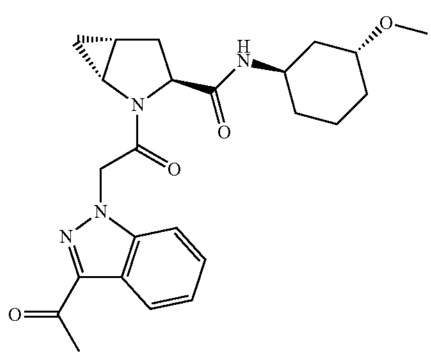 [SMILES: CO[C@@H]1CCC[C@@H](NC(=O)[C@@H]2C[C@H]3C[C@H]3N2C(=O)Cn2nc(C(C)=O)c3ccccc32)C1] | (1R,3S,5R)-2-[2-(3-Acetyl-indazol-1-yl)-acetyl]-2-aza-bicyclo[3.1.0]hexane-3-carboxylic acid ((1R,3R)-3-methoxy-cyclohexyl)-amide | (4, 7, 11); 439.1 [M+H]+, 461.0 [M+Na]+; t$_R$ (b): 4.16 min |
| 44 | 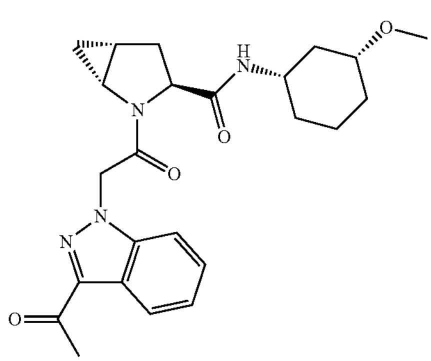 [SMILES: CO[C@@H]1CCC[C@H](NC(=O)[C@@H]2C[C@H]3C[C@H]3N2C(=O)Cn2nc(C(C)=O)c3ccccc32)C1] | (1R,3S,5R)-2-[2-(3-Acetyl-indazol-1-yl)-acetyl]-2-aza-bicyclo[3.1.0]hexane-3-carboxylic acid ((1S,3R)-3-methoxy-cyclohexyl)-amide | (4, 7, 11); 439.1 [M+H]+, 461.0 [M+Na]+; t$_R$ (b): 4.10 min |

TABLE 5-continued

| Example | Structure | Name | Characterization (end-table notes); MS (LC/MS); $t_R$ (HPLC conditions) |
|---|---|---|---|
| 45 | 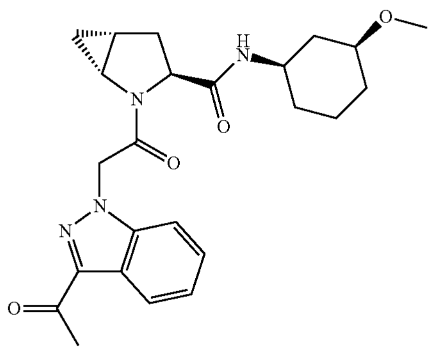 [SMILES: CO[C@H]1CCC[C@@H](NC(=O)[C@@H]2C[C@H]3C[C@H]3N2C(=O)Cn2nc(C(C)=O)c3ccccc32)C1] | (1R,3S,5R)-2-[2-(3-Acetyl-indazol-1-yl)-acetyl]-2-aza-bicyclo[3.1.0]hexane-3-carboxylic acid ((1R,3S)-3-methoxy-cyclohexyl)-amide | (4, 7, 11); 439.1 [M+H]+, 461.0 [M+Na]+; $t_R$ (b): 4.11 min |
| 46 | 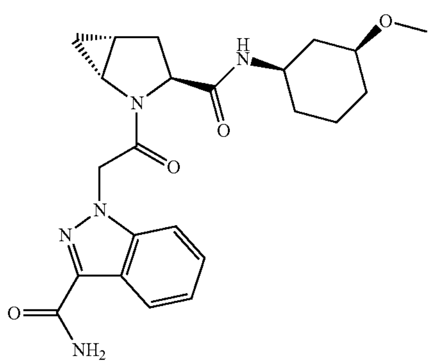 [SMILES: CO[C@H]1CCC[C@@H](NC(=O)[C@@H]2C[C@H]3C[C@H]3N2C(=O)Cn2nc(C(N)=O)c3ccccc32)C1] | 1-{2-[(1R,3S,5R)-3-((1R,3S)-3-Methoxy-cyclohexylcarbamoyl)-2-aza-bicyclo[3.1.0]hex-2-yl]-2-oxo-ethyl}-1H-indazole-3-carboxylic acid amide | (4, 7); 440.0 [M+H]+, 462.1 [M+Na]+; $t_R$ (b): 3.53 min |
| 47 | 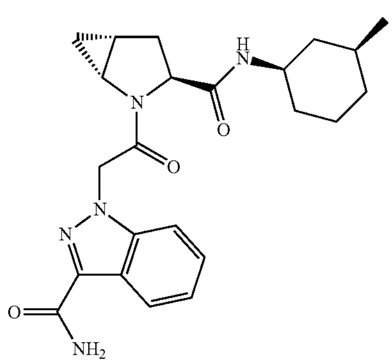 [SMILES: C[C@H]1CCC[C@@H](NC(=O)[C@@H]2C[C@H]3C[C@H]3N2C(=O)Cn2nc(C(N)=O)c3ccccc32)C1] | 1-{2-[(1R,3S,5R)-3-((1R,3S)-3-Methyl-cyclohexylcarbamoyl)-2-aza-bicyclo[3.1.0]hex-2-yl]-2-oxo-ethyl}-1H-indazole-3-carboxylic acid amide | (5[A6], 9[Method 4]); 424.0 [M+H]+, 446.0 [M+Na]+; $t_R$ (b): 4.19 min. |
| 48 | 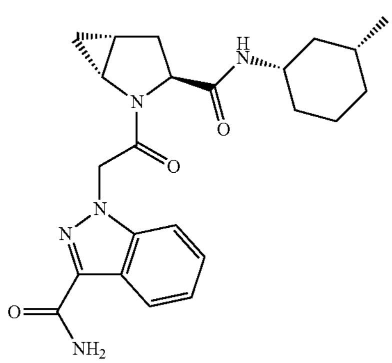 [SMILES: C[C@@H]1CCC[C@H](NC(=O)[C@@H]2C[C@H]3C[C@H]3N2C(=O)Cn2nc(C(N)=O)c3ccccc32)C1] | 1-{2-[(1R,3S,5R)-3-((1S,3R)-3-Methyl-cyclohexylcarbamoyl)-2-aza-bicyclo[3.1.0]hex-2-yl]-2-oxo-ethyl}-1H-indazole-3-carboxylic acid amide | (5[A6], 9[Method 4]); 424.1 [M+H]+, 446.0 [M+Na]+; $t_R$ (b): 4.18 min. |

TABLE 5-continued

| Example | Structure | Name | Characterization (end-table notes); MS (LC/MS); $t_R$ (HPLC conditions) |
|---|---|---|---|
| 49 | 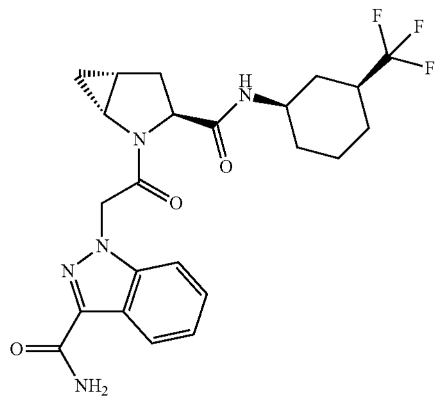 [SMILES: NC(=O)c1nn(CC(=O)N2[C@@H]3C[C@@H]3C[C@H]2C(=O)N[C@@H]2CCC[C@H](C(F)(F)F)C2)c2ccccc12] | 1-{2-Oxo-2-[(1R,3S,5R)-3-((1R,3S)-3-trifluoromethyl-cyclohexylcarbamoyl)-2-aza-bicyclo[3.1.0]hex-2-yl]ethyl}-1H-indazole-3-carboxylic acid amide | (2[C5], 5[A6]); 478.0 [M+H]+, 500.0 [M+Na]+; $t_R$ (b): 4.23 min. |
| 50 | 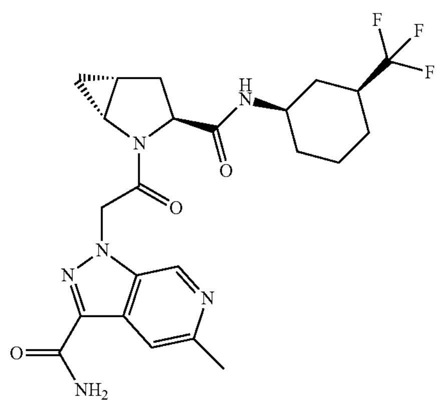 [SMILES: Cc1cc2c(C(N)=O)nn(CC(=O)N3[C@@H]4C[C@@H]4C[C@H]3C(=O)N[C@@H]3CCC[C@H](C(F)(F)F)C3)c2cn1] | 5-Methyl-1-{2-oxo-2-[(1R,3S,5R)-3-((1R,3S)-3-trifluoromethyl-cyclohexylcarbamoyl)-2-aza-bicyclo[3.1.0]hex-2-yl]ethyl}-1H-pyrazolo[3,4-c]pyridine-3-carboxylic acid amide | (2[C5], 5[A8]); 493.0 [M+H]+, 515.0 [M+Na]+; $t_R$ (b): 3.53 min. |
| 51 | 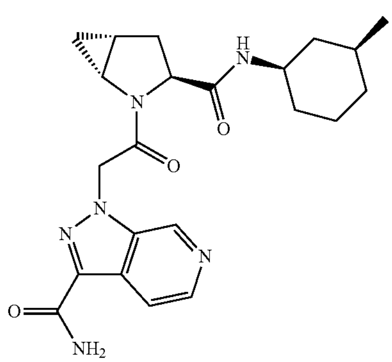 | 1-{2-[(1R,3S,5R)-3-((1R,3S)-3-Methyl-cyclohexylcarbamoyl)-2-aza-bicyclo[3.1.0]hex-2-yl]-2-oxo-ethyl}-1H-pyrazolo[3,4-c]pyridine-3-carboxylic acid amide | (5[A7], 9[Method 4]); 425.0 [M+H]+, 447.1 [M+Na]+; $t_R$ (b): 3.41 min. |
| 52 | 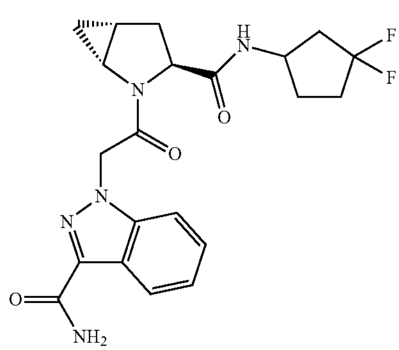 [SMILES: NC(=O)c1nn(CC(=O)N2[C@@H]3C[C@@H]3C[C@H]2C(=O)NC2CCC(F)(F)C2)c2ccccc12] | 1-{2-[(1R,3S,5R)-3-(3,3-Difluoro-cyclopentylcarbamoyl)-2-aza-bicyclo[3.1.0]hex-2-yl]-2-oxo-ethyl}-1H-indazole-3-carboxylic acid amide | (5[A6]); 432.0 [M+H]+, 454.0 [M+Na]+; $t_R$ (d): 2.76 min. |

TABLE 5-continued

| Example | Structure | Name | Characterization (end-table notes); MS (LC/MS); $t_R$ (HPLC conditions) |
|---|---|---|---|
| 53 | 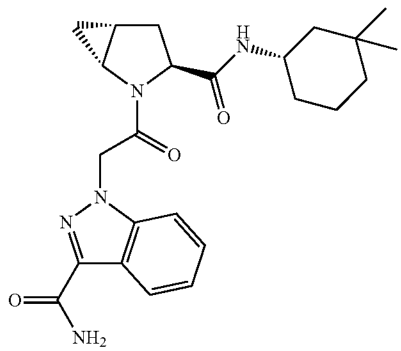 [SMILES: CC1(C)CCC[C@H](NC(=O)[C@@H]2C[C@H]3C[C@H]3N2C(=O)Cn2nc(C(N)=O)c3ccncc32)C1] | 1-{2-[(1R,3S,5R)-3-((S)-3,3-Dimethyl-cyclohexylcarbamoyl)-2-aza-bicyclo[3.1.0]hex-2-yl]-2-oxo-ethyl}-1H-indazole-3-carboxylic acid amide | (5[A6], 9[Method 2]); 438.1 [M+H]+, 460.1 [M+Na]+; $t_R$ (d): 3.26 min. |
| 54 | 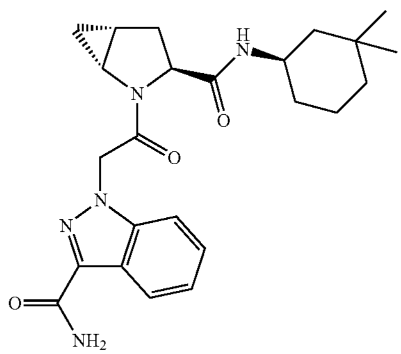 [SMILES: CC1(C)CCC[C@@H](NC(=O)[C@@H]2C[C@H]3C[C@H]3N2C(=O)Cn2nc(C(N)=O)c3ccncc32)C1] | 1-{2-[(1R,3S,5R)-3-((R)-3,3-Dimethyl-cyclohexylcarbamoyl)-2-aza-bicyclo[3.1.0]hex-2-yl]-2-oxo-ethyl}-1H-indazole-3-carboxylic acid amide | (5[A6], 9[Method 2]); 438.1 [M+H]+, 460.0 [M+Na]+; $t_R$ (d): 3.26 min. |
| 55 | 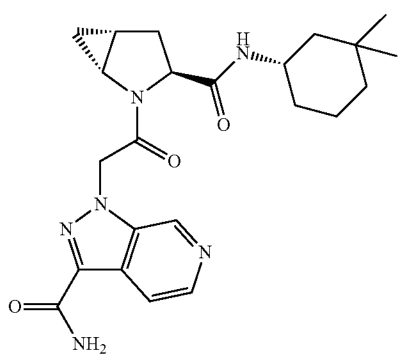 | 1-{2-[(1R,3S,5R)-3-((S)-3,3-Dimethyl-cyclohexylcarbamoyl)-2-aza-bicyclo[3.1.0]hex-2-yl]-2-oxo-ethyl}-1H-pyrazolo[3,4-c]pyridine-3-carboxylic acid amide | (5[A7], 9[Method 2]); 439.1 [M+H]+, 461.0 [M+Na]+; $t_R$ (d): 2.81 min. |
| 56 | 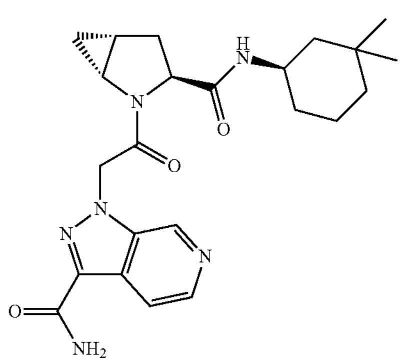 | 1-{2-[(1R,3S,5R)-3-((R)-3,3-Dimethyl-cyclohexylcarbamoyl)-2-aza-bicyclo[3.1.0]hex-2-yl]-2-oxo-ethyl}-1H-pyrazolo[3,4-c]pyridine-3-carboxylic acid amide | (5[A7], 9[Method 2]); 439.1 [M+H]+, 461.0 [M+Na]+; $t_R$ (d): 2.80 min. |

TABLE 5-continued

| Example | Structure | Name | Characterization (end-table notes); MS (LC/MS); $t_R$ (HPLC conditions) |
|---|---|---|---|
| 57 | 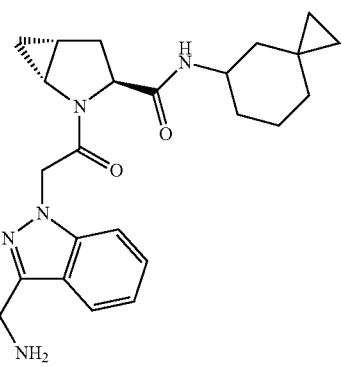 | 1-{2-Oxo-2-[(1R,3S,5R)-3-(spiro[2.5]oct-5-ylcarbamoyl)-2-aza-bicyclo[3.1.0]hex-2-yl]-ethyl}-1H-indazole-3-carboxylic acid amide-Dia 1 | (2[C6], 5[A6], 9[Method 6]); 436.0 [M+H]+, 458.0 [M+Na]+; $t_R$ (d): 3.18 min. |
| 58 | 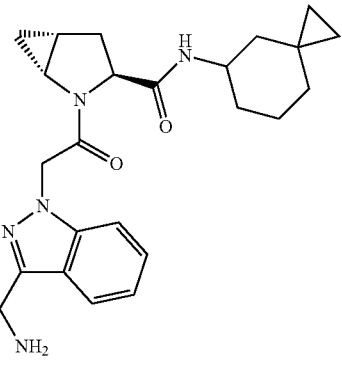 | 1-{2-Oxo-2-[(1R,3S,5R)-3-(spiro[2.5]oct-5-ylcarbamoyl)-2-aza-bicyclo[3.1.0]hex-2-yl]-1H-indazole-3-carboxylic acid amide-Dia 2 | (2[C6], 5[A6], 9[Method 6]); 436.0 [M+H]+, 458.0 [M+Na]+; $t_R$ (d): 3.18 min. |
| 59 | 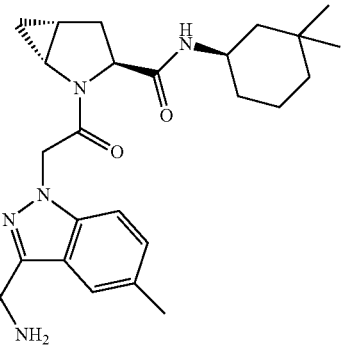 | 1-{2-[(1R,3S,5R)-3-((R)-3,3-Dimethyl-cyclohexylcarbamoyl)-2-aza-bicyclo[3.1.0]hex-2-yl]-2-oxo-ethyl}-5-methyl-1H-indazole-3-carboxylic acid amide | (5[A10], 9[Method 2]); 452.0 [M+H]+, 474.1 [M+Na]+; $t_R$ (b): 4.55 min. |
| 60 | 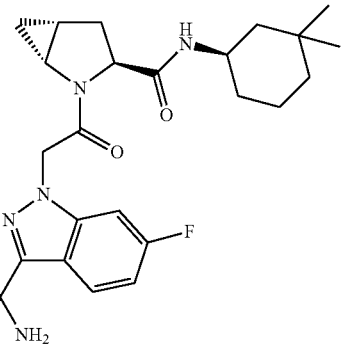 | 1-{2-[(1R,3S,5R)-3-((R)-3,3-Dimethyl-cyclohexylcarbamoyl)-2-aza-bicyclo[3.1.0]hex-2-yl]-2-oxo-ethyl}-6-fluoro-1H-indazole-3-carboxylic acid amide | (5[A9], 9[Method 2]); 456.1 [M+H]+, 478.0 [M+Na]+; $t_R$ (b): 4.49 min. |

TABLE 5-continued

| Example | Structure | Name | Characterization (end-table notes); MS (LC/MS); $t_R$ (HPLC conditions) |
|---|---|---|---|
| 61 | 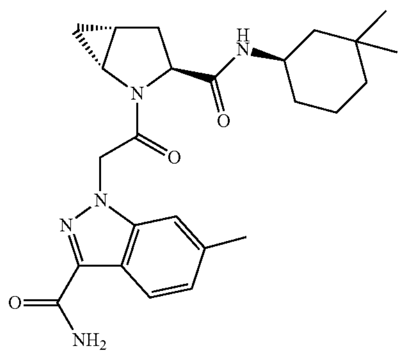 | 1-{2-[(1R,3S,5R)-3-((R)-3,3-Dimethyl-cyclohexylcarbamoyl)-2-aza-bicyclo[3.1.0]hex-2-yl]-2-oxo-ethyl}-6-methyl-1H-indazole-3-carboxylic acid amide | (5[A9], 9[Method 2]); 452.0 [M+H]+, 474.1 [M+Na]+; $t_R$ (e): 3.00 min. |
| 62 | 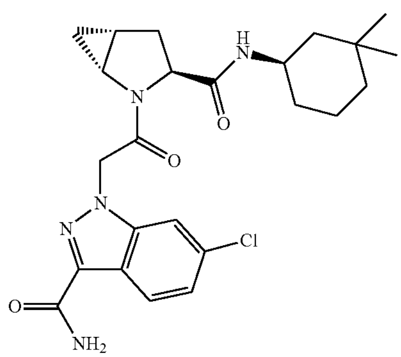 | 6-Chloro-1-{2-[(1R,3S,5R)-3-((R)-3,3-dimethyl-cyclohexyl carbamoyl)-2-aza-bicyclo[3.1.0]hex-2-yl]-2-oxo-ethyl}-1H-indazole-3-carboxylic acid amide | (5[A9], 9[Method 2]); 472.0 [M+H]+; $t_R$ (e): 3.10 min. |
| 63 | 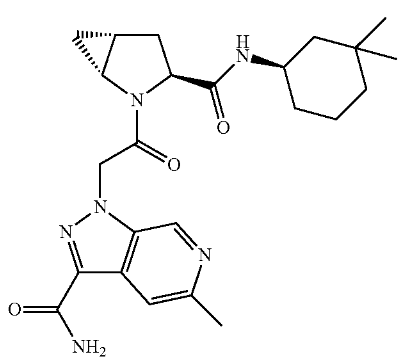 [SMILES: Cc1cc2c(C(N)=O)nn(CC(=O)N3[C@@H]4C[C@@H]4C[C@H]3C(=O)N[C@@H]3CCCC(C)(C)C3)c2cn1] | 1-{2-[(1R,3S,5R)-3-((R)-3,3-Dimethyl-cyclohexylcarbamoyl)-2-aza-bicyclo[3.1.0]hex-2-yl]-2-oxo-ethyl}-5-methyl-1H-pyrazolo[3,4-c]pyridine-3-carboxylic acid amide | (5[A8], 9[Method 2]); 453.1 [M+H]+, 475.0 [M+Na]+; $t_R$ (b): 3.66 min. |
| 64 | 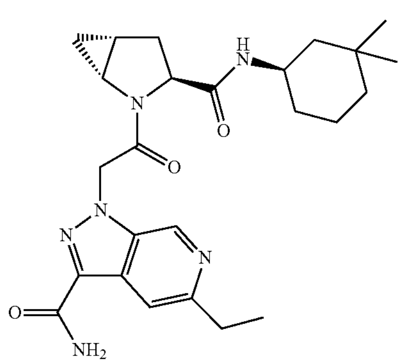 [SMILES: CCc1cc2c(C(N)=O)nn(CC(=O)N3[C@@H]4C[C@@H]4C[C@H]3C(=O)N[C@@H]3CCCC(C)(C)C3)c2cn1] | 1-{2-[(1R,3S,5R)-3-((R)-3,3-Dimethyl-cyclohexylcarbamoyl)-2-aza-bicyclo[3.1.0]hex-2-yl]-2-oxo-ethyl}-5-ethyl-1H-pyrazolo[3,4-c]pyridine-3-carboxylic acid amide | (5[A7], 9[Method 2]); 467.0 [M+H]+, 489.1 [M+Na]+; $t_R$ (b): 3.74 min. |

TABLE 5-continued

| Example | Structure | Name | Characterization (end-table notes); MS (LC/MS); $t_R$ (HPLC conditions) |
|---|---|---|---|
| 65 | 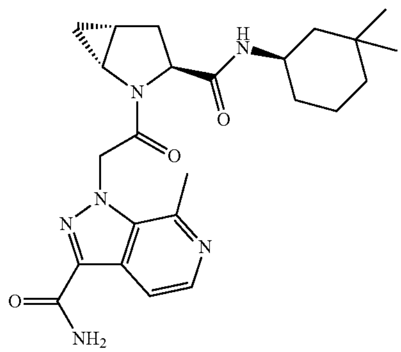 [SMILES: Cc1nccc2c(C(N)=O)nn(CC(=O)N3[C@@H]4C[C@@H]4C[C@H]3C(=O)N[C@@H]3CCCC(C)(C)C3)c12] | 1-{2-[(1R,3S,5R)-3-((R)-3,3-Dimethyl-cyclohexylcarbamoyl)-2-aza-bicyclo[3.1.0]hex-2-yl]-2-oxo-ethyl}-7-methyl-1H-pyrazolo[3,4-c]pyridine-3-carboxylic acid amide | (5[A7], 9[Method 2]); 453.1 [M+H]+, 475.1 [M+Na]+; $t_R$ (d): 2.73 min. |
| 66 | 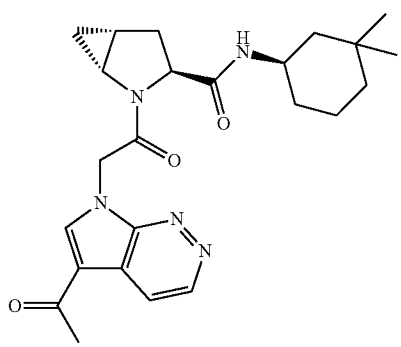 [SMILES: CC(=O)c1cn(CC(=O)N2[C@@H]3C[C@@H]3C[C@H]2C(=O)N[C@@H]2CCCC(C)(C)C2)c2nnccc12] | (1R,3S,5R)-2-[2-(5-Acetyl-pyrrolo[2,3-c]pyridazin-7-yl)-acetyl]-2-aza-bicyclo[3.1.0] hexane-3-carboxylic acid ((R)-3,3-dimethyl-cyclohexyl)-amide | (5[A4], 9[Method 2]); 438.4 [M+H]+, 460.3 [M+Na]+; $t_R$ (d): 2.93 min. |
| 67 | 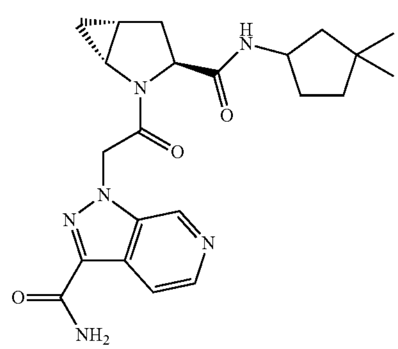 [SMILES: CC1(C)CCC(NC(=O)[C@@H]2C[C@H]3C[C@H]3N2C(=O)Cn2nc(C(N)=O)c3ccncc32)C1] | 1-{2-[(1R,3S,5R)-3-(3,3-Dimethyl-cyclopentylcarbamoyl)-2-aza-bicyclo[3.1.0]hex-2-yl]-2-oxo-ethyl}-1H-pyrazolo[3,4-c]pyridine-3-carboxylic acid amide-Dia 1 | (5[A7], 9[Method 7]); 425.3 [M+H]+, 447.3 [M+Na]+; $t_R$ (b): 3.40 min. |
| 68 | 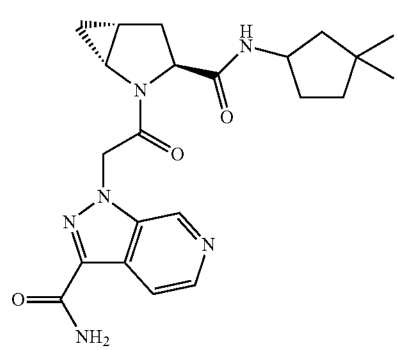 [SMILES: CC1(C)CCC(NC(=O)[C@@H]2C[C@H]3C[C@H]3N2C(=O)Cn2nc(C(N)=O)c3ccncc32)C1] | 1-{2-[(1R,3S,5R)-3-(3,3-Dimethyl-cyclopentylcarbamoyl)-2-aza-bicyclo[3.1.0]hex-2-yl]-2-oxo-ethyl}-1H-pyrazolo[3,4-c]pyridine-3-carboxylic acid amide-Dia 2 | (5[A7], 9[Method 7]); 425.3 [M+H]+, 447.3 [M+Na]+; $t_R$ (b): 3.40 min. |

TABLE 5-continued

| Example | Structure | Name | Characterization (end-table notes); MS (LC/MS); $t_R$ (HPLC conditions) |
|---|---|---|---|
| 69 | 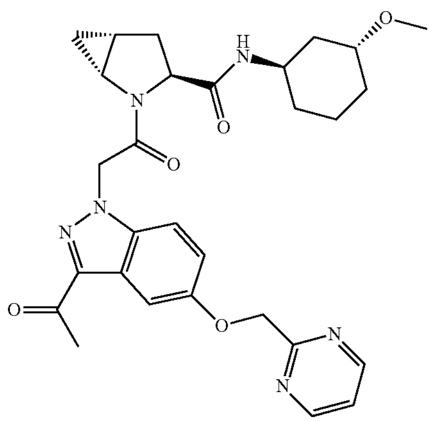 [SMILES: CO[C@@H]1CCC[C@@H](NC(=O)[C@@H]2C[C@H]3C[C@H]3N2C(=O)Cn2nc(C(C)=O)c3cc(OCc4ncccn4)ccc32)C1] | (1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((1R,3R)-3-methoxy-cyclohexyl)-amide | (4, 5[A3], 7); 547.2 [M+H]+, 569.0 [M+Na]+; $t_R$ (b): 3.86 min. |
| 70 | 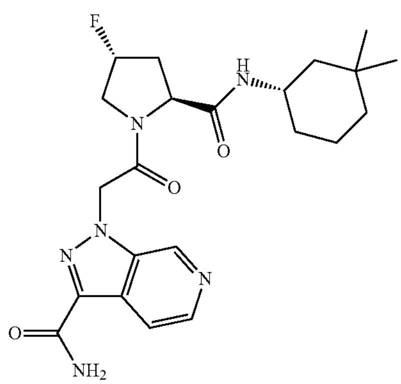 [SMILES: CC1(C)CCC[C@H](NC(=O)[C@@H]2C[C@@H](F)CN2C(=O)Cn2nc(C(N)=O)c3ccncc32)C1] | 1-{2-[(2S,4R)-2-((S)-3,3-Dimethyl-cyclohexylcarbamoyl)-4-fluoro-pyrrolidin-1-yl]-2-oxo-ethyl}-1H-pyrazolo[3,4-c]pyridine-3-carboxylic acid amide | (5[A7], 9[Method 5]); 445.4 [M+H]+, 489.3 [M+HCOO]−; $t_R$ (b): 3.54 min. |
| 71 | 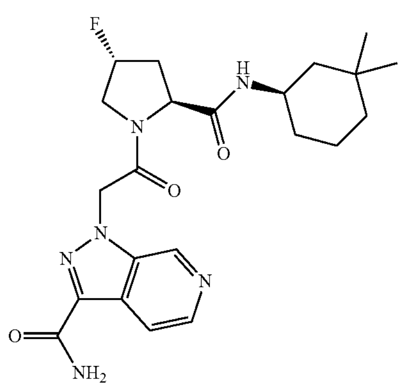 [SMILES: CC1(C)CCC[C@@H](NC(=O)[C@@H]2C[C@@H](F)CN2C(=O)Cn2nc(C(N)=O)c3ccncc32)C1] | 1-{2-[(2S,4R)-2-((R)-3,3-Dimethyl-cyclohexylcarbamoyl)-4-fluoro-pyrrolidin-1-yl]-2-oxo-ethyl}-1H-pyrazolo[3,4-c]pyridine-3-carboxylic acid amide | (5[A7], 9[Method 5]); 445.4 [M+H]+, 489.5 [M+HCOO]−; $t_R$ (b): 3.51 min. |
| 72 | 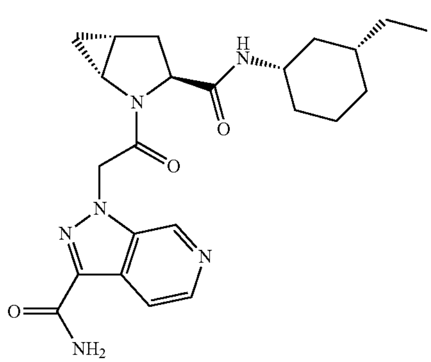 [SMILES: CC[C@@H]1CCC[C@H](NC(=O)[C@@H]2C[C@H]3C[C@H]3N2C(=O)Cn2nc(C(N)=O)c3ccncc32)C1] | 1-{2-[(1R,3S,5R)-3-((1S,3R)-3-Ethyl-cyclohexylcarbamoyl)-2-aza-bicyclo[3.1.0]hex-2-yl]-2-oxo-ethyl}-1H-pyrazolo[3,4-c]pyridine-3-carboxylic acid amide | (5[A7], 9[Method 3]); 439.3 [M+H]+, 461.3 [M+Na]+; $t_R$ (b): 3.70 min. |

TABLE 5-continued

| Example | Structure | Name | Characterization (end-table notes); MS (LC/MS); t_R (HPLC conditions) |
|---|---|---|---|
| 73 | 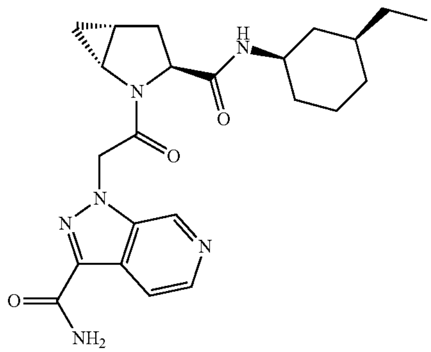 [SMILES: CC[C@H]1CCC[C@@H](NC(=O)[C@@H]2C[C@H]3C[C@H]3N2C(=O)Cn2nc(C(N)=O)c3ccncc32)C1] | 1-{2-[(1R,3S,5R)-3-((1S,3R)-3-Ethyl-cyclohexylcarbamoyl)-2-aza-bicyclo[3.1.0]hex-2-yl]-2-oxo-ethyl}-1H-pyrazolo[3,4-c]pyridine-3-carboxylic acid amide | (5[A7], 9[Method 3]); 439.3 [M+H]+, 483.4 [M+HCOO]−; $t_R$ (b): 3.66 min. |
| 74 | 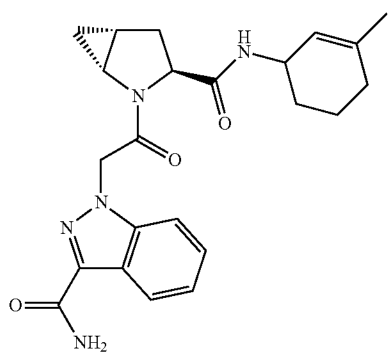 [SMILES: CC1=CC(NC(=O)[C@@H]2C[C@H]3C[C@H]3N2C(=O)Cn2nc(C(N)=O)c3ccccc32)CCC1] | 1-{2-[(1R,3S,5R)-3-(3-Methyl-cyclohex-2-enylcarbamoyl)-2-aza-bicyclo[3.1.0]hex-2-yl]-2-oxo-ethyl}-1H-indazole-3-carboxylic acid amide | (2[C7], 3, 4, 5[A6], 6); 439.2 [M+NH_4]+, 466.3 [M+HCOO]−; $t_R$ (c): 1.68 min. |
| 75 | 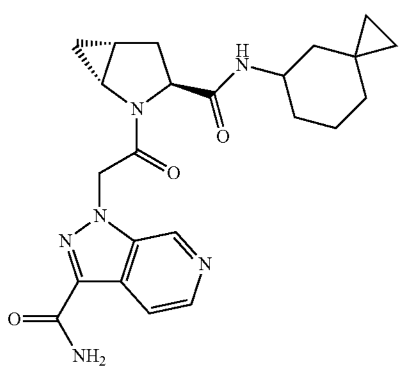 | 1-{2-Oxo-2-[(1R,3S,5R)-3-(spiro[2.5]oct-5-ylcarbamoyl)-2-aza-bicyclo[3.1.0]hex-2-yl]-ethyl}-1H-pyrazolo[3,4-c]pyridine-3-carboxylic acid amide-Dia 1 | (2[C6], 5[A7], 9[Method 8]); 437.4 [M+H]+, 481.3 [M+HCOO]−; $t_R$ (d): 2.74 min. |
| 76 | 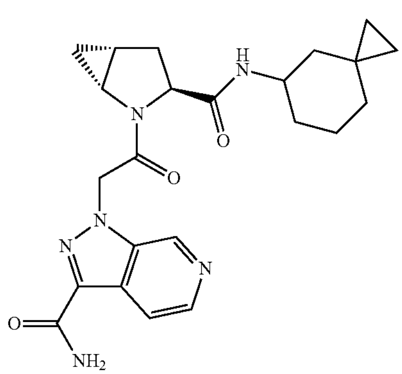 | 1-{2-Oxo-2-[(1R,3S,5R)-3-(spiro[2.5]oct-5-ylcarbamoyl)-2-aza-bicyclo[3.1.0]hex-2-yl]-ethyl}-1H-pyrazolo[3,4-c]pyridine-3-carboxylic acid amide-Dia 2 | (2[C6], 5[A7], 9[Method 8]); 437.3 [M+H]+, 481.4 [M+HCOO]−; $t_R$ (d): 2.71 min. |

TABLE 5-continued

| Example | Structure | Name | Characterization (end-table notes); MS (LC/MS); $t_R$ (HPLC conditions) |
|---|---|---|---|
| 77 | 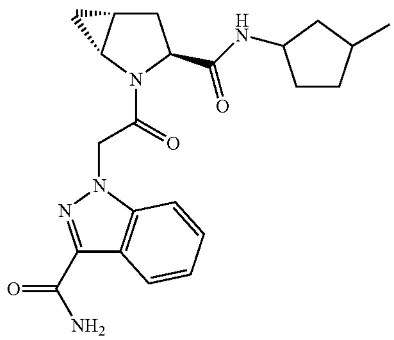 [SMILES: CC1CCC(NC(=O)[C@@H]2C[C@H]3C[C@H]3N2C(=O)Cn2nc(C(N)=O)c3ccccc32)C1] | 1-{2-[(1R,3S,5R)-3-(3-Methyl-cyclopentylcarbamoyl)-2-aza-bicyclo[3.1.0]hex-2-yl]-2-oxo-ethyl}-1H-indazole-3-carboxylic acid amide-Dia 1 | (2[C10], 5[A6], 9[Method 9]); 410.0 [M+H]+, 432.0 [M+Na]+; $t_R$ (d): 3.03 min. |
| 78 | 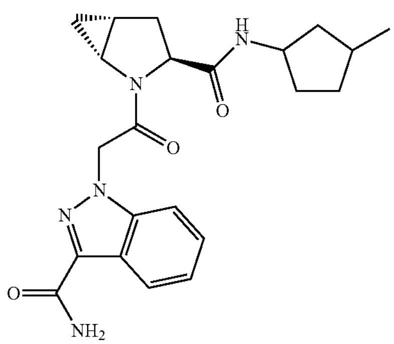 [SMILES: CC1CCC(NC(=O)[C@@H]2C[C@H]3C[C@H]3N2C(=O)Cn2nc(C(N)=O)c3ccccc32)C1] | 1-{2-[(1R,3S,5R)-3-(3-Methyl-cyclopentylcarbamoyl)-2-aza-bicyclo[3.1.0]hex-2-yl]-2-oxo-ethyl}-1H-indazole-3-carboxylic acid amide-Dia 2 | (2[C10], 5[A6], 9[Method 9]); 410.3 [M+H]+, 454.3 [M+HCOO]−; $t_R$ (d): 3.03 min. |
| 79 | 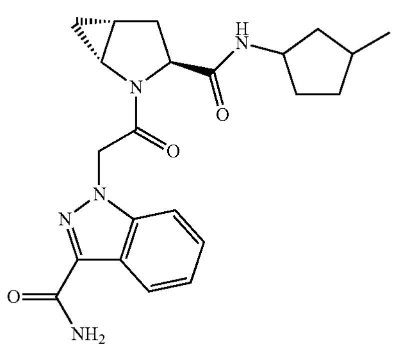 [SMILES: CC1CCC(NC(=O)[C@@H]2C[C@H]3C[C@H]3N2C(=O)Cn2nc(C(N)=O)c3ccccc32)C1] | 1-{2-[(1R,3S,5R)-3-(3-Methyl-cyclopentylcarbamoyl)-2-aza-bicyclo[3.1.0]hex-2-yl]-2-oxo-ethyl}-1H-indazole-3-carboxylic acid amide-Dia 3 | (2[C10], 5[A6], 9[Method 9]); 410.3 [M+H]+, 454.3 [M+HCOO]−; $t_R$ (d): 3.01 min. |
| 80 | 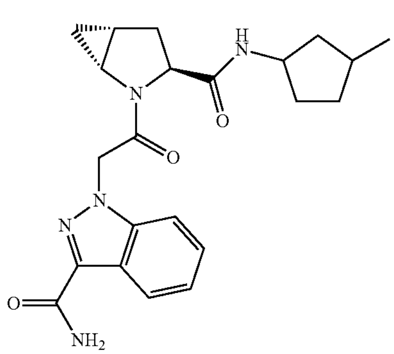 [SMILES: CC1CCC(NC(=O)[C@@H]2C[C@H]3C[C@H]3N2C(=O)Cn2nc(C(N)=O)c3ccccc32)C1] | 1-{2-[(1R,3S,5R)-3-(3-Methyl-cyclopentylcarbamoyl)-2-aza-bicyclo[3.1.0]hex-2-yl]-2-oxo-ethyl}-1H-indazole-3-carboxylic acid amide-Dia 4 | (2[C10], 5[A6], 9[Method 9]); 410.2 [M+H]+, 454.4 [M+HCOO]−; $t_R$ (d): 3.02 min. |

TABLE 5-continued

| Example | Structure | Name | Characterization (end-table notes); MS (LC/MS); t_R (HPLC conditions) |
|---|---|---|---|
| 81 | 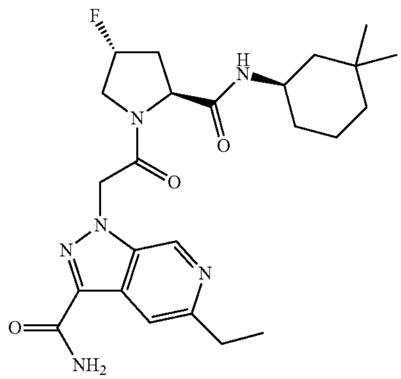 [SMILES: CCc1cc2c(C(N)=O)nn(CC(=O)N3C[C@H](F)C[C@H]3C(=O)N[C@@H]3CCCC(C)(C)C3)c2cn1] | 1-{2-[(2S,4R)-2-((R)-3,3-Dimethyl-cyclohexylcarbamoyl)-4-fluoro-pyrrolidin-1-yl]-2-oxo-ethyl}-5-ethyl-1H-pyrazolo[3,4-c]pyridine-3-carboxylic acid amide | (5[A7], 9[Method 5]); 473.3 [M+H]+, 517.5 [M+HCOO]−; t_R (b): 3.70 min. |
| 82 | 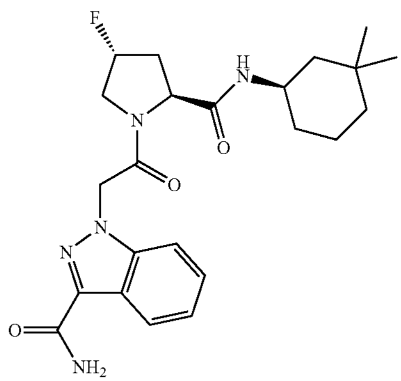 [SMILES: CC1(C)CCC[C@@H](NC(=O)[C@@H]2C[C@@H](F)CN2C(=O)Cn2nc(C(N)=O)c3ccccc32)C1] | 1-{2-[(2S,4R)-2-((R)-3,3-Dimethyl-cyclohexylcarbamoyl)-4-fluoro-pyrrolidin-1-yl]-2-oxo-ethyl}-1H-indazole-3-carboxylic acid amide | (5[A6], 9[Method 5]); 444.3 [M+H]+, 488.5 [M+HCOO]−; t_R (b): 4.25 min. |
| 83 | 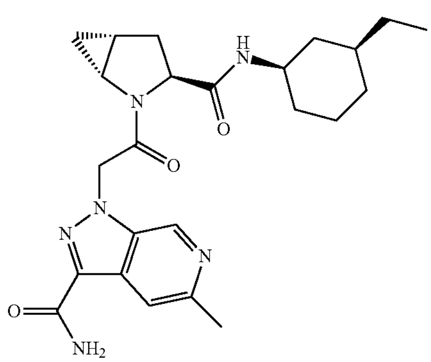 | 1-{2-[(1R,3S,5R)-3-((1R,3S)-3-Ethyl-cyclohexylcarbamoyl)-2-aza-bicyclo[3.1.0]hex-2-yl]-2-oxo-ethyl}-5-methyl-1H-pyrazolo[3,4-c]pyridine-3-carboxylic acid amide | (5[A8], 9[Method 3]); 453.4 [M+H]+, 497.4 [M+HCOO]−; t_R (b): 3.72 min. |
| 84 | 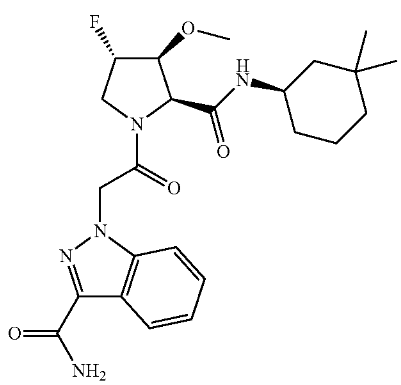 [SMILES: CO[C@H]1[C@@H](C(=O)N[C@@H]2CCCC(C)(C)C2)N(C(=O)Cn2nc(C(N)=O)c3ccccc32)C[C@@H]1F] | 1-{2-[(2S,3S,4S)-2-((R)-3,3-Dimethyl-cyclohexylcarbamoyl)-4-fluoro-3-methoxy-pyrrolidin-1-yl]-2-oxo-ethyl}-1H-indazole-3-carboxylic acid amide | (1[B4], 5[A6], 9[Method 10]); 474.2 [M+H]+, 496.1 [M+Na]+; t_R (b): 4.32 min. |

TABLE 5-continued

| Example | Structure | Name | Characterization (end-table notes); MS (LC/MS); t_R (HPLC conditions) |
|---|---|---|---|
| 85 | 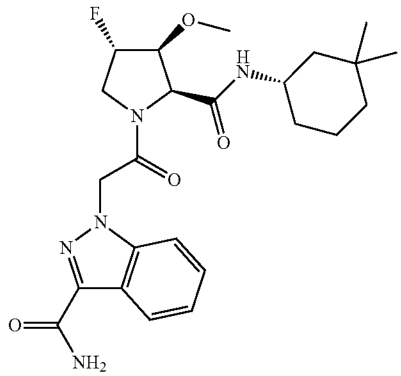 [SMILES: CO[C@H]1[C@@H](C(=O)N[C@H]2CCCC(C)(C)C2)N(C(=O)Cn2nc(C(N)=O)c3ccccc32)C[C@@H]1F] | 1-{2-[(2S,3S,4S)-2-((S)-3,3-Dimethyl-cyclohexylcarbamoyl)-4-fluoro-3-methoxy-pyrrolidin-1-yl]-2-oxo-ethyl}-1H-indazole-3-carboxylic acid amide | (1[B4], 5[A6], 9[Method 10]); 474.2 [M+H]+, 518.0 [M+HCOO]−; t_R (b): 4.33 min. |
| 86 | 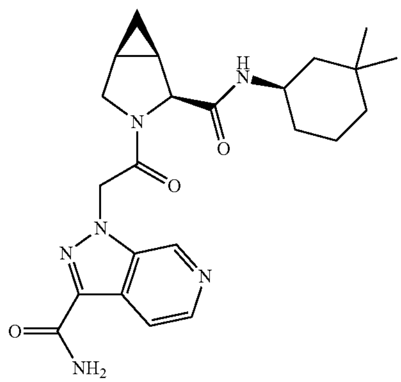 [SMILES: CC1(C)CCC[C@@H](NC(=O)[C@@H]2[C@@H]3C[C@@H]3CN2C(=O)Cn2nc(C(N)=O)c3ccncc32)C1] | 1-{2-[(1R,2S,5S)-2-((R)-3,3-Dimethyl-cyclohexylcarbamoyl)-3-aza-bicyclo[3.1.0]hex-3-yl]-2-oxo-ethyl}-1H-pyrazolo[3,4-c]pyridine-3-carboxylic acid amide | (5[A7], 9[Method 11]); 439.3 [M+H]+, 461.4 [M+Na]+; t_R (b): 3.58 min. |
| 87 | 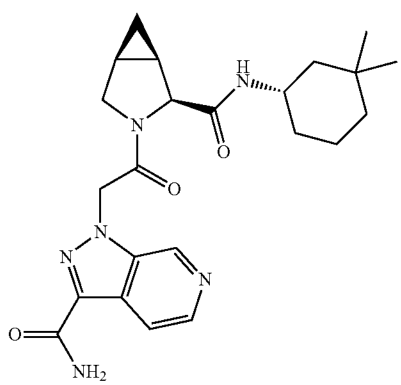 | 1-{2-[(1R,2S,5S)-2-((S)-3,3-Dimethyl-cyclohexylcarbamoyl)-3-aza-bicyclo[3.1.0]hex-3-yl]-2-oxo-ethyl}-1H-pyrazolo[3,4-c]pyridine-3-carboxylic acid amide | (5[A7], 9[Method 11]); 439.3 [M+H]+, 461.3 [M+Na]+; t_R (b): 3.59 min. |
| 88 | 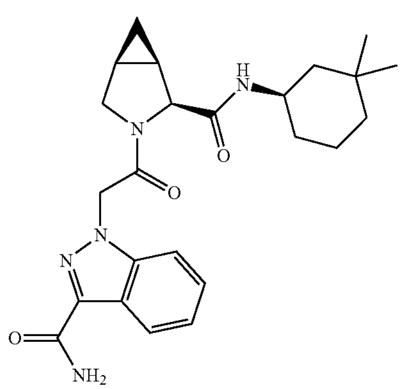 [SMILES: CC1(C)CCC[C@@H](NC(=O)[C@@H]2[C@@H]3C[C@@H]3CN2C(=O)Cn2nc(C(N)=O)c3ccccc32)C1] | 1-{2-[(1R,2S,5S)-2-((R)-3,3-Dimethyl-cyclohexylcarbamoyl)-3-aza-bicyclo[3.1.0]hex-3-yl]-2-oxo-ethyl}-1H-indazole-3-carboxylic acid amide | (5[A6], 9[Method 12]); 438.3 [M+H]+, 455.3 [M+NH_4]+; t_R (f): 3.78 min. |

TABLE 5-continued

| Example | Structure | Name | Characterization (end-table notes); MS (LC/MS); $t_R$ (HPLC conditions) |
|---|---|---|---|
| 89 | 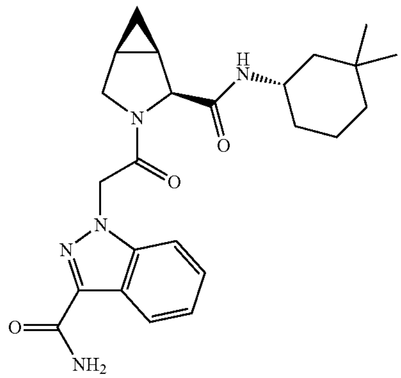 [SMILES: CC1(C)CCC[C@H](NC(=O)[C@@H]2[C@@H]3C[C@@H]3CN2C(=O)Cn2nc(C(N)=O)c3ccccc32)C1] | 1-{2-[(1R,2S,5S)-2-((S)-3,3-Dimethyl-cyclohexylcarbamoyl)-3-aza-bicyclo[3.1.0]hex-3-yl]-2-oxo-ethyl}-1H-indazole-3-carboxylic acid amide | (5[A6], 9[Method 12]); 438.3 [M+H]+, 455.3 [M+NH$_4$]+; $t_R$ (f): 3.77 min. |
| 90 | 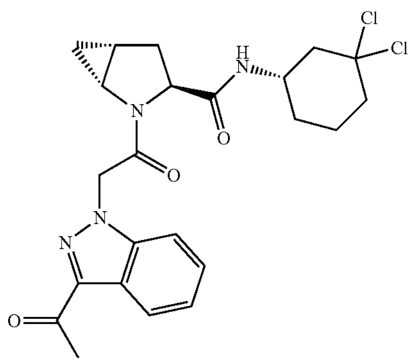 [SMILES: CC(=O)c1nn(CC(=O)N2[C@@H]3C[C@@H]3C[C@H]2C(=O)N[C@H]2CCCC(Cl)(Cl)C2)c2ccccc12] | (1R,3S,5R)-2-[2-(3-Acetyl-indazol-1-yl)-acetyl]-2-aza-bicyclo[3.1.0]hexane-3-carboxylic acid ((S)-3,3-dichloro-cyclohexyl)-amide | (2[C8], 3, 5[A2], 6, 9[Method 13]); 495.2-497.2 [M+NH$_4$]+; $t_R$ (f): 3.37 min. |
| 91 | 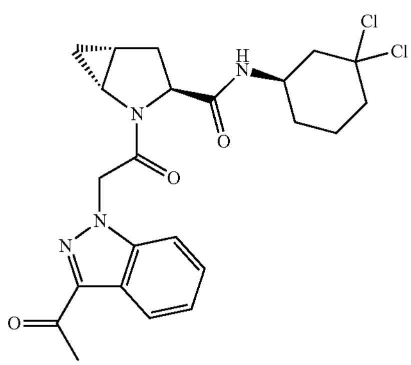 [SMILES: CC(=O)c1nn(CC(=O)N2[C@@H]3C[C@@H]3C[C@H]2C(=O)N[C@@H]2CCCC(Cl)(Cl)C2)c2ccccc12] | (1R,3S,5R)-2-[2-(3-Acetyl-indazol-1-yl)-acetyl]-2-aza-bicyclo[3.1.0]hexane-3-carboxylic acid ((R)-3,3-dichloro-cyclohexyl)-amide | (2[C8], 3, 5[A2], 6, 9[Method 13]); 495.2-497.2 [M+NH$_4$]+; $t_R$ (f): 3.39 min. |
| 92 | 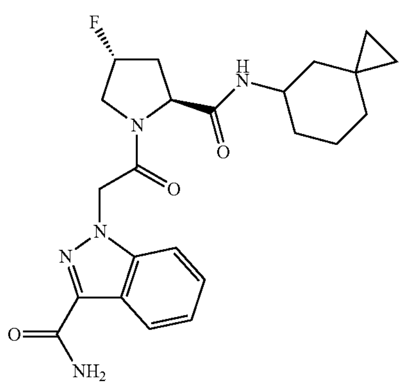 [SMILES: NC(=O)c1nn(CC(=O)N2C[C@H](F)C[C@H]2C(=O)NC2CCCC3(CC3)C2)c2ccccc12] | 1-{2-[(2S,4R)-4-Fluoro-2-(spiro[2.5]oct-5-ylcarbamoyl)-pyrrolidin-1-yl]-2-oxo-ethyl}-1H-indazole-3-carboxylic acid amide-Dia 1 | (2[C6], 5[A6], 9[Method 14]); 442.3 [M+H]+, 486.3 [M+HCOO]−; $t_R$ (f): 3.45 min. |

TABLE 5-continued

| Example | Structure | Name | Characterization (end-table notes); MS (LC/MS); $t_R$ (HPLC conditions) |
|---------|-----------|------|------------------------------------------------------------------------|
| 93 | 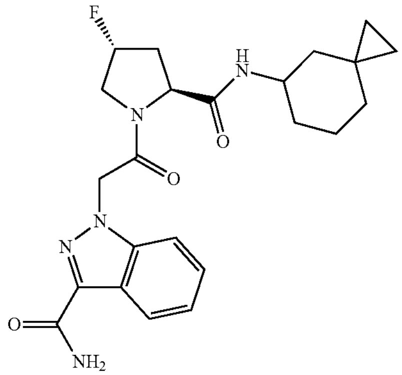 [SMILES: NC(=O)c1nn(CC(=O)N2C[C@H](F)C[C@H]2C(=O)NC2CCCC3(CC3)C2)c2ccccc12] | 1-{2-[(2S,4R)-4-Fluoro-2-(spiro[2.5]oct-5-ylcarbamoyl)-pyrrolidin-1-yl]-2-oxo-ethyl}-1H-indazole-3-carboxylic acid amide-Dia 2 | (2[C6], 5[A6], 9[Method 14]); 442.3 [M+H]+, 486.3 [M+HCOO]−; $t_R$ (f): 3.43 min. |
| 94 | 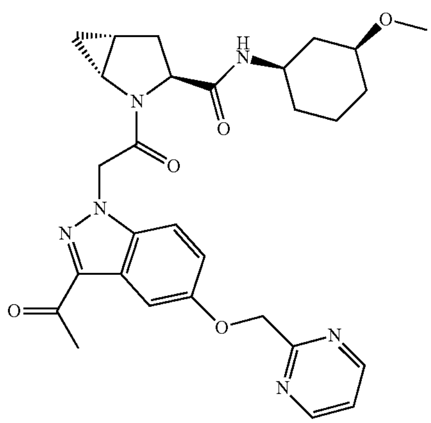 [SMILES: CO[C@H]1CCC[C@@H](NC(=O)[C@@H]2C[C@H]3C[C@H]3N2C(=O)Cn2nc(C(C)=O)c3cc(OCc4ncccn4)ccc32)C1] | (1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((1R,3S)-3-methoxy-cyclohexyl)-amide | (4, 7); 547.2 [M+H]+, 591.2 [M+HCOO]−; $t_R$ (b): 3.85 min |
| 95 | 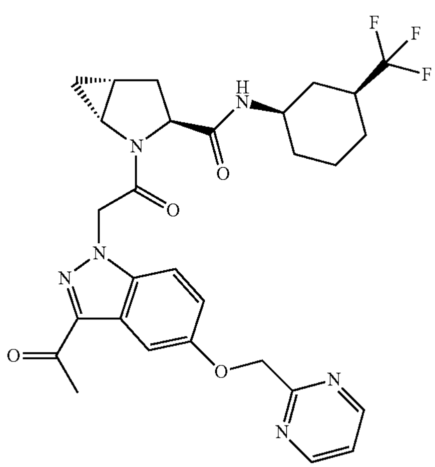 [SMILES: CC(=O)c1nn(CC(=O)N2[C@@H]3C[C@@H]3C[C@H]2C(=O)N[C@@H]2CCC[C@H](C(F)(F)F)C2)c2ccc(OCc3ncccn3)cc12] | (1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((1R,3S)-3-trifluoromethyl-cyclohexyl)-amide | (2[C5], 5[A3]); 585.1 [M+H]+, 629.2 [M+HCOO]−; $t_R$ (b): 4.45 min. |

TABLE 5-continued

| Example | Structure | Name | Characterization (end-table notes); MS (LC/MS); $t_R$ (HPLC conditions) |
|---|---|---|---|
| 96 | 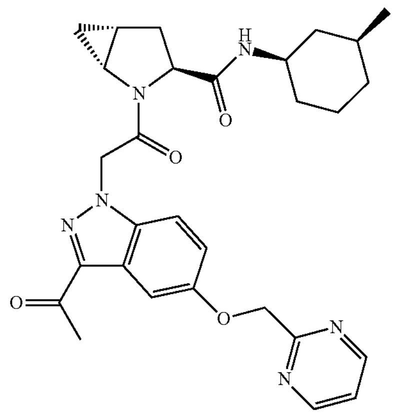 [SMILES: CC(=O)c1nn(CC(=O)N2[C@@H]3C[C@@H]3C[C@H]2C(=O)N[C@@H]2CCC[C@H](C)C2)c2ccc(OCc3ncccn3)cc12] | (1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((1R,3S)-3-methyl-cyclohexyl)-amide | (2[C], 5[A3], 9 [Method 4]); 531.1 [M+H]+, 553.2 [M+Na]+; $t_R$ (b): 4.43 min. |
| 97 | 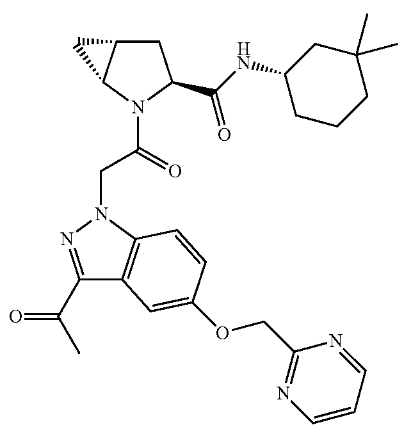 [SMILES: CC(=O)c1nn(CC(=O)N2[C@@H]3C[C@@H]3C[C@H]2C(=O)N[C@H]2CCCC(C)(C)C2)c2ccc(OCc3ncccn3)cc12] | (1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((S)-3,3-dimethyl-cyclohexyl)-amide | (5[A3], 9[Method 2]); 545.0 [M+H]+, 589.2 [M+HCOO]−; $t_R$ (d): 3.38 min. |
| 98 | 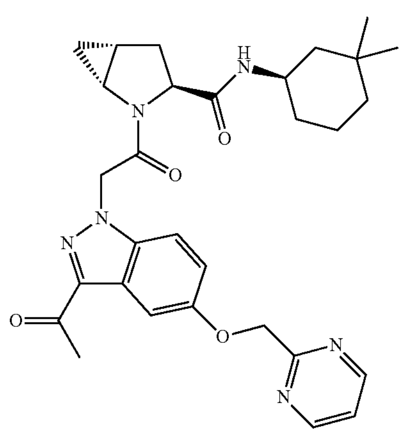 [SMILES: CC(=O)c1nn(CC(=O)N2[C@@H]3C[C@@H]3C[C@H]2C(=O)N[C@@H]2CCCC(C)(C)C2)c2ccc(OCc3ncccn3)cc12] | (1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((R)-3,3-dimethyl-cyclohexyl)-amide | (5[A3], 9[Method 2]); 567.1 [M+Na]+; 589.2 [M+HCOO]−; $t_R$ (d): 3.30 min. |

TABLE 5-continued

| Example | Structure | Name | Characterization (end-table notes); MS (LC/MS); $t_R$ (HPLC conditions) |
|---|---|---|---|
| 99 | 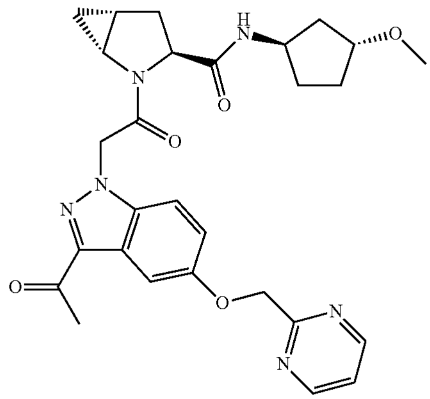 [SMILES: CO[C@@H]1CC[C@@H](NC(=O)[C@@H]2C[C@H]3C[C@H]3N2C(=O)Cn2nc(C(C)=O)c3cc(OCc4ncccn4)ccc32)C1] | (1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((1R,3R)-3-methoxy-cyclopentyl)-amide | (4, 5[A3], 7); 555.1 [M+Na]+; $t_R$ (b): 3.65 min. |
| 100 | 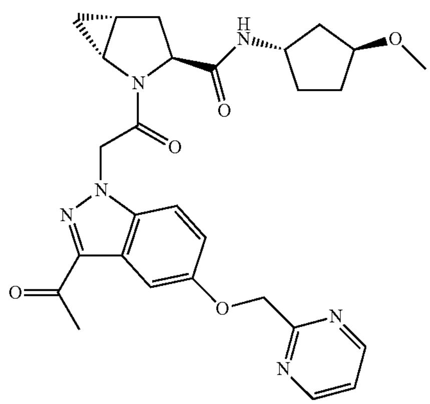 [SMILES: CO[C@H]1CC[C@H](NC(=O)[C@@H]2C[C@H]3C[C@H]3N2C(=O)Cn2nc(C(C)=O)c3cc(OCc4ncccn4)ccc32)C1] | (1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((1S,3S)-3-methoxy-cyclopentyl)-amide | (4, 5[A3], 7); 555.1 [M+Na]+; $t_R$ (b): 3.66 min. |
| 101 | 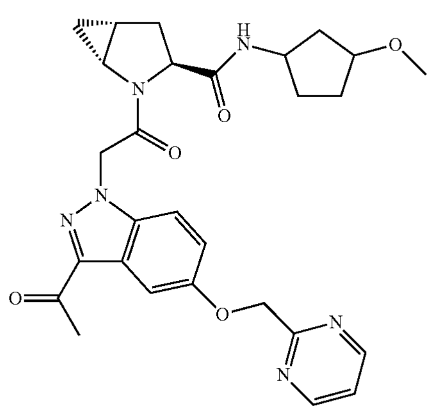 [SMILES: COC1CCC(NC(=O)[C@@H]2C[C@H]3C[C@H]3N2C(=O)Cn2nc(C(C)=O)c3cc(OCc4ncccn4)ccc32)C1] | (1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((1S,3R) or (1R,3S)-3-methoxy-cyclopentyl)-amide | (4, 5[A3], 7); 533.2 [M+H]+, 555.1 [M+Na]+; $t_R$ (b): 3.61 min. |

TABLE 5-continued

| Example | Name | Characterization (end-table notes); MS (LC/MS); $t_R$ (HPLC conditions) |
|---|---|---|
| 102 | (1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((1S,3R) or (1R,3S)-3-methoxy-cyclopentyl)-amide | (4, 5[A3], 7); 533.2 [M+H]+, 555.1 [M+Na]+; $t_R$ (b): 3.74 min. |
| 103 | (1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid (3,3-dimethyl-cyclobutyl)-amide | (2[C1], 4, 5[A3], 7); 517 [M+H]+; $t_R$ (f): 3.54 min. |
| 104 | (1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid (3,3-difluoro-cyclobutyl)-amide | (4, 5[A3], 7); 525 [M+H]+; $t_R$ (f): 2.94 min. |
| 105 | 1-{2-[(1R,3S,5R)-3-((1S,5S)-5-Methoxy-3,3-dimethyl-cyclohexylcarbamoyl)-2-aza-bicyclo[3.1.0]hex-2-yl]-2-oxo-ethyl}-1H-indazole-3-carboxylic acid amide | (2[C4], 3, 5[A6], 9[Method 15], 10); 468.3 [M+H]+, 512.3 [M+HCOO]−; $t_R$ (f): 3.40 min. |

TABLE 5-continued

| Example | Structure | Name | Characterization (end-table notes); MS (LC/MS); t_R (HPLC conditions) |
|---------|-----------|------|----------------------------------------------------------------------|
| 106 | 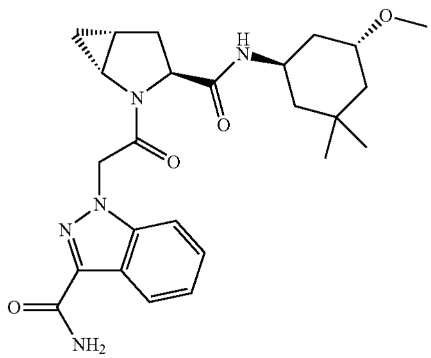 [SMILES: CO[C@H]1C[C@H](NC(=O)[C@@H]2C[C@H]3C[C@H]3N2C(=O)Cn2nc(C(N)=O)c3ccccc32)CC(C)(C)C1] | 1-{2-[(1R,3S,5R)-3-((1R,5R)-5-Methoxy-3,3-dimethyl-cyclohexylcarbamoyl)-2-aza-bicyclo[3.1.0]hex-2-yl]-2-oxo-ethyl}-1H-indazole-3-carboxylic acid amide | (2[C4], 3, 5[A6], 9[Method 15], 10); 468.3 [M+H]+, 512.3 [M+HCOO]−; t_R (f): 3.38 min. |
| 107 | 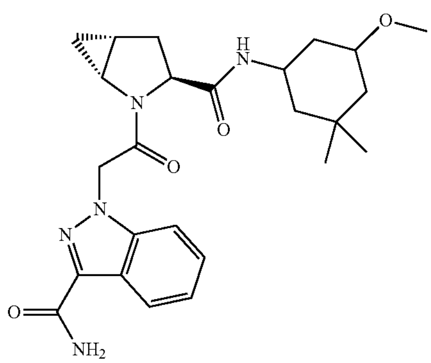 [SMILES: COC1CC(NC(=O)[C@@H]2C[C@H]3C[C@H]3N2C(=O)Cn2nc(C(N)=O)c3ccccc32)CC(C)(C)C1] | 1-{2-[(1R,3S,5R)-3-(cis-5-Methoxy-3,3-dimethyl-cyclohexylcarbamoyl)-2-aza-bicyclo[3.1.0]hex-2-yl]-2-oxo-ethyl}-1H-indazole-3-carboxylic acid amide (mixture of 2 diastereoisomers) | (2[C4], 3, 5[A6], 10); 468.3 [M+H]+, 512.3 [M+HCOO]−; t_R (f): 3.11 min. |
| 108 | 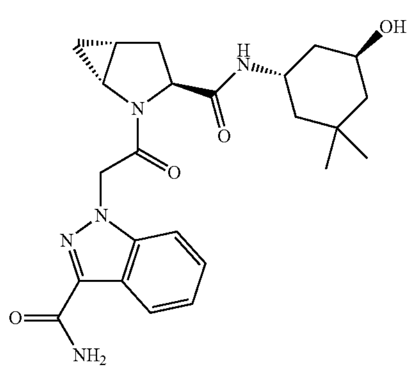 [SMILES: CC1(C)C[C@H](O)C[C@@H](NC(=O)[C@@H]2C[C@H]3C[C@H]3N2C(=O)Cn2nc(C(N)=O)c3ccccc32)C1] | 1-{2-[(1R,3S,5R)-3-((1S,5S)-5-Hydroxy-3,3-dimethyl-cyclohexylcarbamoyl)-2-aza-bicyclo[3.1.0]hex-2-yl]-2-oxo-ethyl}-1H-indazole-3-carboxylic acid amide | (2[C4], 3, 5[A6], 9[Method 16], 10); 454.3 [M+H]+, 498.3 [M+HCOO]−; t_R (f): 2.69 min. |

TABLE 5-continued

| Example | Structure | Name | Characterization (end-table notes); MS (LC/MS); $t_R$ (HPLC conditions) |
|---|---|---|---|
| 109 | 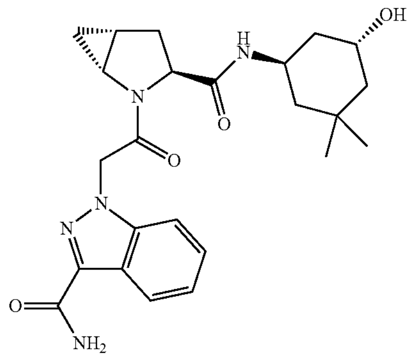 [SMILES: CC1(C)C[C@@H](O)C[C@H](NC(=O)[C@@H]2C[C@H]3C[C@H]3N2C(=O)Cn2nc(C(N)=O)c3ccccc32)C1] | 1-{2-[(1R,3S,5R)-3-((1R,5R)-5-Hydroxy-3,3-dimethyl-cyclohexylcarbamoyl)-2-aza-bicyclo[3.1.0]hex-2-yl]-2-oxo-ethyl}-1H-indazole-3-carboxylic acid amide | (2[C4], 3, 5[A6], 9[Method 16], 10); 454.3 [M+H]+, 498.3 [M+HCOO]−; $t_R$ (f): 2.66 min. |

(1) The substituted acid derivative used in step A was prepared as described in Part B [Scheme];
(2) The substituted amine derivative used in step A was prepared as described in Part C [Scheme];
(3) T₃P was used instead of HBTU in step A and the reaction was performed in CH₂Cl₂;
(4) TFA in CH₂Cl₂ was used instead of HCl in dioxane in step B;
(5) The substituted acid derivative used in step C was prepared as described in Part A [Scheme];
(6) T₃P was used instead of HBTU in step C and the reaction was performed in CH₂Cl₂;
(7) CH₂Cl₂ was used instead of DMF in step A;
(8) CH₃CN was used instead of DMF in step A;
(9) For details concerning the separation of diastereoisomers and assignement of stereochemistry see Separation section [Method];
(10) EDC/HOAT was used instead of HBTU in step C and the reaction was performed in CH₂Cl₂;
(11) CH₂Cl₂ was used instead of DMF in step C Scheme D6: General protocol described for the preparation of Example 110: 1-{2-[(1R, 3S, 5S)-3-(3,3-dimethyl-cyclohexylcarbamoyl)-5-hydroxymethyl-2-aza-bicyclo[3.1.0]hex-2-yl]-2-oxo-thy}-1H-indazole-3-carboxylic acid amide

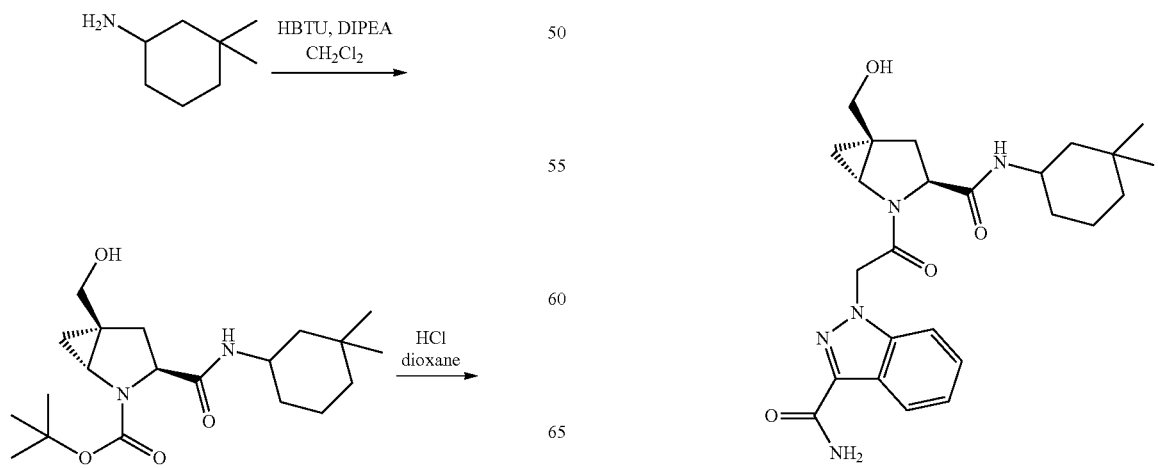

A. (1R,3S,5S)-3-(3,3-Dimethyl-cyclohexylcarbamoyl)-5-hydroxymethyl-2-aza-bicyclo[3.1.0]hexane-2-carboxylic acid tert-butyl ester To a solution of (1R,3S,5S)-5-hydroxymethyl-2-aza-bicyclo[3.1.0]hexane-2,3-dicarboxylic acid 2-tert-butyl ester (prepared as described in part B, 150 mg, 0.583 mmol), 3,3-dimethylcyclohexanamine (95 mg, 0.583 mmol) and HBTU (332 mg, 0.875 mmol) in $CH_2Cl_2$ (1.9 mL) was added DIPEA (305 µL, 1.75 mmol). The reaction mixture was stirred at RT for 2 h, diluted in EtOAc and washed successively with 1N aq. HCl and 5% aq. $NaHCO_3$. The organic layer was dried (phase separator), concentrated and the product was purified by preparative HPLC (XBridge C18OBD, 5 µm, 30×100, eluent: 20 to 100% $CH_3CN$ in $H_2O$ in 12 min, $CH_3CN$ and $H_2O$ contain 7.3 mM of $NH_3$). The pure fractions were combined and lyophilized to afford the title compound. MS (LC/MS): 367.1 [M+H]+, 411.2 [M+HCOO]−.

B. (1R,3S,5S)-5-Hydroxymethyl-2-aza-bicyclo[3.1.0]hexane-3-carboxylic acid (3,3-dimethyl-cyclohexyl)-amide hydrochloride To a solution of (1R,3S,5S)-3-(3,3-dimethyl-cyclohexylcarbamoyl)-5-hydroxymethyl-2-aza-bicyclo[3.1.0]hexane-2-carboxylic acid tert-butyl ester (75 mg, 0.205 mmol) in dioxane (682 µL) was added 4N HCl in dioxane (256 µL, 1.02 mmol). The reaction mixture was stirred at RT for 4 h and lyophilized to afford the title compound. MS (LC/MS): 267.1 [M+H]+.

C. Example 110: 1-{2-[(1R,3S,5S)-3-(3,3-Dimethyl-cyclohexylcarbamoyl)-5-hydroxymethyl-2-aza-bicyclo[3.1.0]hex-2-yl]-2-oxo-thyl}-1H-indazole-3-carboxylic acid amide To a solution of (3-carbamoyl-indazol-1-yl)-acetic acid (prepared as described in part A, 99 mg, 0.45 mmol), (1R,3S,5S)-5-hydroxymethyl-2-aza-bicyclo[3.1.0]hexane-3-carboxylic acid (3,3-dimethyl-cyclohexyl)-amide hydrochloride (65 mg, 0.215 mmol) and HBTU (179 mg, 0.472 mmol) in DMF (715 µL) was added DIPEA (112 µL, 0.644 mmol). The reaction mixture was stirred at RT for 7 h, poured into 5% aq. $NaHCO_3$ and extracted with EtOAc. The combined organic extracts were dried, filtered and concentrated. The residue was dissolved in $H_2O$/THF (1/1, 715 µL) and $LiOH.H_2O$ (45.0 mg, 1.07 mmol) was added. The reaction mixture was stirred at RT for 3 h and the product purified by preparative HPLC (XBridge C18OBD, 5 µm, 30×100, eluent: 5% to 100% $CH_3CN$ in $H_2O$ in 12 min, $CH_3CN$ and $H_2O$ contain 7.3 mM of $NH_3$). The pure fractions were combined and lyophilized to afford the title compound. MS (LC/MS): 468.1 [M+H]+, 512.2 [M+HCOO]−; $t_R$ (HPLC conditions d): 3.06 min.

The examples below were prepared according to the general procedures described in Scheme D6 for the preparation of Example 110 from commercially available building blocks, if not otherwise stated (see notes at the end of table 6). In case a racemic amine is used in step A, the mixture of diastereoisomers can be separated either in step A or C (for details, refer to Separation method section).

TABLE 6

| Example | Structure | Name | Characterization (end-table notes); MS (LC/MS); $t_R$ (HPLC conditions) |
|---|---|---|---|
| 111 | 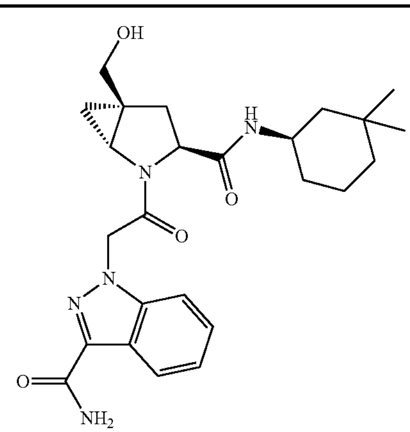 | 1-{2-[(1R,3S,5S)-3-((R)-3,3-Dimethyl-cyclohexylcarbamoyl)-5-hydroxymethyl-2-aza-bicyclo[3.1.0]hex-2-yl]-2-oxo-ethyl}-1H-indazole-3-carboxylic acid amide | (2[A6], 3[Method 17]); 485.4 [M+NH$_4$]+, 512.3 [M+HCOO]−; $t_R$ (d): 3.04 min. |

TABLE 6-continued

| Example | Structure | Name | Characterization (end-table notes); MS (LC/MS); $t_R$ (HPLC conditions) |
|---|---|---|---|
| 112 | 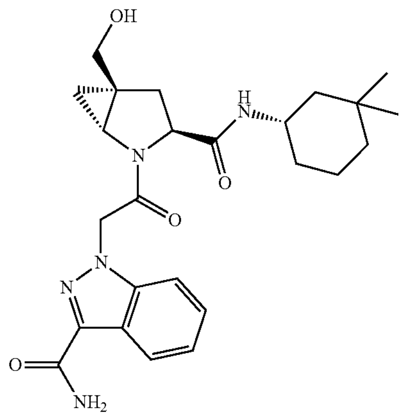 [SMILES: CC1(C)CCC[C@H](NC(=O)[C@@H]2C[C@@]3(CO)C[C@H]3N2C(=O)Cn2nc(C(N)=O)c3ccccc32)C1] | 1-{2-[(1R,3S,5S)-3-((S)-3,3-Dimethyl-cyclohexylcarbamoyl)-5-hydroxymethyl-2-aza-bicyclo[3.1.0]hex-2-yl]-2-oxo-ethyl}-1H-indazole-3-carboxylic acid amide | (2[A6], 3[Method 17]); 485.3 [M+NH$_4$]+, 512.4 [M+HCOO]−; $t_R$ (d): 3.04 min. |
| 113 | 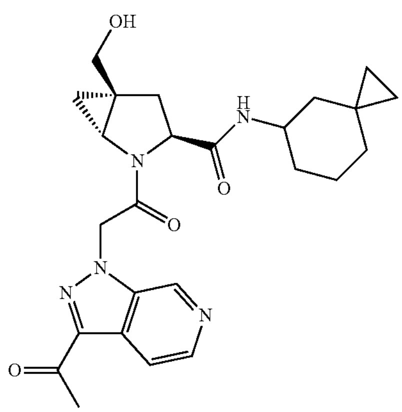 [SMILES: CC(=O)c1nn(CC(=O)N2[C@H](C(=O)NC3CCCC4(CC4)C3)C[C@@]3(CO)C[C@@H]23)c2cnccc12] | (1R,3S,5S)-2-[2-(3-Acetyl-pyrazolo[3,4-c]pyridin-1-yl)-acetyl]-5-hydroxymethyl-2-aza-bicyclo[3.1.0]hexane-3-carboxylic acid spiro[2.5]oct-5-ylamide-Dia 1 | (1[C6], 2[A2], 3[Method 18]); 466.3 [M+H]+, 488.4 [M+Na]+; $t_R$ (b): 3.49 min. |
| 114 | 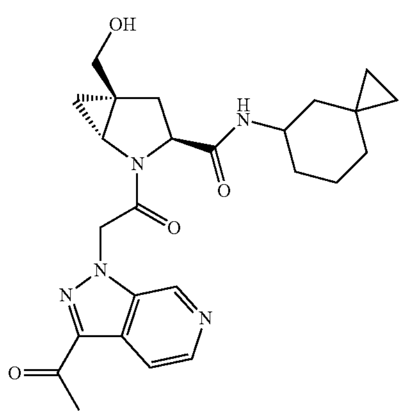 [SMILES: CC(=O)c1nn(CC(=O)N2[C@H](C(=O)NC3CCCC4(CC4)C3)C[C@@]3(CO)C[C@@H]23)c2cnccc12] | (1R,3S,5S)-2-[2-(3-Acetyl-pyrazolo[3,4-c]pyridin-1-yl)-acetyl]-5-hydroxymethyl-2-aza-bicyclo[3.1.0]hexane-3-carboxylic acid spiro[2.5]oct-5-ylamide-Dia 2 | (1[C6], 2[A2], 3[Method 18]); 466.3 [M+H]+, 488.3 [M+Na]+; $t_R$ (b): 3.50 min. |

TABLE 6-continued

| Example | Structure | Name | Characterization (end-table notes); MS (LC/MS); $t_R$ (HPLC conditions) |
|---|---|---|---|
| 115 | 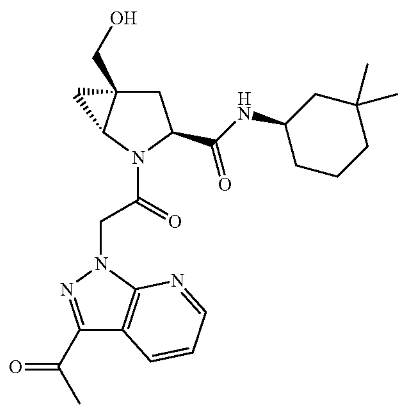 [SMILES: CC(=O)c1nn(CC(=O)N2[C@H](C(=O)N[C@@H]3CCCC(C)(C)C3)C[C@@]3(CO)C[C@@H]23)c2ncccc12] | (1R,3S,5S)-2-[2-(3-Acetyl-pyrazolo[3,4-b]pyridin-1-yl)-acetyl]-5-hydroxymethyl-2-aza-bicyclo[3.1.0]hexane-3-carboxylic acid ((R)-3,3-dimethyl-cyclohexyl)-amide | (2[A2], 3[Method 19]); 468.3 [M+H]+, 512.4 [M+HCOO]− ; $t_R$ (f): 3.64 min. |
| 116 | 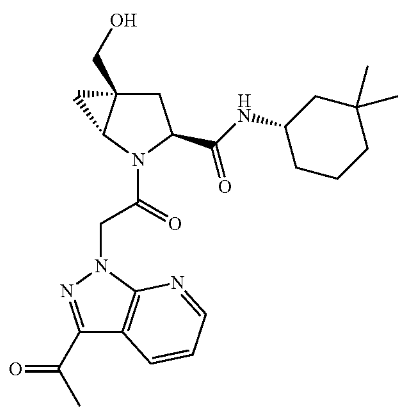 [SMILES: CC(=O)c1nn(CC(=O)N2[C@H](C(=O)N[C@H]3CCCC(C)(C)C3)C[C@@]3(CO)C[C@@H]23)c2ncccc12] | (1R,3S,5S)-2-[2-(3-Acetyl-pyrazolo[3,4-b]pyridin-1-yl)-acetyl]-5-hydroxymethyl-2-aza-bicyclo[3.1.0]hexane-3-carboxylic acid ((S)-3,3-dimethyl-cyclohexyl)-amide | (2[A2], 3[Method 19]); 468.3 [M+H]+, 512.3 [M+HCOO]−; $t_R$ (f): 3.62 min. |
| 117 | 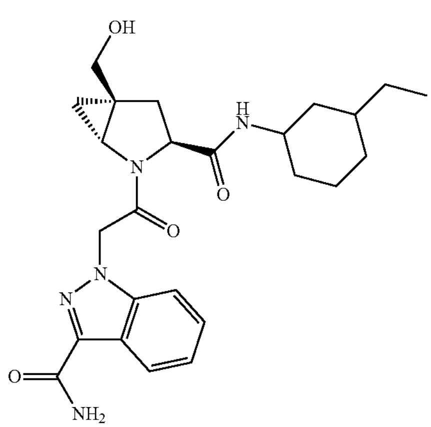 [SMILES: CCC1CCCC(NC(=O)[C@@H]2C[C@@]3(CO)C[C@H]3N2C(=O)Cn2nc(C(N)=O)c3ccccc32)C1] | 1-{2-[(1R,3S,5S)-3-(3-Ethyl-cyclohexylcarbamoyl)-5-hydroxymethyl-2-aza-bicyclo[3.1.0]hex-2-yl]-2-oxo-ethyl}-1H-indazole-3-carboxylic acid amide-Dia 1 | (2[A6], 3[Method 20]); 485.4 [M+NH$_4$]+, 512.2 [M+HCOO]−; $t_R$ (f): 3.41 min. |

TABLE 6-continued

| Example | Structure | Name | Characterization (end-table notes); MS (LC/MS); $t_R$ (HPLC conditions) |
|---|---|---|---|
| 118 | 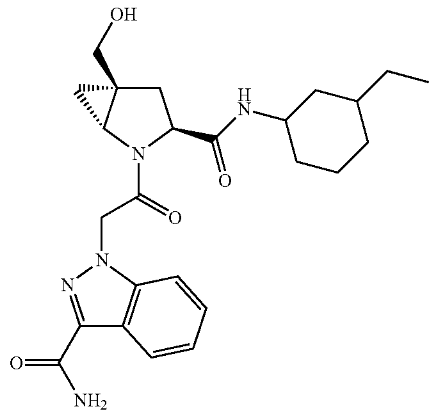 [SMILES: CCC1CCCC(NC(=O)[C@@H]2C[C@@]3(CO)C[C@H]3N2C(=O)Cn2nc(C(N)=O)c3ccccc32)C1] | 1-{2-[(1R,3S,5S)-3-(3-Ethyl-cyclohexylcarbamoyl)-5-hydroxymethyl-2-aza-bicyclo[3.1.0]hex-2-yl]-2-oxo-ethyl}-1H-indazole-3-carboxylic acid amide-Dia 2 | (2[A6], 3[Method 20]); 468.4 [M+H]+, 512.4 [M+HCOO]−; $t_R$ (f): 3.39 min. |
| 119 | 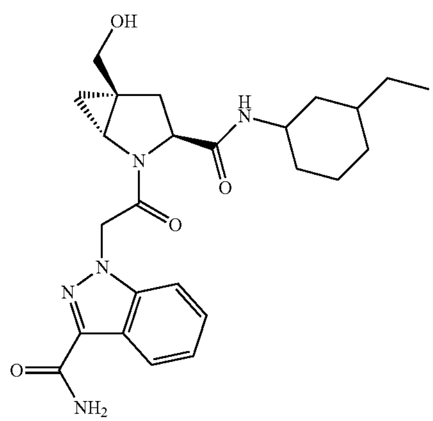 [SMILES: CCC1CCCC(NC(=O)[C@@H]2C[C@@]3(CO)C[C@H]3N2C(=O)Cn2nc(C(N)=O)c3ccccc32)C1] | 1-{2-[(1R,3S,5S)-3-(3-Ethyl-cyclohexylcarbamoyl)-5-hydroxymethyl-2-aza-bicyclo[3.1.0]hex-2-yl]-2-oxo-ethyl}-1H-indazole-3-carboxylic acid amide-Dia 3 | (2[A6], 3[Method 20]); 468.3 [M+H]+, 512.3 [M+HCOO]−; $t_R$ (f): 3.40 min. |
| 120 | 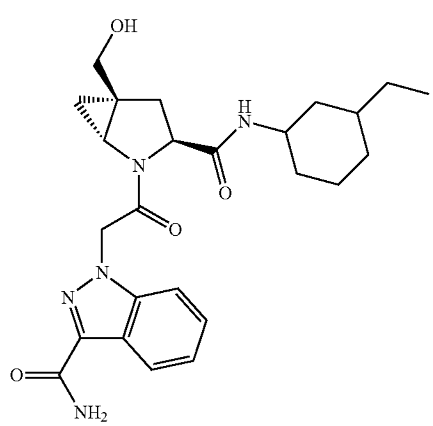 [SMILES: CCC1CCCC(NC(=O)[C@@H]2C[C@@]3(CO)C[C@H]3N2C(=O)Cn2nc(C(N)=O)c3ccccc32)C1] | 1-{2-[(1R,3S,5S)-3-(3-Ethyl-cyclohexylcarbamoyl)-5-hydroxymethyl-2-aza-bicyclo[3.1.0]hex-2-yl]-2-oxo-ethyl}-1H-indazole-3-carboxylic acid amide-Dia 4 | (2[A6], 3[Method 20]); 468.3 [M+H]+, 512.3 [M+HCOO]−; $t_R$ (f): 3.39 min. |

TABLE 6-continued

| Example | Structure | Name | Characterization (end-table notes); MS (LC/MS); $t_R$ (HPLC conditions) |
|---|---|---|---|
| 121 | 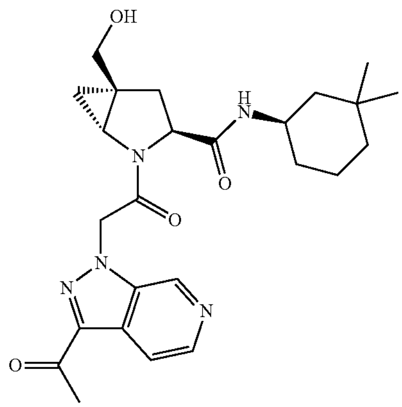 [SMILES: CC(=O)c1nn(CC(=O)N2[C@H](C(=O)N[C@@H]3CCCC(C)(C)C3)C[C@@]3(CO)C[C@@H]23)c2cnccc12] | (1R,3S,5S)-2-[2-(3-Acetyl-pyrazolo[3,4-c]pyridin-1-yl)-acetyl]-5-hydroxymethyl-2-aza-bicyclo[3.1.0]hexane-3-carboxylic acid ((R)-3,3-dimethyl-cyclohexyl)-amide | (2[A2], 3[Method 21]); 468.3 [M+H]+, 512.4 [M+HCOO]− ; $t_R$ (f): 2.87 min. |
| 122 | 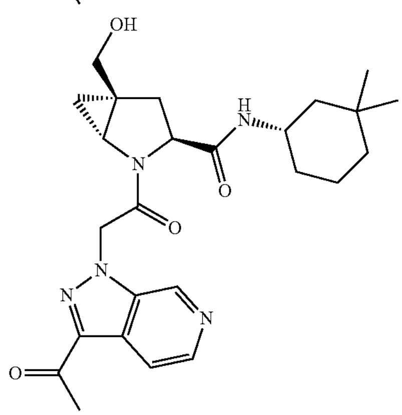 | (1R,3S,5S)-2-[2-(3-Acetyl-pyrazolo[3,4-c]pyridin-1-yl)-acetyl]-5-hydroxymethyl-2-aza-bicyclo[3.1.0]hexane-3-carboxylic acid ((S)-3,3-dimethyl-cyclohexyl)-amide | (2[A2], 3[Method 21]); 468.3 [M+H]+, 512.4 [M+HCOO]−; $t_R$ (f): 2.86 min. |

(1) The substituted amine derivative used in step A was prepared as described in Part C [Scheme];
(2) The substituted acid derivative used in step C was prepared as described in Part A [Scheme];
(3) For details concerning the separation of diastereoisomers and assignement of stereochemistry see Separation section [Method].

Scheme D7: General protocol described for the preparation of Example 123: 1-(2-((1R,3S,5R)-3-(3-hydroxy-3-methylcyclohexylcarbamoyl)-2-azabicyclo[3.1.0]hexan-2-yl)-2-oxoethyl)-1H-indazole-3-carboxamide

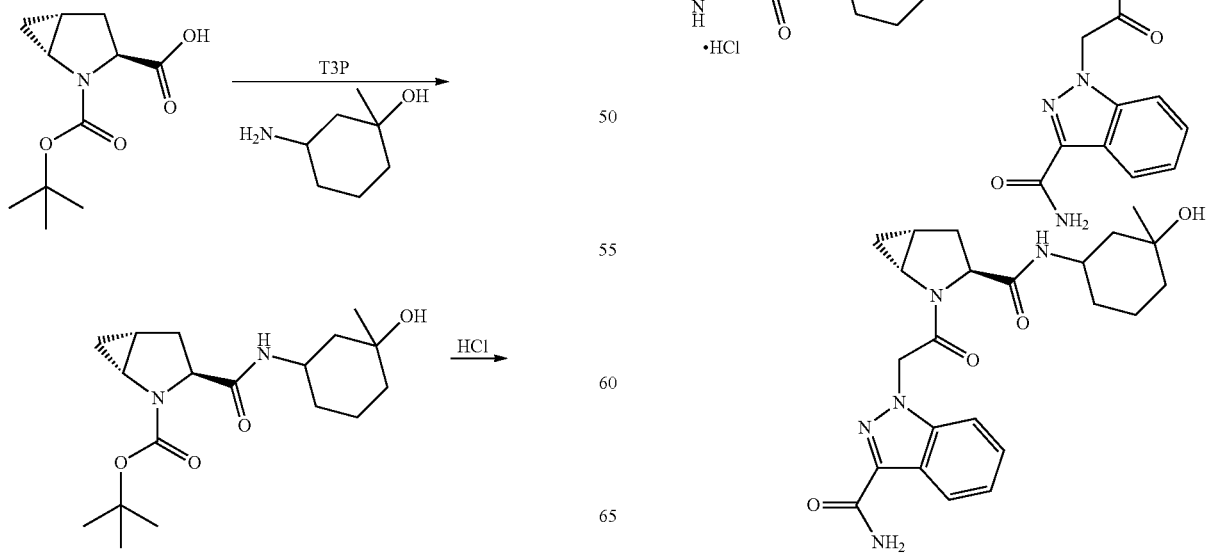

A. (1R,3S,5R)-tert-butyl 3-(3-hydroxy-3-methylcyclohexylcarbamoyl)-2-azabicyclo[3.1.0]hexane-2-carboxylate To a solution of (1R,3S,5R)-2-(tert-butoxycarbonyl)-2-azabicyclo[3.1.0]hexane-3-carboxylic acid (220 mg, 0.968 mmol), 3-amino-1-methylcyclohexanol, hydrochloride salt—Diastereomer 1 (prepared as described in scheme C11, 160 mg, 0.968 mmol) and DIPEA (0.51 mL, 2.90 mmol) in DMF (5 mL) was added propylphosphonic anhydride (50% in DMF, 0.34 mL, 1.16 mmol). The reaction mixture was stirred at 23° C. overnight, then was quenched with H$_2$O (100 mL) and extracted with tert.butylmethyl ether (×3). The combined organic layers were dried (Na$_2$SO$_4$), filtered and concentrated under vacuum. The crude product was purified by flash column chromatography on silica gel (Merck EVF D17, Si60 15×40 µm, 40 g; gradient: c-hexane/EtOAc 95/05 to 70/30) to afford the title compound as a mixture of 2 diastereoisomers. MS (UPLC/MS): 339.3 [M+H]+; t$_R$ (HPLC conditions h): 0.82 min.

B (1R,3S,5R)—N-(3-hydroxy-3-methylcyclohexyl)-2-azabicyclo[3.1.0]hexane-3-carboxamide, hydrochloride salt To a solution of (1R,3S,5R)-tert-butyl 3-(3-hydroxy-3-methylcyclohexylcarbamoyl)-2-azabicyclo[3.1.0]hexane-2-carboxylate (301 mg, 0.89 mmol) in dioxane (4 mL) was added HCl (4N in dioxane, 2.22 mL, 8.89 mmol) and the resulting colorless solution was stirred at RT under nitrogen for 18 h. The reaction mixture was concentrated to dryness to afford the crude title compound which was used without further purification in the subsequent step. MS (UPLC/MS): 239.2 [M+H]+; t$_R$ (HPLC conditions h): 0.37 min.

C. Examples 123: 1-(2-(((1R,3S,5R)-3-(3-hydroxy-3-methylcyclohexylcarbamoyl)-2-azabicyclo[3.1.0]hexan-2-yl)-2-oxoethyl)-1H-indazole-3-carboxamide To a solution of (1R,3S,5R)—N-(3-hydroxy-3-methylcyclohexyl)-2-azabicyclo[3.1.0]hexane-3-carboxamide, hydrochloride salt (258 mg, 0.939 mmol), 2-(3-carbamoyl-1H-indazol-1-yl)acetic acid (206 mg, 0.939 mmol), 1-Hydroxy-7-azabenzotriazole (0.132 g, 0.972 mmol) and DIPEA (0.443 mL, 2.54 mmol) in CH$_2$Cl$_2$ (10 ml) under a nitrogen atmosphere was added EDC (0.178 g, 0.930 mmol) at 23° C. and the reaction mixture was stirred at 23° C. for 2 days. The reaction mixture was quenched with H$_2$O, acidified with aqueous HCl (0.1 N) and extracted with CH$_2$Cl$_2$ (×2). The combined organic layers were washed with a saturated aqueous solution of Na$_2$CO$_3$, dried (Na$_2$SO$_4$), filtered and concentrated under vacuum. The crude product was purified by preparative HPLC (Nucleosil C18 100-10, 5 m, 40×250 mm, eluent: 5% MeCN/95% H$_2$O to 100% CH$_3$CN in 20 min, CH$_3$CN and H$_2$O both containing 0.1% of TFA, flow: 40 mL/min) to afford the title compound as a mixture of 2 diastereoisomers. MS (UPLC/MS): 440.3 [M+H]+; t$_R$ (HPLC conditions f): 2.23 min.

The examples below were prepared according to the general procedures described in Scheme D7 for the preparation of Example 123 from commercially available building blocks or Building blocks described in part C. In case a racemic amine is used in step A, the mixture of diastereoisomers can be separated either in step A or C (for details, refer to Separation method section).

TABLE 7

| Example | Structure | Name | Characterization (end-table notes); MS (LC/MS); t$_R$ (HPLC conditions) |
|---|---|---|---|
| 124 | 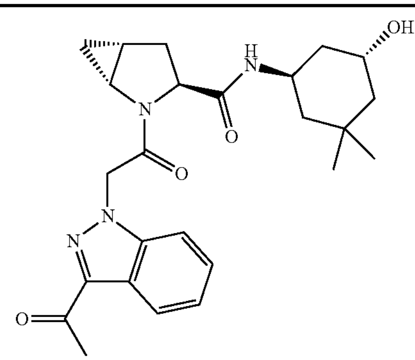 | (1R,3S,5R)-2-(2-(3-acetyl-1H-indazol-1-yl)acetyl)-N-((1R,5R)-5-hydroxy-3,3-dimethylcyclohexyl)-2-azabicyclo[3.1.0]hexane-3-carboxamide | (1, 2[Method 22]); 453.3 [M+H]+; t$_R$ (f): 3.23 min |
| 125 | 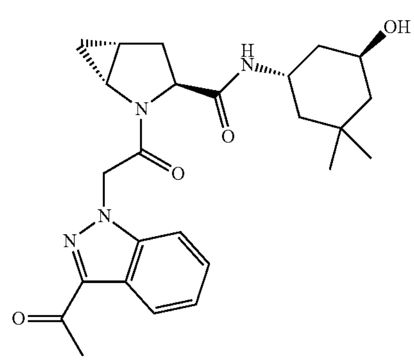 [SMILES: CC(=O)c1nn(CC(=O)N2[C@@H]3C[C@@H]3C[C@H]2C(=O)N[C@@H]2C[C@@H](O)CC(C)(C)C2)c2ccccc12] | (1R,3S,5R)-2-(2-(3-acetyl-1H-indazol-1-yl)acetyl)-N-((1S,5S)-5-hydroxy-3,3-dimethylcyclohexyl)-2-azabicyclo[3.1.0]hexane-3-carboxamide | (1, 2[Method 22]); 453.3 [M+H]+; t$_R$ (f): 3.28 min |

TABLE 7-continued

| Example | Structure | Name | Characterization (end-table notes); MS (LC/MS); $t_R$ (HPLC conditions) |
|---|---|---|---|
| 126 | 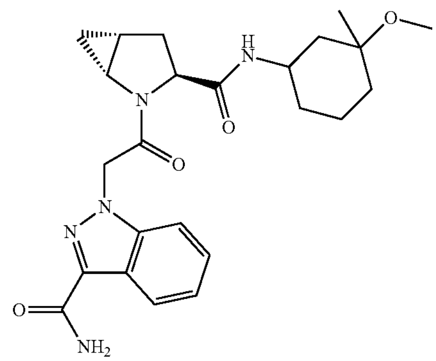 [SMILES: COC1(C)CCCC(NC(=O)[C@@H]2C[C@H]3C[C@H]3N2C(=O)Cn2nc(C(N)=O)c3ccccc32)C1] | 1-(2-((1R,3S,5R)-3-(((1R,3S) and (1S,3R)-3-methoxy-3-methylcyclohexyl)carbamoyl)-2-azabicyclo[3.1.0]hexan-2-yl)-2-oxoethyl)-1H-indazole-3-carboxamide (mixture of 2 diastereosiomers) | (1); 454.3 [M+H]+; $t_R$ (f): 2.73 and 2.81 min |
| 127 | 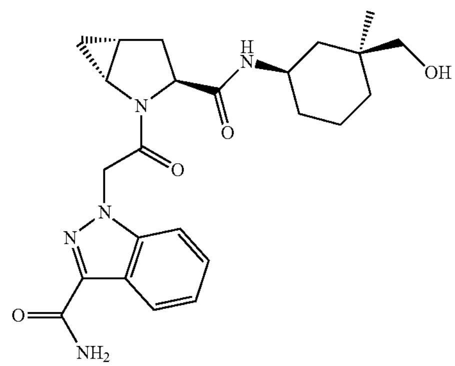 [SMILES: C[C@]1(CO)CCC[C@@H](NC(=O)[C@@H]2C[C@H]3C[C@H]3N2C(=O)Cn2nc(C(N)=O)c3ccccc32)C1] | 1-(2-((1R,3S,5R)-3-(((1R,3S)-3-(hydroxymethyl)-3-methylcyclohexyl)carbamoyl)-2-azabicyclo[3.1.0]hexan-2-yl)-2-oxoethyl)-1H-indazole-3-carboxamide | (1, 2[Method 23]); 454.4 [M+H]+, 471.4 [M+NH4]+; $t_R$ (f): 2.59 min |
| 128 | 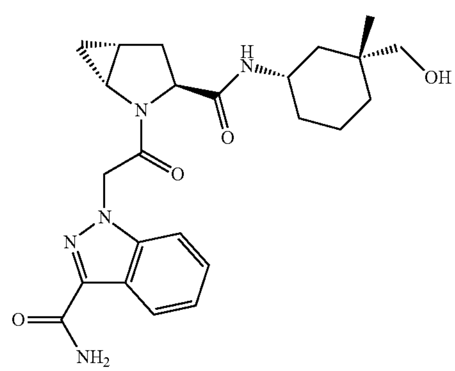 [SMILES: C[C@@]1(CO)CCC[C@H](NC(=O)[C@@H]2C[C@H]3C[C@H]3N2C(=O)Cn2nc(C(N)=O)c3ccccc32)C1] | 1-(2-((1R,3S,5R)-3-(((1S,3R)-3-(hydroxymethyl)-3-methylcyclohexyl)carbamoyl)-2-azabicyclo[3.1.0]hexan-2-yl)-2-oxoethyl)-1H-indazole-3-carboxamide | (1, 2[Method 23]); 454.4 [M+H]+, 471.4 [M+NH4]+; $t_R$ (f): 2.55 min |

(1) The substituted amine derivative used in step A was prepared as described in Part C;
(2) For details concerning the separation of diastereoisomers and assignement of stereochemistry see Separation section [Method].

Separation Section

Method 1:

The mixture of (1R,3S,5R)-3-[(1S,3R) and (1S,3S) and (1R,3R) and (1R,3S)-3-(2,2,2-trifluoro-ethoxy)-cyclohexylcarbamoyl]-2-aza-bicyclo[3.1.0]hexane-2-carboxylic acid tert-butyl ester was separated into its diastereoisomers by preparative chiral HPLC (column: Chiralpak AD, 20 um, 500×50 mm; eluent: heptane:1-propanol 75:25, flow rate: 11 mL/min) to give (1R,3S,5R)-3-[3-(2,2,2-trifluoro-ethoxy)-cyclohexylcarbamoyl]-2-aza-bicyclo[3.1.0]hexane-2-carboxylic acid tert-butyl ester—Dia 1: $t_R$ (Chiralpak AD-H, 5 um, 250×4.6 mm, heptane:1-propanol 85:15, flow rate: 1.1 mL/min, detection: UV at 220 nm): 6.64 min, (1R,3S,5R)-3-[3-(2,2,2-trifluoro-ethoxy)-cyclohexylcarbamoyl]-2-aza-bicyclo[3.1.0]hexane-2-carboxylic acid tert-butyl ester—Dia 2: $t_R$ (Chiralpak AD-H, 5 um, 250×4.6 mm, heptane:1-propanol 85:15, flow rate: 1.1 mL/min, detection: UV at 220 nm): 8.55 min, (1R,3S,5R)-3-[3-(2,2,2-trifluoro-ethoxy)-cyclohexylcarbamoyl]-2-aza-bicyclo[3.1.0]hexane-2-carboxylic acid tert-butyl ester—Dia 3: $t_R$ (Chiralpak AD-H, 5 um, 250×4.6 mm, heptane:1-propanol 85:15, flow rate: 1.1 mL/min, detection: UV at 220 nm): 9.93 min and (1R,3S,5R)-3-[3-(2,2,2-trifluoro-ethoxy)-cyclohexylcarbamoyl]-2-aza-bicyclo[3.1.0]hexane-2-carboxylic acid tert-butyl ester—Dia 4: $t_R$ (Chiralpak AD-H, 5 um, 250×4.6 mm, heptane:1-propanol 85:15, flow rate: 1.1 mL/min, detection: UV at 220 nm): 11.91 min.

Method 2:

The mixture of (1R,3S,5R)-3-((S) and (R)-3,3-dimethyl-cyclohexylcarbamoyl)-2-aza-bicyclo[3.1.0]hexane-2-carboxylic acid tert-butyl ester was separated into its diastereoisomers by preparative chiral HPLC (column: Chiralpak AS, 20 um, 500×50 mm; eluent: heptane:1-propanol 90:10, flow rate: 40 mL/min) to give (1R,3S,5R)-3-((S)-3,3-dimethyl-cyclohexylcarbamoyl)-2-aza-bicyclo[3.1.0]hexane-2-carboxylic acid tert-butyl ester—Dia 1: $t_R$ (Chiralpak AS-H, 5 um, 250×4.6 mm, heptane:1-propanol 90:10, flow rate: 0.5 mL/min, detection: UV at 220 nm): 8.05 min and (1R,3S,5R)-3-((R)-3,3-dimethyl-cyclohexylcarbamoyl)-2-aza-bicyclo[3.1.0]hexane-2-carboxylic acid tert-butyl ester—Dia 2: $t_R$ (Chiralpak AS-H, 5 um, 250×4.6 mm, heptane:1-propanol 90:10, flow rate: 0.5 mL/min, detection: UV at 220 nm): 8.70 min.

The absolute stereochemistry of Example 56 prepared from Dia 2 was assigned by X-ray crystallography to 1-{2-[(1R,3S,5R)-3-((R)-3,3-dimethyl-cyclohexylcarbamoyl)-2-aza-bicyclo[3.1.0]hex-2-yl]-2-oxo-ethyl}-1H-pyrazolo[3,4-c]pyridine-3-carboxylic acid amide. Based on these data, the absolute stereochemistry of Example 55 was assigned to 1-{2-[(1R,3S,5R)-3-((S)-3,3-dimethyl-cyclohexylcarbamoyl)-2-aza-bicyclo[3.1.0]hex-2-yl]-2-oxo-ethyl}-1H-pyrazolo[3,4-c]pyridine-3-carboxylic acid amide. As a consequence, the absolute stereochemistry of Dia 2 was assigned to: (1R,3S,5R)-3-((R)-3,3-dimethyl-cyclohexylcarbamoyl)-2-aza-bicyclo[3.1.0]hexane-2-carboxylic acid tert-butyl ester and the absolute stereochemistry of Dia 1 to (1R,3S,5R)-3-((S)-3,3-dimethyl-cyclohexylcarbamoyl)-2-aza-bicyclo[3.1.0]hexane-2-carboxylic acid tert-butyl ester.

Method 3:

The mixture of (1R,3S,5R)-3-((1R,3R) and (1S,3R) and (1R,3S) and (1S,3S)-3-ethyl-cyclohexylcarbamoyl)-2-aza-bicyclo[3.1.0]hexane-2-carboxylic acid tert-butyl ester was separated by flash column chromatography on silica gel (c-hexane/EtOAc 10:0 to 4:6) to give a mixture (Mix-TRANS) containing the two trans-diastereoisomers (1R,3S,5R)-3-((1R,3R)-3-ethyl-cyclohexylcarbamoyl)-2-aza-bicyclo[3.1.0]hexane-2-carboxylic acid tert-butyl ester and (1R,3S,5R)-3-((1S,3S)-3-ethyl-cyclohexylcarbamoyl)-2-aza-bicyclo[3.1.0]hexane-2-carboxylic acid tert-butyl ester: TLC, $R_f$ (c-hexane/EtOAc 7/3)=0.31 and a mixture (Mix-CIS) containing the two cis-diastereoisomers (1R,3S,5R)-3-((1R,3S)-3-ethyl-cyclohexylcarbamoyl)-2-aza-bicyclo[3.1.0]hexane-2-carboxylic acid tert-butyl ester and (1R,3S,5R)-3-((1S,3R)-3-ethyl-cyclohexylcarbamoyl)-2-aza-bicyclo[3.1.0]hexane-2-carboxylic acid tert-butyl ester: TLC, $R_f$ (c-hexane/EtOAc 7/3)=0.22.

Mix-CIS was separated by preparative chiral HPLC (column: Chiralpak AD, 20 um, 393×76.5 mm; eluent: heptane:i-PrOH 90:10, flow rate: 80 mL/min) to give (1R,3S,5R)-3-((1R,3S)-3-ethyl-cyclohexylcarbamoyl)-2-aza-bicyclo[3.1.0]hexane-2-carboxylic acid tert-butyl ester—Dia 1: $t_R$ (Chiralpak AD-H, 5 um, 250×4.6 mm, heptane:i-PrOH 90:10, flow rate: 1 mL/min, detection: UV at 210 nm): 12.19 min and (1R,3S,5R)-3-((1S,3R)-3-ethyl-cyclohexylcarbamoyl)-2-aza-bicyclo[3.1.0]hexane-2-carboxylic acid tert-butyl ester—Dia 2: $t_R$ (Chiralpak AD-H, 5 um, 250×4.6 mm, heptane:i-PrOH 90:10, flow rate: 1 mL/min, detection: UV at 210 nm):15.44 min. The absolute stereochemistry of Example 23 and Example 24 prepared respectively from CIS-Dia 1 and CIS-Dia 2 were assigned based on biological data and comparison with Example 73 and Example 72. Based on these data, the absolute stereochemistry of CIS-Dia 1 was assigned to (1R,3S,5R)-3-((1R,3S)-3-ethyl-cyclohexylcarbamoyl)-2-aza-bicyclo[3.1.0]hexane-2-carboxylic acid tert-butyl ester and CIS-Dia 2 to: (1R,3S,5R)-3-((1S,3R)-3-ethyl-cyclohexylcarbamoyl)-2-aza-bicyclo[3.1.0]hexane-2-carboxylic acid tert-butyl ester.

The absolute stereochemistry of Example 73 was assigned based on X-ray crystallography to: 1-{2-[(1R,3S,5R)-3-((1R,3S)-3-ethyl-cyclohexylcarbamoyl)-2-aza-bicyclo[3.1.0]hex-2-yl]-2-oxo-ethyl}-1H-pyrazolo[3,4-c]pyridine-3-carboxylic acid amide. As a consequence, the absolute stereochemistry of Example 72 was attributed to: 1-{2-[(1R,3S,5R)-3-((1S,3R)-3-ethyl-cyclohexylcarbamoyl)-2-aza-bicyclo[3.1.0]hex-2-yl]-2-oxo-ethyl}-1H-pyrazolo[3,4-c]pyridine-3-carboxylic acid amide.

Method 4:

The mixture of (1R,3S,5R)-3-((1R,3R) and (1S,3R) and (1R,3S) and (1S,3S)-3-methyl-cyclohexylcarbamoyl)-2-aza-bicyclo[3.1.0]hexane-2-carboxylic acid tert-butyl ester was separated by flash column chromatography on silica gel (GOLD column, c-hexane/EtOAc 10:0 to 6:4) to give a mixture (Mix-TRANS) containing the two trans diastereoisomers (1R,3S,5R)-3-((1R,3R)-3-methyl-cyclohexylcarbamoyl)-2-aza-bicyclo[3.1.0]hexane-2-carboxylic acid tert-butyl ester and (1R,3S,5R)-3-((1S,3S)-3-methyl-cyclohexylcarbamoyl)-2-aza-bicyclo[3.1.0]hexane-2-carboxylic acid tert-butyl ester: $t_R$ (HPLC conditions b): 4.94 min and a mixture (Mix-CIS) containing the two cis diastereoisomers (1R,3S,5R)-3-((1S,3R)-3-methyl-cyclohexylcarbamoyl)-2-aza-bicyclo[3.1.0]hexane-2-carboxylic acid tert-butyl ester and (1R,3S,5R)-3-((1R,3S)-3-methyl-cyclohexylcarbamoyl)-2-aza-bicyclo[3.1.0]hexane-2-carboxylic acid tert-butyl ester: $t_R$ (HPLC conditions b): 4.82 min.

Mix-TRANS was separated into its diastereoisomers by preparative chiral SFC (column: Chiralpak AD-H, 5 um, 250×30 mm; eluent: scCO$_2$:i-PrOH 90:10, flow rate: 120 mL/min, pressure 150 bar) to give (1R,3S,5R)-3-(3-methyl-cyclohexylcarbamoyl)-2-aza-bicyclo[3.1.0]hexane-2-carboxylic acid tert-butyl ester—Trans Dia 1: $t_R$ (Chiralpak AD-H, 5 um, 250×4.6 mm, scCO$_2$:i-PrOH 90:10, flow rate: 3 mL/min, pressure 150 bar, detection: UV at 215 nm): 5.22 min and (1R,3S,5R)-3-(3-methyl-cyclohexylcarbamoyl)-2-aza-bicyclo[3.1.0]hexane-2-carboxylic acid tert-butyl ester—Trans Dia 2: $t_R$ (Chiralpak AD-H, 5 um, 250×4.6 mm, scCO$_2$:i-PrOH 90:10, flow rate: 3 mL/min, pressure 150 bar, detection: UV at 215 nm): 6.18 min.

Mix-CIS was separated into its diastereoisomers by preparative chiral HPLC (column Chiralpak AS, 20 um, 500×50 mm; eluent: heptane:i-PrOH 90:10, flow rate: 80 mL/min) to give (1R,3S,5R)-3-((1S,3R)-3-methyl-cyclohexylcarbamoyl)-2-aza-bicyclo[3.1.0]hexane-2-carboxylic acid tert-butyl ester—Cis Dia 3: $t_R$ (Chiralpak AS, 10 um, 250×4.6 mm, heptane:i-PrOH 87:13, flow rate: 1 mL/min, detection: UV at 210 nm): 4.94 min and (1R,3S,5R)-3-((1R,3S)-3-methyl-cyclohexylcarbamoyl)-2-aza-bicyclo[3.1.0]hexane-2-carboxylic acid tert-butyl ester—Cis Dia 4: $t_R$ (Chiralpak AS, 10 um, 250×4.6 mm, heptane:i-PrOH 87:13, flow rate: 1 mL/min, detection: UV at 210 nm): 6.62 min.

Cis/trans relative stereochemistry was assigned based on NMR. Dia 1 and Dia 2 display a trans relative stereochemistry, Dia 3 and Dia 4 display a cis relative stereochemistry. The absolute stereochemistry of Example 47 (prepared from Cis Dia 4) was assigned by X-ray crystallography to: 1-{2-[(1R,3S,5R)-3-((1R,3S)-3-methyl-cyclohexylcarbamoyl)-2-aza-bicyclo[3.1.0]hex-2-yl]-2-oxo-ethyl}-1H-indazole-3-carboxylic acid amide. The absolute stereochemistry of Cis Dia 4 was assigned to (1R,3S,5R)-3-((1R,3S)-3-methyl-cyclohexylcarbamoyl)-2-aza-bicyclo[3.1.0]hexane-2-carboxylic acid tert-butyl ester and Cis Dia 3 vice versa was assigned to (1R,3S,5R)-3-((1S,3R)-3-methyl-cyclohexylcarbamoyl)-2-aza-bicyclo[3.1.0]hexane-2-carboxylic acid tert-butyl ester.

Method 5:

The mixture of (2S,4R)-2-((S) and (R)-3,3-dimethyl-cyclohexylcarbamoyl)-4-fluoro-pyrrolidine-1-carboxylic acid tert-butyl ester was separated into its diastereoisomers by preparative chiral HPLC (column: Chiralpak IA, 20 um, 3× (106×50 mm); eluent: heptane:TBME:CH$_3$CN 60:40:10, flow rate: 60 mL/min) to give (2S,4R)-2-((S)-3,3-dimethyl-cyclohexylcarbamoyl)-4-fluoro-pyrrolidine-1-carboxylic acid tert-butyl ester—Dia 1: $t_R$ (Chiralpak IA, 5 um, 250×4.6 mm, heptane:TBME:CH$_3$CN 40:50:10, flow rate: 1 mL/min, detection: UV at 210 nm): 6.43 min and (2S,4R)-2-((R)-3,3-dimethyl-cyclohexylcarbamoyl)-4-fluoro-pyrrolidine-1-carboxylic acid tert-butyl ester—Dia 2: $t_R$ (Chiralpak IA, 5 um, 250×4.6 mm, heptane:TBME:CH$_3$CN 40:50:10, flow rate: 1 mL/min, detection: UV at 210 nm): 8.11 min.

The absolute stereochemistry of Example 70 prepared from Dia 1 and Example 71 prepared from Dia 2 was assigned based on biological data and in comparison with Example 56. Based on these data, the absolute stereochemistry of Dia 1 was assigned to (2S,4R)-2-((S)-3,3-dimethyl-cyclohexylcarbamoyl)-4-fluoro-pyrrolidine-1-carboxylic acid tert-butyl ester and vice versa Dia 2 to: (2S,4R)-2-((R)-3,3-dimethyl-cyclohexylcarbamoyl)-4-fluoro-pyrrolidine-1-carboxylic acid tert-butyl ester.

Method 6:

The mixture of 1-{2-oxo-2-[(1R,3S,5R)-3-((S) and (R)-spiro[2.5]oct-5-ylcarbamoyl)-2-aza-bicyclo[3.1.0]hex-2-yl]-ethyl}-1H-indazole-3-carboxylic acid amide was separated into its diastereoisomers by preparative chiral HPLC (column: Chiralpak AD, 20 um, 393×76.5 mm; eluent: EtOH 100, flow rate: 60 mL/min) to give 1-{2-oxo-2-[(1R,3S,5R)-3-((S) or (R)-spiro[2.5]oct-5-ylcarbamoyl)-2-aza-bicyclo[3.1.0]hex-2-yl]-ethyl}-1H-indazole-3-carboxylic acid amide—Dia 1: $t_R$ (Chiralpak AD-H, 5 um, 250×4.6 mm, EtOH 100, flow rate: 0.7 mL/min, detection: UV at 210 nm): 13.49 min and 1-{2-oxo-2-[(1R,3S,5R)-3-((S) or (R)-spiro[2.5]oct-5-ylcarbamoyl)-2-aza-bicyclo[3.1.0]hex-2-yl]-ethyl}-1H-indazole-3-carboxylic acid amide—Dia 2: $t_R$ (Chiralpak AD-H, 5 um, 250×4.6 mm, EtOH 100, flow rate: 0.7 mL/min, detection: UV at 210 nm): 15.50 min.

Method 7:

The mixture of (1R,3S,5R)-3-((S) and (R)-3,3-dimethyl-cyclopentylcarbamoyl)-2-aza-bicyclo[3.1.0]hexane-2-carboxylic acid tert-butyl ester was separated into its diastereoisomers by preparative chiral HPLC (column: Chiralpak AD, 20 um, 393×76.5 mm; eluent: heptane:EtOH 85:15, flow rate: 60 mL/min) to give (1R,3S,5R)-3-((S) or (R)-3,3-dimethyl-cyclopentylcarbamoyl)-2-aza-bicyclo[3.1.0]hexane-2-carboxylic acid tert-butyl ester—Dia 1: $t_R$ (Chiralpak AD-H, 5 um, 250×4.6 mm, heptane:EtOH 90:10, flow rate: 1 mL/min, detection: UV at 210 nm): 5.16 min and (1R,3S,5R)-3-((S) or (R)-3,3-dimethyl-cyclopentylcarbamoyl)-2-aza-bicyclo[3.1.0]hexane-2-carboxylic acid tert-butyl ester—Dia 2: $t_R$ (Chiralpak AD-H, 5 um, 250×4.6 mm, heptane:EtOH 90:10, flow rate: 1 mL/min, detection: UV at 210 nm): 6.84 min.

Method 8:

The mixture of 1-{2-oxo-2-[(1R,3S,5R)-3-((S) and (R)-spiro[2.5]oct-5-ylcarbamoyl)-2-aza-bicyclo[3.1.0]hex-2-yl]-ethyl}-1H-pyrazolo[3,4-c]pyridine-3-carboxylic acid amide was separated into its diastereoisomers by preparative chiral HPLC (column: Chiralpak IA, 20 um, 3× (106×50 mm); eluent: heptane:EtOH:MeOH 60:20:20, flow rate: 60 mL/min) to give 1-{2-oxo-2-[(1R,3S,5R)-3-((S) or (R)-spiro[2.5]oct-5-ylcarbamoyl)-2-aza-bicyclo[3.1.0]hex-2-yl]-ethyl}-1H-pyrazolo[3,4-c]pyridine-3-carboxylic acid amide—Dia 1: $t_R$ (Chiralpak IA, 5 um, 250×4.6 mm, heptane:EtOH:MeOH 60:20:20, flow rate: 0.7 mL/min, detection: UV at 210 nm): 11.28 min and 1-{2-oxo-2-[(1R,3S,5R)-3-((S) or (R)-spiro[2.5]oct-5-ylcarbamoyl)-2-aza-bicyclo[3.1.0]hex-2-yl]-ethyl}-1H-pyrazolo[3,4-c]pyridine-3-carboxylic acid amide—Dia 2: $t_R$ (Chiralpak IA, 5 um, 250×4.6 mm, heptane:EtOH:MeOH 60:20:20, flow rate: 0.7 mL/min, detection: UV at 210 nm): 13.71 min.

Method 9:

The mixture of 1-{2-[(1R,3S,5R)-3-((1S,3R) and (1R,3R) and (1S,3S) and (1R,3S)-3-methyl-cyclopentylcarbamoyl)-2-aza-bicyclo[3.1.0]hex-2-yl]-2-oxo-ethyl}-1H-indazole-3-carboxylic acid amide was separated into its diastereoisomers by preparative chiral HPLC (column: Chiralpak AD, 20 um, 500×50 mm; eluent: heptane:i-PrOH:MeOH 70:15:15, flow rate: 60 mL/min then column: Chiralpak Adi+Chiralpak AD-H, 2×250+2×250 mm; eluent: heptane:i-PrOH 75:25, flow rate: 9 mL/min) to give 1-{2-[(1R,3S,5R)-3-(3-methyl-cyclopentylcarbamoyl)-2-aza-bicyclo[3.1.0]hex-2-yl]-2-oxo-ethyl}-1H-indazole-3-carboxylic acid amide—Dia 1: $t_R$ (HPLC conditions d): 3.03 min, 1-{2-[(1R,3S,5R)-3-(3-methyl-cyclopentylcarbamoyl)-2-aza-bicyclo[3.1.0]hex-2-yl]-2-oxo-ethyl}-1H-indazole-3-carboxylic acid amide—Dia 2: $t_R$ (Kromasyl 3-amycoat, 3 um, 150×4.6 mm, heptane:i-PrOH 75:25, flow rate: 0.7 mL/min, detection: UV at 206 nm): 10.52 min, 1-{2-[(1R,3S,5R)-3-(3-methyl-cyclopentylcarbamoyl)-2-aza-bicyclo[3.1.0]hex-2-yl]-2-oxo-ethyl}-1H-indazole-3-carboxylic acid amide—Dia 3: $t_R$ (Kromasyl 3-amycoat, 3 um, 150×4.6 mm, heptane:i-PrOH 75:25, flow rate: 0.7 mL/min, detection: UV at 206 nm): 11.50 min and 1-{2-[(1R,3S,5R)-3-(3-methyl-cyclopentylcarbamoyl)-2-aza-bicyclo[3.1.0]hex-2-yl]-2-oxo-ethyl}-1H-indazole-3-carboxylic acid amide—Dia 4: $t_R$ (Kromasyl 3-amycoat, 3 um, 150×4.6 mm, heptane:i-PrOH 75:25, flow rate: 0.7 mL/min, detection: UV at 206 nm): 12.24 min.

Method 10:

The mixture of 1-{2-[(2S,3S,4S)-2-((S) and (R)-3,3-dimethyl-cyclohexylcarbamoyl)-4-fluoro-3-methoxy-pyrrolidin-1-yl]-2-oxo-ethyl}-1H-indazole-3-carboxylic acid amide was separated into its diastereoisomers by preparative chiral SFC (column: Chiralpak OD, 20 um, 250×30 mm; eluent: scCO$_2$:i-PrOH 65:35, flow rate: 100 mL/min, pressure: 150 bar) to give 1-{2-[(2S,3S,4S)-2-((R)-3,3-dimethyl-cyclohexylcarbamoyl)-4-fluoro-3-methoxy-pyrrolidin-1-yl]-2-oxo-ethyl}-1H-indazole-3-carboxylic acid amide—Dia 1: $t_R$ (SFC, Chiralpak OD-H, 5 um, 250×4.6 mm, scCO$_2$:i-PrOH 65:35, flow rate: 3 mL/min, detection: UV at 210 nm, pressure: 150 bar): 3.37 min and 1-{2-[(2S,3S,4S)-2-((S)-3,3-dimethyl-cyclohexylcarbamoyl)-4-fluoro-3-methoxy-pyrrolidin-1-yl]-2-oxo-ethyl}-1H-indazole-3-carboxylic acid amide—Dia 2: $t_R$ (SFC, Chiralpak OD-H, 5 um, 250×4.6 mm, scCO$_2$:i-PrOH 65:35, flow rate: 3 mL/min, detection: UV at 210 nm, pressure: 150 bar): 4.45 min.

Tentative assignment of absolute stereochemistry: The absolute stereochemistry of Dia 1 and Dia 2 was assigned following the same reasoning as described in Separation Method 5.

Method 11:

The mixture of 1-{2-[(1R,2S,5S)-2-((S) and (R)-3,3-dimethyl-cyclohexylcarbamoyl)-3-aza-bicyclo[3.1.0]hex-3-yl]-2-oxo-ethyl}-1H-pyrazolo[3,4-c]pyridine-3-carboxylic acid amide was separated into its diastereoisomers by preparative chiral SFC (column: Chiralpak AD-H, 250×30 mm; eluent: scCO$_2$:EtOH 50:50, flow rate: 100 mL/min, pressure:

150 bar) to give 1-{2-[(1R,2S,5S)-2-((R)-3,3-dimethyl-cyclohexylcarbamoyl)-3-aza-bicyclo[3.1.0]hex-3-yl]-2-oxo-ethyl}-1H-pyrazolo[3,4-c]pyridine-3-carboxylic acid amide—Dia 1: $t_R$ (SFC, Chiralpak AD-H, 5 um, 250×4.6 mm, scCO$_2$:EtOH 60:40, flow rate: 3 mL/min, detection: UV at 215 nm, pressure: 150 bar): 3.23 min and 1-{2-[(1R,2S,5S)-2-((S)-3,3-dimethyl-cyclohexylcarbamoyl)-3-aza-bicyclo[3.1.0]hex-3-yl]-2-oxo-ethyl}-1H-pyrazolo[3,4-c]pyridine-3-carboxylic acid amide—Dia 2: $t_R$ (SFC, Chiralpak AD-H, 5 um, 250×4.6 mm, scCO$_2$:EtOH 60:40, flow rate: 3 mL/min, detection: UV at 215 nm, pressure: 150 bar): 5.87 min.

Tentative assignment of absolute stereochemistry: The absolute stereochemistry of Dia 1 and Dia 2 was assigned following the same reasoning as described in Separation Method 5.

Method 12:

The mixture of 1-{2-[(1R,2S,5S)-2-((S) and (R)-3,3-dimethyl-cyclohexylcarbamoyl)-3-aza-bicyclo[3.1.0]hex-3-yl]-2-oxo-ethyl}-1H-indazole-3-carboxylic acid amide was separated into its diastereoisomers by preparative chiral HPLC (column: Chiralpak IC, 20 um, 3×SMB 100×50 mm; eluent: heptane:EtOH 70:30, flow rate: 60 mL/min) to give 1-{2-[(1R,2S,5S)-2-((R)-3,3-dimethyl-cyclohexylcarbamoyl)-3-aza-bicyclo[3.1.0]hex-3-yl]-2-oxo-ethyl}-1H-indazole-3-carboxylic acid amide—Dia 1: $t_R$ (Chiralpak IC, 5 um, 250×4.6 mm, heptane:EtOH 70:30, flow rate: 1 mL/min, detection: UV at 210 nm): 12.45 min and 1-{2-[(1R,2S,5S)-2-((S)-3,3-dimethyl-cyclohexylcarbamoyl)-3-aza-bicyclo[3.1.0]hex-3-yl]-2-oxo-ethyl}-1H-indazole-3-carboxylic acid amide—Dia 2: $t_R$ (Chiralpak IC, 5 um, 250×4.6 mm, heptane:EtOH 70:30, flow rate: 1 mL/min, detection: UV at 210 nm): 15.57 min.

Tentative assignment of absolute stereochemistry: The absolute stereochemistry of Dia 1 and Dia 2 was assigned following the same reasoning as described in Separation Method 5.

Method 13:

The mixture of (1R,3S,5R)-3-((S) and (R)-3,3-dichloro-cyclohexylcarbamoyl)-2-aza-bicyclo[3.1.0]hexane-2-carboxylic acid tert-butyl ester was separated into its diastereoisomers by flash column chromatography on silica gel (c-hexane/EtOAc 4:1) to give (1R,3S,5R)-3-((S)-3,3-dichloro-cyclohexylcarbamoyl)-2-aza-bicyclo[3.1.0]hexane-2-carboxylic acid tert-butyl ester—Dia 1: TLC, $R_f$ (c-hexane/EtOAc 1:1)=0.33 and (1R,3S,5R)-3-((R)-3,3-dichloro-cyclohexylcarbamoyl)-2-aza-bicyclo[3.1.0]hexane-2-carboxylic acid tert-butyl ester—Dia 2: TLC, $R_f$ (c-hexane/EtOAc 1:1)=0.37.

Tentative assignment of absolute stereochemistry: The absolute stereochemistry of Dia 1 and Dia 2 was assigned following the same reasoning as described in Separation Method 5.

Method 14

The mixture of 1-{2-[(2S,4R)-4-fluoro-2-((S) and (R)-spiro[2.5]oct-5-ylcarbamoyl)-pyrrolidin-1-yl]-2-oxo-ethyl}-1H-indazole-3-carboxylic acid amide was separated into its diastereoisomers by preparative chiral SFC (column: Chiralcel IA, 20 um, 250×30 mm; eluent: scCO$_2$:i-PrOH:IPA 50:50:0.5, flow rate: 80 mL/min, pressure: 150 bar) to give 1-{2-[(2S,4R)-4-fluoro-2-((S) or (R)-spiro[2.5]oct-5-ylcarbamoyl)-pyrrolidin-1-yl]-2-oxo-ethyl}-1H-indazole-3-carboxylic acid amide—Dia 1: $t_R$ (SFC, Chiralcel IA, 5 um, 250×4.6 mm, scCO$_2$:i-PrOH:IPA 50:50:0.5, flow rate: 3 mL/min, detection: UV at 215 nm, pressure: 150 bar): 3.65 min and 1-{2-[(2S,4R)-4-fluoro-2-((S) or (R)-spiro[2.5]oct-5-ylcarbamoyl)-pyrrolidin-1-yl]-2-oxo-ethyl}-1H-indazole-3-carboxylic acid amide—Dia 2: $t_R$ (SFC, Chiralcel IA, 5 um, 250×4.6 mm, scCO$_2$:i-PrOH:IPA 50:50:0.5, flow rate: 3 mL/min, detection: UV at 215 nm, pressure: 150 bar): 5.46 min.

Method 15:

The mixture of 1-{2-[(1R,3S,5R)-3-((1S,5S) and (1R,5R)-5-methoxy-3,3-dimethyl-cyclohexylcarbamoyl)-2-aza-bicyclo[3.1.0]hex-2-yl]-2-oxo-ethyl}-1H-indazole-3-carboxylic acid amide was separated into its diastereoisomers by preparative chiral HPLC (column: Chiralpak IA, 5 um, 250×20 mm; eluent: heptane:EtOH:MeOH 80:10:10, flow rate: 12 mL/min) to give 1-{2-[(1R,3S,5R)-3-((1S,5S)-5-methoxy-3,3-dimethyl-cyclohexylcarbamoyl)-2-aza-bicyclo[3.1.0]hex-2-yl]-2-oxo-ethyl}-1H-indazole-3-carboxylic acid amide: $t_R$ (Chiralpak IA, 5 um, 250×4.6 mm, heptane:EtOH:MeOH 80:10:10, flow rate: 1 mL/min, detection: UV at 220 nm): 9.61 min and 1-{2-[(1R,3S,5R)-3-((1R,5R)-5-methoxy-3,3-dimethyl-cyclohexylcarbamoyl)-2-aza-bicyclo[3.1.0]hex-2-yl]-2-oxo-ethyl}-1H-indazole-3-carboxylic acid amide: $t_R$ (Chiralpak IA, 5 um, 250×4.6 mm, heptane:EtOH:MeOH 80:10:10, flow rate: 1 mL/min, detection: UV at 220 nm): 14.21 min.

Tentative assignment of absolute stereochemistry: The absolute stereochemistry of Dia 1 and Dia 2 was assigned following the same reasoning as described in Separation Method 5.

Method 16:

The mixture of 1-{2-[(1R,3S,5R)-3-((1S,5S) and (1R,5R)-5-hydroxy-3,3-dimethyl-cyclohexylcarbamoyl)-2-aza-bicyclo[3.1.0]hex-2-yl]-2-oxo-ethyl}-1H-indazole-3-carboxylic acid amide was separated into its diastereoisomers by preparative chiral HPLC (column: Chiralpak IA, 5 um, 250×20 mm; eluent: heptane:EtOH:MeOH 70:15:15, flow rate: 12 mL/min) to give 1-{2-[(1R,3S,5R)-3-((1S,5S)-5-hydroxy-3,3-dimethyl-cyclohexylcarbamoyl)-2-aza-bicyclo[3.1.0]hex-2-yl]-2-oxo-ethyl}-1H-indazole-3-carboxylic acid amide: $t_R$ (Chiralpak IA, 5 um, 250×4.6 mm, heptane:EtOH:MeOH 75:15:15, flow rate: 1 mL/min, detection: UV at 220 nm): 7.56 min and 1-{2-[(1R,3S,5R)-3-((1R,5R)-5-hydroxy-3,3-dimethyl-cyclohexylcarbamoyl)-2-aza-bicyclo[3.1.0]hex-2-yl]-2-oxo-ethyl}-1H-indazole-3-carboxylic acid amide: $t_R$ (Chiralpak IA, 5 um, 250×4.6 mm, heptane:EtOH:MeOH 75:15:15, flow rate: 1 mL/min, detection: UV at 220 nm): 9.37 min.

Tentative assignment of absolute stereochemistry: The absolute stereochemistry of Dia 1 and Dia 2 was assigned following the same reasoning as described in Separation Method 5.

Method 17:

The mixture of 1-{2-[(1R,3S,5S)-3-((R) and (S)-3,3-dimethyl-cyclohexylcarbamoyl)-5-hydroxymethyl-2-aza-bicyclo[3.1.0]hex-2-yl]-2-oxo-ethyl}-1H-indazole-3-carboxylic acid amide was separated into its diastereoisomers by preparative chiral SFC (column: Chiralpak AD-H, 5 um, 250×30 mm; eluent: scCO$_2$:i-PrOH 60:40, flow rate: 130 mL/min, pressure: 150 bar) to give 1-{2-[(1R,3S,5S)-3-((R)-3,3-dimethyl-cyclohexylcarbamoyl)-5-hydroxymethyl-2-aza-bicyclo[3.1.0]hex-2-yl]-2-oxo-ethyl}-1H-indazole-3-carboxylic acid amide—Dia 1: $t_R$ (SFC, Chiralpak AD-H, 5 um, 250×4.6 mm, scCO$_2$:i-PrOH 55:45, flow rate: 3 mL/min, pressure: 150 bar, detection: UV at 210 nm): 2.35 min and 1-{2-[(1R,3S,5S)-3-((S)-3,3-dimethyl-cyclohexylcarbamoyl)-5-hydroxymethyl-2-aza-bicyclo[3.1.0]hex-2-yl]-2-oxo-ethyl}-1H-indazole-3-carboxylic acid amide—Dia 2: $t_R$ (SFC, Chiralpak AD-H, 5 um, 250×4.6 mm, scCO$_2$:i-PrOH 55:45, flow rate: 3 mL/min, pressure: 150 bar, detection: UV at 210 nm): 3.37 min.

Tentative assignment of absolute stereochemistry: The absolute stereochemistry of Dia 1 and Dia 2 was assigned following the same reasoning as described in Separation Method 5.

Method 18:

The mixture of (1R,3S,5S)-2-[2-(3-acetyl-pyrazolo[3,4-c]pyridin-1-yl)-acetyl]-5-hydroxymethyl-2-aza-bicyclo[3.1.0]hexane-3-carboxylic acid (S) and (R)-spiro[2.5]oct-5-ylamide was separated into its diastereoisomers by preparative chiral SFC (column: Chiralpak AD-H, 20 um, 250×30 mm; eluent: scCO$_2$:EtOH 60:40, flow rate: 80 mL/min, pressure: 150 bar) to give (1R,3S,5S)-2-[2-(3-acetyl-pyrazolo[3,4-c]pyridin-1-yl)-acetyl]-5-hydroxymethyl-2-aza-bicyclo[3.1.0]hexane-3-carboxylic acid (S) or (R)-spiro[2.5]oct-5-ylamide—Dia 1: t$_R$ (SFC, Chiralpak AD-H, 5 um, 250×4.6 mm, scCO$_2$:EtOH 60:40, flow rate: 3 mL/min, pressure: 150 bar, detection: UV at 215 nm): 6.71 min and (1R,3S,5S)-2-[2-(3-acetyl-pyrazolo[3,4-c]pyridin-1-yl)-acetyl]-5-hydroxymethyl-2-aza-bicyclo[3.1.0]hexane-3-carboxylic acid (S) or (R)-spiro[2.5]oct-5-ylamide—Dia 2: t$_R$ (SFC, Chiralpak AD-H, 5 um, 250×4.6 mm, scCO$_2$:EtOH 60:40, flow rate: 3 mL/min, pressure: 150 bar, detection: UV at 215 nm): 9.01 min.

Method 19:

The mixture of (1R,3S,5S)-2-[2-(3-acetyl-pyrazolo[3,4-b]pyridin-1-yl)-acetyl]-5-hydroxymethyl-2-aza-bicyclo[3.1.0]hexane-3-carboxylic acid ((S) and (R)-3,3-dimethyl-cyclohexyl)-amide was separated into its diastereoisomers by preparative chiral SFC (column: Chiralcel AD-H, 5 um, 250×30 mm; eluent: scCO$_2$:i-PrOH 80:20, flow rate: 80 mL/min, pressure: 150 bar) to give (1R,3S,5S)-2-[2-(3-acetyl-pyrazolo[3,4-b]pyridin-1-yl)-acetyl]-5-hydroxymethyl-2-aza-bicyclo[3.1.0]hexane-3-carboxylic acid ((R)-3,3-dimethyl-cyclohexyl)-amide—Dia 1: t$_R$ (SFC, Chiralcel AD-H, 5 um, 250×4.6 mm, scCO$_2$:i-PrOH 80:20, flow rate: 3 mL/min, pressure: 150 bar, detection: UV at 215 nm): 1.94 min and (1R,3S,5S)-2-[2-(3-acetyl-pyrazolo[3,4-b]pyridin-1-yl)-acetyl]-5-hydroxymethyl-2-aza-bicyclo[3.1.0]hexane-3-carboxylic acid ((S)-3,3-dimethyl-cyclohexyl)-amide—Dia 2: t$_R$ (SFC, Chiralcel AD-H, 5 um, 250×4.6 mm, scCO$_2$:i-PrOH 80:20, flow rate: 3 mL/min, pressure: 150 bar, detection: UV at 215 nm): 2.49 min.

Tentative assignment of absolute stereochemistry: The absolute stereochemistry of Dia 1 and Dia 2 was assigned following the same reasoning as described in Separation Method 5.

Method 20:

The mixture of (1R,3S,5S)-3-((1S,3R) and (1R,3R) and (1S,3S) and (1R,3S)-3-ethyl-cyclohexylcarbamoyl)-5-hydroxymethyl-2-aza-bicyclo[3.1.0]hexane-2-carboxylic acid tert-butyl ester was separated into its diastereoisomers by preparative chiral HPLC (column: Chiralpak AD-H, 20 um, 500×50 mm; eluent: heptane:i-PrOH 90:10 then Chiralpak AD, 20 um, 500×50 mm; eluent: heptane:EtOH 95:5 then EtOH:MeOH 50:50, flow rate: 90 mL/min) to give ((1R,3S,5S)-3-(3-ethyl-cyclohexylcarbamoyl)-5-hydroxymethyl-2-aza-bicyclo[3.1.0]hexane-2-carboxylic acid tert-butyl ester—Dia 1: t$_R$ (Chiralpak AD-H, 5 um, 250×4.6 mm, heptane:EtOH 90:10, flow rate: 1 mL/min, detection: UV at 210 nm): 19.61 min, (1R,3S,5S)-3-(3-ethyl-cyclohexylcarbamoyl)-5-hydroxymethyl-2-aza-bicyclo[3.1.0]hexane-2-carboxylic acid tert-butyl ester—Dia 2: t$_R$ (Chiralpak AD-H, 5 um, 250×4.6 mm, heptane:EtOH 90:10, flow rate: 1 mL/min, detection: UV at 210 nm): 17.03 min, ((1R,3S,5S)-3-(3-ethyl-cyclohexylcarbamoyl)-5-hydroxymethyl-2-aza-bicyclo[3.1.0]hexane-2-carboxylic acid tert-butyl ester—Dia 3: t$_R$ (Chiralpak AD-H, 5 um, 250×4.6 mm, heptane: EtOH 90:10, flow rate: 1 mL/min, detection: UV at 210 nm): 6.12 min and (1R,3S,5S)-3-(3-ethyl-cyclohexylcarbamoyl)-5-hydroxymethyl-2-aza-bicyclo[3.1.0]hexane-2-carboxylic acid tert-butyl ester—Dia 4: t$_R$ (Chiralpak AD-H, 5 um, 250×4.6 mm, heptane:EtOH 90:10, flow rate: 1 mL/min, detection: UV at 210 nm): 8.3 min.

Method 21:

The mixture of (1R,3S,5S)-2-[2-(3-acetyl-pyrazolo[3,4-c]pyridin-1-yl)-acetyl]-5-hydroxymethyl-2-aza-bicyclo[3.1.0]hexane-3-carboxylic acid ((R) and (S)-3,3-dimethyl-cyclohexyl)-amide was separated into its diastereoisomers by preparative chiral HPLC (column: Chiralpak AD, 20 um, 500×50 mm; eluent: heptane:EtOH 50:50 (flow rate: 110 mL/min), after 33 min EtOH 100 (flow rate: 80 mL/min)) to give (1R,3S,5S)-2-[2-(3-acetyl-pyrazolo[3,4-c]pyridin-1-yl)-acetyl]-5-hydroxymethyl-2-aza-bicyclo[3.1.0]hexane-3-carboxylic acid ((R)-3,3-dimethyl-cyclohexyl)-amide—Dia 1: t$_R$ (Chiralpak AD-H, 5 um, 250×4.6 mm, EtOH 100%, flow rate: 0.6 mL/min, detection: UV at 215 nm): 16.44 min and (1R,3S,5S)-2-[2-(3-acetyl-pyrazolo[3,4-c]pyridin-1-yl)-acetyl]-5-hydroxymethyl-2-aza-bicyclo[3.1.0]hexane-3-carboxylic acid ((S)-3,3-dimethyl-cyclohexyl)-amide—Dia 2: t$_R$ (Chiralpak AD-H, 5 μm, 250×4.6 mm, EtOH 100%, flow rate: 0.6 mL/min, detection: UV at 215 nm): 22.69 min.

Tentative assignment of absolute stereochemistry: The absolute stereochemistry of Dia 1 and Dia 2 was assigned following the same reasoning as described in Separation Method 5.

Method 22:

The mixture of (1R,3S,5R)-2-(2-(3-acetyl-1H-indazol-1-yl)acetyl)-N-((1R,5R)-5-hydroxy-3,3-dimethylcyclohexyl)-2-azabicyclo[3.1.0]hexane-3-carboxamide and (1R,3S,5R)-2-(2-(3-acetyl-1H-indazol-1-yl)acetyl)-N-((1S,5S)-5-hydroxy-3,3-dimethylcyclohexyl)-2-azabicyclo[3.1.0]hexane-3-carboxamide was separated by preparative chiral HPLC (column: Chiralpak IC 5 μm, 250×20 mm; heptane/EtOH 70:30, flow rate: 16 mL/min; detection UV at 210 nm). The two separated fractions containing the title compounds were evaporated to dryness, then separately dissolved in CH$_3$CN and water, freeze-dried and lyophilized to afford (1R,3S,5R)-2-(2-(3-acetyl-1H-indazol-1-yl)acetyl)-N-((1S,5S)-5-hydroxy-3,3-dimethylcyclohexyl)-2-azabicyclo[3.1.0]hexane-3-carboxamide: t$_R$ (Chiralpak IC, 5 μm, 250×4.6 mm, heptane/EtOH 70:30, flow 1 mL/min): 7.02 min and (1R,3S,5R)-2-(2-(3-acetyl-1H-indazol-1-yl)acetyl)-N-((1R,5R)-5-hydroxy-3,3-dimethylcyclohexyl)-2-azabicyclo[3.1.0]hexane-3-carboxamide: t$_R$ (Chiralpak IC, 5 μm, 250×4.6 mm, heptane/EtOH 70:30, flow 1 mL/min): 9.91 min.

Tentative assignment of absolute stereochemistry: The absolute stereochemistry of Example 124 and Example 125 was assigned following the same reasoning as described in Separation Method 5.

Method 23:

The mixture of 1-(2-((1R,3S,5R)-3-(((1R,3S)-3-(hydroxymethyl)-3-methylcyclohexyl)carbamoyl)-2-azabicyclo[3.1.0]hexan-2-yl)-2-oxoethyl)-1H-indazole-3-carboxamide and 1-(2-((1R,3S,5R)-3-(((1S,3R)-3-(hydroxymethyl)-3-methylcyclohexyl)carbamoyl)-2-azabicyclo[3.1.0]hexan-2-yl)-2-oxoethyl)-1H-indazole-3-carboxamide was separated by preparative chiral HPLC (Chiralpak IC, 20 μm, 37.3×7.65 cm; heptane/CH$_2$Cl$_2$/MeOH 60:25:15, flow rate: 110 mL/min detection UV 300 nm). The two separated fractions containing the title compounds were evaporated to dryness, then separately dissolved in CH$_3$CN and water, freeze-dried and lyophilized to afford 1-(2-((1R,3S,5R)-3-(((1R,3S)-3-(hydroxymethyl)-3- methylcyclohexyl) carbamoyl)-2-azabicyclo[3.1.0]hexan-2-yl)-2-oxoethyl)-1H-indazole-3-carboxamide: $t_R$ (Chiralpak IC, 20 μm, 250×4.6 mm, heptane/CH$_2$Cl$_2$/MeOH 60/25/15, flow 1 mL/min): 10.64 min and 1-(2-((1R,3S,5R)-3-(((1S,3R)-3-(hydroxymethyl)-3-methylcyclohexyl)carbamoyl)-2-azabicyclo[3.1.0]hexan-2-yl)-2-oxoethyl)-1H-indazole-3-carboxamide: $t_R$ (Chiralpak IC, 20 μm, 250×4.6 mm, heptane/CH$_2$Cl$_2$/MeOH 60/25/15, flow 1 mL/min): 13.52 min.

Tentative assignment of absolute stereochemistry: The absolute stereochemistry of Example 127 and Example 128 was assigned following the same reasoning as described in Separation Method 5.

$^1$H NMR Data for Selected Compounds:

Example 1: $^1$H NMR (400 MHz, DMSO-d$_6$) δ ppm: 9.13 (s, 1 H), 8.37 (d, 1 H), 8.00 (d, 1 H), 7.84 (d, 1 H), 5.96 (d, 1 H), 5.61 (d, 1 H), 3.97-4.11 (m, 2 H), 3.62-3.69 (m, 1 H), 2.59 (s, 3H), 2.07-2.19 (m, 1 H), 1.95-2.07 (m, 1 H), 1.83-1.92 (m, 2 H), 1.69-1.83 (m, 1 H), 1.51-1.69 (m, 2 H), 0.96-1.09 (m, 6 H), 0.88-0.96 (m, 1 H), 0.71-0.78 (m, 1 H)

Example 21: $^1$H NMR (400 MHz, DMSO-d$_6$) δ ppm: 8.47-8.52 (m, 1 H), 8.28 (d, 1 H), 7.98 (s, 1 H), 7.78 (d, 1 H), 7.69-7.75 (m, 1 H), 7.41 (br. s., 2 H), 7.27 (t, 1 H), 7.19 (t, 1 H), 4.08 (t, 1 H), 3.75-3.81 (m, 2 H), 3.14-3.27 (m, 4 H), 2.26 (dd, 1 H), 1.99-2.13 (m, 2 H), 1.82-1.89 (m, 1 H), 1.60-1.79 (m, 3 H), 1.04-1.29 (m, 4 H), 0.80-0.88 (m, 1 H), 0.50 (m, 1 H)

Example 32: $^1$H NMR (400 MHz, DMSO-d$_6$) δ ppm: 8.20 (d, 1 H), 7.69 (d, 2 H), 7.45-7.52 (m, 1 H), 7.37 (t, 1 H), 5.87 (d, 1 H), 5.53 (d, 1 H), 4.73 (br. s., 1 H), 4.13-4.19 (m, 1 H), 3.78-3.88 (m, 1 H), 3.74 (br. s., 1 H), 2.64 (s, 3 H), 2.17-2.28 (m, 1 H), 2.06-2.15 (m, 1 H), 1.78-1.88 (m, 2 H), 1.68-1.76 (m, 1 H), 1.53-1.67 (m, 5 H), 1.19-1.31 (m, 1 H), 0.97-1.04 (m, 1H), 0.72-0.77 (m, 1 H)

Example 35: $^1$H NMR (400 MHz, DMSO-d$_6$) δ ppm: 9.14 (s, 1 H), 8.35 (d, 1 H), 8.05 (d, 1 H), 7.93 (d, 1 H), 7.74-7.88 (m, 1 H), 7.53 (br. s., 1 H), 5.93 (d, 1 H), 5.60 (d, 1 H), 4.27-4.37 (m, 1 H), 3.98-4.08 (m, 1 H), 3.69-3.77 (m, 1 H), 2.20-2.30 (m, 1 H), 1.97-2.11 (m, 2 H), 1.80-1.88 (m, 1 H), 1.56-1.70 (m, 3 H), 1.38-1.48 (m, 1 H), 1.26-1.38 (m, 3 H), 0.93-1.06 (m, 1H), 0.66-0.79 (m, 1 H)

Example 36: $^1$H NMR (400 MHz, DMSO-d$_6$) δ ppm: 8.85 (d, 2 H), 7.93 (d, 1 H), 7.53-7.64 (m, 2 H), 7.48 (t, 1 H), 7.22 (dd, 1 H), 5.85 (d, 1 H), 5.49 (d, 1 H), 5.36 (s, 2 H), 4.31 (dd, 1 H), 3.73-3.79 (m, 1 H), 2.58 (s, 3 H), 2.19-2.24 (m, 1 H), 1.96-2.13 (m, 3 H), 1.73-1.91 (m, 2H), 1.55-1.70 (m, 3 H), 1.29-1.44 (m, 3 H), 0.95-1.04 (m, 1 H), 0.69-0.76 (m, 1 H)

Example 37: $^1$H NMR (400 MHz, DMSO-d$_6$) δ ppm: 8.85 (d, 2 H), 7.82 (d, 1 H), 7.63 (d, 1 H), 7.56 (d, 1 H), 7.47 (t, 1 H), 7.22 (dd, 1 H), 5.84 (d, 1 H), 5.48 (d, 1 H), 5.36 (s, 2 H), 4.28 (dd, 1H), 3.97-4.13 (m, 1 H), 3.73 (t, 1 H), 2.58 (s, 3 H), 2.21-2.30 (m, 1 H), 1.97-2.13 (m, 2 H), 1.59-1.89 (m, 5 H), 1.32-1.53 (m, 3 H), 0.96-1.03 (m, 1 H), 0.73-0.79 (m, 1 H)

Example 43: $^1$H NMR (400 MHz, DMSO-d$_6$) δ ppm: 8.20 (d, 1 H), 7.70 (d, 1 H), 7.43-7.58 (m, 2 H), 7.37 (t, 1 H), 5.88 (d, 1 H), 5.54 (d, 1 H), 4.15-4.21 (m, 1 H), 3.71-3.83 (m, 2 H), 3.44-3.49 (m, 1 H), 3.16 (s, 3 H), 2.64 (s, 3 H), 2.06-2.26 (m, 2 H), 1.79-1.89 (m, 1 H), 1.75 (d, 1 H), 1.60 (t, 2 H), 1.41-1.53 (m, 2 H), 1.27-1.41 (m, 2 H), 1.12-1.25 (m, 1 H), 1.01 (m, 1H), 0.71-0.77 (m, 1 H)

Example 45: $^1$H NMR (400 MHz, DMSO-d$_6$) δ ppm: 8.20 (d, 1 H), 7.60-7.74 (m, 2 H), 7.49 (t, 1 H), 7.37 (t, 1 H), 5.87 (d, 1 H), 5.54 (d, 1 H), 4.11-4.20 (m, 1 H), 3.48-3.60 (m, 2 H), 3.22 (s, 3 H), 3.09-3.18 (m, 1 H), 2.64 (s, 3 H), 2.18-2.27 (m, 1 H), 2.06-2.16 (m, 1 H), 2.01 (d, 1H), 1.81-1.95 (m, 2 H), 1.55-1.71 (m, 2 H), 1.12-1.27 (m, 1 H), 0.95-1.11 (m, 4 H), 0.73-0.78 (m, 1 H)

Example 46: $^1$H NMR (400 MHz, DMSO-d$_6$) δ ppm: 8.19 (d, 1 H), 7.62-7.69 (m, 3 H), 7.36-7.48 (m, 2 H), 7.28 (t, 1 H), 5.76 (d, 1 H), 5.45 (d, 1 H), 4.14 (dd, 1 H), 3.67-3.74 (m, 2 H), 3.22 (s, 3 H), 3.09-3.19 (m, 1 H), 2.22 (dd, 1 H), 2.05-2.15 (m, 1 H), 2.01 (d, 1 H), 1.80-1.95 (m, 2 H), 1.57-1.71 (m, 2 H), 1.12-1.22 (m, 1 H), 0.94-1.10 (m, 4 H), 0.69 (m, 1 H)

Example 47: $^1$H NMR (400 MHz, DMSO-d$_6$) δ ppm: 8.18 (d, 1 H), 7.59-7.70 (m, 2 H), 7.50-7.58 (m, 1 H), 7.43 (t, 1 H), 7.37 (bs., 1 H), 7.27 (t, 1 H), 5.75 (d, 1 H), 5.43 (d, 1 H), 4.12 (m, 1H), 3.66-3.72 (m, 1 H), 3.41-3.52 (m, 1 H), 2.01-2.23 (m, 2 H), 1.77-1.87 (m, 1 H), 1.65 (d, 2 H), 1.57 (d, 2 H), 1.39 (m, 1 H), 1.13-1.29 (m, 2 H), 0.95-1.04 (m, 2 H), 0.84 (d, 3 H), 0.69-0.81 (m, 2 H)

Example 49: $^1$H NMR (400 MHz, DMSO-d$_6$) δ ppm: 8.18 (d, 1 H), 7.59-7.72 (m, 3 H), 7.42 (m, 1 H), 7.37 (bs., 1 H), 7.26 (t, 1 H), 5.74 (d, 1 H), 5.44 (d, 1 H), 4.12 (m, 1 H), 3.67-3.73 (m, 1 H), 3.57 (m, 1 H), 2.34-2.43 (m, 1 H), 2.21 (m, 1 H), 2.00-2.15 (m, 1 H), 1.68-1.91 (m, 5 H), 1.21-1.40 (m, 1 H), 1.02-1.21 (m, 3 H), 0.94-1.02 (m, 1 H), 0.68 (m, 1 H)

Example 55: $^1$H NMR (400 MHz, DMSO-d$_6$) δ ppm: 9.13 (s, 1 H), 8.35 (d, 1 H), 8.05 (dd, 1 H), 7.84 (bs., 1 H), 7.44-7.59 (m, 2 H), 5.90 (d, 1 H), 5.57 (d, 1 H), 4.12 (m, 1 H), 3.51-3.75 (m, 2 H), 2.13-2.26 (m, 1 H), 1.96-2.13 (m, 1 H), 1.76-1.91 (m, 1 H), 1.67 (d, 1 H), 1.46-1.59 (m, 1 H), 1.18-1.46 (m, 3 H), 0.81-1.10 (m, 11 H), 0.72 (m, 1 H)

Example 56: $^1$H NMR (400 MHz, DMSO-d$_6$) δ ppm: 9.12 (s, 1 H), 8.36 (d, 1 H), 8.06 (d, 1 H), 7.85 (bs., 1 H), 7.45-7.60 (m, 2 H), 5.90 (d, 1 H), 5.59 (d, 1 H), 4.14 (m, 1 H), 3.52-3.81 (m, 2 H), 2.20 (dd, 1 H), 1.93-2.14 (m, 1 H), 1.75-1.93 (m, 1 H), 1.67 (d, 1 H), 1.46-1.58 (m, 1H), 1.18-1.46 (m, 3 H), 0.81-1.09 (m, 11 H), 0.58-0.77 (m, 1 H)

Example 69: $^1$H NMR (400 MHz, DMSO-d$_6$) δ ppm: 8.85 (d, 2 H), 7.60-7.65 (m, 1 H), 7.55-7.58 (m, 1 H), 7.50-7.55 (m, 1 H), 7.48 (t, 1 H), 7.22 (dd, 1 H), 5.83 (d, 1 H), 5.49 (d, 1 H), 5.36 (s, 2 H), 4.17 (dd, 1 H), 3.74-3.83 (m, 1 H), 3.68-3.74 (m, 1 H), 3.16 (s, 3 H), 2.58 (s, 3H), 2.19 (dd, 1 H), 2.05-2.14 (m, 1 H), 1.71-1.88 (m, 2 H), 1.53-1.67 (m, 2 H), 1.28-1.53 (m, 5 H), 1.12-1.24 (m, 1 H), 0.95-1.03 (m, 1 H), 0.69-0.76 (m, 1 H)

Example 73: $^1$H NMR (400 MHz, DMSO-d$_6$) δ ppm: 9.15 (s, 1 H), 8.37 (d, 1 H), 8.07 (dd, 1 H), 7.85 (bs., 1 H), 7.49-7.60 (m, 2 H), 5.92 (d, 1 H), 5.60 (d, 1 H), 4.16 (dd, 1 H), 3.71 (t, 1 H), 3.41-3.53 (m, 1 H), 2.16-2.27 (m, 1 H), 2.06-2.16 (m, 1 H), 1.80-1.90 (m, 1 H), 1.57-1.80 (m, 4 H), 1.19 (m, 4 H), 0.94-1.09 (m, 2 H), 0.68-0.90 (m, 6 H)

Example 74: $^1$H NMR (400 MHz, DMSO-d$_6$) δ ppm: 8.18 (d, 1H), 7.71-7.60 (m, 3H), 7.43 (t, 1H), 7.37 (bs, 1H), 7.27 (t, 1H), 5.76 (m, 1H), 5.43 (m, 1H), 5.18 (m, 1H), 4.17 (m, 2H), 3.69 (m, 1H), 2.23-2.05 (m, 2H), 1.84 (m, 3H), 1.68-1.55 (m, 5H), 1.47 (m, 1H), 1.38-1.20 (m, 1H), 0.99 (m, 1H), 0.67 (m, 1H)

Example 99: $^1$H NMR (400 MHz, DMSO-d$_6$) δ ppm: 8.85 (d, 2 H), 7.69 (d, 1 H), 7.63 (d, 1 H), 7.57 (d, 1 H), 7.48 (t, 1 H), 7.23 (dd, 1 H), 5.82 (d, 1 H), 5.49 (d, 1 H), 5.37 (s, 2 H), 3.99-4.16 (m, 2 H), 3.69-3.87 (m, 2 H), 3.14 (s, 3 H), 2.58 (s, 3 H), 2.05-2.24 (m, 2 H), 1.79-1.92 (m, 4 H), 1.48-1.58 (m, 2 H), 1.23-1.37 (m, 1 H), 0.95-1.02 (m, 1 H), 0.71-0.76 (m, 1 H)

Example 100: $^1$H NMR (400 MHz, DMSO-d$_6$) δ ppm: 8.85 (d, 2 H), 7.70 (d, 1 H), 7.63 (d, 1 H), 7.57 (d, 1 H), 7.48 (t, 1 H), 7.23 (dd, 1 H), 5.82 (d, 1 H), 5.49 (d, 1 H), 5.36 (s, 2 H), 3.99-4.17 (m, 2 H), 3.68-3.82 (m, 2 H), 3.14 (s, 3 H), 2.58 (s, 3 H), 2.05-2.24 (m, 2 H), 1.79-1.92 (m, 4 H), 1.45-1.59 (m, 2 H), 1.28-1.38 (m, 1 H), 0.95-1.03 (m, 1 H), 0.71-0.77 (m, 1 H)

Example 101: $^1$H NMR (400 MHz, DMSO-$d_6$) δ ppm: 8.85 (d, 2 H), 7.61-7.69 (m, 2 H), 7.57 (d, 1 H), 7.48 (t, 1 H), 7.22 (dd, 1 H), 5.82 (d, 1 H), 5.49 (d, 1 H), 5.37 (s, 2 H), 4.17 (dd, 1 H), 3.90-4.01 (m, 1 H), 3.67-3.75 (m, 2 H), 3.16 (s, 3 H), 2.58 (s, 3 H), 2.06-2.24 (m, 3 H), 1.58-1.88 (m, 4 H), 1.34-1.49 (m, 2 H), 0.93-1.04 (m, 1 H), 0.75 (td, 1 H)

Example 102: $^1$H NMR (400 MHz, DMSO-$d_6$) δ ppm: 8.85 (d, 2 H), 7.60-7.71 (m, 2 H), 7.57 (d, 1 H), 7.48 (t, 1 H), 7.22 (dd, 1 H), 5.83 (d, 1 H), 5.49 (d, 1 H), 5.36 (s, 2 H), 4.17 (dd, 1 H), 3.89-4.01 (m, 1 H), 3.67-3.75 (m, 2 H), 3.16 (s, 3 H), 2.58 (s, 3 H), 2.04-2.24 (m, 3 H), 1.57-1.88 (m, 4 H), 1.32-1.51 (m, 2 H), 0.95-1.04 (m, 1 H), 0.72-0.77 (m, 1 H)

Example 123: $^1$H NMR (400 MHz, CDCl$_3$-d6) δ ppm: 8.40 (d, 1 H), 7.31-7.51 (m, 3 H), 5.39 (d, 2 H), 4.55 (m, 1 H), 3.95-4.07 (m, 1 H), 3.36 (m, 1 H), 2.83-2.94 (m, 1 H), 1.64-2.09 (m, 6 H), 1.14-1.27 (m, 6 H), 0.95-1.12 (m, 1 H), 0.77-0.94 (m, 1 H), 0.62 (m, 1 H)I.

Example 126: $^1$H NMR (400 MHz, DMSO-d6) δ ppm: mixture of 2 diastereosiomers: 8.20 (d, 1 H), 7.65-7.73 (m, 3 H), 7.35-7.47 (m, 2 H), 7.28 (t, 1 H), 5.80 (d, 0.5 H), 5.75 (d, 0.5 H), 5.48 (d, 0.5 H), 5.43 (d, 0.5 H), 4.15 (m, 1 H), 3.7 (bs, 2 H), 3.12 (s, 1.5 H), 3.09 (s, 1.5 H), 2.11-2.22 (m, 2 H), 1.85 (bs, 1 H), 1.15-1.66 (m, 8 H), 1.10 (s, 3 H), 1.01 (m, 1 H), 0.70 (m, 1 H). The relative stereochemistry was tentatively assigned based on NMR-ROESY experiments.

Example 127: $^1$H NMR (600 MHz, DMSO-$d_6$) δ ppm: 8.19 (d, 1 H) 7.60-7.73 (m, 2 H), 7.42-7.53 (m, 2 H), 7.37 (br. s., 1 H), 7.28 (t, 1 H), 5.71-5.79 (m, 1 H), 5.45 (d, 1 H), 4.50 (t, 1 H), 4.14 (dd, 1 H), 3.64-3.74 (m, 2 H), 3.04 (d, 2 H), 2.15-2.24 (m, 1 H), 2.10 (dd, 1 H), 1.83 (dd, 1 H), 1.67 (d, 1 H), 1.51-1.58 (m, 1 H), 1.41 (d, 1 H), 1.23-1.34 (m, 2 H), 1.06-1.20 (m, 2H), 0.93-1.04 (m, 2 H), 0.78-0.90 (m, 3 H), 0.64-0.71 (m, 1 H)

| Factor D inhibition data using Method 1 to determine the IC$_{50}$ values | |
|---|---|
| Example | IC$_{50}$ (μM) |
| 1 | 0.204 |
| 2 | 6.904 |
| 3 | 4.789 |
| 4 | 5.129 |
| 5 | 0.022 |
| 6 | 0.056 |
| 7 | 1.683 |
| 8 | 2.392 |
| 9 | 1.484 |
| 10 | 1.822 |
| 11 | 3.015 |
| 12 | 12.708 |
| 13 | 5.966 |
| 14 | 2.430 |
| 15 | 1.761 |
| 16 | 3.152 |
| 17 | 0.691 |
| 18 | 1.698 |
| 19 | 0.790 |
| 20 | 1.233 |
| 21 | 0.486 |
| 22 | 0.015 |
| 23 | 0.016 |
| 24 | 0.401 |
| 25 | 0.028 |
| 26 | 0.026 |
| 27 | 0.040 |
| 28 | 0.100 |
| 29 | 0.028 |
| 30 | 0.010 |
| 31 | 0.900 |
| 32 | 0.063 |
| 33 | 0.121 |
| 34 | 0.728 |
| 35 | 0.774 |
| 36 | 0.734 |
| 37 | 0.024 |
| 38 | 0.282 |
| 39 | 0.085 |
| 40 | 4.47 |
| 41 | 0.114 |
| 42 | 1.070 |
| 43 | 0.323 |
| 44 | 1.881 |
| 45 | 0.405 |
| 46 | 0.478 |
| 47 | 0.091 |
| 48 | 1.325 |
| 49 | 0.029 |
| 50 | 0.118 |
| 51 | 0.226 |
| 52 | 0.999 |
| 53 | 0.905 |
| 54 | 0.057 |
| 55 | 2.212 |
| 56 | 0.037 |
| 57 | 1.932 |
| 58 | 0.041 |
| 59 | 0.043 |
| 60 | 0.022 |
| 61 | 0.032 |
| 62 | 0.024 |
| 63 | 0.049 |
| 64 | 0.024 |
| 65 | 0.038 |
| 66 | 1.211 |
| 67 | 0.318 |
| 68 | 1.922 |
| 69 | 0.143 |
| 70 | 2.092 |
| 71 | 0.041 |
| 72 | 1.703 |
| 73 | 0.029 |
| 74 | 0.132 |
| 75 | 1.574 |
| 76 | 0.156 |
| 77 | 0.254 |
| 78 | 0.105 |
| 79 | 2.414 |
| 80 | 0.469 |
| 81 | 0.039 |
| 82 | 0.038 |
| 83 | 0.050 |
| 84 | 0.060 |
| 85 | 0.585 |
| 86 | 0.058 |
| 87 | 6.622 |
| 88 | 0.034 |
| 89 | 2.130 |
| 90 | 0.095 |
| 91 | 0.006 |
| 92 | 2.000 |
| 93 | 0.092 |
| 94 | 0.138 |
| 95 | 0.025 |
| 96 | 0.090 |
| 97 | 0.341 |
| 98 | 0.011 |
| 99 | 0.432 |
| 100 | 0.942 |
| 101 | 0.102 |
| 102 | 0.247 |
| 103 | 0.036 |
| 104 | 0.273 |

Factor D inhibition data using Method 1 to determine the IC$_{50}$ values

| Example | IC$_{50}$ (μM) |
|---|---|
| 105 | 0.225 |
| 106 | 0.018 |
| 107 | 0.467 |
| 108 | 2.230 |
| 109 | 0.028 |
| 110 | 0.048 |
| 111 | 0.010 |
| 112 | 0.370 |
| 113 | 0.090 |
| 114 | 1.276 |
| 115 | 0.022 |
| 116 | 1.599 |
| 117 | 0.016 |
| 118 | 0.403 |
| 119 | 0.183 |
| 120 | 0.997 |
| 121 | 0.015 |
| 122 | 2.20 |
| 123 | 0.920 |
| 124 | 0.010 |
| 125 | 1.10 |
| 126 | 0.200 |
| 127 | 0.080 |
| 128 | 2.21 |

What is claimed is:

1. A compound, or a salt thereof, according to the formula (I)

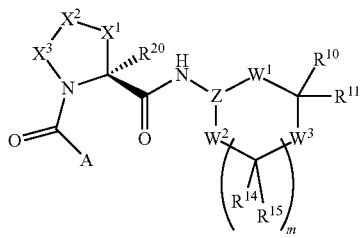

(I)

Wherein
A is a group selected from:

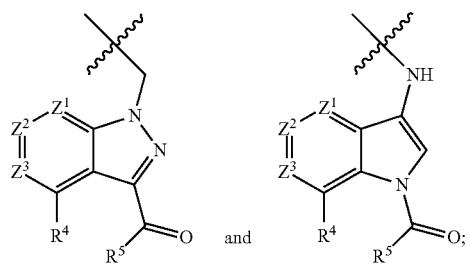

and

Wherein
$Z^1$ is $C(R^1)$ or N;
$Z^2$ is $C(R^2)$ or N;
$Z^3$ is $C(R^3)$ or N, wherein at least one of $Z^1$, $Z^2$ or $Z^3$ is not N;
$R^1$ is selected from the group consisting of hydrogen, halogen, $C_1$-$C_6$alkyl, $C_1$-$C_6$alkoxy, haloC-$C_6$alkyl, haloC-$C_6$alkoxy $C_1$-$C_6$alkoxycarbonyl, $CO_2H$ and $C(O)NR^AR^B$;

$R^2$ and $R^3$ are independently selected from the group consisting of hydrogen, halogen, hydroxy, $NR^CR^D$, cyano, $CO_2H$, $CONR^AR^B$, $SO_2C_1$-$C_6$alkyl, and $SO_2NH_2$, $SO_2NR^AR^B$, $C_1$-$C_6$alkoxycarbonyl, —C(NR$^A$)NR$^C$R$^D$, $C_1$-$C_6$alkyl, haloC$_1$-$C_6$alkyl, $C_2$-$C_6$alkenyl, $C_1$-$C_6$alkoxy, haloC$_1$-$C_6$alkoxy, $C_2$-$C_6$alkenyloxy, wherein each alkyl, alkenyl, alkoxy and alkenyloxy is unsubstituted or substituted with up to 4 substitutents independently selected from halogen, hydroxy, cyano, tetrazole, $C_1$-$C_4$alkoxy, $C_1$-$C_4$haloalkoxy, $CO_2H$, $C_1$-$C_6$alkoxycarbonyl, $C(O)NR^AR^B$, $NR^CR^D$, optionally substituted phenyl, heterocycle having 4 to 7 ring atoms and 1, 2, or 3 ring heteroatoms selected from N, O or S, heteroaryl having 5 or 6 ring atoms and 1, 2 or 3 ring heteroatoms selected from N, O or S, and wherein optional phenyl and heteroaryl substituents are selected from halogen, hydroxy, $C_1$-$C_4$alkyl, $C_1$-$C_4$alkoxy and $CO_2H$;
$R^4$ is selected from the group consisting of hydrogen, halogen, and $C_1$-$C_6$alkyl;
$R^5$ is $C_1$-$C_4$alkyl, hydroxyC$_1$-$C_4$alkyl, haloC$_1$-$C_4$alkyl $C_1$-$C_4$alkoxyC$_1$-$C_4$alkyl, amino, methylamino;
$X^1$ is $CR^9R^{22}$ or sulfur;
$X^2$ is $CR^7R^8$, oxygen, sulfur, N(H) or N(C$_1$-$C_6$alkyl), wherein at least one of $X^1$ and $X^2$ is carbon; or
$X^1$ and $X^2$, in combination, forms an olefin of the formula —C(R$^7$)=C(H)— or —C(R$^7$)=C(C$_1$-$C_4$alkyl)-, wherein the C(R$^7$) is attached to $X^3$;
$X^3$ is (CR$^6$R$^{21}$)$_q$ or N(H) wherein q is 0, 1 or 2, wherein $X^3$ is CR$^6$R$^{21}$ or (CR$^6$R$^{21}$)$_2$ when either $X^1$ or $X^2$ is sulfur or $X^2$ is oxygen; or
$X^2$ and $X^3$, taken in combination, are —N=C(H)— or —N=C(C$_1$-$C_4$alkyl)- in which the C(H) or C(C$_1$-$C_4$alkyl) is attached to $X^1$;
$R^6$ is selected from the group consisting of hydrogen and $C_1$-$C_6$alkyl;
$R^7$ is hydrogen, halogen, hydroxy, cyano, $C_1$-$C_6$alkyl, $C_1$-$C_6$alkoxy, hydroxyC$_1$-$C_6$alkyl, $C_1$-$C_6$alkoxyC$_1$-$C_6$alkyl, haloC$_1$-$C_6$alkyl, or $C_1$-$C_6$haloalkoxy;
$R^8$ is hydrogen, halogen, hydroxy, azide, cyano, COOH, $C_1$-$C_6$alkoxycarbonyl, $C_1$-$C_6$alkyl, $C_1$-$C_6$alkoxy, $C_1$-$C_6$haloalkyl, $C_1$-$C_6$haloalkoxy, $NR^AR^B$, N(H)C(O)$C_1$-$C_6$alkyl, hydroxyC$_1$-$C_6$alkyl, $C_1$-$C_6$alkoxyC$_1$-$C_6$alkyl, or $C_1$-$C_6$alkyl substituted with $NR^AR^B$, N(H)C(O)H or N(H)C(O)(C$_1$-$C_4$alkyl);
$R^9$ is selected from the group consisting of hydrogen, hydroxy, halogen, $C_1$-$C_6$alkyl, haloC$_1$-$C_6$alkyl, $C_2$-$C_6$alkenyl, $C_2$-$C_6$alkynyl, $C_1$-$C_6$alkoxy, haloC$_1$-$C_6$alkoxy, $NR^AR^B$, N(H)C(O)$C_1$-$C_6$alkyl, N(H)C(O)OC$_1$-$C_6$alkyl and OC(O)NR$^C$R$^D$ each of alkyl, alkoxy, alkenyl, and alkynyl substituents may be substituted with 0, 1, or 2 groups independently selected at each occurrence from the group consisting of halogen, hydroxy, $C_1$-$C_6$alkyl, $C_1$-$C_6$alkoxy, and $NR^AR^B$;
$R^{20}$ is hydrogen or $C_1$-$C_6$alkyl;
$R^{21}$ is selected from the group consisting of hydrogen, phenyl and $C_1$-$C_6$alkyl, which alkyl group is unsubstituted or substituted with hydroxy, amino, azide, and NHC(O)$C_1$-$C_6$alkyl;
$R^{22}$ is selected from the group consisting of hydrogen, halogen, hydroxy, amino and $C_1$-$C_6$alkyl;
CR$^7$R$^8$, taken in combination forms a spirocyclic 3 to 6 membered carbocycle which is substituted with 0, 1, or 2 substituents independently selected from the group consisting of halogen and methyl; or
$R^7$ and $R^8$, taken in combination, form an exocyclic methylidene (=CH$_2$);

R$^7$ and R$^{22}$ or R$^8$ and R$^9$, taken in combination form an epoxide ring or a 3 to 6 membered carbocyclic ring system which carbocyclic ring is substituted with 0, 1, or 2 substituents independently selected from the group consisting of halogen, methyl, ethyl, hydroxyC$_1$-C$_4$alkyl, C$_1$-C$_6$alkoxyC$_1$-C$_4$alkyl, C$_1$-C$_4$alkoxycarbonyl, CO$_2$H, and C$_1$-C$_4$alkyl substituted with NR$^A$R$^B$;

R$^6$ and R$^7$ or R$^8$ and R$^{21}$, taken in combination, form a fused 3 membered carbocyclic ring system which is substituted with 0, 1, or 2 substituents independently selected from the group consisting of halogen, methyl, ethyl, hydroxyC$_1$-C$_4$alkyl, C$_1$-C$_6$alkoxyC$_1$-C$_4$alkyl, C$_1$-C$_4$alkoxycarbonyl, CO$_2$H, and C$_1$-C$_4$alkyl substituted with NR$^A$R$^B$;

R$^{20}$ and R$^{22}$ taken in combination form a fused 3 carbocyclic ring system;

R$^9$ and R$^{21}$ taken in combination form a form 1 to 3 carbon alkylene linker;

R$^7$ and R$^{20}$ taken in combination form 1 to 3 carbon alkylene linker;

Z is N or CR$^{16}$;

W$^1$ is a bond or CR$^{17}$R$^{18}$;

W$^2$ is a bond or CH$_2$;

W$^3$ is CR$^{12}$R$^{13}$; or W$^3$ is oxygen when (a) neither W$^1$ or W$^2$ is a bond and m is 1 or (b) W$^1$ is a bond, W$^2$ is CH$_2$ and m is 2;

R$^{10}$ is selected from the group consisting of hydrogen, C$_1$-C$_4$alkyl, C$_1$-C$_4$alkoxy, halogen, hydroxyC$_1$-C$_4$alkyl, haloC$_1$-C$_4$alkyl, haloC$_1$-C$_4$alkoxy, CO$_2$C$_1$-C$_4$alkyl, and C(O)NH$_2$;

R$^{11}$ is selected from the group consisting of hydrogen, C$_1$-C$_4$alkyl, haloC$_1$-C$_4$alkyl, C$_1$-C$_4$alkoxy, hydroxy and halogen;

or CR$^{10}$R$^{11}$, taken in combination form a spirocyclic carbocycle having 3 to 6 ring carbon atoms or a spirocyclic heterocycle having 3 to 6 ring atoms and one ring heteroatom selected from N O or S;

R$^{12}$ and R$^{13}$ are independently selected from the group consisting of hydrogen, C$_1$-C$_4$alkyl and halogen;

R$^{14}$ and R$^{15}$ are independently selected from hydrogen, C$_1$-C$_4$alkyl, C$_1$-C$_4$alkoxy, halogen, haloC$_1$-C$_4$alkyl and hydroxy;

R$^{16}$ is hydrogen, C$_1$-C$_4$alkyl optionally substituted by fluoro, hydroxy or methoxy;

R$^{17}$ is hydrogen or fluoro;

R$^{18}$ is hydrogen or fluoro; or

CR$^{17}$R$^{18}$—CR$^{10}$R$^{11}$, taken in combination, form a vinyl group of the formula —C(R$^{18}$)=C(R$^{11}$)—;

R$^A$ and R$^B$, are each independently selected from the group consisting of hydrogen, C$_1$-C$_6$alkyl, haloC$_1$-C$_6$alkyl, C$_1$-C$_6$alkoxyC$_1$-C$_6$alkyl, or hydroxyC$_1$-C$_6$alkyl; and R$^C$ and R$^D$ are independently selected from the group consisting of hydrogen, and C$_1$-C$_6$alkyl, haloC$_1$-C$_6$alkyl, C$_1$-C$_6$alkoxyC$_1$-C$_6$alkyl, hydroxyC$_1$-C$_6$alkyl, or NR$^C$R$^D$, taken in combination, form a heterocycle having 4 to 7 ring atoms and 0 or 1 additional ring N, O or S atoms, which heterocycle is substituted with 0, 1, or 2 substituents independently selected from the group consisting of C$_1$-C$_4$alkyl, halogen, hydroxy, C$_1$-C$_4$alkoxy; and m is 0, 1, or 2.

2. A compound, or a salt thereof, according to formula (II):

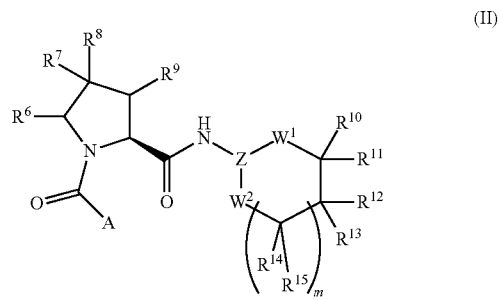

(II)

Wherein

A is a group selected from:

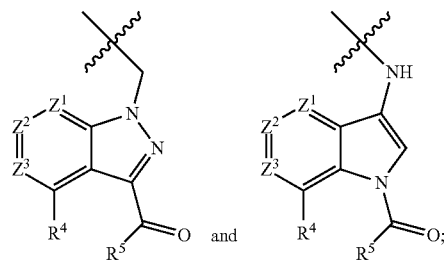

Z$^1$ is C(R$^1$) or N;

Z$^2$ is C(R$^2$) or N;

Z$^3$ is C(R$^3$) or N, wherein at least one of Z$^1$, Z$^2$ or Z$^3$ is not N;

R$^1$ is selected from the group consisting of hydrogen, halogen, C$_1$-C$_6$alkyl, C$_1$-C$_6$alkoxy, haloC-C$_6$alkyl, haloC-C$_6$alkoxy C$_1$-C$_6$alkoxycarbonyl, CO$_2$H and C(O)NR$^A$R$^B$;

R$^2$ and R$^3$ are independently selected from the group consisting of hydrogen, halogen, hydroxy, NR$^C$R$^D$, cyano, CO$_2$H, CONR$^A$R$^B$, SO$_2$C$_1$-C$_6$alkyl, and SO$_2$NH$_2$, SO$_2$NR$^A$R$^B$, C$_1$-C$_6$alkoxycarbonyl, —C(NR$^A$)NR$^C$R$^D$, C$_1$-C$_6$alkyl, haloC$_1$-C$_6$alkyl, C$_2$-C$_6$alkenyl, C$_1$-C$_6$alkoxy, haloC$_1$-C$_6$alkoxy, C$_2$-C$_6$alkenyloxy, wherein each alkyl, alkenyl, alkoxy and alkenyloxy is unsubstituted or substituted with up to 4 substitutents independently selected from halogen, hydroxy, cyano, tetrazole, C$_1$-C$_4$alkoxy, C$_1$-C$_4$haloalkoxy, CO$_2$H, C$_1$-C$_6$alkoxycarbonyl, C(O)NR$^A$R$^B$, NR$^C$R$^D$, optionally substituted phenyl, heterocycle having 4 to 7 ring atoms and 1, 2, or 3 ring heteroatoms selected from N, O or S, heteroaryl having 5 or 6 ring atoms and 1, 2 or 3 ring heteroatoms selected from N, O or S, and wherein optional phenyl and heteroaryl substituents are selected from halogen, hydroxy, C$_1$-C$_4$alkyl, C$_1$-C$_4$alkoxy and CO$_2$H;

R$^4$ is selected from the group consisting of hydrogen, halogen, and C$_1$-C$_6$alkyl;

R$^5$ is C$_1$-C$_4$alkyl, haloC-C$_4$alkyl, hydroxyC$_1$-C$_4$alkyl, C$_1$-C$_4$alkoxyC$_1$-C$_4$alkyl, amino, and methylamino;

R$^6$ is hydrogen;

R$^7$ is hydrogen or fluoro;

R$^8$ is hydrogen, methyl or hydroxymethyl;

R$^9$ is hydrogen, halogen, hydroxy or methoxy; or $R^6$ and $R^7$, taken in combination, form a cyclopropane ring; or $R^8$ and $R^9$, taken in combination, form a cyclopropane ring;

Z is N or $CR^{16}$;

$W^1$ is a bond or $CR^{17}R^{18}$;

$W^2$ is a bond or $CH_2$;

$R^{10}$ is selected from the group consisting of hydrogen, $C_1$-$C_4$alkyl, $C_1$-$C_4$alkoxy, halogen, hydroxy$C_1$-$C_4$alkyl, halo$C_1$-$C_4$alkyl, halo$C_1$-$C_4$alkoxy, $CO_2C_1$-$C_4$alkyl, and $C(O)NH_2$;

$R^{11}$ is selected from the group consisting of hydrogen, $C_1$-$C_4$alkyl, halo$C_1$-$C_4$alkyl, $C_1$-$C_4$alkoxy, hydroxy and halogen;

or $CR^{10}R^{11}$, taken in combination form a spirocyclic carbocycle having 3 to 6 ring carbon atoms or a spirocyclic heterocycle having 3 to 6 ring atoms and one ring heteroatom selected from N O or S;

$R^{12}$ and $R^{13}$ are independently selected from the group consisting of hydrogen, $C_1$-$C_4$alkyl and halogen;

$R^{14}$ and $R^{15}$ are independently selected from hydrogen, $C_1$-$C_4$alkyl, $C_1$-$C_4$alkoxy, halogen, halo$C_1$-$C_4$alkyl and hydroxy;

$R^{16}$ is hydrogen, $C_1$-$C_4$alkyl optionally substituted by fluoro, hydroxy or methoxy;

$R^{17}$ is hydrogen or fluoro;

$R^{18}$ is hydrogen or fluoro; or $CR^{17}R^{18}$—$CR^{10}R^{11}$, taken in combination, form a vinyl group of the formula —$C(R^{18})$=$C(R^{11})$—;

$R^A$ and $R^B$, are each independently selected from the group consisting of hydrogen, $C_1C_6$alkyl, halo$C_1$-$C_6$alkyl, $C_1$-$C_6$alkoxy$C_1$-$C_6$alkyl, or hydroxy$C_1$-$C_6$alkyl; and $R^C$ and $R^D$ are independently selected from the group consisting of hydrogen, and $C_1$-$C_6$alkyl, halo$C_1$-$C_6$alkyl, $C_1$-$C_6$alkoxy$C_1$-$C_6$alkyl, hydroxy$C_1$-$C_6$alkyl, or $NR^CR^D$, taken in combination, form a heterocycle having 4 to 7 ring atoms and 0 or 1 additional ring N, O or S atoms, which heterocycle is substituted with 0, 1, or 2 substituents independently selected from the group consisting of $C_1$-$C_4$alkyl, halogen, hydroxy, $C_1$-$C_4$alkoxy; and m is 0, 1, or 2.

3. The compound of claim 1, or a salt thereof, according to formula (III) or (IV):

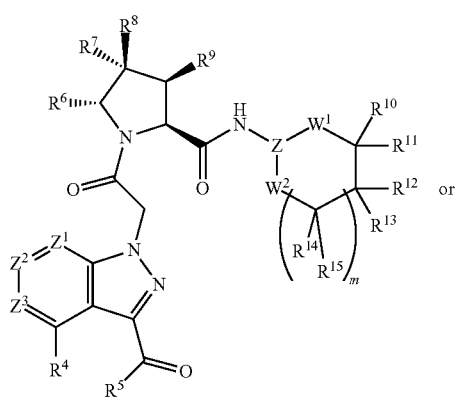

(III)

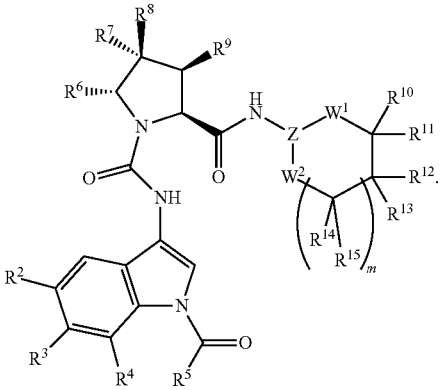

(IV)

4. The compound of claim 1, or a salt thereof, wherein at least two of $Z^1$, $Z^2$ and $Z^3$ are not N.

5. The compound of claim 1, or a salt thereof, wherein $R^4$ is hydrogen.

6. The compound of claim 1, or a salt thereof, wherein $Z^1$ is N or $CR^1$; $Z^2$ is N or $CR^2$, wherein at least one of $Z^1$ and $Z^2$ are not N;

$Z^3$ is $CR^3$;

$R^1$ is hydrogen, halogen or $C_1$-$C_4$alkyl;

$R^2$ is selected from the group consisting of hydrogen, halogen, $CO_2H$, $C_1$-$C_4$alkyl and $C_1$-$C_4$alkoxy;

$R^3$ is selected from the group consisting of hydrogen, halogen, $CO_2H$, $C_1$-$C_4$alkyl and $C_1$-$C_4$alkoxy, wherein the alkoxy is optionally substituted by pyridyl or pyrimidinyl;

$R^4$ is hydrogen; and $R^5$ is amino or $C_1$-$C_4$alkyl.

7. The compound of claim 1, or a salt thereof, wherein $R^6$ and $R^7$ taken in combination form a cyclopropane ring;

$R^8$ is hydrogen, methyl or hydroxymethyl; and $R^9$ is hydrogen.

8. The compound of claim 1, or a salt thereof, wherein $R^6$ and $R^7$ are hydrogen; and $R^8$ and $R^9$ taken in combination form a cyclopropane ring.

9. The compound of claim 1, or a salt thereof, wherein $R^6$ and $R^8$ are hydrogen;

$R^7$ is fluoro; and $R^9$ is hydrogen or methoxy.

10. The compound of claim 1, or a salt thereof, wherein $W^1$ is $CH_2$ and $W^2$ is a bond or $CH_2$.

11. The compound of claim 1, or a salt thereof, wherein $R^{10}$ is selected from the group consisting of hydrogen, $C_1$-$C_4$alkyl, $C_1$-$C_4$alkoxy, halogen and halo$C_1$-$C_4$alkyl;

$R^{11}$ is selected from the group consisting of hydrogen, $C_1$-$C_4$alkyl, $C_1$-$C_4$alkoxy and halogen;

or $CR^{10}R^{11}$, taken in combination form a spirocyclic cyclopropyl;

$R^{12}$ and $R^{13}$ are hydrogen; and $R^{14}$ and $R^{15}$ are independently selected from hydrogen, hydroxyl, $C_1$-$C_4$alkyl and $C_1$-$C_4$alkoxy.

12. A method for the treatment of a respiratory disorder, comprising the step of administering a therapeutically effective amount of a compound according to claim 1 to a subject in need thereof.

13. The compound of claim 1, wherein Z is CH.

14. The compound of claim 1, or a salt thereof, represented by formula (V) or (VI):

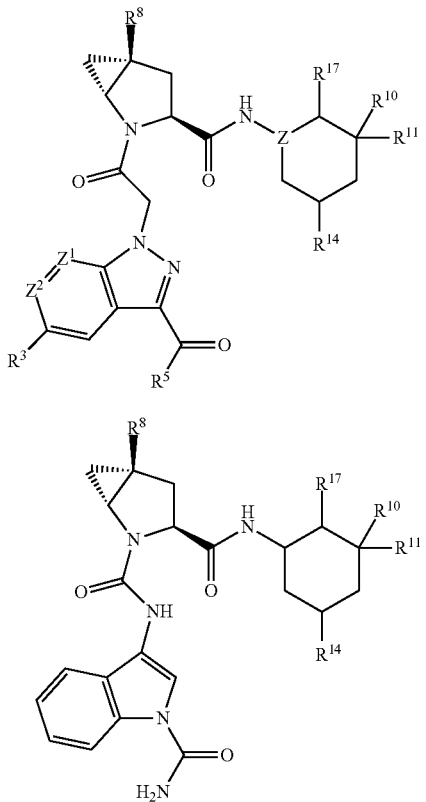

Wherein
$Z^1$ is CH or N;
$Z^2$ is $CR^2$ or N;
$R^2$ is hydrogen, $C_1$-$C_4$alkyl, or halogen;
$R^3$ is hydrogen, $C_1$-$C_4$alkyl, or pyrimidinylmethoxy;
$R^5$ is methyl or amino;
$R^8$ is hydrogen or hydroxymethyl;
$R^{10}$ is $C_1$-$C_4$alkyl, halogen, or trifluoromethyl;
$R^{11}$ is hydrogen, halogen, $C_1$-$C_4$alkyl or methoxy; or
$R^{10}$ and $R^{11}$ together form a spirocyclopropyl;
$R^{14}$ is hydrogen, hydroxyl, $C_1$-$C_4$alkyl or methoxy;
$R^{17}$ is hydrogen; or
$CHR^{17}CR^{10}R^{11}$, taken in combination forms a vinly group of the formula $CH=CR^{11}$.

15. The compound of claim 2, or a salt thereof, selected from the group consisting of (1R,3S,5R)-2-[2-(3-Acetyl-pyrazolo[3,4-c]pyridin-1-yl)-acetyl]-2-aza-bicyclo[3.1.0]hexane-3-carboxylic acid (3,3-dimethyl-cyclobutyl)-amide;
(1R,3S,5R)-2-[2-(3-Acetyl-pyrazolo[3,4-b]pyridin-1-yl)-acetyl]-2-aza-bicyclo[3.1.0]hexane-3-carboxylic acid (2,2-dimethyl-cyclopropyl)-amide;
(1R,3S,5R)-2-[2-(3-Acetyl-pyrazolo[3,4-b]pyridin-1-yl)-acetyl]-2-aza-bicyclo[3.1.0]hexane-3-carboxylic acid (2,2-difluoro-cyclopropyl)-amide;
(1R,3S,5R)-2-[2-(3-Acetyl-pyrazolo[3,4-b]pyridin-1-yl)-acetyl]-2-aza-bicyclo[3.1.0]hexane-3-carboxylic acid ((1R,2S)-2-fluoro-cyclopropyl)-amide;
(1R,3S,5R)-2-[2-(3-Acetyl-pyrazolo[3,4-b]pyridin-1-yl)-acetyl]-2-aza-bicyclo[3.1.0]hexane-3-carboxylic acid (3,3,5-trimethyl-cyclohexyl)-amide;
(1R,3S,5R)-2-[2-(3-Acetyl-pyrazolo[3,4-b]pyridin-1-yl)-acetyl]-2-aza-bicyclo[3.1.0]hexane-3-carboxylic acid (3,3,5,5-tetramethyl-cyclohexyl)-amide;
(1R,3S,5R)-2-[2-(3-Acetyl-pyrazolo[3,4-c]pyridin-1-yl)-acetyl]-2-aza-bicyclo[3.1.0]hexane-3-carboxylic acid (2,2-dimethyl-tetrahydro-pyran-4-yl)-amide;
(1R,3S,5R)-2-[2-(3-Acetyl-pyrazolo[3,4-c]pyridin-1-yl)-acetyl]-2-aza-bicyclo[3.1.0]hexane-3-carboxylic acid (3,3-difluoro-cyclobutyl)-amide;
(1R,3S,5R)-2-[2-(3-Acetyl-pyrazolo[3,4-c]pyridin-1-yl)-acetyl]-2-aza-bicyclo[3.1.0]hexane-3-carboxylic acid (3,3-difluoro-cyclohexyl)-amide;
(1R,3S,5R)-2-[2-(3-Acetyl-pyrazolo[3,4-c]pyridin-1-yl)-acetyl]-2-aza-bicyclo[3.1.0]hexane-3-carboxylic acid (1-hydroxymethyl-cyclohexyl)-amide;
(1R,3S,5R)-2-[2-(3-Acetyl-pyrazolo[3,4-c]pyridin-1-yl)-acetyl]-2-aza-bicyclo[3.1.0]hexane-3-carboxylic acid (4,4-difluoro-cyclohexyl)-amide;
(1R,3S,5R)-2-[2-(3-Acetyl-pyrazolo[3,4-b]pyridin-1-yl)-acetyl]-2-aza-bicyclo[3.1.0]hexane-3-carboxylic acid ((1R,3R)-3-carbamoyl-cyclopentyl)-amide;
(1R,3R)-3-({(1R,3S,5R)-2-[2-(3-Acetyl-pyrazolo[3,4-b]pyridin-1-yl)-acetyl]-2-aza-bicyclo[3.1.0]hexane-3-carbonyl}-amino)-cyclopentanecarboxylic acid methyl ester;
(1R,3S)-3-({(1R,3S,5R)-2-[2-(3-Acetyl-pyrazolo[3,4-b]pyridin-1-yl)-acetyl]-2-aza-bicyclo[3.1.0]hexane-3-carbonyl}-amino)-cyclohexanecarboxylic acid methyl ester;
(1R,3S,5R)-2-Aza-bicyclo[3.1.0]hexane-2,3-dicarboxylic acid 2-[(1-carbamoyl-1H-indol-3-yl)-amide]3-cyclohexylamide;
(1R,3S,5R)-2-Aza-bicyclo[3.1.0]hexane-2,3-dicarboxylic acid 2-[(1-carbamoyl-1H-indol-3-yl)-amide]3-(S)-cyclohex-2-enylamide;
(1R,3S,5R)-2-Aza-bicyclo[3.1.0]hexane-2,3-dicarboxylic acid 2-[(1-carbamoyl-1H-indol-3-yl)-amide]3-{[(1S,3R)-3-(2,2,2-trifluoro-ethoxy)-cyclohexyl]-amide};
(1R,3S,5R)-2-Aza-bicyclo[3.1.0]hexane-2,3-dicarboxylic acid 2-[(1-carbamoyl-1H-indol-3-yl)-amide]3-{[(1R,3S)-3-(2,2,2-trifluoro-ethoxy)-cyclohexyl]-amide};
(1R,3S,5R)-2-Aza-bicyclo[3.1.0]hexane-2,3-dicarboxylic acid 2-[(1-carbamoyl-1H-indol-3-yl)-amide]3-{[(1S,3S)-3-(2,2,2-trifluoro-ethoxy)-cyclohexyl]-amide};
(1R,3S,5R)-2-Aza-bicyclo[3.1.0]hexane-2,3-dicarboxylic acid 2-[(1-carbamoyl-1H-indol-3-yl)-amide]3-{[(1R,3R)-3-(2,2,2-trifluoro-ethoxy)-cyclohexyl]-amide};
(1R,3S,5R)-2-Aza-bicyclo[3.1.0]hexane-2,3-dicarboxylic acid 2-[(1-carbamoyl-1H-indol-3-yl)-amide]3-[((1R,3S)-3-methoxy-cyclohexyl)-amide];
(1R,3S,5R)-2-Aza-bicyclo[3.1.0]hexane-2,3-dicarboxylic acid 2-[(1-carbamoyl-1H-indol-3-yl)-amide]3-[((R)-3,3-dimethyl-cyclohexyl)-amide];
(1R,3S,5R)-2-Aza-bicyclo[3.1.0]hexane-2,3-dicarboxylic acid 2-[(1-carbamoyl-1H-indol-3-yl)-amide]3-[((1R,3S)-3-ethyl-cyclohexyl)-amide];
(1R,3S,5R)-2-Aza-bicyclo[3.1.0]hexane-2,3-dicarboxylic acid 2-[(1-carbamoyl-1H-indol-3-yl)-amide]3-[((1S,3R)-3-ethyl-cyclohexyl)-amide];
(1R,3S,5R)-2-Aza-bicyclo[3.1.0]hexane-2,3-dicarboxylic acid 2-[(1-carbamoyl-1H-indol-3-yl)-amide]3-[((1R,3S)-3-methyl-cyclohexyl)-amide];

(1R,3S,5R)-2-Aza-bicyclo[3.1.0]hexane-2,3-dicarboxylic acid 2-[(1-carbamoyl-1H-indol-3-yl)-amide]3-[((1R,3S)-3-trifluoromethyl-cyclohexyl)-amide];

(2S,4R)-4-Fluoro-pyrrolidine-1,2-dicarboxylic acid 1-[(1-carbamoyl-1H-indol-3-yl)-amide]2-[((R)-3,3-dimethyl-cyclohexyl)-amide];

1-{2-[(1R,3S,5R)-3-(3,3-Dimethyl-piperidin-1-ylcarbamoyl)-2-aza-bicyclo[3.1.0]hex-2-yl]-2-oxo-ethyl}-6-methyl-1H-indazole-3-carboxylic acid amide;

1-{2-[(1R,3S,5R)-3-(3,3-Dimethyl-piperidin-1-ylcarbamoyl)-2-aza-bicyclo[3.1.0]hex-2-yl]-2-oxo-ethyl}-5-methyl-1H-pyrazolo[3,4-c]pyridine-3-carboxylic acid amide;

(1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid (3,3-dimethyl-piperidin-1-yl)-amide;

(1R,3S,5R)-2-[2-(3-Acetyl-pyrazolo[3,4-c]pyridin-1-yl)-acetyl]-2-aza-bicyclo[3.1.0]hexane-3-carboxylic acid (3-hydroxy-3-trifluoromethyl-cyclohexyl)-amide;

(1R,3S,5R)-2-[2-(3-Acetyl-indazol-1-yl)-acetyl]-2-aza-bicyclo[3.1.0]hexane-3-carboxylic acid (trans-3-trifluoromethoxy-cyclohexyl)-amide;

1-{2-Oxo-2-[(1R,3S,5R)-3-(trans-3-trifluoromethoxy-cyclohexylcarbamoyl)-2-aza-bicyclo[3.1.0]hex-2-yl]-ethyl}-1H-indazole-3-carboxylic acid amide;

1-{2-[(1R,3S,5R)-3-(3-Hydroxy-3-trifluoromethyl-cyclohexylcarbamoyl)-2-aza-bicyclo[3.1.0]hex-2-yl]-2-oxo-ethyl}-1H-pyrazolo[3,4-c]pyridine-3-carboxylic acid amide;

1-{2-[(1R,3S,5R)-3-(2,2-Difluoro-cyclohexylcarbamoyl)-2-aza-bicyclo[3.1.0]hex-2-yl]-2-oxo-ethyl}-1H-pyrazolo[3,4-c]pyridine-3-carboxylic acid amide;

(1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((S)-2,2-difluoro-cyclohexyl)-amide;

(1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((R)-2,2-difluoro-cyclohexyl)-amide;

(1R,3S,5R)-2-{2-[3-acetyl-5-(pyrimidin-2-ylmethoxy)-indazol-1-yl]-acetyl}-2-aza-bicyclo[3.1.0]hexane-3-carboxylic acid (2-fluoro-cyclohex-2-enyl)-amide;

1-{2-[(1R,3S,5R)-3-(3-Methoxy-3-trifluoromethyl-cyclohexylcarbamoyl)-2-aza-bicyclo[3.1.0]hex-2-yl]-2-oxo-ethyl}-1H-indazole-3-carboxylic acid amide;

1-{2-[(1R,3S,5R)-3-(3-Methoxy-3-trifluoromethyl-cyclohexylcarbamoyl)-2-aza-bicyclo[3.1.0]hex-2-yl]-2-oxo-ethyl}-1H-indazole-3-carboxylic acid amide;

1-{2-Oxo-2-[(1R,3S,5R)-3-((1R,3S)-3-trifluoromethyl-cyclohexylcarbamoyl)-2-aza-bicyclo[3.1.0]hex-2-yl]-ethyl}-1H-pyrazolo[3,4-c]pyridine-3-carboxylic acid amide;

(1R,3S,5R)-2-[2-(3-Acetyl-indazol-1-yl)-acetyl]-2-aza-bicyclo[3.1.0]hexane-3-carboxylic acid ((1S,3S)-3-methoxy-cyclohexyl)-amide;

(1R,3S,5R)-2-[2-(3-Acetyl-indazol-1-yl)-acetyl]-2-aza-bicyclo[3.1.0]hexane-3-carboxylic acid ((1R,3R)-3-methoxy-cyclohexyl)-amide;

(1R,3S,5R)-2-[2-(3-Acetyl-indazol-1-yl)-acetyl]-2-aza-bicyclo[3.1.0]hexane-3-carboxylic acid ((1S,3R)-3-methoxy-cyclohexyl)-amide;

(1R,3S,5R)-2-[2-(3-Acetyl-indazol-1-yl)-acetyl]-2-aza-bicyclo[3.1.0]hexane-3-carboxylic acid ((1R,3S)-3-methoxy-cyclohexyl)-amide;

1-{2-[(1R,3S,5R)-3-((1R,3S)-3-Methoxy-cyclohexylcarbamoyl)-2-aza-bicyclo[3.1.0]hex-2-yl]-2-oxo-ethyl}-1H-indazole-3-carboxylic acid amide;

1-{2-[(1R,3S,5R)-3-((1R,3S)-3-Methyl-cyclohexylcarbamoyl)-2-aza-bicyclo[3.1.0]hex-2-yl]-2-oxo-ethyl}-1H-indazole-3-carboxylic acid amide;

1-{2-[(1R,3S,5R)-3-((1S,3R)-3-Methyl-cyclohexylcarbamoyl)-2-aza-bicyclo[3.1.0]hex-2-yl]-2-oxo-ethyl}-1H-indazole-3-carboxylic acid amide;

1-{2-Oxo-2-[(1R,3S,5R)-3-((1R,3S)-3-trifluoromethyl-cyclohexylcarbamoyl)-2-aza-bicyclo[3.1.0]hex-2-yl]-ethyl}-1H-indazole-3-carboxylic acid amide;

5-Methyl-1-{2-oxo-2-[(1R,3S,5R)-3-((1R,3S)-3-trifluoromethyl-cyclohexylcarbamoyl)-2-aza-bicyclo[3.1.0]hex-2-yl]-ethyl}-1H-pyrazolo[3,4-c]pyridine-3-carboxylic acid amide;

1-{2-[(1R,3S,5R)-3-((1R,3S)-3-Methyl-cyclohexylcarbamoyl)-2-aza-bicyclo[3.1.0]hex-2-yl]-2-oxo-ethyl}-1H-pyrazolo[3,4-c]pyridine-3-carboxylic acid amide;

1-{2-[(1R,3S,5R)-3-(3,3-Difluoro-cyclopentylcarbamoyl)-2-aza-bicyclo[3.1.0]hex-2-yl]-2-oxo-ethyl}-1H-indazole-3-carboxylic acid amide;

1-{2-[(1R,3S,5R)-3-((S)-3,3-Dimethyl-cyclohexylcarbamoyl)-2-aza-bicyclo[3.1.0]hex-2-yl]-2-oxo-ethyl}-1H-indazole-3-carboxylic acid amide;

1-{2-[(1R,3S,5R)-3-((R)-3,3-Dimethyl-cyclohexylcarbamoyl)-2-aza-bicyclo[3.1.0]hex-2-yl]-2-oxo-ethyl}-1H-indazole-3-carboxylic acid amide;

1-{2-[(1R,3S,5R)-3-((S)-3,3-Dimethyl-cyclohexylcarbamoyl)-2-aza-bicyclo[3.1.0]hex-2-yl]-2-oxo-ethyl}-1H-pyrazolo[3,4-c]pyridine-3-carboxylic acid amide;

1-{2-[(1R,3S,5R)-3-((R)-3,3-Dimethyl-cyclohexylcarbamoyl)-2-aza-bicyclo[3.1.0]hex-2-yl]-2-oxo-ethyl}-1H-pyrazolo[3,4-c]pyridine-3-carboxylic acid amide;

1-{2-Oxo-2-[(1R,3S,5R)-3-((S)-spiro[2.5]oct-5-ylcarbamoyl)-2-aza-bicyclo[3.1.0]hex-2-yl]-ethyl}-1H-indazole-3-carboxylic acid amide;

1-{2-Oxo-2-[(1R,3S,5R)-3-((R)-spiro[2.5]oct-5-ylcarbamoyl)-2-aza-bicyclo[3.1.0]hex-2-yl]-ethyl}-1H-indazole-3-carboxylic acid amide;

1-{2-[(1R,3S,5R)-3-((R)-3,3-Dimethyl-cyclohexylcarbamoyl)-2-aza-bicyclo[3.1.0]hex-2-yl]-2-oxo-ethyl}-5-methyl-1H-indazole-3-carboxylic acid amide;

1-{2-[(1R,3S,5R)-3-((R)-3,3-Dimethyl-cyclohexylcarbamoyl)-2-aza-bicyclo[3.1.0]hex-2-yl]-2-oxo-ethyl}-6-fluoro-1H-indazole-3-carboxylic acid amide;

1-{2-[(1R,3S,5R)-3-((R)-3,3-Dimethyl-cyclohexylcarbamoyl)-2-aza-bicyclo[3.1.0]hex-2-yl]-2-oxo-ethyl}-6-methyl-1H-indazole-3-carboxylic acid amide;

6-Chloro-1-{2-[(1R,3S,5R)-3-((R)-3,3-dimethyl-cyclohexylcarbamoyl)-2-aza-bicyclo[3.1.0]hex-2-yl]-2-oxo-ethyl}-1H-indazole-3-carboxylic acid amide;

1-{2-[(1R,3S,5R)-3-((R)-3,3-Dimethyl-cyclohexylcarbamoyl)-2-aza-bicyclo[3.1.0]hex-2-yl]-2-oxo-ethyl}-5-methyl-1H-pyrazolo[3,4-c]pyridine-3-carboxylic acid amide;

1-{2-[(1R,3S,5R)-3-((R)-3,3-Dimethyl-cyclohexylcarbamoyl)-2-aza-bicyclo[3.1.0]hex-2-yl]-2-oxo-ethyl}-5-ethyl-1H-pyrazolo[3,4-c]pyridine-3-carboxylic acid amide;

1-{2-[(1R,3S,5R)-3-((R)-3,3-Dimethyl-cyclohexylcarbamoyl)-2-aza-bicyclo[3.1.0]hex-2-yl]-2-oxo-ethyl}-7-methyl-1H-pyrazolo[3,4-c]pyridine-3-carboxylic acid amide;

(1R,3S,5R)-2-[2-(5-Acetyl-pyrrolo[2,3-c]pyridazin-7-yl)-acetyl]-2-aza-bicyclo[3.1.0]hexane-3-carboxylic acid ((R)-3,3-dimethyl-cyclohexyl)-amide;

1-{2-[(1R,3S,5R)-3-((S)-3,3-Dimethyl-cyclopentylcarbamoyl)-2-aza-bicyclo[3.1.0]hex-2-yl]-2-oxo-ethyl}-1H-pyrazolo[3,4-c]pyridine-3-carboxylic acid amide;

1-{2-[(1R,3S,5R)-3-((R)-3,3-Dimethyl-cyclopentylcarbamoyl)-2-aza-bicyclo[3.1.0]hex-2-yl]-2-oxo-ethyl}-1H-pyrazolo[3,4-c]pyridine-3-carboxylic acid amide;
(1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((1R,3R)-3-methoxy-cyclohexyl)-amide;
1-{2-[(2S,4R)-2-((S)-3,3-Dimethyl-cyclohexylcarbamoyl)-4-fluoro-pyrrolidin-1-yl]-2-oxo-ethyl}-1H-pyrazolo[3,4-c]pyridine-3-carboxylic acid amide;
1-{2-[(2S,4R)-2-((R)-3,3-Dimethyl-cyclohexylcarbamoyl)-4-fluoro-pyrrolidin-1-yl]-2-oxo-ethyl}-1H-pyrazolo[3,4-c]pyridine-3-carboxylic acid amide;
1-{2-[(1R,3S,5R)-3-((1S,3R)-3-Ethyl-cyclohexylcarbamoyl)-2-aza-bicyclo[3.1.0]hex-2-yl]-2-oxo-ethyl}-1H-pyrazolo[3,4-c]pyridine-3-carboxylic acid amide;
1-{2-[(1R,3S,5R)-3-((1R,3S)-3-Ethyl-cyclohexylcarbamoyl)-2-aza-bicyclo[3.1.0]hex-2-yl]-2-oxo-ethyl}-1H-pyrazolo[3,4-c]pyridine-3-carboxylic acid amide;
1-{2-[(1R,3S,5R)-3-(3-Methyl-cyclohex-2-enylcarbamoyl)-2-aza-bicyclo[3.1.0]hex-2-yl]-2-oxo-ethyl}-1H-indazole-3-carboxylic acid amide;
1-{2-Oxo-2-[(1R,3S,5R)-3-((S)-spiro[2.5]oct-5-ylcarbamoyl)-2-aza-bicyclo[3.1.0]hex-2-yl]-ethyl}-1H-pyrazolo[3,4-c]pyridine-3-carboxylic acid amide;
1-{2-Oxo-2-[(1R,3S,5R)-3-((R)-spiro[2.5]oct-5-ylcarbamoyl)-2-aza-bicyclo[3.1.0]hex-2-yl]-ethyl}-1H-pyrazolo[3,4-c]pyridine-3-carboxylic acid amide;
1-{2-[(1R,3S,5R)-3-((1S,3R)-3-Methyl-cyclopentylcarbamoyl)-2-aza-bicyclo[3.1.0]hex-2-yl]-2-oxo-ethyl}-1H-indazole-3-carboxylic acid amide;
1-{2-[(1R,3S,5R)-3-((1S,3S)-3-Methyl-cyclopentylcarbamoyl)-2-aza-bicyclo[3.1.0]hex-2-yl]-2-oxo-ethyl}-1H-indazole-3-carboxylic acid amide;
1-{2-[(1R,3S,5R)-3-((1R,3R)-3-Methyl-cyclopentylcarbamoyl)-2-aza-bicyclo[3.1.0]hex-2-yl]-2-oxo-ethyl}-1H-indazole-3-carboxylic acid amide;
1-{2-[(1R,3S,5R)-3-((1R,3S)-3-Methyl-cyclopentylcarbamoyl)-2-aza-bicyclo[3.1.0]hex-2-yl]-2-oxo-ethyl}-1H-indazole-3-carboxylic acid amide;
1-{2-[(2S,4R)-2-((R)-3,3-Dimethyl-cyclohexylcarbamoyl)-4-fluoro-pyrrolidin-1-yl]-2-oxo-ethyl}-5-ethyl-1H-pyrazolo[3,4-c]pyridine-3-carboxylic acid amide;
1-{2-[(2S,4R)-2-((R)-3,3-Dimethyl-cyclohexylcarbamoyl)-4-fluoro-pyrrolidin-1-yl]-2-oxo-ethyl}-1H-indazole-3-carboxylic acid amide;
1-{2-[(1R,3S,5R)-3-((1R,3S)-3-Ethyl-cyclohexylcarbamoyl)-2-aza-bicyclo[3.1.0]hex-2-yl]-2-oxo-ethyl}-5-methyl-1H-pyrazolo[3,4-c]pyridine-3-carboxylic acid amide;
1-{2-[(2S,3S,4S)-2-((R)-3,3-Dimethyl-cyclohexylcarbamoyl)-4-fluoro-3-methoxy-pyrrolidin-1-yl]-2-oxo-ethyl}-1H-indazole-3-carboxylic acid amide;
1-{2-[(2S,3S,4S)-2-((S)-3,3-Dimethyl-cyclohexylcarbamoyl)-4-fluoro-3-methoxy-pyrrolidin-1-yl]-2-oxo-ethyl}-1H-indazole-3-carboxylic acid amide;
1-{2-[(1R,2S,5S)-2-((R)-3,3-Dimethyl-cyclohexylcarbamoyl)-3-aza-bicyclo[3.1.0]hex-3-yl]-2-oxo-ethyl}-1H-pyrazolo[3,4-c]pyridine-3-carboxylic acid amide;
1-{2-[(1R,2S,5S)-2-((S)-3,3-Dimethyl-cyclohexylcarbamoyl)-3-aza-bicyclo[3.1.0]hex-3-yl]-2-oxo-ethyl}-1H-pyrazolo[3,4-c]pyridine-3-carboxylic acid amide;
1-{2-[(1R,2S,5S)-2-((R)-3,3-Dimethyl-cyclohexylcarbamoyl)-3-aza-bicyclo[3.1.0]hex-3-yl]-2-oxo-ethyl}-1H-indazole-3-carboxylic acid amide;
1-{2-[(1R,2S,5S)-2-((S)-3,3-Dimethyl-cyclohexylcarbamoyl)-3-aza-bicyclo[3.1.0]hex-3-yl]-2-oxo-ethyl}-1H-indazole-3-carboxylic acid amide;
(1R,3S,5R)-2-[2-(3-Acetyl-indazol-1-yl)-acetyl]-2-aza-bicyclo[3.1.0]hexane-3-carboxylic acid ((S)-3,3-dichloro-cyclohexyl)-amide;
(1R,3S,5R)-2-[2-(3-Acetyl-indazol-1-yl)-acetyl]-2-aza-bicyclo[3.1.0]hexane-3-carboxylic acid ((R)-3,3-dichloro-cyclohexyl)-amide;
1-{2-[(2S,4R)-4-Fluoro-2-((S)-spiro[2.5]oct-5-ylcarbamoyl)-pyrrolidin-1-yl]-2-oxo-ethyl}-1H-indazole-3-carboxylic acid amide;
1-{2-[(2S,4R)-4-Fluoro-2-((R)-spiro[2.5]oct-5-ylcarbamoyl)-pyrrolidin-1-yl]-2-oxo-ethyl}-1H-indazole-3-carboxylic acid amide;
(1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((1R,3S)-3-methoxy-cyclohexyl)-amide;
(1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((1R,3S)-3-trifluoromethyl-cyclohexyl)-amide;
(1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((1R,3S)-3-methyl-cyclohexyl)-amide;
(1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((S)-3,3-dimethyl-cyclohexyl)-amide;
(1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((R)-3,3-dimethyl-cyclohexyl)-amide;
(1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((1R,3R)-3-methoxy-cyclopentyl)-amide;
(1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((1S,3S)-3-methoxy-cyclopentyl)-amide;
(1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((1S,3R)-3-methoxy-cyclopentyl)-amide;
(1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid ((1R,3S)-3-methoxy-cyclopentyl)-amide;
(1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid (3,3-dimethyl-cyclobutyl)-amide;
(1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid (3,3-difluoro-cyclobutyl)-amide;
1-{2-[(1R,3S,5R)-3-((1S,5S)-5-Methoxy-3,3-dimethyl-cyclohexylcarbamoyl)-2-aza-bicyclo[3.1.0]hex-2-yl]-2-oxo-ethyl}-1H-indazole-3-carboxylic acid amide;
1-{2-[(1R,3S,5R)-3-((1R,5R)-5-Methoxy-3,3-dimethyl-cyclohexylcarbamoyl)-2-aza-bicyclo[3.1.0]hex-2-yl]-2-oxo-ethyl}-1H-indazole-3-carboxylic acid amide;
1-{2-[(1R,3S,5R)-3-(cis-5-Methoxy-3,3-dimethyl-cyclohexylcarbamoyl)-2-aza-bicyclo[3.1.0]hex-2-yl]-2-oxo-ethyl}-1H-indazole-3-carboxylic acid amide;
1-{2-[(1R,3S,5R)-3-((1S,5S)-5-Hydroxy-3,3-dimethyl-cyclohexylcarbamoyl)-2-aza-bicyclo[3.1.0]hex-2-yl]-2-oxo-ethyl}-1H-indazole-3-carboxylic acid amide;

1-{2-[(1R,3S,5R)-3-((1R,5R)-5-Hydroxy-3,3-dimethyl-cyclohexylcarbamoyl)-2-aza-bicyclo[3.1.0]hex-2-yl]-2-oxo-ethyl}-1H-indazole-3-carboxylic acid amide;

1-{2-[(1R,3S,5S)-3-(3,3-dimethyl-cyclohexylcarbamoyl)-5-hydroxymethyl-2-aza-bicyclo[3.1.0]hex-2-yl]-2-oxo-thyl}-1H-indazole-3-carboxylic acid amide;

1-{2-[(1R,3S,5S)-3-((R)-3,3-Dimethyl-cyclohexylcarbamoyl)-5-hydroxymethyl-2-aza-bicyclo[3.1.0]hex-2-yl]-2-oxo-ethyl}-1H-indazole-3-carboxylic acid amide;

1-{2-[(1R,3S,5S)-3-((S)-3,3-Dimethyl-cyclohexylcarbamoyl)-5-hydroxymethyl-2-aza-bicyclo[3.1.0]hex-2-yl]-2-oxo-ethyl}-1H-indazole-3-carboxylic acid amide;

(1R,3S,5S)-2-[2-(3-Acetyl-pyrazolo[3,4-c]pyridin-1-yl)-acetyl]-5-hydroxymethyl-2-aza-bicyclo[3.1.0]hexane-3-carboxylic acid (S)-spiro[2.5]oct-5-ylamide;

(1R,3S,5S)-2-[2-(3-Acetyl-pyrazolo[3,4-c]pyridin-1-yl)-acetyl]-5-hydroxymethyl-2-aza-bicyclo[3.1.0]hexane-3-carboxylic acid (R)-spiro[2.5]oct-5-ylamide;

(1R,3S,5S)-2-[2-(3-Acetyl-pyrazolo[3,4-b]pyridin-1-yl)-acetyl]-5-hydroxymethyl-2-aza-bicyclo[3.1.0]hexane-3-carboxylic acid ((R)-3,3-dimethyl-cyclohexyl)-amide;

(1R,3S,5S)-2-[2-(3-Acetyl-pyrazolo[3,4-b]pyridin-1-yl)-acetyl]-5-hydroxymethyl-2-aza-bicyclo[3.1.0]hexane-3-carboxylic acid ((S)-3,3-dimethyl-cyclohexyl)-amide;

1-{2-[(1R,3S,5S)-3-((1S,3R)-3-Ethyl-cyclohexylcarbamoyl)-5-hydroxymethyl-2-aza-bicyclo[3.1.0]hex-2-yl]-2-oxo-ethyl}-1H-indazole-3-carboxylic acid amide;

1-{2-[(1R,3S,5S)-3-((1S,3S)-3-Ethyl-cyclohexylcarbamoyl)-5-hydroxymethyl-2-aza-bicyclo[3.1.0]hex-2-yl]-2-oxo-ethyl}-1H-indazole-3-carboxylic acid amide;

1-{2-[(1R,3S,5S)-3-((1R,3R)-3-Ethyl-cyclohexylcarbamoyl)-5-hydroxymethyl-2-aza-bicyclo[3.1.0]hex-2-yl]-2-oxo-ethyl}-1H-indazole-3-carboxylic acid amide;

1-{2-[(1R,3S,5S)-3-((1R,3S)-3-Ethyl-cyclohexylcarbamoyl)-5-hydroxymethyl-2-aza-bicyclo[3.1.0]hex-2-yl]-2-oxo-ethyl}-1H-indazole-3-carboxylic acid amide;

(1R,3S,5S)-2-[2-(3-Acetyl-pyrazolo[3,4-c]pyridin-1-yl)-acetyl]-5-hydroxymethyl-2-aza-bicyclo[3.1.0]hexane-3-carboxylic acid ((R)-3,3-dimethyl-cyclohexyl)-amide; and (1R,3S,5S)-2-[2-(3-Acetyl-pyrazolo[3,4-c]pyridin-1-yl)-acetyl]-5-hydroxymethyl-2-aza-bicyclo[3.1.0]hexane-3-carboxylic acid ((S)-3,3-dimethyl-cyclohexyl)-amide.

16. The compound of claim 1, or a salt thereof, selected from the group consisting of 1-(2-((1R,3S,5R)-3-(3-hydroxy-3-methylcyclohexylcarbamoyl)-2-azabicyclo[3.1.0]hexan-2-yl)-2-oxoethyl)-1H-indazole-3-carboxamide;

(1R,3S,5R)-2-(2-(3-acetyl-1H-indazol-1-yl)acetyl)-N-((1R,5R)-5-hydroxy-3,3-dimethylcyclohexyl)-2-azabicyclo[3.1.0]hexane-3-carboxamide;

(1R,3S,5R)-2-(2-(3-acetyl-1H-indazol-1-yl)acetyl)-N-((1S,5S)-5-hydroxy-3,3-dimethylcyclohexyl)-2-azabicyclo[3.1.0]hexane-3-carboxamide;

1-(2-((1R,3S,5R)-3-((3-methoxy-3-methylcyclohexyl)carbamoyl)-2-azabicyclo[3.1.0]hexan-2-yl)-2-oxoethyl)-1H-indazole-3-carboxamide;

1-(2-((1R,3S,5R)-3-(((1R,3S)-3-(hydroxymethyl)-3-methylcyclohexyl)carbamoyl)-2-azabicyclo[3.1.0]hexan-2-yl)-2-oxoethyl)-1H-indazole-3-carboxamide; and 1-(2-((1R,3S,5R)-3-(((1S,3R)-3-(hydroxymethyl)-3-methylcyclohexyl)carbamoyl)-2-azabicyclo[3.1.0]hexan-2-yl)-2-oxoethyl)-1H-indazole-3-carboxamide.

17. A pharmaceutical composition comprising one or more pharmaceutically acceptable carriers and a therapeutically effective amount of a compound of claim 1.

* * * * *